United States Patent
Miller et al.

(10) Patent No.: US 9,006,228 B2
(45) Date of Patent: Apr. 14, 2015

(54) SUBSTITUTED CYCLOPROPYL COMPOUNDS, COMPOSITIONS CONTAINING SUCH COMPOUNDS, AND METHODS OF TREATMENT

(75) Inventors: Michael Miller, Scotch Plains, NJ (US); Andrew Stamford, Chatham Township, NJ (US); Kallol Basu, Hillsborough, NJ (US); Harold B. Wood, Westfield, NJ (US); Duane DeMong, Somerset, NJ (US); Wanying Sun, Edison, NJ (US); Joie Garfunkle, Metuchen, NJ (US); Christopher Moyes, Westfield, NJ (US); Zhiyong Hu, Livingston, NJ (US); Ping Liu, Westfield, NJ (US); Scott D. Edmondson, Clark, NJ (US); Xing Dai, Cranford, NJ (US); Byron Gabriel DuBois, New York, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/126,685

(22) PCT Filed: Jun. 11, 2012

(86) PCT No.: PCT/US2012/041847
§ 371 (c)(1),
(2), (4) Date: Dec. 16, 2013

(87) PCT Pub. No.: WO2012/173917
PCT Pub. Date: Dec. 20, 2012

(65) Prior Publication Data
US 2014/0128368 A1    May 8, 2014

Related U.S. Application Data

(60) Provisional application No. 61/655,010, filed on Jun. 4, 2012, provisional application No. 61/497,703, filed on Jun. 16, 2011.

(51) Int. Cl.
| | | |
|---|---|---|
| C07D 417/14 | (2006.01) |
| C07D 211/24 | (2006.01) |
| C07D 401/04 | (2006.01) |
| C07D 401/14 | (2006.01) |
| C07D 405/14 | (2006.01) |
| C07D 413/04 | (2006.01) |
| C07D 413/14 | (2006.01) |
| C07D 211/22 | (2006.01) |

(52) U.S. Cl.
CPC ............ *C07D 211/24* (2013.01); *C07D 401/14* (2013.01); *C07D 405/14* (2013.01); *C07D 413/14* (2013.01); *C07D 401/04* (2013.01); *C07D 413/04* (2013.01); *C07D 417/14* (2013.01); *C07D 211/22* (2013.01)

(58) Field of Classification Search
None
See application file for complete search history.

(56) References Cited

U.S. PATENT DOCUMENTS

| | | |
|---|---|---|
| 6,054,587 A | 4/2000 | Reddy et al. |
| 6,110,903 A | 8/2000 | Kasibhatla et al. |
| 6,284,748 B1 | 9/2001 | Dang et al. |
| 6,399,782 B1 | 6/2002 | Kasibhatla et al. |
| 6,489,476 B1 | 12/2002 | Dang et al. |
| 6,699,871 B2 | 3/2004 | Edmondson et al. |
| 6,730,690 B2 | 5/2004 | Olson et al. |
| 2009/0270409 A1 | 10/2009 | Alper et al. |
| 2010/0022591 A1 | 1/2010 | Bertram et al. |
| 2010/0286112 A1 | 11/2010 | Barba et al. |
| 2011/0028501 A1 | 2/2011 | Wood et al. |
| 2011/0212939 A1 | 9/2011 | Bartram et al. |
| 2012/0053180 A1 | 3/2012 | Kang et al. |
| 2012/0142706 A1 | 6/2012 | Wood et al. |

FOREIGN PATENT DOCUMENTS

| | | |
|---|---|---|
| WO | 98/04528 A2 | 2/1998 |
| WO | 99/01423 A1 | 1/1999 |
| WO | 00/39088 A1 | 7/2000 |
| WO | 00/69810 A1 | 11/2000 |
| WO | 02/08188 A1 | 1/2002 |
| WO | 02/060388 A2 | 8/2002 |

(Continued)

OTHER PUBLICATIONS

Charette, et al., Enantioselective Cyclpropanation of Allylic Alcohols with Dioxaborolane Ligands: Scope and Synthetic Applications, vol. 120, pp. 11943-11952 (1998).
Charette, et al., Stability, Reactivity, Solution, and Solid-State Structure of Halomethylzinc Alkoxides, vol. 123, pp. 12160-12167 (2001).
Costanzi, et al., "On the applicability of GPCR Homology Models . . . ", J. Med. Chem., vol. 51, pp. 2907-2914 (2008).
Eymery, et al., "The Usefullness of Phosphorus Compounds in Alkyne Synthesis", Synthesis, No. 2, pp. 185-213 (2000).
Lima, et al., "Bioisosterism: A Useful Strategy for Molecular Modification and Drug Design", Current Medicinal Chemistry, vol. 12, pp. 23-49 (2005).
Chaki, et al., "Recent Advances in feeding suppressing agents: potential therapeutic strategy for the treatment of obesity", Expert Opinion Ther. Patents, vol. 11, No. 11, pp. 1677-1692 (2001).
Spanswick, et al., "Emerging antiobesity drugs", Expert Opinion Emerging Drugs, vol. 8, No. 1, pp. 217-237 (2003).

(Continued)

*Primary Examiner* — Timothy R Rozof
(74) *Attorney, Agent, or Firm* — Anna L. Cocuzzo; Catherine D. Fitch

(57) ABSTRACT

Substituted cyclopropyl compounds of the formula I: and pharmaceutically acceptable salts thereof are disclosed as useful for treating or preventing type 2 diabetes and similar conditions. The compounds are useful as agonists of the G-protein coupled receptor GPR-119. Pharmaceutical compositions and methods of treatment are also included.

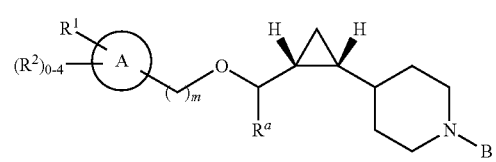

19 Claims, No Drawings

(56) References Cited

FOREIGN PATENT DOCUMENTS

| WO | 03/104207 A2 | 12/2003 |
|---|---|---|
| WO | 2004/019869 A2 | 3/2004 |
| WO | 2004/020408 A1 | 3/2004 |
| WO | 2004/020409 A1 | 3/2004 |
| WO | 2004/058741 A1 | 7/2004 |
| WO | 2004/066963 A2 | 8/2004 |
| WO | 2006/067531 A1 | 6/2006 |
| WO | 2006/067532 A1 | 6/2006 |
| WO | 2007/003962 A2 | 1/2007 |
| WO | 2007/003964 A1 | 1/2007 |
| WO | 2009/011836 A1 | 1/2009 |
| WO | 2009/034388 A1 | 3/2009 |
| WO | 2009/042053 A2 | 4/2009 |
| WO | 2009/129036 A1 | 10/2009 |
| WO | 2009/000087 A1 | 12/2009 |
| WO | 2010/004343 A1 | 1/2010 |
| WO | 2010/004344 A1 | 1/2010 |
| WO | 2010/004346 A1 | 1/2010 |
| WO | 2010/004347 A1 | 1/2010 |
| WO | 2010/004348 A1 | 1/2010 |
| WO | 2010/146605 A1 | 12/2010 |
| WO | 2011/008663 A2 | 1/2011 |
| WO | 2011/019538 A1 | 2/2011 |
| WO | 2011/113947 A1 | 9/2011 |
| WO | 2012/138845 A1 | 10/2012 |
| WO | 2012/173917 A1 | 12/2012 |
| WO | 2013/048916 A1 | 4/2013 |
| WO | 2013/062838 A1 | 5/2013 |
| WO | 2013/074388 A1 | 5/2013 |
| WO | 2013/122821 A1 | 8/2013 |
| WO | 2014/025379 A1 | 4/2014 |

OTHER PUBLICATIONS

Fernandez-Lopez, et al., "Pharmacological Approaches for the Treatment of Obesity", Drugs, vol. 62, No. 6, pp. 915-944 (2002).

Gadde, et al., "Combination pharmaceutical therapies for obesity", Expert Opin. Pharmacother., vol. 10, No. 6, pp. 921-925 (2009).

Szewczyk, et al., "Design of potent and selective GPR119 agonists for type II diabetes", Bioorganic & Medicinal Chemistry Letters, vol. 21, pp. 2665-2668 (2011).

International Search Report for PCT/US2012/41847, mailed Sep. 5, 2012.

SUBSTITUTED CYCLOPROPYL COMPOUNDS, COMPOSITIONS CONTAINING SUCH COMPOUNDS, AND METHODS OF TREATMENT

CROSS-REFERENCE TO RELATED APPLICATIONS

This application is a U.S. National Phase application under 35 U.S.C. §371 of PCT Application No. PCT/US2012/041847, filed Jun. 11, 2012, which published as WO 2012/173917 on Dec. 20, 2012, and claims priority under 35 U.S.C. §119 from U.S. Provisional Application No. 61/497,703, filed Jun. 16, 2011 and U.S. Provisional Application No. 61/655,010, filed Jun. 4, 2012.

BACKGROUND OF THE INVENTION

The present invention relates to G-protein coupled receptor agonists. In particular, the present invention is directed to agonists of GPR 119 that are useful for the treatment of diabetes, especially type 2 diabetes, as well as related diseases and conditions such as obesity and metabolic syndrome.

Diabetes is a disease derived from multiple causative factors. It is characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (T2DM), insulin is still produced in the body, and patients demonstrate resistance to the effects of insulin in stimulating glucose and lipid metabolism in the main insulin-sensitive tissues, namely, muscle, liver and adipose tissue. These patients often have normal levels of insulin, and may have hyperinsulinemia (elevated plasma insulin levels), as they compensate for the reduced effectiveness of insulin by secreting increased amounts of insulin.

There has been renewed focus on pancreatic islet-based insulin secretion that is controlled by glucose-dependent insulin secretion (GDIS). In this regard, several orphan G-protein coupled receptors (GPCR's) have recently been identified that are preferentially expressed in the β-cell and are implicated in GDIS. GPR119 is a cell-surface GPCR that is highly expressed in human (and rodent) islets as well as in insulin-secreting cell lines. Synthetic GPR119 agonists augment the release of insulin from isolated static mouse islets only under conditions of elevated glucose, and improve glucose tolerance in diabetic mice and diet-induced obese (DIO) C57/B6 mice without causing hypoglycemia. Novel GPR119 agonists therefore have the potential to function as anti-hyperglycemic agents that produce weight loss.

SUMMARY OF THE INVENTION

The present invention addresses a compound represented by the formula:

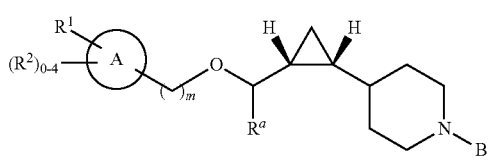

as well as the pharmaceutically acceptable salts thereof. The present invention further relates to methods of treating diabetes and related diseases and conditions.

DETAILED DESCRIPTION OF THE INVENTION

The present invention addresses a compound represented by the formula:

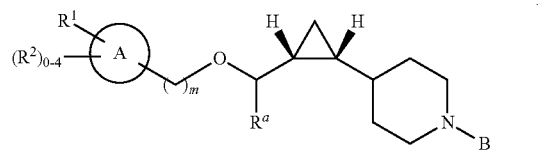

or a pharmaceutically acceptable salt thereof, wherein:

ring A represents a 5- or 6-membered aryl or heteroaryl ring, the heteroaryl ring containing 1-4 heteroatoms, 1-4 of which are nitrogen atoms, and 0-1 of which are oxygen or sulfur atoms;

m is an integer selected from 1-3;

$R^a$ is selected from: H; $C_{1-4}$alkyl; hydroxy$C_{1-4}$alkyl; or $C_{1-4}$alkoxy$C_{1-4}$alkyl;

$R^1$ is selected from:

$C_{1-6}$alkyl;

$OC_{1-6}$alkyl;

$C(O)C_{1-6}$alkyl;

$C(O)C_{3-6}$cycloalkyl;

$C(O)NHC_{1-6}$alkyl;

$S(O)_{0-2}C_{1-6}$alkyl;

$SO_2C_{3-6}$cycloalkyl;

$SO_2NR^bR^e$, wherein $R^b$ and $R^e$ are independently selected from H or $C_{1-6}$alkyl;

—$CH_2CONR^dR^e$ wherein $R^d$ and $R^e$ are independently selected from the group consisting of H, $C_{1-6}$alkyl, $C_{3-6}$cycloalkyl, halo$C_{1-6}$alkyl, halo$C_{3-6}$cycloalkyl, $C_{1-6}$alkoxy, and $C_{3-6}$cycloalkyl$C_{1-6}$alkoxy; wherein $R^d$ and $R^e$, if individually alkyl or alkoxy, can together form a 4-6-membered saturated heterocyclic ring having 1 nitrogen atom which 4-6-membered ring may be optionally substituted with 1-3 substituents independently selected from halogen, hydroxy, oxo, $C_{1-6}$alkyl, $C_{1-6}$alkoxy; or $CO_2C_{1-6}$alkyl;

—$CH_2$-heteroaryl, wherein heteroaryl is a 5-6 membered heteroaryl ring containing 1-4 heteroatoms selected from nitrogen or oxygen;

—$CH_2CH_3CONR^dR^e$; with $R^d$ and $R^e$ defined above;

or a 5-6 membered heteroaryl ring containing 1-4 heteroatoms, 1-4 of which are nitrogen atoms, and 0-1 of which are oxygen or sulfur atoms, wherein the $R^1$ alkyl, cycloalkyl and heteroaryl moiety is optionally substituted with 1-3 of halogen; hydroxy; $C_{1-6}$alkyl; $NH^2$; and O—$C_{1-6}$alkyl;

each $R^2$ is independently selected from halogen, CN, $C_{1-6}$alkyl and halo$C_{1-6}$alkyl;

B represents (a) a 6 membered aryl ring or a 5-6 membered heteroaryl ring containing 1-4 heteroatoms, 1-4 of which are nitrogen atoms, and 0-1 of which are oxygen or sulfur atoms, said ring being optionally substituted with 1-3 groups selected from $R^3$, wherein
each $R^3$ is independently selected from:
halogen;
hydroxyl;
$C_{1-6}$alkyl;
$C(O)OC_{1-6}$alkyl;
C=O;
CN;
$C_{1-6}$alkoxy;
$C_{3-6}$cycloalkyl;
$C(=O)-(O)_n-R'$, wherein n is an integer from 0-3 and R' is $C_{1-6}$alkyl or H;
5-6 membered heteroaryl ring containing 1-4 heteroatoms selected from nitrogen or oxygen;
$C(=O)-R^f$, wherein $R^f$ is a 5-6 membered heteroaryl ring containing 1-4 heteroatoms selected from nitrogen or oxygen;
and halo$C_{1-6}$alkoxy;
wherein the $R^3$ alkyl moiety is optionally substituted with 1-3 substituents independently selected from:
halogen,
hydroxy,
$C_{1-6}$alkyl, or
$C_{1-6}$alkoxy;
or b) $CO_2R^4$, wherein
$R^4$ is selected from:
$C_{1-6}$alkyl; or
$C_{3-6}$cycloalkyl,
wherein the alkyl and cycloalkyl are optionally substituted with 1-3 substituents independently selected from:
halogen,
$C_{1-6}$alkyl, or
$C_{3-6}$cycloalkyl.

The present invention is further directed to a compound in accordance with formula I-a:

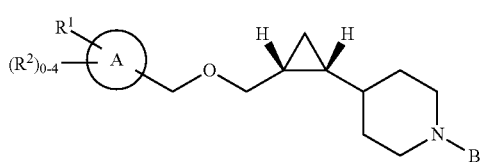

or a pharmaceutically acceptable salt thereof, wherein:
ring A is a substituted phenyl or pyridyl;
B represents a) a pyrimidine ring optionally substituted with 1-2 groups selected from $R^3$, wherein each $R^3$ is independently selected from:
halogen;
hydroxyl;
$C_{1-6}$alkyl;
$C(O)OC_{1-6}$alkyl;
C=O;
CN;
$C_{1-6}$alkoxy;
$C_{3-6}$cycloalkyl;
$C(=O)-(O)_n-R'$, wherein n is an integer from 0-3 and R' is $C_{1-6}$alkyl or H;
5-6 membered heteroaryl ring containing 1-4 heteroatoms selected from nitrogen or oxygen;
$C(=O)-R^f$, wherein $R^f$ is a 5-6 membered heteroaryl ring containing 1-4 heteroatoms selected from nitrogen or oxygen;
or halo$C_{1-6}$alkoxy;
wherein the $R^3$ alkyl moiety is optionally substituted with 1-3 substituents independently selected from:
halogen,
hydroxy,
$C_{1-6}$alkyl, or
$C_{1-6}$alkoxy;
b) 1,2,4-oxadiazol optionally substituted with 1-3 substituents independently selected from:
$C_{1-6}$alkyl,
$C_{1-6}$alkoxy; or
$C_{3-6}$cycloalkyl;
wherein the alkyl, alkoxy and cycloalkyl are optionally substituted with 1-3 substituents independently selected from:
Halogen;
$C_{1-6}$alkyl, or
$C_{3-6}$cycloalkyl;
or c) $CO_2R^4$, wherein
$R^4$ is selected from:
$C_{1-6}$alkyl; or
$C_{3-6}$cycloalkyl,
wherein the alkyl and cycloalkyl are optionally substituted with 1-3 substituents independently selected from:
halogen,
$C_{1-6}$alkyl, or
$C_{3-6}$cycloalkyl;
$R^1$ is selected from:
$C_{1-6}$alkyl;
$OC_{1-6}$alkyl;
$C(O)C_{1-6}$alkyl;
$C(O)C_{3-6}$cycloalkyl;
$C(O)NHC_{1-6}$alkyl;
$S(O)_{0-2}C_{1-6}$alkyl;
$SO_2C_{3-6}$cycloalkyl;
—$CH_2CONR^dR^e$ wherein $R^d$ and $R^e$ are independently selected from H, $C_{1-6}$alkyl, $C_{3-6}$cycloalkyl, halo$C_{1-6}$alkyl, halo $C_{3-6}$cycloalkyl, $C_{1-6}$alkoxy, or $C_{3-6}$cycloalkyl$C_{1-6}$alkoxy; wherein $R^d$ and $R^e$, if individually alkyl or alkoxy, can together form a 4-6-membered saturated heterocyclic ring having 1 nitrogen atom which 4-6-membered ring may be optionally substituted with 1-3 substituents independently selected from halogen, hydroxy, oxo, $C_{1-6}$alkyl, $C_{1-6}$alkoxy; or $CO_2C_{1-6}$alkyl;
—$CH_2$-heteroaryl, wherein the heteroaryl is a 5-6 membered heteroaryl ring containing 1-4 heteroatoms independently selected from nitrogen or oxygen
—$CH_2CH_3CONR^dR^e$, with $R^d$ and $R^e$ defined above;
or a 5-6 membered heteroaryl ring containing 1-4 heteroatoms, 1-4 of which are nitrogen atoms, and 0-1 of which are oxygen or sulfur atoms,
wherein the $R^1$ alkyl and cycloalkyl moiety is optionally substituted with 1-3 substituents independently selected from: halogen; hydroxy; $C_{1-6}$alkyl; $NH^2$; or O—$C_{1-6}$alkyl;
and $R^2$ is halogen which is further selected from fluoro or chloro.

In a particular embodiment of the present invention, ring A is pyridyl.

In another embodiment, ring A is phenyl.

The present invention is further directed to compounds of Formula I or pharmaceutically acceptable salts thereof, wherein B represents (b) $CO_2R^4$, wherein $R^4$ is
$C_{1-6}$alkyl, or
$C_{3-6}$cycloalkyl,
wherein the alkyl and cycloalkyl are optionally substituted with 1-3 substituents independently selected from:
halogen,
$C_{1-6}$alkyl,
or $C_{3-6}$cycloalkyl.

The present invention is also directed to compounds of Formula I or pharmaceutically acceptable salts thereof, wherein B is pyrimidine, optionally substituted with 1-3 substituents independently selected from:
halogen;
hydroxyl;
$C_{1-6}$alkyl;
$C(O)OC_{1-6}$alkyl;
C=O;
CN;
$C_{1-6}$alkoxy;
$C_{3-6}$cycloalkyl;
C(=O)—(O)$_n$—R', wherein n is an integer from 0-3 and R' is $C_{1-6}$alkyl or H;
5-6 membered heteroaryl ring containing 1-4 heteroatoms selected from nitrogen or oxygen;
C(=O)—R', wherein R' is a 5-6 membered heteroaryl ring containing 1-4 heteroatoms selected from nitrogen or oxygen;
or halo$C_{1-6}$alkoxy;
wherein the alkyl moiety is optionally substituted with 1-3 substituents independently selected from:
halogen,
hydroxy,
$C_{1-6}$alkyl, or
$C_{1-6}$alkoxy.

The present invention is further directed to compounds of Formula I or pharmaceutically acceptable salts thereof, wherein B is 1,2,4-oxadiazol optionally substituted with 1-3 substituents independently selected from
$C_{1-6}$alkyl;
$C_{1-6}$alkoxy; or
$C_{3-6}$cycloalkyl, wherein the alkyl, alkoxy and cycloalkyl are optionally substituted with 1-3 substituents independently selected from:
halogen,
$C_{1-6}$alkyl, or
$C_{3-6}$cycloalkyl.

In a particular embodiment of the present invention directed to compounds of formula I or pharmaceutically acceptable salts thereof, each $R^3$ is independently selected from halogen which is further selected from F, Cl or Br, $C_{1-4}$alkyl, $C_{1-3}$alkoxy or $C_{3-6}$cycloalkyl.

In a particular embodiment of the present invention, B is methoxymethyl-pyrimidine.

The present invention further encompasses compounds of Formula I or pharmaceutically acceptable salts thereof, wherein $R^2$ is halogen which is further selected from fluoro and chloro.

In other embodiments, $R^1$ is at the 4 position and is selected from: $C_{1-6}$alkyl; $OC_{1-6}$alkyl; $C(O)C_{1-6}$alkyl; $C(O)C_{3-6}$cycloalkyl; $C(O)NHC_{1-6}$alkyl; $S(O)_{0-2}C_{1-6}$alkyl; $SO_2C_{3-6}$cycloalkyl; $SO_2NR^bR^c$, wherein $R^b$ and $R^e$ are selected from H or $C_{1-6}$alkyl; or a 5-6 membered heteroaryl ring containing 1-4 heteroatoms, 1-4 of which are nitrogen atoms, and 0-1 of which are O or S atoms, wherein the $R^1$ alkyl, cycloalkyl and heteroaryl moiety is optionally substituted with 1-3 substituents independently selected from: halogen; hydroxy; $C_{1-6}$alkyl or O—$C_{1-6}$alkyl.

In one embodiment, $R^1$ is methylsulfonyl.

In another embodiment, the compound of formula I is

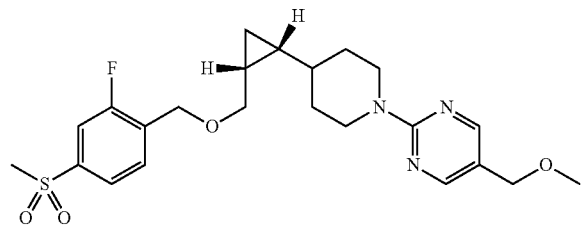

or a pharmaceutically acceptable salt thereof.

For compounds of formula I or a pharmaceutically acceptable salt thereof, the cyclopropyl ring is the cis cyclopropyl isomer.

Yet another aspect of the invention that is of interest relates to compounds of formula I, as well as the pharmaceutically acceptable salts thereof, selected from:

| Example | Compound Name |
|---|---|
| 1 | 5-chloro-2-{4-[(1R,2R)-2-({[5-(methylsulfonyl)pyridin-2-yl]methoxy}methyl)cyclopropyl]piperidin-1-yl}pyrimidine |
| 2 | 5-methyl-2-{4-[(1R,2R)-2-({[5-(methylsulfonyl)pyridin-2-yl]methoxy}methyl)cyclopropyl]piperidin-1-yl}pyrimidine |
| 3 | 5-ethyl-2-{4-[(1R,2R)-2-({[5-(methylsulfonyl)pyridin-2-yl]methoxy}methyl)cyclopropyl]piperidin-1-yl}pyrimidine |
| 4 | 5-bromo-2-{4-[(1R,2R)-2-({[5-(methylsulfonyl)pyridin-2-yl]methoxy}methyl)cyclopropyl]piperidin-1-yl}pyrimidine |
| 5 | 5-fluoro-2-{4-[(1R,2R)-2-({[5-(methylsulfonyl)pyridin-2-yl]methoxy}methyl)cyclopropyl]piperidin-1-yl}pyrimidine |
| 6 | 5-methoxy-2-{4-[(1R,2R)-2-({[5-(methylsulfonyl)pyridin-2-yl]methoxy}methyl)cyclopropyl]piperidin-1-yl}pyrimidine |
| 7 | 2-{4-[(1R,2S)-2-({[5-(methylsulfonyl)pyridin-2-yl]methoxy}methyl)cyclopropyl]piperidin-1-yl}-5-(1H-pyrazol-4-yl)pyrimidine |
| 8 | propyl 4-[(1R,2R)-2-({[4-(methylsulfonyl)benzyl]oxy}methyl)cyclopropyl]piperidine-1-carboxylate |
| 9 | isopropyl 4-[(1R,2R)-2-({[4-(methylsulfonyl)benzyl]oxy}methyl)cyclopropyl]piperidine-1-carboxylate |

-continued

| Example | Compound Name |
|---|---|
| 10 | isobutyl 4-[(1R,2R)-2-({[4-(methylsulfonyl)benzyl]oxy}methyl)cyclopropyl]piperidine-1-carboxylate |
| 11 | 1-methylcyclopropyl 4-[(1R,2R)-2-({[4-(methylsulfonyl)benzyl]oxy}methyl)cyclopropyl]piperidine-1-carboxylate |
| 12 | cyclobutyl 4-[(1R,2R)-2-({[4-(methylsulfonyl)benzyl]oxy}methyl)cyclopropyl]piperidine-1-carboxylate |
| 13 | cyclopropylmethyl 4-[(1R,2R)-2-({[4-(methylsulfonyl)benzyl]oxy}methyl)cyclopropyl]piperidine-1-carboxylate |
| 14 | 5-chloro-2-{4-[(1R,2R)-2-({[4-(methylsulfonyl)benzyl]oxy}methyl)cyclopropyl]piperidin-1-yl}pyrimidine |
| 15 | 5-methoxy-2-{4-[(1R,2R)-2-({[4-(methylsulfonyl)benzyl]oxy}methyl)cyclopropyl]piperidin-1-yl}pyrimidine |
| 16 | 5-fluoro-2-{4-[(1R,2R)-2-({[4-(methylsulfonyl)benzyl]oxy}methyl)cyclopropyl]piperidin-1-yl}pyrimidine |
| 17 | methyl 2-{4-[(1R,2R)-2-({[4-(methylsulfonyl)benzyl]oxy}methyl)cyclopropyl]piperidin-1-yl}pyrimidine-5-carboxylate |
| 18 | 5-cyclopropyl-2-{4-[(1R,2R)-2-({[4-(methylsulfonyl)benzyl]oxy}methyl)cyclopropyl]piperidin-1-yl}pyrimidine |
| 19 | 5-isobutyl-2-{4-[(1R,2R)-2-({[4-(methylsulfonyl)benzyl]oxy}methyl)cyclo propyl]piperidin-1-yl}pyrimidine |
| 20 | 5-ethyl-2-{4-[(1R,2R)-2-({[4-(methylsulfonyl)benzyl]oxy}methyl)cyclopropyl]piperidin-1-yl}pyrimidine |
| 21 | 5-methyl-2-{4-[(1R,2R)-2-({[4-(methylsulfonyl)benzyl]oxy}methyl)cyclopropyl]piperidin-1-yl}pyrimidine |
| 22 | 2-{4-[(1R,2R)-2-({[4-(methylsulfonyl)benzyl]oxy}methyl)cyclopropyl]piperidin-1-yl}-5-propylpyrimidine |
| 23 | 5-isopropyl-2-{4-[(1R,2R)-2-({[4-(methylsulfonyl)benzyl]oxy}methyl)cyclo propyl]piperidin-1-yl}pyrimidine |
| 24 | 1-(3-isopropyl-1,2,4-oxadiazol-5-yl)-4-[(1R,2R)-2-({[4-(methylsulfonyl)benzyl]oxy}methyl)cyclo propyl]piperidine |
| 25 | 4-[(1R,2R))-2-({[4-(cyclopropylsulfonyl)benzyl]oxy}methyl)cyclopropyl]-1-(3-isopropyl-1,2,4-oxadiazol-5-yl)piperidine |
| 26 | 4-[(1R,2R)-2-({[4-(ethylsulfonyl)benzyl]oxy}methyl)cyclopropyl]-1-(3-isopropyl-1,2,4-oxadiazol-5-yl)piperidine |
| 27 | 1-(3-cyclopropyl-1,2,4-oxadiazol-5-yl)-4-[(1R,2R)-2-({[4-(methylsulfonyl)benzyl]oxy}methyl) cyclopropyl]piperidine |
| 28 | 1-(3-cyclopropyl-1,2,4-oxadiazol-5-yl)-4-[(1R,2R)-2-({[4-(cyclopropylsulfonyl)benzyl]oxy}methyl) cyclopropyl]piperidine |
| 29 | 1-(3-cyclopropyl-1,2,4-oxadiazol-5-yl)-4-[(1R,2R)-2-({[4-(ethylsulfonyl)benzyl]oxy}methyl) cyclopropyl]piperidine |
| 30 | 1-(3-ethyl-1,2,4-oxadiazol-5-yl)-4-[(1R,2R)-2-({[4-(methylsulfonyl)benzyl]oxy}methyl) cyclopropyl]piperidine |
| 31 | 1-(3-cyclobutyl-1,2,4-oxadiazol-5-yl)-4-[(1R,2R)-2-({[4-(cyclopropylsulfonyl)benzyl]oxy}methyl) cyclopropyl]piperidine |
| 32 | 1-(3-cyclobutyl-1,2,4-oxadiazol-5-yl)-4-[(1R,2R)-2-({[4-(ethylsulfonyl)benzyl]oxy}methyl) cyclopropyl]piperidine |
| 33 | tert-butyl 4-[(1R,2R)-2-({[3-fluoro-4-(methylsulfonyl)benzyl]oxy}methyl) cyclopropyl]piperidine-1-carboxylate |
| 34 | tert-butyl 4-[(1R,2R)-2-({[4-(ethylsulfonyl)-3-fluorobenzyl]oxy}methyl) cyclopropyl]piperidine-1-carboxylate |
| 35 | 4-[(1R,2R)-2-({[3-fluoro-4-(methylsulfonyl)benzyl]oxy}methyl)cyclopropyl]-1-(3-isopropyl-1,2,4-oxadiazol-5-yl)piperidine |
| 36 | 1-(3-ethyl-1,2,4-oxadiazol-5-yl)-4-[(1R,2R)-2-({[3-fluoro-4-(methylsulfonyl)benzyl]oxy}methyl) cyclopropyl]piperidine |
| 37 | 1-(3-cyclopropyl-1,2,4-oxadiazol-5-yl)-4-[(1R,2R)-2-({[3-fluoro-4-(methylsulfonyl)benzyl]oxy}methyl) cyclopropyl]piperidine |
| 38 | 4-[(1R,2R)-2-({[3-fluoro-4-(ethylsulfonyl)benzyl]oxy}methyl)cyclopropyl]-1-(3-isopropyl-1,2,4-oxadiazol-5-yl)piperidine |
| 39 | 1-(3-cyclopropyl-1,2,4-oxadiazol-5-yl)-4-[(1R,2R)-2-({[3-fluoro-4-(ethylsulfonyl)benzyl]oxy}methyl) cyclopropyl]piperidine |
| 40 | 5-ethyl-2-{4-[(1R,2R)-2-({[3-fluoro-4-(methylsulfonyl)benzyl]oxy}methyl)cyclopropyl]piperidin-1-yl}pyrimidine |
| 41 | 5-chloro-2-{4-[(1R,2R)-2-({[3-fluoro-4-(methylsulfonyl)benzyl]oxy}methyl)cyclopropyl]piperidin-1-yl}pyrimidine |
| 42 | isopropyl 4-[(1R,2R)-2-({[3-fluoro-4-(methylsulfonyl)benzyl]oxy}methyl)cyclopropyl]piperidine-1-carboxylate |
| 43 | 1-methylcyclopropyl 4-[(1R,2R)-2-({[3-fluoro-4-(methylsulfonyl)benzyl]oxy}methyl)cyclopropyl] piperidine-1-carboxylate |
| 44 | tert-butyl 4-[(1R,2R)-2-({[3,5-difluoro-4-(methylsulfonyl)benzyl]oxy}methyl) cyclopropyl]piperidine-1-carboxylate |
| 45 | 5-chloro-2-{4-[(1R,2R)-2-({[3,5-difluoro-4-(methylsulfonyl)benzyl]oxy}methyl) cyclopropyl]piperidin-1-yl}pyrimidine |
| 46 | 5-chloro-2-{4-[(1R,2R)-2-({[3,5-difluoro-4-(methylsulfonyl)benzyl]oxy}methyl) cyclopropyl]piperidin-1-yl}pyrimidine |

-continued

| Example | Compound Name |
| --- | --- |
| 47 | 2-{4-[(1R,2R)-2-({[3,5-difluoro-4-(methylsulfonyl)benzyl]oxy}methyl)cyclopropyl]piperidin-1-yl}-5-fluoropyrimidine |
| 48 | 5-cyclopropyl-2-{4-[(1R,2R)-2-({[3,5-difluoro-4-(methylsulfonyl)benzyl]oxy}methyl) cyclopropyl] piperidin-1-yl}pyrimidine |
| 49 | 1-methylcyclopropyl 4-[(1R,2R)-2-({[3,5-difluoro-4-(methylsulfonyl)benzyl]oxy}methyl)cyclopropyl] piperidine-1-carboxylate |
| 50 | isopropyl 4-[(1R,2R)-2-({[3,5-difluoro-4-(methylsulfonyl)benzyl]oxy}methyl)cyclopropyl] piperidine-1-carboxylate |
| 51 | 4-[(1R,2R)-2-[1-(5-chloropyrimidin-2-yl)piperidin-4-yl]cyclopropyl}methoxy)methyl]-2-fluoro phenyl}(cyclopropyl)methanone |
| 52 | tert-butyl 4-[(1R,2R)-2-({[4-(cyclopropylcarbonyl)-3,5-difluorobenzyl]oxy}methyl)cyclopropyl] piperidine-1-carboxylate |
| 53 | 4-[(1R,2R)-2-[1-(5-chloropyrimidin-2-yl)piperidin-4-yl]cyclopropyl}methoxy)methyl]-2,6-difluoro phenyl}(cyclopropyl)methanone |
| 54 | 5-ethyl-2-{4-[(1R,2R)-2-({[4-(1,3-oxazol-2-yl)benzyl]oxy}methyl)cyclopropyl] piperidin-1-yl} pyrimidine |
| 55 | 5-ethyl-2-{4-[(1R,2R)-2-({[4-(1,3-thiazol-5-yl)benzyl]oxy}methyl)cyclopropyl] piperidin-1-yl} pyrimidine |
| 56 | 2-{4-[(1R,2R)-2-({[4-(cyclopropylsulfonyl)benzyl]oxy}methyl)cyclopropyl] piperidin-1-yl}-5-ethyl pyrimidine |
| 57 | 5-ethyl-2-{4-[(1R,2R)-2-({[4-(ethylsulfonyl)benzyl]oxy}methyl)cyclopropyl]piperidin-1-yl}pyrimidine |
| 58 | (2R)-1-{4-[({(1R,2R)-2-[1-(5-ethylpyrimidin-2-yl)piperidin-4-yl]cyclopropyl}methoxy)methyl]phenyl}propan-2-ol |
| 59 | (2S)-1-{4-[({(1R,2R)-2-[1-(5-ethylpyrimidin-2-yl)piperidin-4-yl]cyclopropyl}methoxy)methyl]phenyl} propan-2-ol |
| 60 | 2-{4-[({(1R,2R)-2-[1-(5-ethylpyrimidin-2-yl)piperidin-4-yl]cyclopropyl}methoxy)methyl]phenyl} ethanol |
| 61 | 5-ethyl-2-{4-[(1R,2R)-2-({[4-(1H-tetrazol-1-yl)benzyl]oxy}methyl)cyclopropyl] piperidin-1-yl} pyrimidine |
| 62 | 5-ethyl-2-{4-[(1R,2R)-2-({[4-(1H-1,2,3-triazol-1-yl)benzyl]oxy}methyl)cyclo propyl]piperidin-1-yl} pyrimidine |
| 63 | 5-ethyl-2-{4-[(1R,2R)-2-({[4-(1,2,4-oxadiazol-5-yl)benzyl]oxy}methyl)cyclopropyl]piperidin-1-yl} pyrimidine |
| 64 | (2S)-)-4-({4-[({(1R,2R)-2-[1-(5-ethylpyrimidin-2-yl)piperidin-4-yl]cyclopropyl}methoxy)methyl]phenyl}sulfonyl)butan-2-ol |
| 65 | 5-ethyl-2-{4-[(1R,2R)-2-((1R)-2-methoxy-1-{[4-(methylsulfonyl)benzyl]oxy ethyl)cyclopropyl]piperidin-1-yl}pyrimidine |
| 66 | 5-ethyl-2-{4-[(1R,2R)-2-((1S)-2-methoxy-1-{[4-(methylsulfonyl)benzyl]oxy ethyl)cyclopropyl]piperidin-1-yl}pyrimidine |
| 67 | 5-ethyl-2-{4-[(1R,2R)-2-((1S)-2-methoxy-1-{[4-(ethylsulfonyl)benzyl]oxy ethyl)cyclopropyl]piperidin-1-yl}pyrimidine |
| 68 | 5-chloro-2-{4-[(1R,2R)-2-({[3,5-difluoro-4-(methylsulfonyl)benzyl]oxy}methyl) cyclopropyl]piperidin-1-yl}pyrimidine |
| 69 | 5-fluoro-2-{4-[(1R,2R)-2-({[3,5-difluoro-4-(methylsulfonyl)benzyl]oxy}methyl) cyclopropyl]piperidin-1-yl}pyrimidine |
| 70 | 5-bromo-2-{4-[(1R,2R)-2-({[3,5-difluoro-4-(methylsulfonyl)benzyl]oxy}methyl) cyclopropyl]piperidin-1-yl}pyrimidine |
| 71 | 2-{4-[(1R,2R)-2-({[2-fluoro-4-(methylsulfonyl)benzyl]oxy}methyl)cyclopropyl]piperidin-1-yl} pyrimidine-5-carbaldehyde |
| 72 | 5-cyano-2-{4-[(1R,2R)-2-({[3,5-difluoro-4-(methylsulfonyl)benzyl]oxy}methyl) cyclopropyl]piperidin-1-yl}pyrimidine |
| 73 | 5-methoxy-2-{4-[(1R,2R)-2-({[3,5-difluoro-4-(methylsulfonyl)benzyl]oxy}methyl) cyclopropyl] piperidin-1-yl}pyrimidine |
| 74 | 5-methyl-2-{4-[(1R,2R)-2-({[3,5-difluoro-4-(methylsulfonyl)benzyl]oxy}methyl) cyclopropyl]piperidin-1-yl}pyrimidine |
| 75 | 2-(2-{4-[(1R,2R)-2-({[2-fluoro-4-(methylsulfonyl)benzyl]oxy}methyl)cyclopropyl]piperidin-1-yl} pyrimidin-5-yl)propan-2-ol |
| 76 | 2-(5-{4-[(1R,2R))-2-({[2-fluoro-4-(methylsulfonyl)benzyl]oxy}methyl)cyclopropyl]piperidin-1-yl} pyrazin-2-yl)propan-2-ol |
| 77 | 2-{4-[(1R,2R)-2-({[2-fluoro-4-(methylsulfonyl)benzyl]oxy}methyl)cyclopropyl]piperidin-1-yl}-5-(methoxymethyl)pyrimidine |
| 78 | 4-[(1R,2R)-2-({[2-fluoro-4-(methylsulfonyl)benzyl]oxy}methyl)cyclopropyl]-1-(3-isopropyl-1,2,4-oxadiazol-5-yl)piperidine |
| 79 | tert-butyl 4-{(1R,2R)-2-[({2-fluoro-4-[(2-hydroxyethyl)sulfonyl]benzyl} oxy)methyl] cyclopropyl}piperidine-1-carboxylate |
| 80 | 2-({4-[({(1R,2R))-2-[1-(5-chloropyrimidin-2-yl)piperidin-4-yl]cyclopropyl}methoxy)methyl]-3-fluorophenyl}sulfonyl)ethanol |
| 81 | 2-({4-[({(1R,2R))-2-[1-(5-bromopyrimidin-2-yl)piperidin-4-yl]cyclopropyl]}methoxy)methyl]-3-fluorophenyl}sulfonyl)ethanol |
| 82 | 2-({4-[({(1R,2R))-2-[1-(5-methylpyrimidin-2-yl)piperidin-4-yl]cyclopropyl]}methoxy)methyl]-3-fluorophenyl}sulfonyl)ethanol |

| Example | Compound Name |
|---|---|
| 83 | 2-({4-[({(1R,2R))-2-[1-(5-ethylpyrimidin-2-yl)piperidin-4-yl]cyclopropyl]}methoxy)methyl]-3-fluorophenyl}sulfonyl)ethanol |
| 84 | 2-({4-[({(1R,2R))-2-[1-(5-propylpyrimidin-2-yl)piperidin-4-yl]cyclopropyl}methoxy)methyl]-3-fluorophenyl}sulfonyl)ethanol |
| 85 | 2-[(3-fluoro-4-{[(((1R,2R)-2-{1-[5-(3-furyl)pyrimidin-2-yl]piperidin-4-yl}cyclopropyl)methoxy]methyl}phenyl)sulfonyl]ethanol |
| 86 | 2-({6-[({(1R,2R)-2-[1-(5-chloropyrimidin-2-yl)piperidin-4-yl]cyclopropyl}methoxy)methyl]pyridin-3-yl}sulfonyl)ethanol |
| 87 | 2-({6-[({(1R,2R)-2-[1-(5-bromopyrimidin-2-yl)piperidin-4-yl]cyclopropyl}methoxy)methyl]pyridin-3-yl}sulfonyl)ethanol |
| 88 | 2-({6-[({(1R,2R)-2-[1-(5-ethylpyrimidin-2-yl)piperidin-4-yl]cyclopropyl}methoxy)methyl]pyridin-3-yl}sulfonyl)ethanol |
| 89 | 2-({6-[({(1R,2R)-2-[1-(5-propylpyrimidin-2-yl)piperidin-4-yl]cyclopropyl}methoxy)methyl]pyridin-3-yl}sulfonyl)ethanol |
| 90 | 2-({6-[({(1R,2R)-2-[1-(5-cyclopropylpyrimidin-2-yl)piperidin-4-yl]cyclopropyl}methoxy)methyl] pyridin-3-yl}sulfonyl)ethanol |
| 91 | tert-butyl 4-(1R,2R)-2-[({4-[(2-oxopropyl)thio]benzyl}oxy)methyl]cyclopropyl} piperidine-1-carboxylate |
| 92 | tert-butyl 4-(1R,2R)-2-[({4-[(2-hydroxy-2-methylpropyl)thio]benzyl}oxy)methyl]cyclopropyl} piperidine-1-carboxylate |
| 93 | tert-butyl 4-(1R,2R)-2-[({4-[(2R/S-hydroxypropyl)thio]benzyl}oxy)methyl]cyclo propyl}piperidine-1-carboxylate |
| 94 | tert-butyl 4-(1R,2R)-2-[({4-[(2R/S-hydroxypropyl)sulfonyl]benzyl}oxy)methyl] cyclopropyl}piperidine-1-carboxylate |
| 95 | 1-({4-[({(1R,2R)-2-[1-(5-chloropyrimidin-2-yl)piperidin-4-yl]cyclopropyl]}methoxy)methyl]-3-fluoro phenyl}sulfonyl)propan-2-ol |
| 96 | 1-({4-[({(1R,2R)-2-[1-(5-fluoropyrimidin-2-yl)piperidin-4-yl]cyclopropyl}methoxy)methyl]-3-fluoro phenyl}sulfonyl)propan-2-ol |
| 97 | 1-({4-[({(1R,2R)-2-[1-(5-bromopyrimidin-2-yl)piperidin-4-yl]cyclopropyl}methoxy)methyl]-3-fluoro phenyl}sulfonyl)propan-2-ol |
| 98 | 1-({4-[({(1R,2R)-2-[1-(5-chloropyrazin-2-yl)piperidin-4-yl]cyclopropyl}methoxy)methyl]-3-fluoro phenyl}sulfonyl)propan-2-ol |
| 99 | 3-{4-[({(1R,2R)-2-[1-(5-ethylpyrimidin-2-yl)piperidin-4-yl]cyclopropyl} methoxy)methyl]-3-fluorophenyl}pyridazine |
| 100 | 3-{4-[({(1R,2R)-2-[1-(5-ethylpyrimidin-2-yl)piperidin-4-yl]cyclopropyl} methoxy)methyl]-3-fluorophenyl}-6-methylpyridazine |
| 101 | 3-{4-[({(1R,2R)-2-[1-(5-ethylpyrimidin-2-yl)piperidin-4-yl]cyclopropyl} methoxy)methyl]-3-fluorophenyl}-6-methoxypyridazine |
| 102 | 4-{4-[({(1R,2R)-2-[1-(5-ethylpyrimidin-2-yl)piperidin-4-yl]cyclopropyl} methoxy)methyl]-3-fluorophenyl}pyridazine |
| 103 | 5-{4-[({(1R,2R)-2-[1-(5-ethylpyrimidin-2-yl)piperidin-4-yl]cyclopropyl}methoxy)methyl]-3-fluorophenyl}pyrimidin-2-amine |
| 104 | 5-{4-[({(1R,2R)-2-[1-(5-ethylpyrimidin-2-yl)piperidin-4-yl]cyclopropyl}methoxy)methyl]-3-fluorophenyl}-2-methoxypyrimidine |
| 105 | 4-{4-[({(1R,2R)-2-[1-(5-ethylpyrimidin-2-yl)piperidin-4-yl]cyclopropyl}methoxy)methyl]-3-fluorophenyl}pyrimidin-2-amine |
| 106 | 4-{4-[({(1R,2R)-2-[1-(5-ethylpyrimidin-2-yl)piperidin-4-yl]cyclopropyl}methoxy)methyl]-3-fluorophenyl}-2-methoxypyrimidine |
| 107 | 2-{4-[({(1R,2R)-2-[1-(5-ethylpyrimidin-2-yl)piperidin-4-yl]cyclopropyl}methoxy)methyl]-3-fluorophenyl}pyrazin-2-amine |
| 108 | 5-{4-[({(1R,2R)-2-[1-(5-ethylpyrimidin-2-yl)piperidin-4-yl]cyclopropyl}methoxy)methyl]-3-fluorophenyl}pyrimidine |
| 109 | 2-{4-[({(1R,2R)-2-[1-(5-ethylpyrimidin-2-yl)piperidin-4-yl]cyclopropyl}methoxy)methyl]-3-fluorophenyl}pyrazine |
| 110 | 4-{4-[({(1R,2R)-2-[1-(5-ethylpyrimidin-2-yl)piperidin-4-yl]cyclopropyl}methoxy)methyl]-3-fluorophenyl}pyrimidine |
| 111 | 5-ethyl-2-{4-[(1R,2R)-2-({[2-fluoro-4-(2-methyl-1,3-thiazol-5-yl)benzyl]oxy}methyl)cyclopropyl] piperidin-1-yl}pyrimidine |
| 112 | 4-{4-[({(1R,2R)-2-[1-(5-ethylpyrimidin-2-yl)piperidin-4-yl]cyclopropyl}methoxy)methyl]-2-fluorophenyl}pyrimidine |
| 113 | 5-{4-[({(1R,2R)-2-[1-(5-ethylpyrimidin-2-yl)piperidin-4-yl]cyclopropyl}methoxy)methyl]-2-fluorophenyl}pyrimidine |
| 114 | 3-{4-[({(1R,2R)-2-[1-(5-ethylpyrimidin-2-yl)piperidin-4-yl]cyclopropyl}methoxy)methyl]-2-fluorophenyl}pyridazine |
| 115 | 4-{4-[({(1R,2R)-2-[1-(5-ethylpyrimidin-2-yl)piperidin-4-yl]cyclopropyl}methoxy)methyl]-2-fluorophenyl}pyridazine |
| 116 | 4-{4-[({(1R,2R)-2-[1-(5-ethylpyrimidin-2-yl)piperidin-4-yl]cyclopropyl}methoxy)methyl]-2-fluorophenyl}-6-methoxypyridazine |
| 117 | 4-{4-[({(1R,2R)-2-[1-(5-ethylpyrimidin-2-yl)piperidin-4-yl]cyclopropyl}methoxy)methyl]-2-fluorophenyl}-6-methylpyridazine |
| 118 | 5-{4-[({(1R,2R)-2-[1-(5-ethylpyrimidin-2-yl)piperidin-4-yl]cyclopropyl}methoxy)methyl]-2-fluorophenyl}pyrimidin-2-amine |
| 119 | 4-{4-[({(1R,2R)-2-[1-(5-ethylpyrimidin-2-yl)piperidin-4-yl]cyclopropyl}methoxy)methyl]-3-fluorophenyl}-2-methoxypyrimidine |
| 120 | 5-ethyl-2-[4-((1R,2R))-2-{[(4-pyrimidin-5-ylbenzyl)oxy]methyl}cyclopropyl)piperidin-1-yl]pyrimidine |

-continued

| Example | Compound Name |
|---|---|
| 121 | 5-ethyl-2-[4-((1R,2R))-2-{[(4-pyridazin-4-ylbenzyl)oxy]methyl}cyclopropyl)piperidin-1-yl]pyrimidine |
| 122 | 5-ethyl-2-[4-((1R,2R))-2-{[(4-pyridazin-4-ylbenzyl)oxy]methyl}cyclopropyl)piperidin-1-yl]pyrimidine |
| 123 | 5-ethyl-2-[4-((1R,2R))-2-{[(4-pyrazin-2-ylbenzyl)oxy]methyl}cyclopropyl)piperidin-1-yl]pyrimidine |
| 124 | 2-(4-((1R,2R)-2-((2-fluoro-4-(methylsulfonyl)benzyloxy)methyl)cyclopropyl)piperidin-1-yl)-5-(methoxymethyl)pyrimidine |
| 125 | 2-(4-((1R,2R)-2-((2-fluoro-4-(methylsulfonyl)benzyloxy)methyl)cyclopropyl)piperidin-1-yl)-5-(1-methoxyethyl)pyrimidine |
| 126 | 2-(4-((1R,2R)-2-((2-fluoro-4-(methylsulfonyl)benzyloxy)methyl)cyclopropyl)piperidin-1-yl)-5-(1-methoxyethyl)pyrimidine |
| 127 | 2-(4-((1R,2R)-2-((4-(ethylsulfonyl)-2-fluorobenzyloxy)methyl)cyclopropyl)piperidin-1-yl)-5-(methoxymethyl)pyrimidine |
| 128 | 2-(4-((1R,2R)-2-((3,5-difluoro-4-(methylsulfonyl)benzyloxy)methyl)cyclopropyl)piperidin-1-yl)-5-(methoxymethyl)pyrimidine |
| 129 | 5-ethoxy-2-(4-((1R,2R)-2-((3-fluoro-4-(methylsulfonyl)benzyloxy)methyl)cyclopropyl)piperidin-1-yl)pyrimidine |
| 130 | 2-(4-((1R,2R)-2-((3-fluoro-4-(methylsulfonyl)benzyloxy)methyl)cyclopropyl)piperidin-1-yl)-5-(1-methoxyethyl)pyrimidine |
| 131 | 2-(4-((1R,2R)-2-((3-fluoro-4-(methylsulfonyl)benzyloxy)methyl)cyclopropyl)piperidin-1-yl)-5-(1-methoxyethyl)pyrimidine |
| 132 | 2-(4-((1R,2R)-2-((3-fluoro-4-(1H-tetrazol-1-yl)benzyloxy)methyl)cyclopropyl)piperidin-1-yl)-5-(methoxymethyl)pyrimidine |
| 133 | 2-(4-((1R,2R)-2-(((5-(1H-tetrazol-1-yl)pyridin-2-yl)methoxy)methyl)cyclopropyl)piperidin-1-yl)-5-ethylpyrimidine |
| 134 | 5-(4-((1R,2R)-2-((2-fluoro-4-(1H-tetrazol-1-yl)benzyloxy)methyl)cyclopropyl)piperidin-1-yl)-3-isopropyl-1,2,4-oxadiazole |
| 135 | 5-(4-((1R,2R)-2-((2-fluoro-4-(1H-tetrazol-1-yl)benzyloxy)methyl)cyclopropyl)piperidin-1-yl)-3-(methoxymethyl)-1,2,4-oxadiazole |
| 136 | 1-methylcyclopropyl 4-((1R,2R)-2-((2-fluoro-4-(1H-tetrazol-1-yl)benzyloxy)methyl)cyclopropyl)piperidine-1-carboxylate |
| 137 | 2-(3-fluoro-4-((((1R,2R)-2-(1-(3-isopropyl-1,2,4-oxadiazol-5-yl)piperidin-4-yl)cyclopropyl)methoxy)methyl)phenyl)-N,N-dimethylacetamide |
| 138 | 2-(3-fluoro-4-((((1R,2R)-2-(1-(3-isopropyl-1,2,4-oxadiazol-5-yl)piperidin-4-yl)cyclopropyl)methoxy)methyl)phenyl)-1-(3-methoxyazetidin-1-yl)ethanone |
| 139 | 2-(3-fluoro-4-((((1R,2R)-2-(1-(3-isopropyl-1,2,4-oxadiazol-5-yl)piperidin-4-yl)cyclopropyl)methoxy)methyl)phenyl)-1-(3-fluoroazetidin-1-yl)ethanone |
| 140 | 2-(2-fluoro-4-((((1R,2R)-2-(1-(3-isopropyl-1,2,4-oxadiazol-5-yl)piperidin-4-yl)cyclopropyl)methoxy)methyl)phenyl)-N,N-dimethylacetamide |
| 141 | 2-(2-fluoro-4-((((1R,2R)-2-(1-(3-isopropyl-1,2,4-oxadiazol-5-yl)piperidin-4-yl)cyclopropyl)methoxy)methyl)phenyl)-1-morpholinoethanone |
| 142 | 2-(2-fluoro-4-((((1R,2R)-2-(1-(3-isopropyl-1,2,4-oxadiazol-5-yl)piperidin-4-yl)cyclopropyl)methoxy)methyl)phenyl)-1-(3-methoxyazetidin-1-yl)ethanone |
| 143 | 2-(2-fluoro-4-((((1R,2R)-2-(1-(3-isopropyl-1,2,4-oxadiazol-5-yl)piperidin-4-yl)cyclopropyl)methoxy)methyl)phenyl)-1-(3-hydroxyazetidin-1-yl)ethanone |
| 144 | 1-(azetidin-1-yl)-2-(2-fluoro-4-((((1R,2R)-2-(1-(3-(methoxymethyl)-1,2,4-oxadiazol-5-yl)piperidin-4-yl)cyclopropyl)methoxy)methyl)phenyl)ethanone |
| 145 | 1-(azetidin-1-yl)-2-(3-fluoro-4-((((1R,2R)-2-(1-(5-(methoxymethyl)pyrimidin-2-yl)piperidin-4-yl)cyclopropyl)methoxy)methyl)phenyl)ethanone |
| 146 | 2-(3-fluoro-4-((((1R,2R)-2-(1-(5-(methoxymethyl)pyrimidin-2-yl)piperidin-4-yl)cyclopropyl)methoxy)methyl)phenyl)-1-morpholinoethanone |
| 147 | 2-(3-fluoro-4-((((1R,2R)-2-(1-(5-(methoxymethyl)pyrimidin-2-yl)piperidin-4-yl)cyclopropyl)methoxy)methyl)phenyl)-N,N-dimethylacetamide; or |
| 148 | 2-(3-fluoro-4-((((1R,2R)-2-(1-(5-(methoxymethyl)pyrimidin-2-yl)piperidin-4-yl)cyclopropyl)methoxy)methyl)phenyl)-1-(3-fluoroazetidin-1-yl)ethanone |

The present invention also relates to pharmaceutical compositions comprising compounds of formula I or a pharmaceutically acceptable salt thereof, and a pharmaceutically acceptable carrier.

Additionally, the present invention relates to use of a compound of Formula I or a pharmaceutically acceptable salt thereof, in the manufacture of a medicament for use in treating a condition selected from the group consisting of obesity and diabetes.

The present invention relates to the use of a compound of Formula I or a pharmaceutically acceptable salt thereof, in the treatment of diabetes.

The present invention further relates to a method for the treatment of a condition selected from obesity or diabetes comprising administering to an individual a pharmaceutical composition comprising the compound of Formula I.

Another embodiment of the present invention includes a method of treating a condition selected from: (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension or other conditions and disorders where insulin resistance is a component, in a mammalian patient in need of such treatment, comprising administering to the patient a compound in accordance with claim 1, or a pharmaceutically acceptable salt thereof, in an amount that is effective to treat said condition.

Yet another embodiment of the present invention include a method of treating a condition selected from: (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension or other conditions and disorders where insulin resistance is a component, in a mammalian patient in need of such treatment, comprising administering to the patient a compound in accordance with Formula I, or a pharmaceutically acceptable salt thereof, and a compound selected from:
  (a) DPP-IV inhibitors;
  (b) insulin sensitizers selected from the group consisting of
    (i) PPAR agonists and (ii) biguanides;
  (c) insulin and insulin mimetics;
  (d) sulfonylureas and other insulin secretagogues;
  (e) α-glucosidase inhibitors;
  (f) glucagon receptor antagonists;
  (g) GLP-1, GLP-1 mimetics, and GLP-1 receptor agonists;
  (h) GIP, GIP mimetics, and GIP receptor agonists;
  (i) PACAP, PACAP mimetics, and PACAP receptor 3 agonists;
  (j) cholesterol lowering agents selected from
    (i) HMG-CoA reductase inhibitors, (ii) sequestrants, (iii) nicotinyl alcohol, nicotinic acid and salts thereof, (iv) PPARα agonists, (v) PPARα/γ dual agonists, (vi) inhibitors of cholesterol absorption, (vii) acyl CoA: cholesterol acyltransferase inhibitors, or (viii) antioxidants;
  (k) PPARδ agonists;
  (l) antiobesity compounds;
  (m) ileal bile acid transporter inhibitors;
  (n) anti-inflammatory agents excluding glucocorticoids;
  (o) protein tyrosine phosphatase-1B (PTP-1B) inhibitors; or
  (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan, said compounds being administered to the patient in an amount that is effective to treat said condition.

The invention is described herein in detail using the terms defined below unless otherwise specified.

The invention is described herein in detail using the terms defined below unless otherwise specified. "Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

As used herein, "cycloalkyl" means a saturated cyclic hydrocarbon radical having the number of carbon atoms designated. If no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Alkoxy" refers to an alkyl group linked to oxygen.

"Haloalkoxy" and "haloalkylO" are used interchangeably and refer to halo substituted alkyl groups linked through the oxygen atom. Haloalkoxy include mono-substituted as well as multiple halo substituted alkoxy groups, up to perhalo substituted alkoxy. For example, trifluoromethoxy is included.

"Haloalkyl" include mono-substituted as well as multiple halo substituted alkyl groups, up to perhalo substituted alkyl. For example, trifluoromethyl is included.

As used herein, "heterocycle" or "heterocyclic" refers to nonaromatic cyclic ring structures in which one or more atoms in the ring, the heteroatom(s), is an element other than carbon. Heteroatoms are typically O, S or N atoms.

"Heteroaryl" (HAR) unless otherwise specified, means an aromatic or partially aromatic heterocycle that contains at least one ring heteroatom selected from oxygen ("O"), sulfur ("S") and nitrogen ("N"). Heteroaryls thus includes heteroaryls fused to other kinds of rings, such as aryls, cycloalkyls and heterocycles that are not aromatic. Examples of heteroaryl groups include: pyrrolyl or pyrrole, isoxazolyl or isoxazole, isothiazolyl or isothiazole, pyrazolyl or pyrazole, pyridyl, oxazolyl or oxazole, oxadiazolyl or oxadiazole, thiadiazolyl or thiadiazole, thiazolyl or thiazole, imidazolyl or imidazole, triazolyl or triazole, tetrazolyl or tetrazole, furyl, triazinyl, thienyl, pyrimidyl, benzisoxazolyl or benzisoxazole, benzoxazolyl or benzoazole, benzothiazolyl or benzothiazole, benzothiadiazolyl or benzothiadiazole, dihydrobenzofuranyl or dihydrobenzofurane, indolinyl or indoline, pyridazinyl or pyridazine, indazolyl or indazole, isoindolyl or isoindole, dihydrobenzothienyl, indolizinyl or indolizine, cinnolinyl or cinnoline, phthalazinyl or phthalazine, quinazolinyl or quinazoline, naphthyridinyl or naphthyridine, carbazolyl or carbazole, benzodioxolyl or benzodioxole, quinoxalinyl or quinoxaline, purinyl or purine, furazanyl or furazane, isobenzylfuranyl or isobenzylfurane, benzimidazolyl or benzimidazole, benzofuranyl or benzofurane, benzothienyl or benzothiene, quinolyl or quinoline, oxo-dihydroqunoline, indolyl or indole, oxindole, isoquinolyl or isoquinoline, dibenzofuranyl or dibenzofurane, and the like. For heterocyclic and heteroaryl groups, rings and ring systems containing from 5-15 atoms are included, forming 1-3 rings.

"Halogen" (Halo) includes fluorine, chlorine, bromine and iodine.

Unless expressly depicted or described otherwise, variables depicted in a structural formula with a "floating" bond, such as each of substituents $R^1$ and $R^2$, are permitted on any available carbon atom in the ring to which each is attached.

Substitution, where applicable, may be on any available carbon atom that results in a stable structure.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1$H) and deuterium ($^2$H). Protium is the predominant hydrogen isotope found in nature. Enriching for deuterium may yield certain therapeutic advantages, such as increasing in vivo half-life or reducing dosage requirements, or may provide a compound useful as a standard for characterization of biological samples. Isotopically-enriched compounds within the formulas described herein can be prepared without undue experimentation by conventional techniques well known to those skilled in the art or by processes analogous to those described in the Schemes and Examples herein using appropriate isotopically-enriched reagents and/or intermediates.

The individual tautomers of the compounds of the formulas described herein, as well as mixture thereof, are encompassed with compounds of the formulas described herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds of the formulas described herein may be separated into diastereoisomeric pairs of enantiomers by, for example, fractional crystallization from a suitable solvent. The pair of enantiomers thus obtained may be separated into individual stereoisomers by conventional means, for example by the use of an optically active amine or acid as a resolving agent or on a chiral HPLC column.

Alternatively, any enantiomer of a compound of the formulas described herein may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of Formula I and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I or Ia may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of the structural formulas described herein are also included in the present invention.

Compounds of the present invention are potent agonists of the GPR 119 receptor. These compounds and pharmaceutically acceptable salts thereof are modulators of the receptor known as GPR 119, and are therefore useful in the treatment of diseases that are modulated by GPR119 ligands and agonists. Many of these diseases are summarized below. Said compounds may be used for the manufacture of a medicament for treating one or more of diseases or conditions, including, without limitation:

(1) noninsulin dependent diabetes mellitus (type 2 diabetes);
(2) hyperglycemia;
(3) metabolic syndrome/syndrome X;
(4) obesity;
(5) ischemia and myocardial infarction;
(6) neurological disorders such as Alzheimer's disease, schizophrenia, and impaired cognition;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) Hyperapobetalipoproteinemia; and
(11) atherosclerosis.

Because the compounds are agonists of the GPR119 receptor, the compounds will be useful for lowering glucose, lipids, and insulin resistance in diabetic patients and in non-diabetic patients who have impaired glucose tolerance and/or are in a pre-diabetic condition. The compounds are useful to ameliorate hyperinsulinemia, which often occurs in diabetic or pre-diabetic patients, by modulating the swings in the level of serum glucose that often occurs in these patients. The compounds are useful for treating or reducing insulin resistance. The compounds are useful for treating or preventing gestational diabetes.

Additionally, by keeping hyperglycemia under control, the compounds are useful to delay or for preventing vascular restenosis and diabetic retinopathy.

The compounds of this invention are useful in improving or restoring β-cell function, so that they may be useful in treating type 1 diabetes or in delaying or preventing a patient with type 2 diabetes from needing insulin therapy.

The compounds, compositions, and medicaments as described herein are further useful for reducing the risks of adverse sequelae associated with metabolic syndrome, or Syndrome X, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

The compounds may be useful for reducing appetite and body weight in obese subjects and may therefore be useful in reducing the risk of co-morbidities associated with obesity such as hypertension, atherosclerosis, diabetes, and dyslipidemia.

By elevating levels of active GLP-1 in vivo, the compounds are useful in treating neurological disorders such as Alzheimer's disease, multiple sclerosis, and schizophrenia.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of the formulas described herein or a pharmaceutically acceptable salt thereof. The compound may be used alone or advantageously may be administered with a cholesterol biosynthesis inhibitor, particularly an HMG-CoA reductase inhibitor (e.g., simvastatin, atorvastatin, and the like). The compound may also be used advantageously in combination with other lipid lowering drugs such as cholesterol absorption inhibitors (e.g., stanol esters, sterol glycosides or azetidinones such as ezetimibe), ACAT inhibitors (e.g., avasimibe), CETP inhibitors (e.g. anacetrapib), niacin, bile acid sequestrants, microsomal triglyceride transport inhibitors, and bile acid reuptake inhibitors. Such combination treatments are useful for the treatment or control of conditions such hypercholesterolemia, atherosclerosis, hyperlipidemia, hypertriglyceridemia, dyslipidemia, high LDL, and low HDL.

Another aspect of the invention provides a method for the treatment and control of obesity or metabolic syndrome, which comprises administering to a patient in need of such treatment a therapeutically effective amount of a compound having the formulas described herein or a pharmaceutically acceptable salt thereof. The compound may be used alone or advantageously may be administered with an anti-obesity agent, such as a lipase inhibitor (e.g., orlistat) or a monoamine neurotransmitter uptake inhibitor (e.g., sibutramine or phentermine). The compound may also be used advantageously in combination with CB-1 inverse agonists or antagonists (e.g., rimonabant or taranabant).

The present invention further relates to a method of treating hyperglycemia, diabetes or insulin resistance in a mammalian patient in need of such treatment which comprises administering to said patient a compound in accordance with the formulas described herein or a pharmaceutically acceptable salt thereof in an amount that is effective to treat hyperglycemia, diabetes or insulin resistance.

Yet another aspect of the invention that is of interest relates to a method of treating atherosclerosis in a mammalian patient in need of such treatment, comprising administering to said patient a compound in accordance with a compound in accordance with the formulas described herein or a pharmaceutically acceptable salt thereof in an amount that is effective to treat atherosclerosis.

Yet another aspect of the invention that is of interest relates to a method of delaying the onset of one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to delay the onset of said condition.

Yet another aspect of the invention that is of interest relates to a method of reducing the risk of developing one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to reduce the risk of developing said condition.

Yet another aspect of the invention that is of interest relates to a method of treating a condition or reducing the risk of developing a condition or delaying the onset of a condition selected from the group consisting of (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with the formulas described herein or a pharmaceutically acceptable salt thereof in an amount that is effective to treat said condition, and a compound selected from the group consisting of:

(a) DPP-IV inhibitors;
(b) insulin sensitizers selected from the group consisting of (i) PPAR agonists and (ii) biguanides;
(c) insulin and insulin mimetics;
(d) sulfonylureas and other insulin secretagogues;
(e) α-glucosidase inhibitors;
(f) glucagon receptor antagonists;
(g) GLP-1, GLP-1 mimetics, and GLP-1 receptor agonists;
(h) GIP, GIP mimetics, and GIP receptor agonists;
(i) PACAP, PACAP mimetics, and PACAP receptor 3 agonists;
(j) cholesterol lowering agents selected from the group consisting of
  (i) HMG-CoA reductase inhibitors, (ii) sequestrants, (iii) nicotinyl alcohol, nicotinic acid and salts thereof, (iv) PPARα agonists, (v) PPAR α/γ dual agonists, (vi) inhibitors of cholesterol absorption, (vii) acyl CoA: cholesterol acyltransferase inhibitors, and (viii) antioxidants;
(k) PPARδ agonists;
(l) antiobesity compounds;
(m) ileal bile acid transporter inhibitors;
(n) anti-inflammatory agents excluding glucocorticoids;
(o) protein tyrosine phosphatase-1B (PTP-1B) inhibitors; and
(p) antihypertensives including those acting on the angiotensin or renin systems, such as angiotensin converting enzyme inhibitors, angiotensin II receptor antagonists or renin inhibitors, (e.g., lisinopril, losartan); said compounds being administered to the patient in an amount that is effective to treat said condition.

For dosing purposes, any suitable route of administration may be employed for providing a mammal, especially a human, with an effective amount of a compound of the present invention. Dosage forms may include tablets, troches, dispersions, suspensions, solutions, capsules, creams, ointments, aerosols, and the like. Most preferably, compounds of the formulas described herein or a pharmaceutically acceptable salt thereof are administered orally. The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus or other diseases for which compounds of the formulas described herein are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response. Oral administration will usually be carried out using tablets or capsules. Examples of doses in tablets and capsules are 0.1 mg, 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 12 mg, 15 mg, 20 mg, 25 mg, 50 mg, 100 mg, 200 mg, 350 mg, 500 mg, 700 mg, 750 mg, 800 mg and 1000 mg. Other oral forms may also have the same or similar dosages.

Another aspect of the invention that is of interest is a pharmaceutical composition comprised of a compound of the formulas described herein or a pharmaceutically acceptable salt thereof in combination with a pharmaceutically acceptable carrier. The pharmaceutical compositions of the present invention comprise a compound of the formulas described herein or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art.

In practical use, compounds of the formulas described herein, or the pharmaceutically acceptable salts thereof can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compound of the formulas described herein or a pharmaceutically acceptable salt thereof may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

As discussed supra, compounds of the present invention may be used in combination with other drugs that may also be useful in the treatment or amelioration of the diseases and conditions described herein. Such other drugs may be administered by a route and in an amount commonly used therefore, contemporaneously or sequentially with a compound of the formulas described herein or a pharmaceutically acceptable salt thereof. In the treatment of patients who have type 2 diabetes, insulin resistance, obesity, metabolic syndrome, neurological disorders, and co-morbidities that accompany these diseases, more than one drug is commonly administered. The compounds of this invention may generally be administered to a patient who is already taking one or more other drugs for these conditions.

When a compound of the formulas described herein is used contemporaneously with one or more other drugs, a pharmaceutical composition in unit dosage form containing such other drugs and the compound of the formulas described herein is preferred. However, the combination therapy also includes therapies in which a compound of the formulas described herein and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the formulas described herein.

Examples of other active ingredients that may be administered separately or in the same pharmaceutical composition in combination with a compound of the formulas described herein include, but are not limited to:

(1) dipeptidyl peptidase-IV (DPP-4) inhibitors;
(2) insulin sensitizers, including
(i) PPARγ agonists, such as the glitazones (e.g. pioglitazone), and other PPAR ligands, including (1) PPARα/γ dual agonists (e.g., muraglitazar); (2) PPARα agonists, such as fenofibric acid derivatives (e.g., gemfibrozil), (3) selective PPARγ modulators (SPPARγM's); and (4) PPARγ partial agonists;
(ii) biguanides, such as metformin and its pharmaceutically acceptable salts, in particular, metformin hydrochloride, and extended-release formulations thereof, such as Glumetza™, Fortamet™, and GlucophageXR™; and
(iii) protein tyrosine phosphatase-1B (PTP-1B) inhibitors;
(3) insulin or insulin analogs;
(4) leptin and leptin derivatives and agonists;
(5) amylin and amylin analogs, such as pramlintide;
(6) sulfonylurea and non-sulfonylurea insulin secretagogues;
(7) α-glucosidase inhibitors (e.g., acarbose);
(8) glucagon receptor antagonists;
(9) incretin mimetics, such as GLP-1, GLP-1 analogs, derivatives, and mimetics; and GLP-1 receptor agonists;
(10) LDL cholesterol lowering agents such as (i) HMG-CoA reductase inhibitors (e.g., simvastatin), (ii) bile acid sequestering agents (e.g., cholestyramine), (iii) inhibitors of cholesterol absorption, (e.g., ezetimibe), and (iv) acyl CoA: cholesterol acyltransferase inhibitors, (e.g., avasimibe);
(11) HDL-raising drugs, (e.g., niacin and nicotinic acid receptor agonists);
(12) antiobesity compounds;
(13) agents intended for use in inflammatory conditions, such as aspirin, non-steroidal anti-inflammatory drugs or NSAIDs, glucocorticoids, and selective cyclooxygenase-2 or COX-2 inhibitors;
(14) antihypertensive agents, such as ACE inhibitors (e.g., lisinopril), A-II receptor blockers (e.g., losartan), renin inhibitors (e.g., aliskiren), beta blockers, and calcium channel blockers;
(15) glucokinase activators (GKAs);
(16) inhibitors of 11β-hydroxysteroid dehydrogenase type 1, (e.g., those disclosed in U.S. Pat. No. 6,730,690);
(17) CETP inhibitors (e.g., anacetrapib);
(18) inhibitors of fructose 1,6-bisphosphatase, (e.g., those disclosed in U.S. Pat. No. 6,054,587);
(19) inhibitors of acetyl CoA carboxylase-1 or 2;
(20) AMP-activated Protein Kinase (AMPK) activators;
(21) other agonists of the G-protein-coupled receptors: GPR-109, GPR-119, and GPR-40;
(22) SSTR3 antagonists;
(23) neuromedin U receptor agonists;
(24) SCD inhibitors;
(25) GPR-105 antagonists;
(26) SGLT inhibitors such as dapagliflozin; canagliflozin; BI-10773; PF-729; tofogliflozin; ipragliflozin; or LX-4211;
(27) inhibitors of acyl coenzyme A:diacylglycerol acyltransferase 1 and 2 (DGAT-1 and DGAT-2);
(28) inhibitors of fatty acid synthase;
(29) inhibitors of acetyl-CoA carboxylase-1 and 2 (ACC-1 and ACC-2);
(30) inhibitors of acyl coenzyme A:monoacylglycerol acyltransferase 1 and 2 (MGAT-1 and MGAT-2);
(31) agonists of the TGR5 receptor (also known as GPBAR1, BG37, GPCR19, GPR131, and M-BAR);
(32) ileal bile acid transporter inhibitors;
(33) PACAP, PACAP mimetics, and PACAP receptor 3 agonists;
(34) PPAR agonists;
(35) protein tyrosine phosphatase-1B (PTP-1B) inhibitors; and
(36) bromocriptine mesylate and rapid-release formulations thereof.

Of particular interest are dipeptidyl peptidase-IV (DPP-4) inhibitors that can be used in combination with compounds of the present invention. Such inhibitors include, without limitation, sitagliptin (disclosed in U.S. Pat. No. 6,699,871), vildagliptin, saxagliptin, alogliptin, denagliptin, carmegliptin, dutogliptin, melogliptin, linagliptin, and pharmaceutically acceptable salts thereof, and fixed-dose combinations of these compounds with metformin hydrochloride, pioglitazone, rosiglitazone, simvastatin, atorvastatin, or a sulfonylurea.

Other dipeptidyl peptidase-IV (DPP-4) inhibitors that can be used in combination with compounds of the formulas described herein include, but are not limited to:
(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;
(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;
(2R,3S,5R)-2-(2,5-difluorophenyl)tetrahydro)-5-(4,6-dihydropyrrolo[3,4-c]pyrazol-5(1H)-yl)tetrahydro-2H-pyran-3-amine;
(3R)-4-[(3R)-3-amino-4-(2,4,5-trifluorophenyl)butanoyl]-hexahydro-3-methyl-2H-1,4-diazepin-2-one;
4-[(3R)-3-amino-4-(2,5-difluorophenyl)butanoyl]hexahydro-1-methyl-2H-1,4-diazepin-2-one hydrochloride; and
(3R)-4-[(3R)-3-amino-4-(2,4,5-trifluorophenyl)butanoyl]-hexahydro-3-(2,2,2-trifluoroethyl)-2H-1,4-diazepin-2-one; and pharmaceutically acceptable salts thereof.

Another aspect of the invention that is of interest relates to the use of a compound in accordance with the formulas described herein or a pharmaceutically acceptable salt thereof in the manufacture of a medicament for use in treating a disease or condition described herein.

The compounds of the invention can be prepared using the synthetic schemes described herein as well as any of several alternate methods which will be apparent to a chemist skilled in the art. The following abbreviations may be used in the synthetic schemes or Examples: BuTMDOB is trans 2-butyl-N,N,N,N-tetramethyl-1,3,2-dioxaborolane-4,5-dicarboxamide, as specified R,R or S,S; CBz is carbobenzyloxy; CPME is cyclopentyl methyl ether; DCM is dichloromethane; DMAP is dimethylaminopyridine; DMF is N,N-dimethylformamide; DMSO is dimethyl sulfoxide; EDC is 1-ethyl-3-[3-(dimethylamino)propyl]-carbodiimide HCl; EtOAc is ethyl acetate; EtOH is ethanol; HCl is hydrochloric acid; HOBt is 1-hydroxybenzotriazole; HPLC is high performance liquid chromatography; iPrOAc is isopropyl acetate; KHMDS is potassium hexamethyldisilazane; LRMS is low resolution mass spectrometry; M is molar; mmol is millimole; NaHMDS is sodium hexamethyldisilazane; n-BuLi is n-butyllithium; RT is RT; OTf is triflate; PPh3 is triphenylphosphine; TEA is triethylamine; TFA is trifluoroacetic acid; THF is tetrahydrofuran; TLC is thin layer chromatography; TPAP is tetrapropylammonium perruthenate.

Reaction Schemes below illustrate in exemplary fashion the methods employed in the synthesis of the compounds of the present invention of Formula I; other routes may be contemplated as well.

General Schemes

Substituted aryl and heteroaryl coupling intermediates shown in the schemes are commercially available or may be prepared from readily accessible aryl, heterocyclic, or other congeners via a host of routes. Many intermediates are accessible through either modification of a pre-formed heteroaryl scaffold or through de novo ring synthesis.

The cyclopropyl residue in the connecting chain of the present examples may be introduced by any of several methods. A particularly convenient method is outlined in Scheme 1 below. Conversion of the readily available piperidine aldehyde to the acetylene by a multistep protocol allows ready access to the indicated cis olefins after Lindlar reduction. Charette's Et$_2$Zn/CH$_2$I$_2$ cyclopropanation yields racemic, diastereomerically or enantiomerically enriched cyclopropyl analogs. In the absence of an auxiliary chiral Lewis acid the cis allylic olefins yield good yields of the desired racemic analogs.

With the addition of the auxiliary chiral Lewis acid RR or SS BuTMDOB, the same cyclopropanation protocol leads to very good ratios of the desired enantiomer.

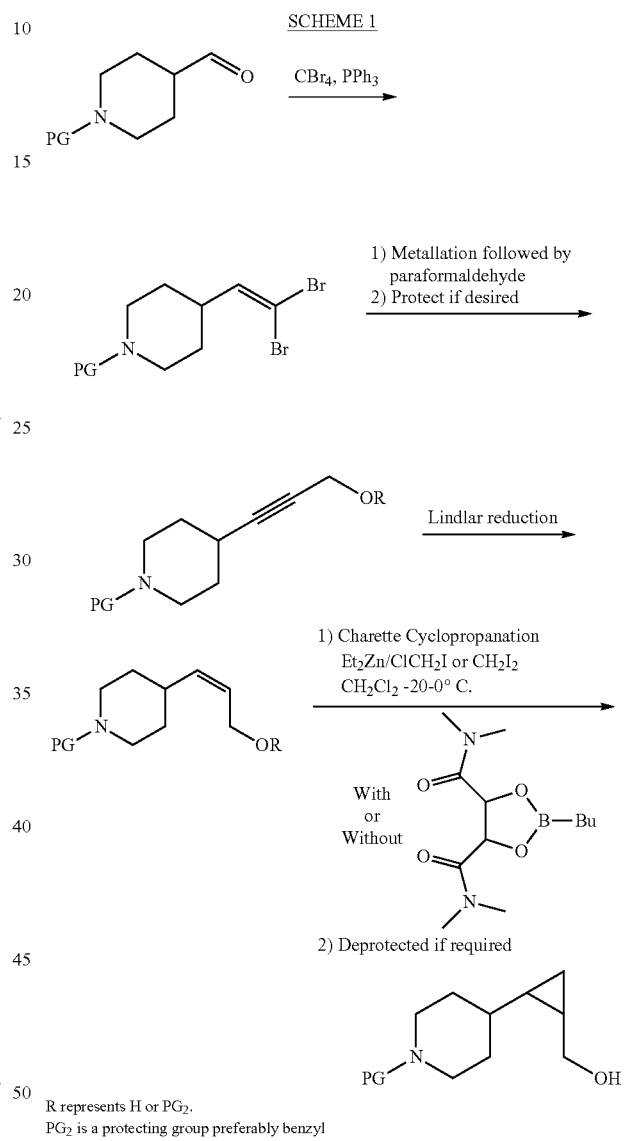

R represents H or PG$_2$.
PG$_2$ is a protecting group preferably benzyl

Using the alcohols prepared as outlined in scheme 1, many analogs may be prepared by different routes. Scheme 2 outlines a particularly convenient method for conversion of the cyclopropyl alcohol to substituted aryl/heteroaryl alkyl ethers via treatment with aryl/heteroaryl alkyl halides in the presence of a base, such as NaHMDS or KHMDS usually heated to 70° C., for a period of 2 to 24 hours. Depending on the amino protecting group, several methods can be used for removal which will be apparent to a chemist skilled in the art. For example, most commonly used t-butylcarbonyl can be removed via treatment with an acid, e.g., HCl or TFA. Another commonly used protecting group is CBz which can be removed via hydrogenation.

SCHEME 2

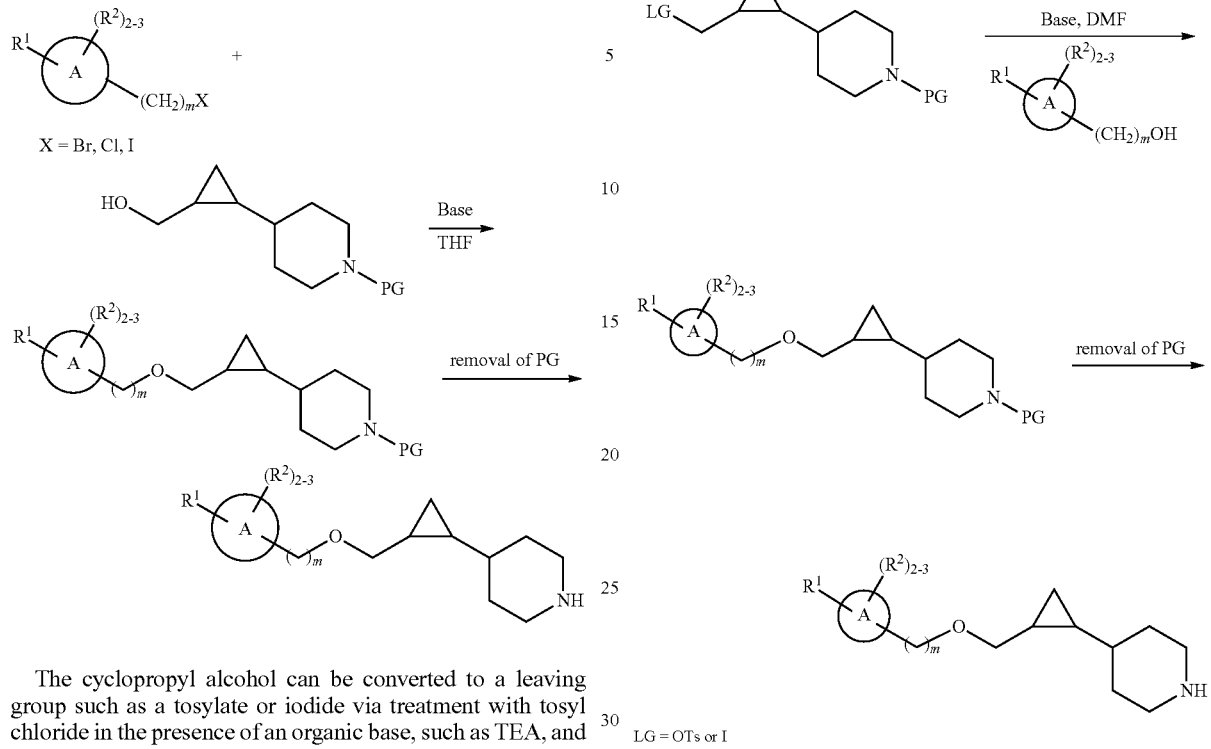

The cyclopropyl alcohol can be converted to a leaving group such as a tosylate or iodide via treatment with tosyl chloride in the presence of an organic base, such as TEA, and an activating agent, such as DMAP, in the appropriate solvent, or by treatment with iodine and triphenylphosphine in the presence of imidazole. This tosylate/iodide can then be treated with the choice of aryl/heteroaryl alkyl alcohols in the presence of base, such as sodium hydride to form the desired aryl/heteroaryl alkyl ethers.

SCHEME 3

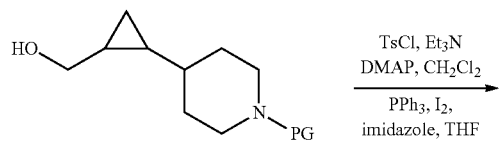

Introduction of the piperidine nitrogen substituent can be accomplished by a particularly wide variety of routes. Some of the most versatile routes for the examples reported here are represented in the following schemes. The formation of carbamate analogs are outlined in Scheme 4. Commercially available alkyl or aryl chloroformates or preformed succinimides can be used in the acylation of the nitrogen of the cyclopropyl intermediate with a base such as DIEA or TEA, to yield the carbamate GPR119 agonist analogs. This procedure is particularly useful for targeting several different carbamate analogs of a particularly interesting aryl or heteroarylalkyl ether.

SCHEME 4

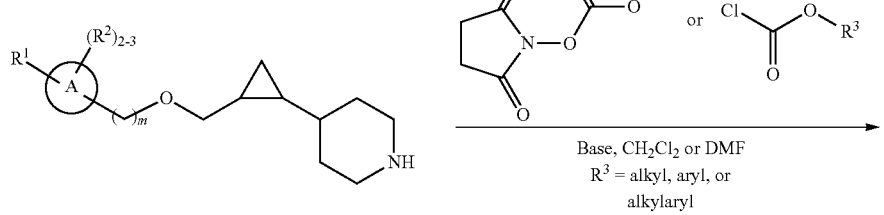

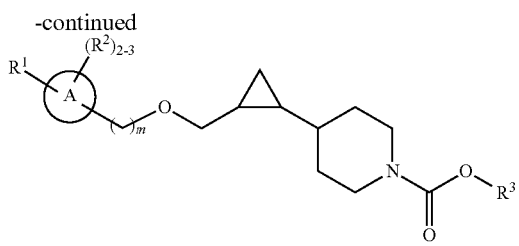

Introduction of the piperidine nitrogen 5-membered heterocyclic substituents can be accomplished by a number of routes. One of the most versatile routes for the examples reported here are represented in scheme 5. The amine of the piperidine is converted to a cyano substituted piperidine by treatment with cyanogen bromide in the presence of base in a suitable chlorinated solvent at temperatures from 0° C. to reflux. The cyano intermediate can then be converted to a 3-substituted 1,2,4-oxadiazole by zinc chloride mediated reaction with an N-hydroxyalkylimidamide or N-hydroxyarylimidamide, followed by acid mediated cyclization.

SCHEME 5

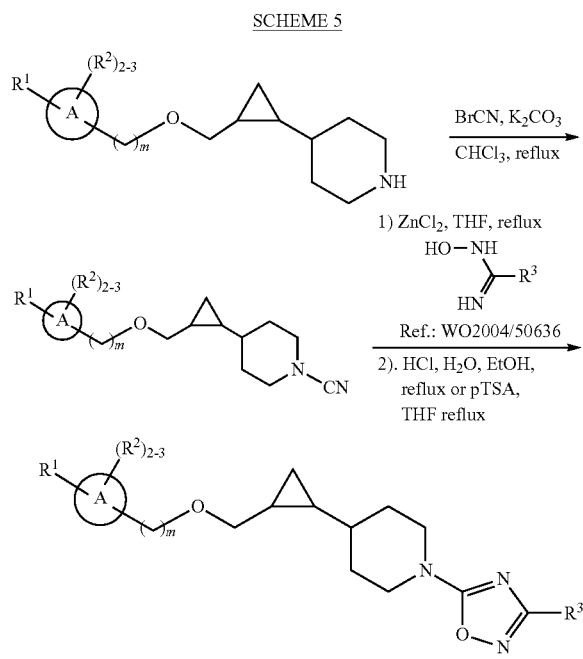

Direct displacement of labile heteroaryl halides or other leaving groups can often be used to introduce the nitrogen substituent directly as shown in scheme 6.

SCHEME 6

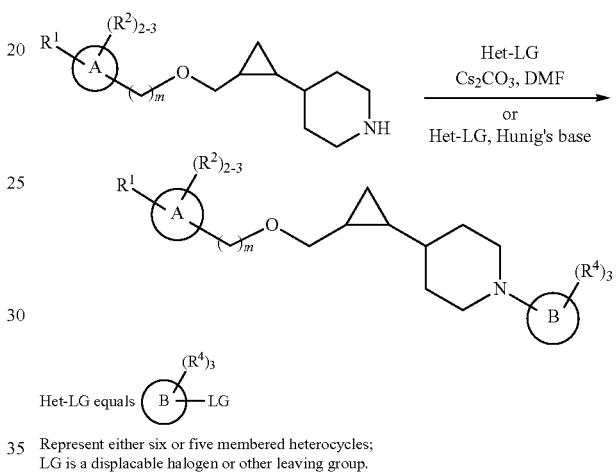

Represent either six or five membered heterocycles; LG is a displacable halogen or other leaving group.

The order of introduction of piperidine N substituents and aryl/heteroarylalkyl ether is easily inverted by removal of piperidine protecting group first. Following derivatisation of the piperidine nitrogen using the methods outlined in the above schemes, further elaboration of the primary alcohol may be achieved by base mediated reaction with aryl/heteroarylalkyl halide, or activation of the alcohol to a leaving group and displacement with aryl/heteroarylalkyl alcohol as outlined in scheme 7.

SCHEME 7

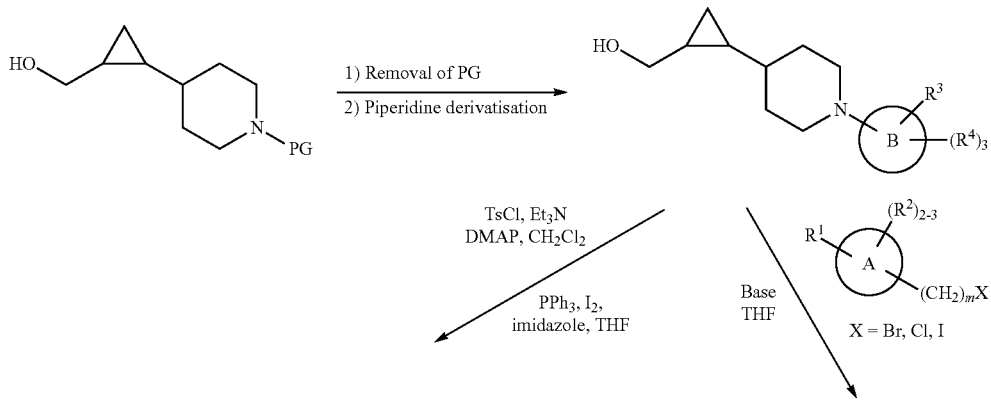

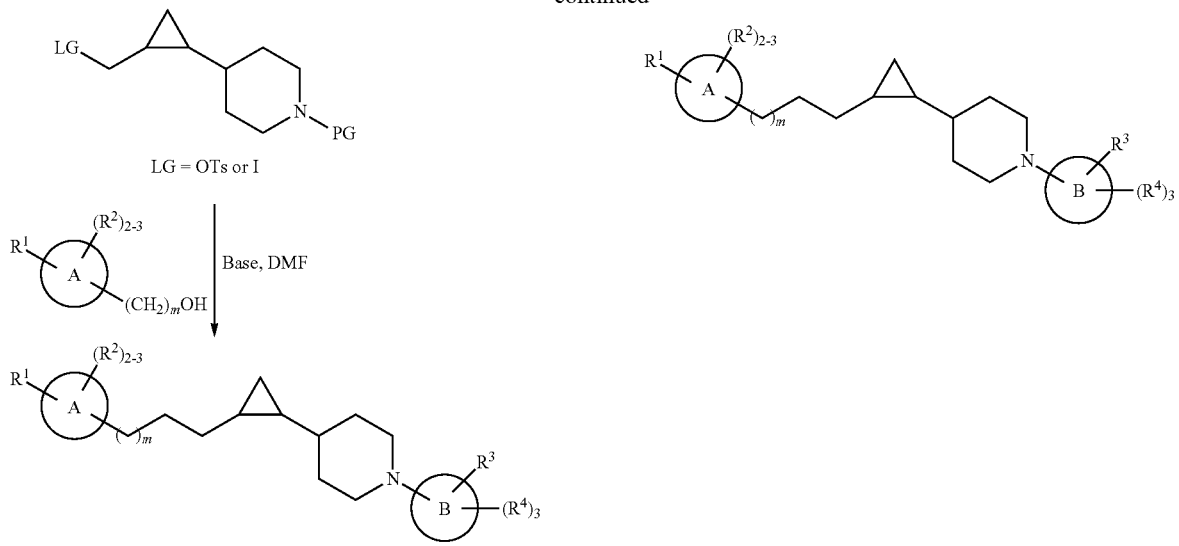

When the N-Aryl or N-heteroaryl residue is substituted with an X group (where X=Cl, Br, I or OTf) it is possible to further functionalize the residue by utilizing palladium mediated coupling reactions. Methods with extraordinarily broad applicability are metal based couplings outlined in scheme 8.

SCHEME 8

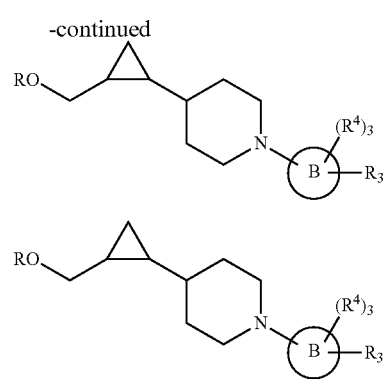

Similarly when the ring A residue is substituted with an X group (where X=Cl, Br, I or OTf), it is possible to further functionalize the residue by utilizing palladium mediated coupling reactions. Methods with extraordinarily broad applicability are metal based couplings outlined in scheme 9.

SCHEME 9

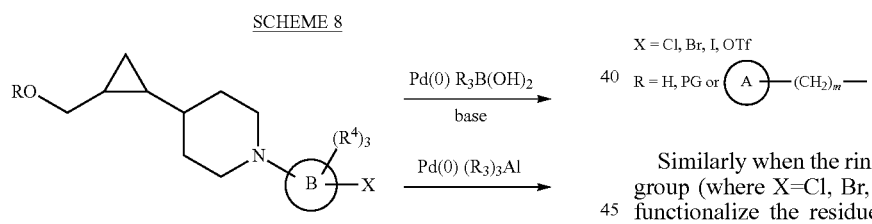

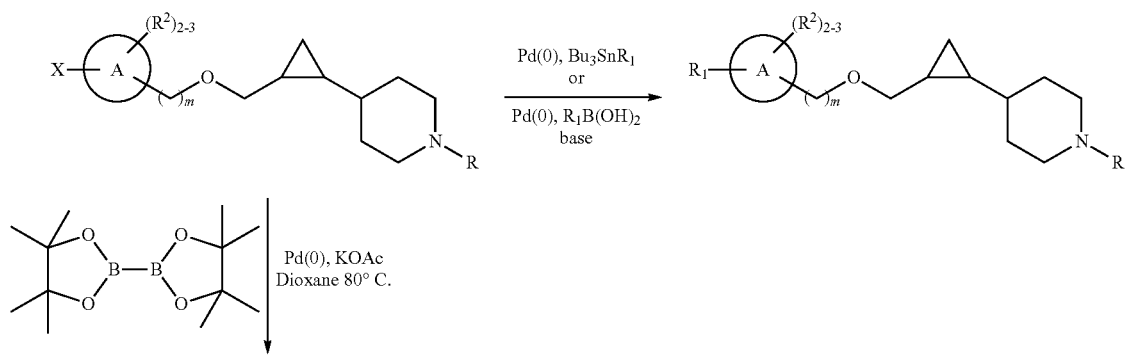

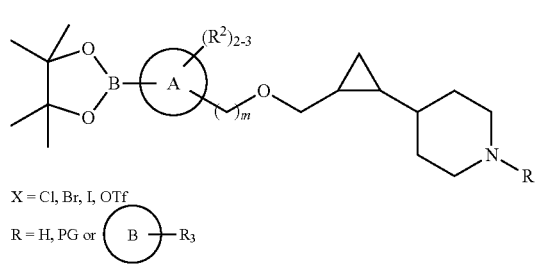
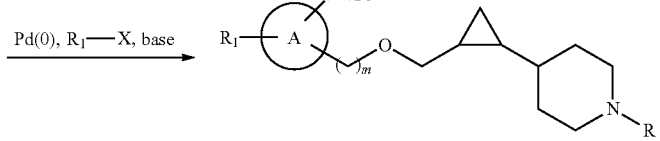

-continued

X = Cl, Br, I, OTf

R = H, PG or (B)—R₃

INTERMEDIATES

Intermediates 1-3

Preparation of cyclopropylmethyl 2,5-dioxopyrrolidin-1-yl carbonate

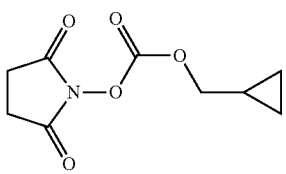

1

Step A: cyclopropylmethyl 2,5-dioxopyrrolidin-1-yl carbonate

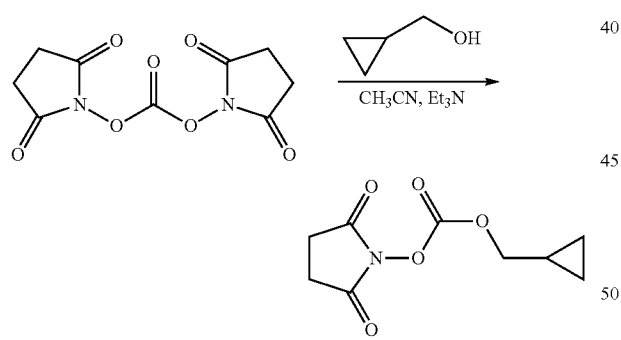

To a stirred solution of cyclopropylmethanol (1.0 g, 13.8 mmol) in acetonitrile (15 mL) was added bis(2,5-dioxopyrrolidin-1-yl) carbonate (7.1 g, 27.7 mmol) and triethylamine (5.8 mL, 41.6 mmol). The reaction was stirred overnight, then quenched with saturated NaHCO3 solution (aq.) and extracted with ethyl acetate (3×50 mL), dried over sodium sulfate, filtered and concentrated under reduced pressure to provide the title compound (3.2 g, quant.) as an amber oil: $^1$H NMR (300 MHz, CDCl$_3$) δ 4.16 (d, J=7.5 Hz, 2H), 2.84 (s, 4H), 1.26 (m, 1H), 0.70-0.64 (m, 2H), 0.40-0.35 (m, 2H).

The remaining examples in Table 1 were synthesized according to the method described above using the appropriate alcohol.

TABLE 1

| Number | Name | Chemical Structure |
|---|---|---|
| 2 | 2,5-dioxopyrrolidin-1-yl 1-methylcyclopropyl carbonate | 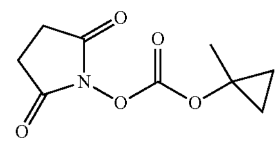 |
| 3 | cyclobutyl 2,5-dioxopyrrolidin-1-yl carbonate | 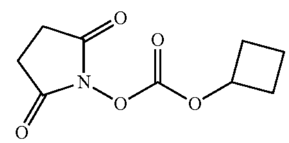 [SMILES: O=C(OC1CCC1)ON1C(=O)CCC1=O] |

Intermediate 4

Preparation of tert-butyl 4-[(1R,2R)-2-(hydroxymethyl)cyclopropyl]piperidine-1-carboxylate

4

Step A: tert-butyl 4-(2,2-dibromovinyl)piperidine-1-carboxylate

Carbon tetrabromide (2.332 g, 7.03 mmol) was dissolved in CH$_2$Cl$_2$ (30.2 ml, 469 mmol) and the solution was cooled in a 0° C. bath. Triphenylphosphine (3.69 g, 14.07 mmol) was added, giving an orange colored solution as it dissolved. After 25 min tert-butyl 4-formylpiperidine-1-carboxylate (1 g, 4.69 mmol) was added in one portion to the 0° C. solution. After 50 min, the solution was concentrated to about ⅓ the original volume, causing a precipitate. Cyclopentylmethyl ether was then added slowly, causing more precipitation. The suspension was filtered, rinsing with CPME. More precipitate appeared in the filtrate, so it was filtered again. The filtrate was partitioned with water. The aqueous layer was removed. The organic layer was washed with dilute aqueous sodium bisulfite followed by water. The final organic layer was concentrated to a mixture of solid and oil. The residue was triturated with 40% ethyl acetate/hexanes and filtered through a pad of silica. The filtrate was concentrated to yield the dibromoalkene as a white solid. $^1$H NMR (500 MHz, CDCl$_3$) δ 6.23 (d, J 8.9 Hz, 1H), 4.15-3.98 (m, 2H), 2.83-2.72 (m, 2H), 2.48-2.40 (m, 1H), 1.75-1.67 (m, 2H), 1.45 (s, 9H), 1.37-1.26 (m, 2H).

Step B: tert-butyl 4-(3-hydroxyprop-1-yn-1-yl)piperidine-1-carboxylate

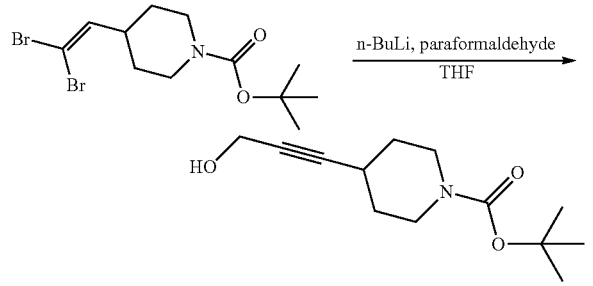

Product from step A (0.5 g, 1.355 mmol) was dissolved in dry THF (4.99 ml, 61.0 mmol) under nitrogen. The solution was cooled in a bath at −45° C. and to it was added n-BuLi (1.6M in hexanes, 1.736 ml, 2.78 mmol) over ca. 2 min. The solution was stirred at −45° C. to −38° C. for 45 min, then paraformaldehyde (0.122 g, 4.06 mmol) was added. The suspension was allowed to warm slowly to room temp. After stirring at room temp overnight, the reaction was quenched with aqueous 10% NH$_4$Cl and extracted with ethyl acetate. The organic layer was washed with water and evaporated to yield a crude material which was subjected to silica gel chromatography (gradient elution 9% to 70% EtOAc in hexanes) to provide the desired product. $^1$H NMR (400 MHz, CDCl$_3$) δ 4.46 (d, 2H), 3.80-3.68 (m, 2H), 3.22-3.11 (m, 2H), 2.68-2.58 (m, 1H), 1.86-1.75 (m, 2H), 1.64-1.53 (m, 2H), 1.49 (s, 9H).

Step C: tert-butyl 4-[(1Z)-3-hydroxyprop-1-en-1-yl]piperidine-1-carboxylate

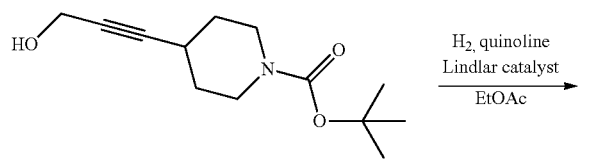

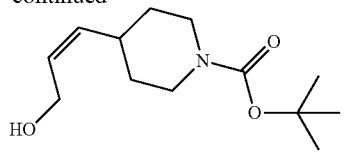

The alkyne from step B (6.5 g, 27.2 mmol) and quinoline (0.55 mL, 4.62 mmol) were dissolved in EtOAc (120 mL). Lindlar's catalyst (740 mg) was added and the reaction was stirred under hydrogen atmosphere (1 atm) for 40 minutes. The reaction was filtered and concentrated to yield a crude residue which was purified by silica gel chromatography (gradient elution, 0% to 100% EtOAc in hexanes) to yield the desired allylic alcohol. $^1$H NMR (500 MHz, CDCl$_3$) δ 5.58 (m, 1H), 5.37 (dd, J 10.8 & 9.6 Hz, 1H), 4.22 (d, 2H), 4.16-3.99 (m, 2H), 2.80-2.78 (m, 2H), 2.52-2.40 (m, 1H), 1.61-1.56 (m, 2H), 1.45 (s, 9H), 1.36-1.22 (m, 2H).

Step D: tert-Butyl 4-[(1R,2R)-2-(hydroxymethyl)cyclopropyl]piperidine-1-carboxylate

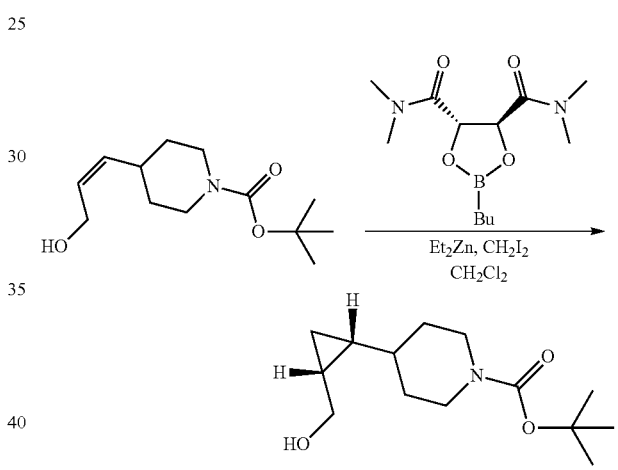

To a 3 L round bottomed flask equipped with overhead stirrer was added CH$_2$Cl$_2$ (850 ml) under a nitrogen atmosphere. The flask was cooled to −30° C. and diethyl zinc (528 mL, 528 mmol) was added, followed by DME (55 mL, 528 mmol). The mixture was stirred for 20 min at −20° C. followed by slow addition of diiodomethane (85 mL, 1057 mmol) over 20 min. The mixture was stirred at −20° C. for 45 min resulting in a white slurry. To a separate 1 L flask was charged the cis allylic alcohol (51 g, 211 mmol) and (4S,5S)-2-butyl-N4,N4,N5,N5-tetramethyl-1,3,2-dioxaborolane-4,5-dicarboxamide (68.5 g, 254 mmol) in DCM (400 mL). This mixture was then added to the diethylzinc solution slowly over 1 h at −15° C. The reaction was stirred overnight, allowing it to warm to RT. The reaction was then cooled to <5° C., quenched with 5% aqueous NH$_4$Cl (500 mL). A solid precipitate formed during the quench. The liquid was decanted liquid into a 4 L Sep funnel, and the layers were separated. Dichloromethane (350 mL) and aqueous NH$_4$Cl (400 mL) were added into the reaction flask and the mixture was stirred for ~1 h to dissolve some of the solids. The layers were separated and both organic layers were combined, washed with 5% aqueous NH$_4$Cl (500 mL), then brine (500 mL), dried over anhydrous MgSO$_4$, filtered and concentrated. The resulting residue was subjected to silica gel chromatography (EtOAc/hexanes) and the product recrystallized from Heptane to give material with >98% de and >98% ee as a white solid. $^1$H NMR (500 MHz, CDCl$_3$) δ 4.18-4.00 (m, 2H), 3.68 (d, J 7.3 Hz, 2H), 2.76-2.63 (m, 2H), 1.83-1.72 (m, 2H), 1.49 (s, 9H), 1.39-1.25 (m, 2H), 1.24-1.14 (m, 1H), 1.05-0.95 (m, 1H), 0.78-0.71 (m, 2H), 0.07-0.01 (m, 1H).

Intermediate 5

Preparation of 5-(methylsulfonyl)-2-({[(1R,2R)-2-piperidin-4-ylcyclopropyl]methoxy}methyl) pyridine

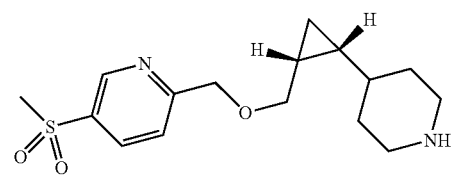

Step A: 5-bromo-2-(bromomethyl)pyridine

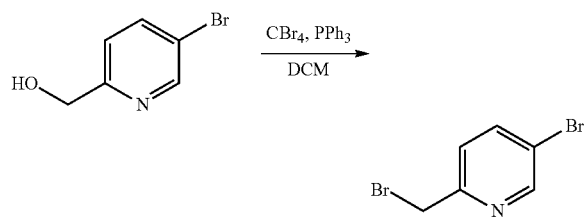

5-Bromo-2-hydroxymethylpyridine (1 g, 5.32 mmol) was dissolved in dichloromethane (26.6 ml) and cooled to 0° C. Triphenylphosphine (1.604 g, 6.12 mmol) was added followed by carbon tetrabromide (2.028 g, 6.12 mmol) which caused the reaction to become yellow and heterogeneous. After 48 h, the mixture was concentrated by half and directly purified by silica gel column chromatography (0-37%, EtOAc-hexanes) to yield the title compound. $^1$H NMR (500 MHz, CDCl$_3$) δ 8.64 (t, J 2.7 Hz, 1H), 7.82 (m, 1H), 7.35 (dd, J 7.8 & 3.1 Hz, 1H), 4.51 (s, 2H).

Step B: tert-butyl 4-((1R,2R)-2-{[(5-bromopyridin-2-yl)methoxy]}cyclopropyl)piperidine-1-carboxylate

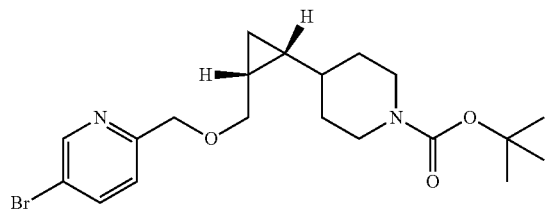 [SMILES: CC(C)(C)OC(=O)N1CCC([C@H]2C[C@H]2COCc2ccc(Br)cn2)CC1]

To a solution of tert-butyl 4-[(1R,2R)-2-(hydroxymethyl)cyclopropyl]piperidine-1-carboxylate (Intermediate 4: 3.5 g, 13.71 mmol) in THF (40 mL) was added NaHMDS (16.45 mL of a 1.0M soln in THF, 16.45 mmol) followed by the product of step A (4.13 g, 16.45 mmol) and the resulting mixture heated at reflux overnight. The mixture was cooled and poured into water (100 mL) and extracted with EtOAc (2×75 mL); combined EtOAc layers washed with sat. NaCl, dried over MgSO$_4$, filtered and evaporated in vacuo. Residue purified by silica gel column chromatography (eluent: gradient 0-25% EtOAc in Hexanes) to give the title compound. $^1$H NMR (500 MHz, CDCl$_3$) δ 8.82 (d, J 2.0 Hz, 1H), 7.84 (dd, J 8.0 & 2.0 Hz, 1H), 7.38 (d, J 8.0 Hz, 1H), 4.65 (d, J 13.5 Hz, 1H), 4.57 (d, J 13.5 Hz, 1H), 4.18-3.97 (br m, 2H), 3.64-3.58 (m, 1H), 3.58-3.52 (m, 1H), 2.74-2.58 (m, 2H), 1.86-1.79 (m, 1H), 1.77-1.69 (m, 1H), 1.47 (s, 9H), 1.36-1.20 (m, 3H), 0.98-0.89 (m, 1H), 0.79-0.68 (m, 2H), 0.07-0.03 (m, 1H).

Step C: tert-butyl 4-[(1R,2R)-2-({[5-(methylthio)pyridin-2-yl]methoxy}methyl)cyclopropyl]piperidine-1-carboxylate

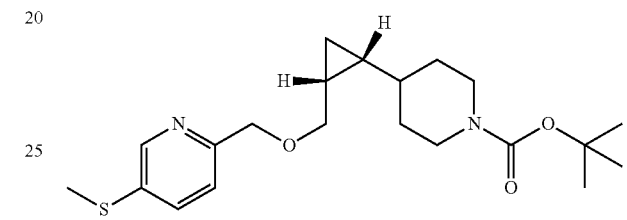

To a solution of the aryl bromide from step B (680 mg, 1.60 mmol) dissolved in THF (10.7 mL) cooled at −78° C. was added N-butyllithium in hexanes (1.5 M, 1.12 mL, 1.68 mmol). After 10 min, dimethyldisulfide (0.16 mL, 1.76 mmol) was added. At 45 min, the reaction was quenched at −78° C. with saturated aqueous NH$_4$Cl (2 mL). The mixture was warmed to room temperature, diluted with EtOAc and washed with H$_2$O (1×) and saturated aqueous NaCl (1×). The aqueous was back-extracted with EtOAc (3×), and the combined organic layer was dried over Na$_2$SO$_4$, filtered and evaporated in vacuo to yield a crude oil that was purified by silica gel column chromatography (10-70%, EtOAc-hexanes) to yield the title compound. $^1$H NMR (500 MHz, CDCl$_3$) δ 8.47 (d, J 2.0 Hz, 1H), 7.62 (dd, J 8.0 & 2.0 Hz, 1H), 7.39 (d, J 8.0 Hz, 1H), 4.68 (d, J 13.5 Hz, 1H), 4.59 (d, J 13.5 Hz, 1H), 4.18-3.98 (br m, 2H), 3.66-3.60 (m, 1H), 3.57-3.51 (m, 1H), 2.75-2.58 (m, 2H), 2.53 (s, 3H), 1.88-1.82 (m, 1H), 1.77-1.69 (m, 1H), 1.47 (s, 9H), 1.37-1.21 (m, 3H), 0.98-0.90 (m, 1H), 0.79-0.68 (m, 2H), 0.07-0.03 (m, 1H).

Step D: tert-butyl 4-[(1R,2R)-2-({[5-(methylsulfonyl)pyridin-2-yl]methoxy}methyl)cyclopropyl]piperidine-1-carboxylate

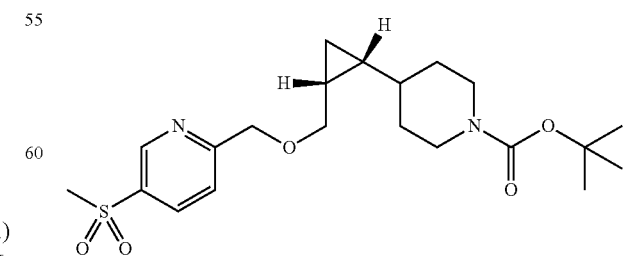

The sulfide from step B (200 mg, 0.509 mmol) was dissolved in MeOH (3.09 mL), and a solution of oxone (940 mg, 1.528 mmol) in water (7.1 mL) was added. The reaction became warm and heterogeneous with a white precipitate. At 45 min, the reaction was diluted with dichloromethane and washed with H₂O (1×) and saturated aqueous NaCl (1×). The aqueous was back-extracted with DCM (2×), and the combined organic layer was dried over Na₂SO₄, filtered and evaporated in vacuo to yield the crude compound that was purified by silica gel column chromatography (20-100%, EtOAc-hexanes) to yield the title compound. ¹H NMR (500 MHz, CDCl₃) δ 9.10 (d, 1H), 8.26 (dd, 1H), 7.73 (d, 1H), 4.81 (d, 1H), 4.73 (d, 1H), 4.20-4.00 (m, 2H), 3.69-3.61 (m, 2H), 3.14 (s, 3H), 2.75-2.60 (m, 2H), 1.87-1.82 (m, 1H), 1.78-1.72 (m, 1H), 1.47 (s, 9H), 1.38-1.24 (m, 3H), 1.02-0.93 (m, 1H), 0.83-0.72 (m, 2H), 0.11-0.06 (m, 1H). MS (ESI) m/z 425 [M+H]⁺.

Step E: 5-(methylsulfonyl)-2-({[(1R,2R)-2-piperidin-4-ylcyclopropyl]methoxy}methyl)pyridine

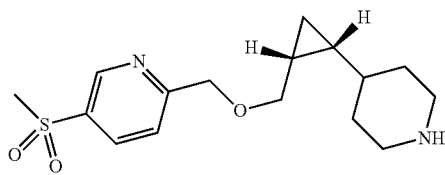 [SMILES: CS(=O)(=O)c1ccc(COC[C@@H]2C[C@@H]2C2CCNCC2)nc1]

The product of step D (207 mg, 0.488 mmol) was dissolved in dichloromethane (1.63 mL) and trifluoroacetic acid (1.62 mL, 21.0 mmol) was added. At 1.75 h the volatiles were removed to yield an oil, which was dissolved in 1 mL of MeOH and 1.5 mL of 7 M NH₃ in MeOH. After 30 min all volatiles were removed. The free base was used without further purification. ¹H NMR (500 MHz, CDCl₃) δ 9.10 (d, 1H), 8.26 (dd, 1H), 7.68 (d, 1H), 4.78 (d, 1H), 4.71 (d, 1H), 3.89-3.84 (m, 1H), 3.53-3.49 (m, 1H), 3.46-3.41 (m, 1H), 3.15 (s, 3H), 2.93-2.81 (m, 2H), 2.19-2.12 (m, 1H), 2.02-1.94 (m, 1H), 1.80-1.68 (m, 2H), 1.80-1.68 (m, 2H), 1.38-1.30 (m, 1H), 1.19-1.09 (m, 1H), 0.89-0.22 (m, 2H), 0.11-0.06 (m, 1H). MS (ESI) m/z 437 [M+H]⁺.

Intermediate 6

Preparation of 2-{[6-({[(1R,2R)-2-piperidin-4-ylcyclopropyl]methoxy}methyl)pyridin-3-yl]sulfonyl}ethanol

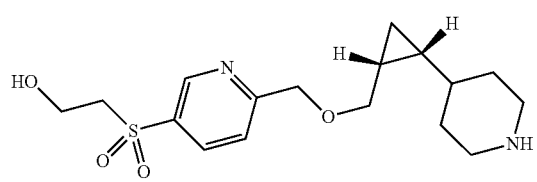 [SMILES: O=S(=O)(CCO)c1ccc(COC[C@@H]2C[C@@H]2C2CCNCC2)nc1]

Step A: tert-butyl 4-[(1R,2R)-2-[({5-[(2-hydroxyethyl)thio]pyridin-2-yl}methoxy)methyl]cyclopropyl]piperidine-1-carboxylate

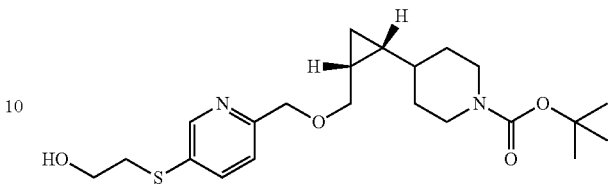

Hunig's base (1.64 mL, 9.4 mmol) was added to a solution of intermediate 5 (step B) (2 g, 4.7 mmol) in 1,4-dioxane (40 mL). The mixture was evacuated and backfilled with N₂ (3×). Pd₂dba₃ (129 mg, 0.14 mmol), 4,5-bis(diphenylphosphino)-9,9-dimethylxanthene (272 mg, 0.47 mmol) and 2-mercaptoethanol (367 mg, 4.7 mmol) were added sequentially and the mixture was degassed 2×. The mixture was heated to reflux for 2 h, the mixture cooled and evaporated. The residue was purified by silica gel column chromatography (gradient 50~100% EtOAC in hexane) to yield the title compound. ¹H NMR (500 MHz, CDCl₃) δ 8.59 (d, 1H), 7.77 (dd, 1H), 7.42 (dd, 1H), 4.69 (d, 1H), 4.59 (d, 1H), 4.17-3.98 (m, 2H), 3.92-3.77 (m, 2H), 3.66 (dd, 1H), 3.57-3.52 (m, 1H), 3.12 (t, 2H), 2.74-2.64 (m, 1H), 1.83 (d, 1H), 1.73 (d, 1H), 1.48 (s, 9H), 1.36-1.21 (m, 3H), 0.97-0.88 (m, 1H), 0.80-0.68 (m, 2H), 0.08-0.03 (m, 1H).

Step B: tert-butyl 4-[(1R,2R)-2-[({5-[(2-hydroxyethyl)sulfonyl]pyridin-2-yl}methoxy)methyl]cyclopropyl]piperidine-1-carboxylate

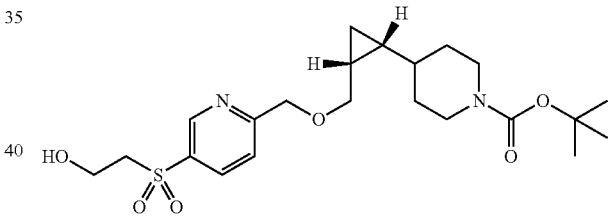

The product of step A (2 g, 4.73 mmol) was oxidized according to the procedure of intermediate 5 (step D) to yield the designed product. ¹H NMR (500 MHz, CDCl₃) δ 9.07 (d, 1H), 8.24 (dd, 1H), 7.73 (dd, 1H), 4.80 (d, 1H), 4.72 (d, 1H), 4.11-3.97 (m, 4H), 3.69 (dd, 1H), 3.65-3.59 (m, 1H), 3.43 (t, 2H), 2.72-2.66 (m, 1H), 1.83 (d, 1H), 1.74 (d, 1H), 1.48 (s, 9H), 1.38-1.23 (m, 3H), 1.00-0.91 (m, 1H), 0.83-0.70 (m, 2H), 0.10-0.06 (m, 1H).

Step C: 2-{[6-({[(1R,2R)-2-piperidin-4-ylcyclopropyl]methoxy}methyl)pyridin-3-yl]sulfonyl}ethanol

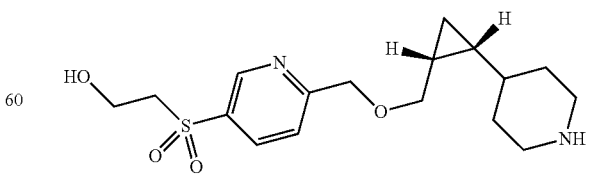

The product of step B (650 mg, 1.430 mmol) was deprotected according to the procedure of intermediate 5 (step E) to yield the designed product. MS (ESI) m/z 355 [M+H]⁺.

Intermediate 7

Preparation of 5-bromo-2-{4-[(1R,2R)-2-({[4-(methylsulfonyl)benzyl]oxy}methyl)cyclopropyl]piperidin-1-yl}pyrimidine

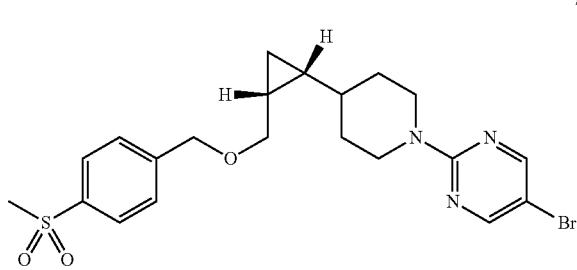

7

Step A:
[1R,2R)-2-piperidin-4-ylcyclopropyl]methanol trifluoroacetate

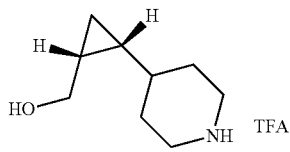 [SMILES: OC[C@@H]1C[C@@H]1C1CCNCC1 ; "TFA"]

tert-Butyl 4-[(1R,2R)-2-(hydroxymethyl)cyclopropyl]piperidine-1-carboxylate (Intermediate 4, 5.0 g, 19.6 mmol) was dissolved in DCM (50 mL) at 0° C., and TFA (100 mL, 1.35 mol) was added. After stirring at 0° C. for 1 hour the solution was concentrated in vacuo to give the title compound which was used without further purification Step B: {(1R,2R)-2-[1-(5-bromopyrimidin-2-yl)piperidin-4-yl]cyclopropyl}methanol

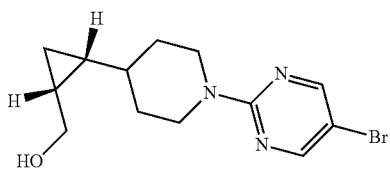 [SMILES: OC[C@@H]1C[C@@H]1C1CCN(c2ncc(Br)cn2)CC1]

The product of step A (4.94 g, 19.6 mmol) was dissolved in DMF (40 mL), and Cs₂CO₃ (35 g, 107 mmol) and 5-bromo-2-chloropyrimidine (3.8 g, 19.6 mmol) were added. After stirring the mixture at RT for 5 hours, the mixture was partitioned between water and EtOAc. The aqueous layer was extracted with EtOAc. The combined organic layers were washed with water and brine. The organic layers were dried with Na₂SO₄ and concentrated in vacuo. The residue was purified via silica gel column chromatography (20/1, DCM/MeOH), yielding the title compound.

Step C: 5-bromo-2-{4-[(1R,2R)-2-({[4-(methylthio)benzyl]oxy}methyl)cyclopropyl]piperidin-1-yl}pyrimidine

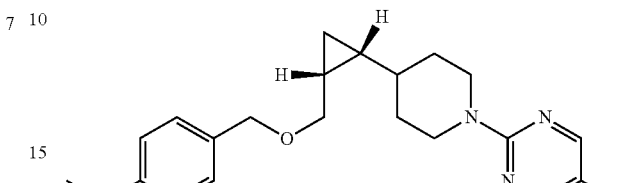

The product of step B (1.5 g, 4.8 mmol) was dissolved in DMF (15 mL), and sodium hydride (60 wt % dispersion in oil, 290 mg, 7.3 mmol) was added. After stirring at RT for 1 hour, (4-(bromomethyl)phenyl)(methyl)sulfane (1.35 g, 6.2 mmol) was added, and the resulting solution was stirred at RT for 18 h. The solution was partitioned between sat. NH₄Cl and EtOAc. The aqueous layer was extracted with EtOAc. The combined organic layers were washed with brine and dried over Na₂SO₄, filtered and concentrated in vacuo. The residue was purified by silica gel column chromatography (5/1 hexanes/EtOAc) to yield the title compound.

Step D: 5-bromo-2-{4-[(1R,2R)-2-({[4-(methylsulfonyl)benzyl]oxy}methyl)cyclopropyl]piperidin-1-yl}pyrimidine The product of step C was oxidized using the conditions outlined in intermediate 6, step B to give the title compound.

Intermediate 8

Preparation of 4-[(1R,2R)-2-({[4-(methylsulfonyl)benzyl]oxy}methyl)cyclopropyl]piperidine trifluoroacetate

8

Step A: tert-butyl-4-[(1R,2R)-2-(iodomethyl)cyclopropyl]piperidine-1-carboxylate

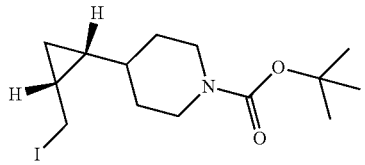 [SMILES: CC(C)(C)OC(=O)N1CCC([C@H]2C[C@H]2CI)CC1]

Intermediate 4 (2.0 g, 7.8 mmol), PPh₃ (2.68 g, 10.2 mmol), imidazole (1.07 g, 15.7 mmol), and iodine (2.98 g, 11.7 mmol) were dissolved in THF (15 mL), and the resulting solution was stirred at RT for 2 h. The solution was quenched with sat. $Na_2S_2O_3$, and extracted with $Et_2O$. The organic layer was dried over $Na_2SO_4$, filtered, and concentrated. The residue was purified by silica gel column chromatography (10/1 hexanes/EtOAc) which provided the title compound.

Step B: tert-butyl-4-[(1R,2R)-2-({[4-(methylsulfonyl)benzyl]oxy}methyl)cyclopropyl]piperidine-1-carboxylate

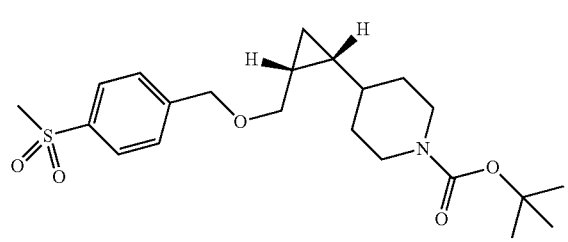

4-(Methylsulfonyl)benzyl alcohol (1.0 g, 5.4 mmol) was dissolved in DMF (12 mL), and sodium hydride (60 wt % dispersion in oil, 320 mg, 8 mmol) was added. The iodide from step A (2.35 g, 6.4 mmol) in DMF (12 mL) was added and the resulting solution was stirred at RT for 15 h. The solution was quenched with sat. $NH_4Cl$, and EtOAc. The organic layer was washed with water and brine. The organic layer was dried over $Na_2SO_4$, filtered, and concentrated. The residue was purified via silica gel column chromatography (2/1 hexanes/EtOAc) which provided the title compound.

Step C: 4-[(1R,2R)-2-({[4-(methylsulfonyl)benzyl]oxy}methyl)cyclopropyl]piperidine trifluoroacetate

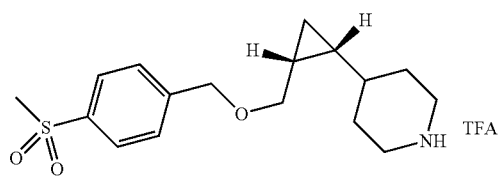 [SMILES: CS(=O)(=O)c1ccc(COC[C@@H]2C[C@@H]2C2CCNCC2)cc1 ; "TFA"]

The product of step B was deprotected using the procedure outlined in intermediate 7, step A.

Intermediates 9-11

Preparation of 4-((1R,2R)-2-({[4-(methylsulfonyl)benzyl]oxy}methyl)cyclopropyl]piperidine-1-carbonitrile

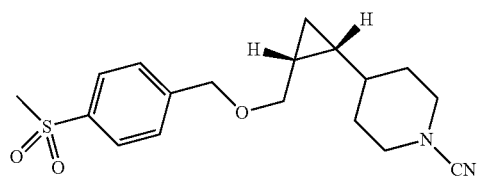

Step A: tert-butyl 4-((1R,2R)-2-{[(4-bromobenzyl)oxy]methyl}cyclopropyl)piperidine-1-carboxylate

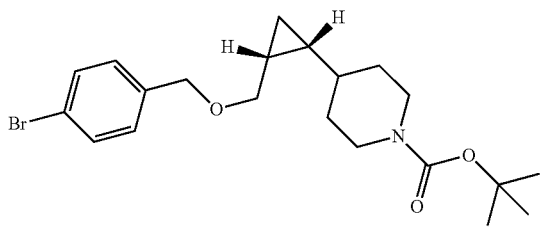 [SMILES: CC(C)(C)OC(=O)N1CCC([C@H]2C[C@H]2COCc2ccc(Br)cc2)CC1]

Using the conditions outlined in intermediate 5 (step C) tert-butyl 4-[(1R,2R)-2-(hydroxymethyl)cyclopropyl]piperidine-1-carboxylate (intermediate 4) and 4-bromobenzyl bromide were reacted to yield the title compound. ¹H NMR (500 MHz, CDCl₃) δ 7.49 (d, J 8.2 Hz, 2H), 7.22 (d, J 8.2 Hz, 2H), 4.53 (d, J 12.3 Hz, 1H), 4.44 (d, J 12.3 Hz, 1H), 4.17-3.18 (m, 2H), 3.58-3.51 (m, 1H), 3.43-3.37 (m, 1H), 2.73-2.58 (m, 2H), 1.84 (d, J 13.2 Hz, 1H), 1.70 (d, J 13.3 Hz, 1H), 1.49 (s, 9H), 1.34-1.24 (m, 2H), 1.24-1.17 (m, 1H), 0.94-0.85 (m, 1H), 0.77-0.66 (m, 2H), 0.03-0.02 (m, 1H).

Step B: 4-((1R,2R)-2-{[(4-bromobenzyl)oxy]methyl}cyclopropyl)piperidine trifluoroacetate

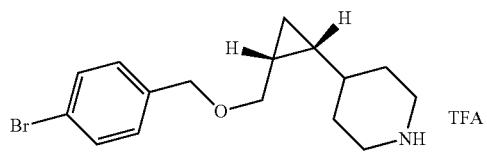 [SMILES: Brc1ccc(COC[C@@H]2C[C@@H]2C2CCNCC2)cc1]

The product of step A was deprotected using the procedure outlined in intermediate 7, step A. ¹H NMR (500 MHz, CDCl₃) δ 7.78 (br s, 2H), 7.45 (d, J 8.2 Hz, 2H), 7.21 (d, J 8.2 Hz, 2H), 4.51 (d, J 12.2 Hz, 1H), 4.42 (d, J 12.2 Hz, 1H), 3.63-3.59 (m, 1H), 3.37-3.25 (m, 3H), 2.82-2.68 (m, 2H), 2.06 (d, J 13.9 Hz, 1H), 1.88 (d, J 13.6 Hz, 1H), 1.67-1.56 (m, 2H), 1.29-1.20 (m, 1H), 1.04-0.9 (m, 1H), 0.80-0.73 (m, 2H), 0.04-0.03 (m, 1H).

Step C: 4-((1R,2R)-2-{[(4-bromobenzyl)oxy]methyl}cyclopropyl)piperidine-1-carbonitrile

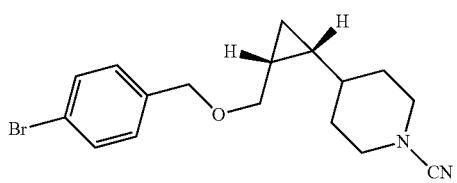 [SMILES: N#CN1CCC([C@H]2C[C@H]2COCc2ccc(Br)cc2)CC1]

The product from step B (1.00 g, 3.08 mmol) and N,N-diisopropylethylamine (1.61 mL, 9.25 mmol) were dissolved in acetonitrile (20 mL). Cyanogen bromide (5M in acetonitrile, 0.746 mL, 3.7 mmol) was added and the reaction was stirred overnight at room temperature. The reaction was concentrated and the residue was partitioned between $CH_2Cl_2$ and water. The organic layer was saved and the aqueous layer was extracted with $CH_2Cl_2$. The organic layers were combined, washed with brine, dried over anhydrous $MgSO_4$, filtered and evaporated to yield a crude material, which was purified by silica gel column chromatography (gradient elution 0% to 100% EtOAc in hexanes) to yield the title compound as a viscous oil.

Step D: 4-((1R,2R)-2-({[4-(methylsulfonyl)benzyl]oxy}methyl)cyclopropyl]piperidine-1-carbonitrile

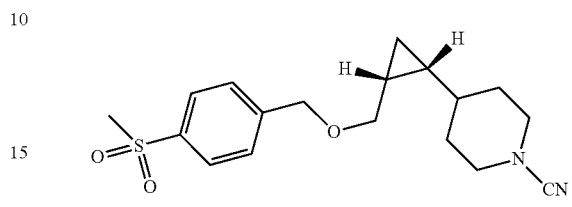

The product of step C (310 mg, 0.89 mmol), sodium methanesulfinate (109 mg, 1.06 mmol), $Cu(OTf)_2 \cdot C_6H_6$ (89 mg, 0.178 mmol), and $MeNHCH_2CH_2NHMe$ (0.038 mL, 0.355 mmol) were combined in dimethyl sulfoxide (5 mL) in a glass pressure tube. The solution was purged with nitrogen, sealed, and heated in a 120° C. oil bath overnight. The crude reaction mixture was directly purified by preparative HPLC (C18 reversed phase, gradient elution 10% to 100% MeCN in water with 0.1% formic acid) to yield the desired product.

The remaining examples in Table 2 were synthesized according to the method described above using the appropriate sodium alkylsulfinate.

TABLE 2

| Number | Name | Chemical Structure |
|---|---|---|
| 10 | 4-((1R,2R)-2-({[4-(cyclopropylsulfonyl)benzyl]oxy}methyl)cyclopropyl]piperidine-1-carbonitrile | 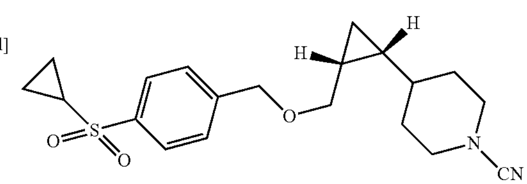 |
| 11 | 4-((1R,2R)-2-({[4-(ethylsulfonyl)benzyl]oxy}methyl)cyclopropyl]piperidine-1-carbonitrile | 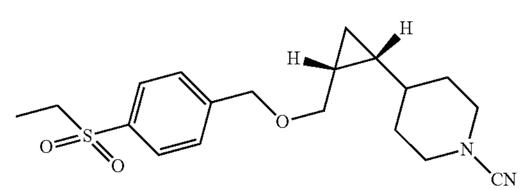 [SMILES: CCS(=O)(=O)c1ccc(COC[C@@H]2C[C@@H]2C2CCN(C#N)CC2)cc1] |

Intermediate 12

Preparation of tert-butyl 4-[(1R,2R)-2-{[(4-bromo-2-fluorobenzyl)oxy]methylcyclopropyl)piperidine-1-carboxylate

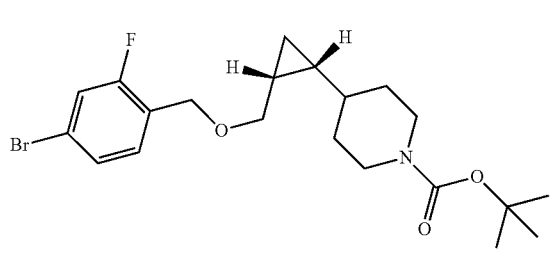

This intermediate was prepared from tert-butyl 4-[(1R,2R)-2-(hydroxymethyl)cyclopropyl]piperidine-1-carboxylate (intermediate 4) and 4-bromo-2-fluorobenzyl bromide according to the conditions outlined in intermediate 5 (step B). $^1$H NMR (500 MHz, CDCl$_3$) δ 7.35-7.24 (m, 3H), 4.58 (d, 1H), 4.50 (d, 1H), 4.20-3.96 (br m, 2H), 3.63-3.58 (m, 1H), 3.45-3.40 (m, 1H), 2.72-2.58 (m, 2H), 1.84 (d, 1H), 1.71 (d, 1H), 1.49 (s, 9H), 1.37-1.18 (m, 3H), 0.95-0.85 (m, 1H), 0.78-0.66 (m, 2H), 0.05-0.00 (m, 1H).

Intermediate 13

Preparation of tert-butyl 4-[(1R,2R)-2-{[(4-bromo-3-fluorobenzyl)oxy]methylcyclopropyl)piperidine-1-carboxylate

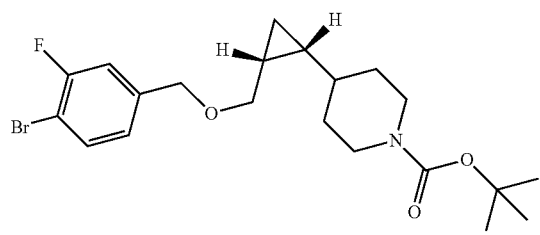

Step A: (4-Bromo-3-fluorophenyl)methanol

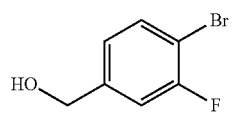

A 0° C. solution of 4-bromo-3-fluoro benzoic acid (2.3 g, 10.50 mmol) in dry THF (52.5 ml) is treated with borane tetrahydrofuran complex (15.75 ml of a 1 M solution in THF, 15.75 mmol) and the resulting mixture stirred at RT for 72 hours. The mixture is then quenched with 1N HCl, stirred for 20 minutes, then extracted with DCM. Concentration and silica gel chromatography (10-50% EtOAc/hexanes) yields the title compound 1.87 g (87% yield) as colorless needles. $^1$H NMR (500 MHz, CDCl$_3$) δ 7.55 (m, 1H), 7.04 (d, J 9.4 Hz, 1H), 7.04 (d, J 8.3 Hz, 1H), 4.70 (d, 2H).

Step B: 3-Fluoro-4-bromobenzyl bromide

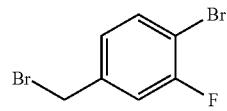

The product from step A was converted to the bromide according to the procedure from example 5 (step A). $^1$H NMR (500 MHz, CDCl$_3$) δ 7.54 (m, 1H), 7.19 (d, 1H), 7.08 (d, 1H), 4.43 (s, 2H).

Step C: tert-butyl 4-[(1R,2R)-2-{[(4-bromo-3-fluorobenzyl)oxy]methylcyclopropyl)piperidine-1-carboxylate

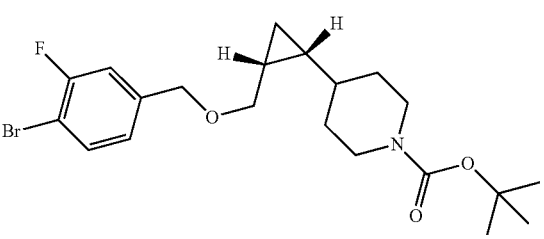 [SMILES: CC(C)(C)OC(=O)N1CCC([C@H]2C[C@H]2COCc2ccc(Br)c(F)c2)CC1]

Using the conditions outlined in intermediate 5 (step B) tert-butyl 4-[(1R,2R)-2-(hydroxymethyl)cyclopropyl]piperidine-1-carboxylate (intermediate 4) and the product from step C were reacted to yield the title compound.

Intermediate 14

Preparation of tert-butyl 4-[(1R,2R)-2-{[(3,5-difluorobenzyl)oxy]methylcyclopropyl)piperidine-1-carboxylate

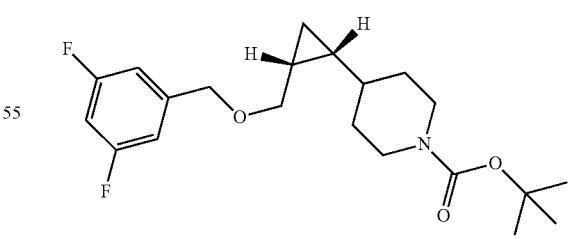

Prepared from tert-butyl 4-[(1R,2R)-2-(hydroxymethyl)cyclopropyl]piperidine-1-carboxylate (intermediate 4) and 3,5-difluorobenzyl bromide according to the conditions outlined in intermediate 5 (step B). $^1$H NMR (500 MHz, CDCl$_3$) δ 6.89 (m, 2H), 6.75 (m, 1H), 4.57 (d, 1H), 4.47 (d, 1H), 4.20-3.98 (br m, 2H), 3.60-3.51 (m, 1H), 3.50-3.41 (m, 1H), 2.77-2.59 (m, 2H), 1.85 (d, 1H), 1.73 (d, 1H), 1.49 (s, 9H), 1.38-1.20 (m, 3H), 0.97-0.87 (m, 1H), 0.80-0.69 (m, 2H), 0.09-0.01 (m, 1H).

Intermediate 15A

Preparation of 5-(Bromomethyl)-1,3-difluoro-2-(methylthio)benzene

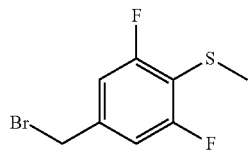

Step A: 3,5-Difluoro-4-(methylthio)benzaldehyde

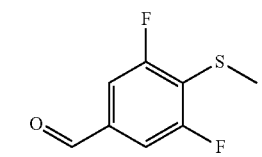

A solution of 3,4,5-trifluorobenzaldehyde (1.0 g, 6.3 mmol) in DMSO (7.8 mL) was treated with a slurry of sodium methanethiolate (0.438 g, 6.25 mmol) in DMSO (0.3 mL). The solution was warmed at 125° C. for 17 min in a microwave. Upon completion, the reaction was diluted with EtOAc and washed with H$_2$O (1×) and saturated aqueous NaCl (1×). The combined aqueous was back-extracted with EtOAc (3×), and the combined organic layer was dried over Na$_2$SO$_4$, filtered and evaporated in vacuo to yield a crude oil that was purified by silica gel column chromatography (0-30%, EtOAc-hexanes) to yield the title compound. $^1$H NMR (500 MHz, CDCl$_3$) δ 9.88 (s, 1H), 7.39 (d, J 7.0 Hz, 2H), 2.58 (s, 3H).

Step B: [3,5-Difluoro-4-(methylthio)phenyl]methanol

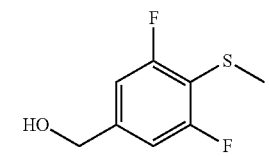

Sodium borohydride (25 mg, 0.66 mmol) was added to a 0° C. slurry of the product of step A (124 mg, 0.659 mmol) in methanol (4.39 mL). After 30 min the reaction mixture was warmed to room temperature, and at 1.5 h the reaction was diluted with DCM and quenched with 0.1 N HCl. The aqueous was extracted with DCM (2×) and then washed with saturated aqueous NaCl (1×). The combined organic layer was dried over Na$_2$SO$_4$, filtered and evaporated in vacuo to yield the title compound. $^1$H NMR (500 MHz, CDCl$_3$) δ 6.81 (d, J 7.5 Hz, 2H), 4.55 (s, 2H), 3.23 (s, 1H), 2.37 (s, 3H).

Step C: 5-(Bromomethyl)-1,3-difluoro-2-(methylthio)benzene

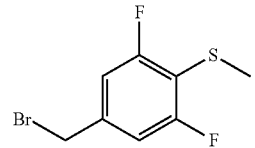

The product from step B was converted to the bromide according to the procedure from intermediate 5 (step A). $^1$H NMR (500 MHz, CDCl$_3$) δ 7.36 (d, J 7.5 Hz, 2H), 4.82 (s, 2H), 2.88 (s, 3H)

Intermediates 15B, 16 and 17

Preparation of 5-ethyl-2-{4-[(1R,2R)-2-({[2-fluoro-4-(4,4,5,5-tetramethyl-1,3,2-dioxaborolan-2-yl)benzyl]oxy}methyl)cyclopropyl]piperidin-1-yl}pyrimidine

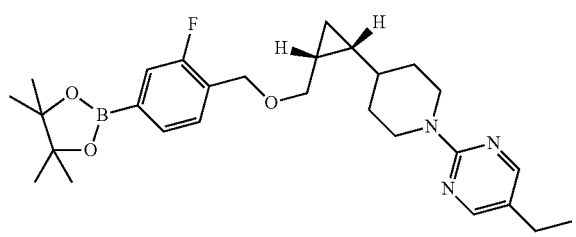

Step A: 4-((1R,2R)-2-{[(4-bromo-2-fluorobenzyl)oxy]methyl}cyclopropyl)piperidine TFA (9.3 mL, 121 mmol) was added to a solution of intermediate 12 (5.34 g, 12.07 mmol) in DCM (20 mL) and the resulting mixture stirred at RT for 2 hours. The mixture was evaporated and the residue partitioned between sat. NaHCO$_3$, and DCM, extracted with DCM (×2); combined DCM layers washed with sat. NaCl, dried over MgSO$_4$, filtered and evaporated to yield the title compound 3.92 g (Yield 95%) as a yellow oil. $^1$H NMR (500 MHz, CDCl$_3$) δ 7.37-7.28 (m, 2H), 7.23 (d, J 9.9 Hz, 1H), 4.56 (d, J 12.5 Hz, 1H), 4.49 (d, J 12.5 Hz, 1H), 3.56 (dd, J 10.0 & 6.5 Hz, 1H), 3.43 (t, J 8.4 Hz, 1H), 3.13-3.05 (m, 2H), 2.63-2.48 (m, 3H), 1.84 (d, J 13.1 Hz, 1H), 1.73 (d, J 12.9 Hz, 1H), 1.36-1.28 (m, 2H), 1.21-1.16 (m, 1H), 0.92-0.82 (m, 1H), 0.76-0.69 (m, 2H), 0.03-0.03 (m, 1H).

Step B: 5-ethyl-2-{4-[(1R,2R)-2-({[4-bromo-2-fluorobenzyl]oxy}methyl)cyclopropyl]piperidin-1-yl}pyrimidine

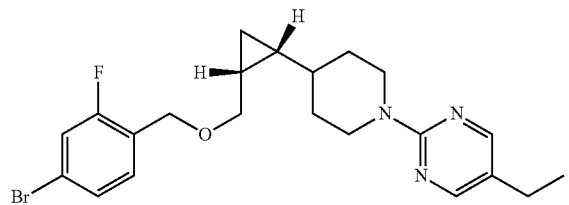 [SMILES: CCc1cnc(N2CCC([C@H]3C[C@H]3COCc3ccc(Br)cc3F)CC2)nc1]

This compound was prepared from the product of step A and 2-chloro-5-ethylpyrimidine according to the conditions outlined in intermediate 7 (step B). $^1$H NMR (500 MHz, CDCl$_3$) δ 8.19 (s, 2H), 7.33-7.31 (m, 2H), 7.26 (d, J 9.0 Hz, 1H), 4.72-4.65 (m, 2H), 4.60 (d, J 12.4 Hz, 1H), 4.52 (d, J 12.4 Hz, 1H), 3.65 (dd, J 10.1 & 6.4 Hz, 1H), 3.47 (t, J 9.6 Hz, 1H), 2.88-2.76 (m, 2H), 2.47 (q, J 7.5 Hz, 1H), 1.95 (d, J 13.0 Hz, 1H), 1.82 (d, J 13.3 Hz, 1H), 1.45-1.35 (m, 2H), 1.21 (t, J 7.5 Hz, 3H), 1.09-1.00 (m, 1H), 0.79-0.69 (m, 2H), 0.09-0.04 (m, 1H).

Step C: 5-ethyl-2-{4-[(1R,2R)-2-({[2-fluoro-4-(4,4,5,5-tetramethyl-1,3,2-dioxaborolan-2-yl)benzyl]oxy}methyl)cyclopropyl]piperidin-1-yl}pyrimidine

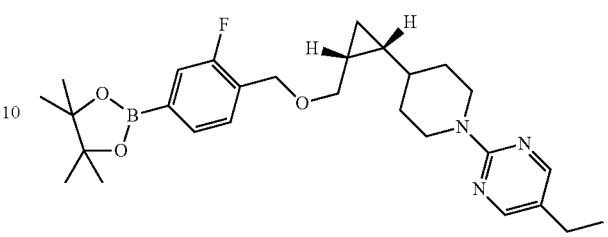

A mixture of the product of step B (2.48 g, 5.5 mmol), bis(pinacolato)diboron (2.81 g, 11 mmol), potassium acetate (1.63 g, 16.6 mmol) and Pd(dppf)Cl$_2$ (452 mg, 0.55 mmol) in 1,4 dioxane (60 mL) was degassed with nitrogen and heated at 80° C. overnight. The cooled reaction mixture was partitioned between EtOAc and water and extracted into EtOAc (×3); combined EtOAc layers washed with sat. NaCl, dried over MgSO$_4$, filtered and evaporated. The residue was purified by silica gel chromatography (eluent:gradient 0-25% EtOAc in Hexanes) to give the title compound 2.2 g (Yield 80%) as a light yellow oil. $^1$H NMR (500 MHz, CDCl$_3$) δ 8.18 (s, 2H), 7.59 (d, J 7.4 Hz, 1H), 7.47-7.44 (m, 2H), 4.73-4.63 (m, 3H), 4.60 (d, J 12.6 Hz, 1H), 3.63 (dd, J 10.2 & 6.5 Hz, 1H), 3.47 (t, J 8.6 Hz, 1H), 2.86-2.76 (m, 2H), 2.47 (q, J 7.6 Hz, 1H), 1.97 (d, J 10.1 Hz, 1H), 1.81 (d, J 13.1 Hz, 1H), 1.36 (s, 12H), 1.31-1.23 (m, 3H), 1.21 (t, J 7.6 Hz, 3H), 1.08-0.99 (m, 1H), 0.78-0.68 (m, 2H), 0.08-0.02 (m, 1H).

The remaining examples in Table 3 were synthesized according to the method described above using the appropriate benzyl bromide.

TABLE 3

| Number | Name | Chemical Structure |
|---|---|---|
| 16 | 5-ethyl-2-{4-[(1R,2R)-2-({[3-fluoro-4-(4,4,5,5-tetramethyl-1,3,2-dioxaborolan-2-yl)benzyl]oxy}methyl)cyclopropyl] piperidin-1-yl}pyrimidine | 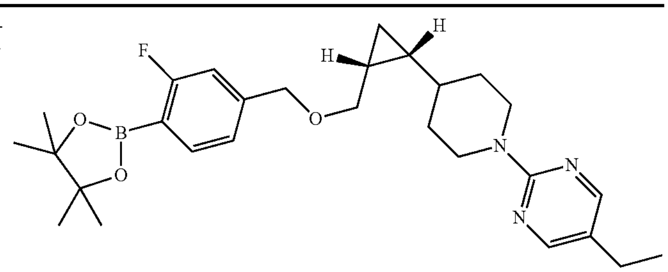 |
| 17 | 5-ethyl-2-{4-[(1R,2R)-2-({[4-(4,4,5,5-tetramethyl-1,3,2-dioxaborolan-2-yl)benzyl]oxy}methyl)cyclopropyl] piperidin-1-yl}pyrimidine | 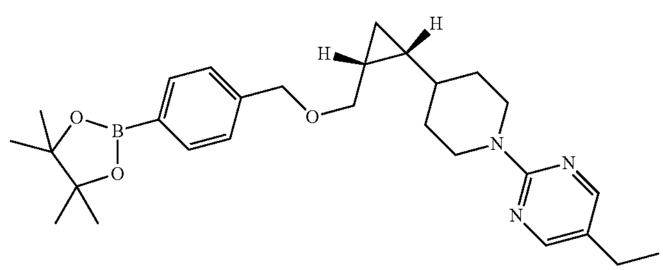 [SMILES: CCc1cnc(N2CCC([C@H]3C[C@H]3COCc3ccc(B4OC(C)(C)C(C)(C)O4)cc3)CC2)nc1] |

Intermediate 18

Preparation of 2-chloro-5-methoxymethylpyrimidine

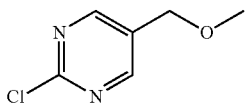

To a solution of 2-chloro-5-hydroxymethyl-pyrimidine (9.0 g, 62 mmol) in 70 ml of anhydrous DMF was added methyl iodide (6 eq. 370 mmol, 23 ml). The mixture was cooled to 0° C., then NaH (2.61 g, 1.05 eq.) was added in portions over 5 mins. The resulting mixture was stirred 25 min. at 0° C., then 25 min. at rt. The reaction mixture was then cooled in ice bath, and quenched by addition of saturated NH$_4$Cl aq. solution (200 ml), extracted with ether (150 ml×3). The combined organic layers were washed by brine, dried over Na$_2$SO$_4$, filtered and concentrated in vacuo. The residue was purified by ISCO column (330 g of silica gel) using ethyl acetate in hexane (0-90% ethyl acetate, 2500 ml, then 1000 ml of ethyl acetate) to give 6.5 g (66%) of the title compound: MS (ESI) m/z 159.2 (M+H); $^1$H NMR (500 MHz, CDCl$_3$) δ 8.60 (s, 2H), 4.48 (s, 2H), 3.45 (s, 3H).

EXAMPLES

Examples 1-6

Preparation of 5-chloro-2-{4-[(1R,2R)-2-({[5-(methylsulfonyl)pyridin-2-yl]methoxy}methyl)cyclopropyl]piperidin-1-yl}pyrimidine

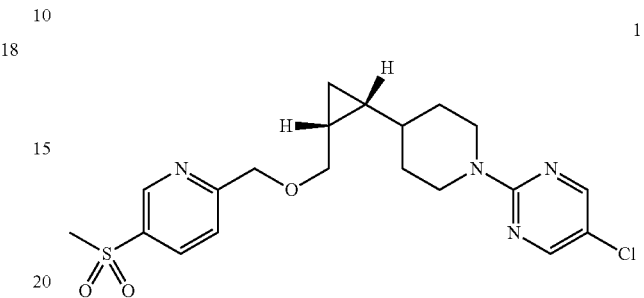

Intermediate 5 (158 mg, 0.488 mmol) was dissolved in DMSO (2 mL) and treated with cesium carbonate (270 mg, 0.830 mmol). After 5 min, 2,5-dichloropyrimidine (80 mg, 0.537 mmol) was added in DMSO (0.4 mL). After stirring at RT for 20 h, the reaction was diluted with EtOAc and washed with H$_2$O (1×) and saturated aqueous NaCl (1×). The combined aqueous was back-extracted with EtOAc (3×), and the combined organic layer was dried over Na$_2$SO$_4$, filtered and evaporated in vacuo to yield a crude oil that was purified by silica gel column chromatography (10-80%, EtOAc-hexanes) to yield the title compound. $^1$H NMR (500 MHz, CDCl$_3$) δ 9.07 (d, J 2.1 Hz, 1H), 8.23 (dd, J 8.2 & 2.1 Hz, 1H), 8.19 (s, 2H), 7.71 (d, J 8.2 Hz, 1H), 4.78 (d, J 14.6 Hz, 1H), 4.71 (d, J 14.6 Hz, 1H), 4.69-4.64 (m, 1H), 4.63-4.58 (m, 1H), 3.70-3.65 (m, 1H), 3.65-3.60 (m, 1H), 3.11 (s, 3H), 2.89-2.78 (m, 2H), 1.95-1.90 (m, 1H), 1.85-1.80 (m, 1H), 1.41-1.31 (m, 2H), 1.30-1.22 (m, 2H), 1.12-1.04 (m, 1H), 0.82-0.76 (m, 1H), 0.76-0.70 (m, 2H), 0.11-0.06 (m, 1H). MS (ESI) m/z 325 [M+H]$^+$. GPR119 Human EC50: 8.7 nM The Examples in Table 4 were synthesized according to the method described in Example 1 employing the appropriate 2-chloropyrimidine reagent.

TABLE 4

| Example # | Chemical Structure | Observed Mass | GPR119 Human EC$_{50}$ |
| --- | --- | --- | --- |
| 2 | 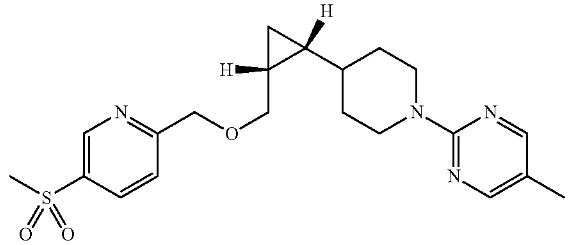 | 417 [M + H]$^+$ | 10.8 nM |

TABLE 4-continued

| Example # | Chemical Structure | Observed Mass | GPR119 Human EC$_{50}$ |
|---|---|---|---|
| 3 | 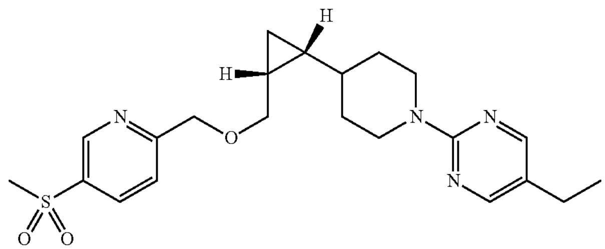 [SMILES: CCc1cnc(N2CCC([C@H]3C[C@H]3COCc3ccc(S(C)(=O)=O)cn3)CC2)nc1] | 431 [M + H]$^+$ | 1.5 nM |
| 4 | 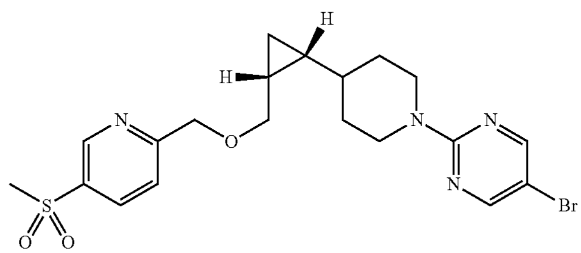 [SMILES: CS(=O)(=O)c1ccc(COC[C@@H]2C[C@@H]2C2CCN(c3ncc(Br)cn3)CC2)nc1] | 481/483 [M + H]$^+$ | 1 nM |
| 5 | 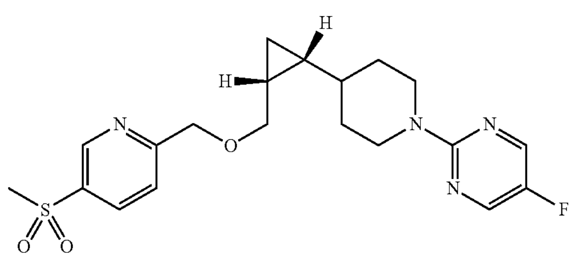 [SMILES: CS(=O)(=O)c1ccc(COC[C@@H]2C[C@@H]2C2CCN(c3ncc(F)cn3)CC2)nc1] | 421 [M + H]$^+$ | 21 nM |
| 6 | 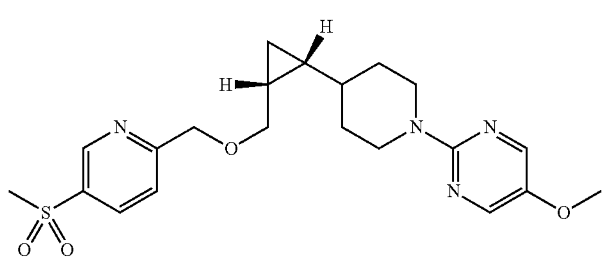 | 433 [M + H]$^+$ | 15 nM |

Example 7

Preparation of 2-{4-[(1R,2R)-2-({[5-(methylsulfonyl)pyridin-2-yl]methoxy}methyl)cyclopropyl]piperidin-1-yl}-5-(1H)-pyrazol-4-yl)pyrimidine

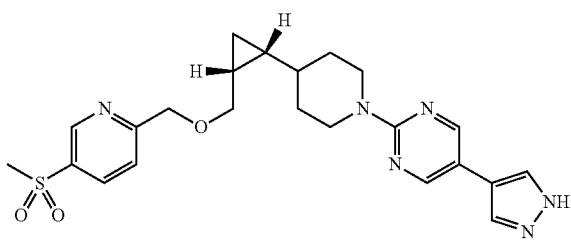

The compound of Example 4 (40 mg, 0.08 mmol), pyrazole-4-boronic acid (14 mg, 0.125 mmol), Pd(dppf)Cl$_2$ (5.4 mg, 0.008 mmol), and 50% aqueous K$_3$PO$_4$ (0.2 mL) were dissolved in DMF (1.5 mL) and the resulting mixture heated in a microwave reactor at 120° C. for 1 hour. The mixture was diluted with EtOAc, washed with sat. NH$_4$Cl, evaporated and purified by preparative thin-layer chromatography (pure EtOAc) to yield the title compound. $^1$H NMR (500 MHz, CDCl$_3$) δ 9.11 (d, 1H), 8.46 (s, 2H), 8.26 (dd, 1H), 7.78 (s, 2H), 7.76 (d, 1H), 4.84-4.68 (m, 3H), 3.76-3.65 (m, 2H), 3.15 (s, 3H), 2.96-2.83 (m, 2H), 2.02-1.96 (m, 1H), 1.92-1.84 (m, 1H), 1.47-1.38 (m, 2H), 1.38-1.23 (m, 2H), 1.18-1.09 (m, 1H), 0.85-0.76 (m, 2H), 0.17-0.12 (m, 1H). MS (ESI) m/z 469 [M+H]$^+$. GPR119 Human EC50: 15.6 nM

Examples 8-17

Preparation of propyl 4-[(1R,2R)-2-({[4-(methylsulfonyl)benzyl]oxy}methyl)cyclopropyl]piperidine-1-carboxylate

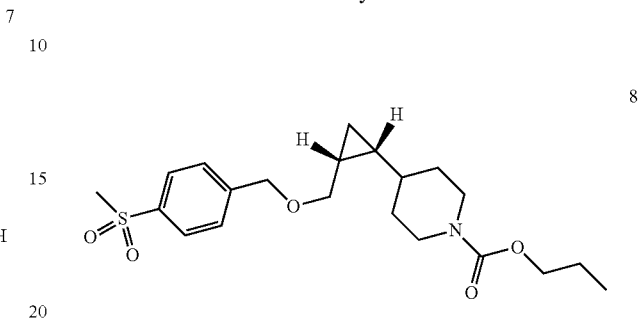

Intermediate 8 (70 mg, 0.17 mmol), n-propylchloroformate (31 mg, 0.25 mmol), and Et$_3$N (84 mg, 0.83 mmol) were dissolved in DCM (2 mL). After stirring at RT for 2 h, the solution was concentrated. The residue was purified via preparative thin-layer chromatography (1/1 hexanes/EtOAc, SiO$_2$) to yield the title compound. MS (ESI) m/z 410 [M+H]$^+$. GPR119 Human EC50: 16 nM The Examples in Table 5 were synthesized using method described in the prior example 8, employing intermediate 8 and the appropriate chloroformate or hydroxysuccinimide reagent.

TABLE 5

| Example # | Chemical Structure | Observed Mass | GPR119 Human EC$_{50}$ |
|---|---|---|---|
| 9 | 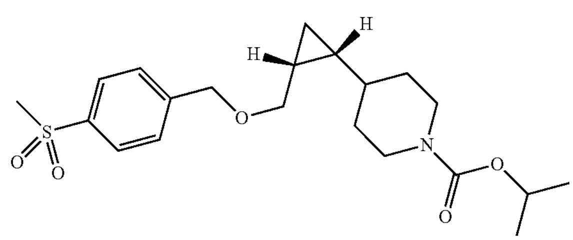 [SMILES: CC(C)OC(=O)N1CCC([C@H]2C[C@H]2COCc2ccc(S(C)(=O)=O)cc2)CC1] | 410 [M + H]$^+$ | 16 nM |
| 10 | 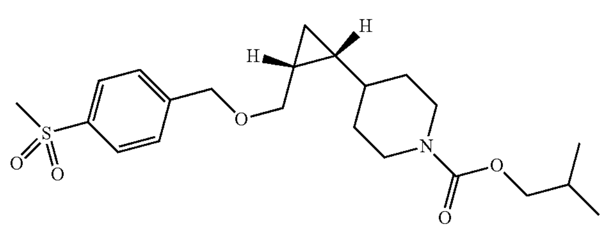 [SMILES: CC(C)COC(=O)N1CCC([C@H]2C[C@H]2COCc2ccc(S(C)(=O)=O)cc2)CC1] | 424 [M + H]$^+$ | 8.2 nM |
| 11 | 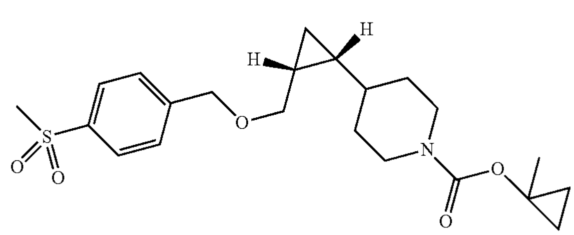 [SMILES: CC1(OC(=O)N2CCC([C@H]3C[C@H]3COCc3ccc(S(C)(=O)=O)cc3)CC2)CC1] | 422 [M + H]$^+$ | 3.9 nM |

TABLE 5-continued

| Example # | Chemical Structure | Observed Mass | GPR119 Human EC$_{50}$ |
|---|---|---|---|
| 12 | 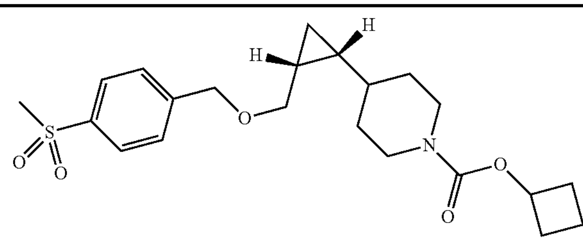 | 422 [M + H]$^+$ | 8.2 nM |
| 13 | 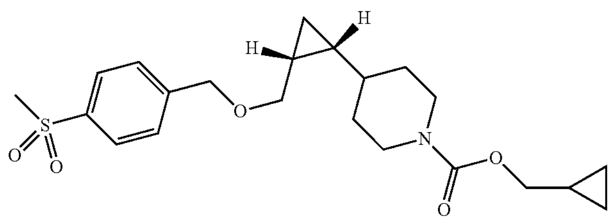 [SMILES: CS(=O)(=O)c1ccc(COC[C@@H]2C[C@@H]2C2CCN(C(=O)OCC3CC3)CC2)cc1] | 422 [M + H]$^+$ | 3.2 nM |

The Examples in Table 6 were synthesized according to the method described in example 1, from intermediate 8 and employing the appropriate 2-chloropyrimidine reagent.

TABLE 6

| Example # | Chemical Structure | Observed Mass | GPR119 Human EC$_{50}$ |
|---|---|---|---|
| 14 | 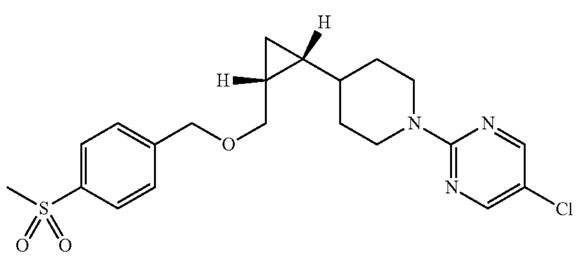 | 425 [M + H]$^+$ | 0.7 nM |
| 15 | 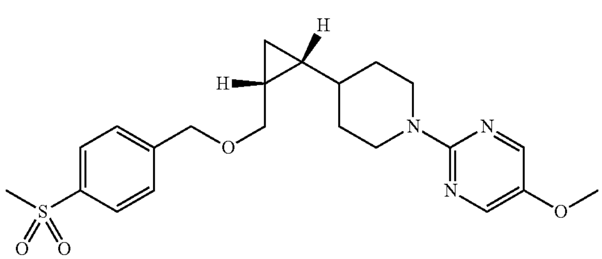 | 432 [M + H]$^+$ | 0.4 nM |
| 16 | 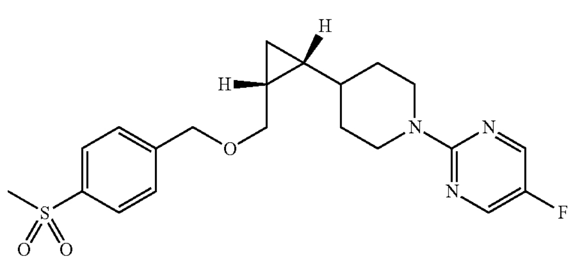 [SMILES: CS(=O)(=O)c1ccc(COC[C@@H]2C[C@@H]2C2CCN(c3ncc(F)cn3)CC2)cc1] | 420 [M + H]$^+$ | 5.8 nM |

TABLE 6-continued

| Example # | Chemical Structure | Observed Mass | GPR119 Human EC$_{50}$ |
|---|---|---|---|
| 17 | 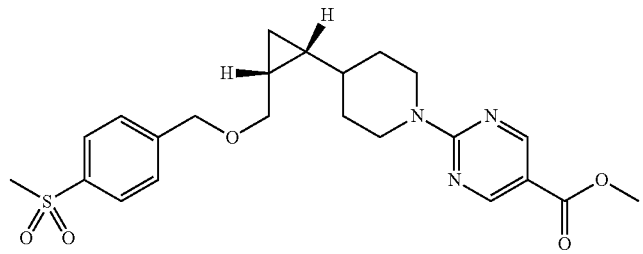 | 460 [M + H]$^+$ | 20 nM |

Example 18

Preparation of 5-cyclopropyl-2-{4-[(1R,2R)-2-({[4-(methylsulfonyl)benzyl]oxy}methyl)cyclopropyl]piperidin-1-yl}pyrimidine

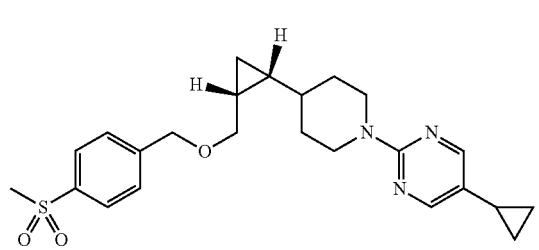

18

Intermediate 7 (60 mg, 0.12 mmol), cyclopropyl boronic acid (64 mg, 0.74 mmol), Pd(dppf)Cl$_2$ (10 mg, 0.012 mmol), and K$_2$CO$_3$ (86 mg, 0.6 mmol) were dissolved in degassed THF/H$_2$O (2 mL/0.2 mL), and the resulting mixture was stirred at 70° C. for 18 hours. The solution was concentrated in vacuo and the residue was purified via preparative thin-layer chromatography (40/1 DCM/MeOH, SiO$_2$) to yield the title compound. MS (ESI) m/z 442 [M+H]$^+$. GPR119 Human EC50: 1 nM

Examples 19-22

Preparation of 5-isobutyl-2-{4-[(1R,2R)-2-({[4-(methylsulfonyl)benzyl]oxy}methyl)cyclopropyl]piperidin-1-yl}pyrimidine

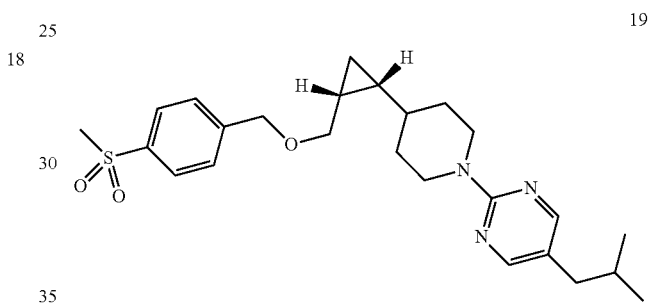

19

Intermediate 7 (75 mg, 0.15 mmol), triisobutylaluminum (0.3 mL of a 1.0 M solution in hexanes, 0.3 mmol), and Pd(PPh$_3$)$_4$ (9 mg, 0.008 mmol) were dissolved in THF (2 mL), and the resulting solution was heated at 70° C. for 15 hours. The solution was quenched with 1N sodium potassium-tartrate and extracted with DCM. The organic layers were dried over Na$_2$SO$_4$, filtered and concentrated in vacuo. The residue was purified via preparative thin-layer chromatography (30/1, DCM/MeOH, SiO$_2$) which provided the title compound. MS (ESI) m/z 458 [M+H]$^+$.

GPR119 Human EC50: 0.13 nM

The Examples in Table 7 were synthesized according to the method described in Example 19, from intermediate 7 and employing the appropriate tri-alkyl aluminum reagents.

TABLE 7

| Example # | Chemical Structure | Observed Mass | GPR119 Human EC$_{50}$ |
|---|---|---|---|
| 20 | 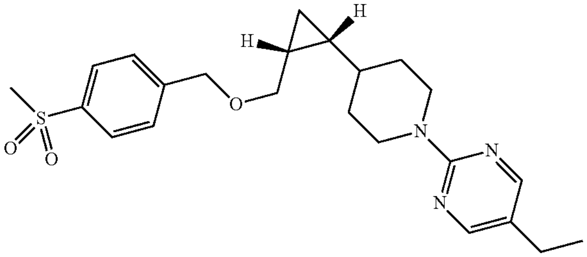 [SMILES: CCc1cnc(N2CCC([C@H]3C[C@H]3COCc3ccc(S(C)(=O)=O)cc3)CC2)nc1] | 430 [M + H]$^+$ | 0.74 nM |

TABLE 7-continued

| Example # | Chemical Structure | Observed Mass | GPR119 Human EC$_{50}$ |
|---|---|---|---|
| 21 | 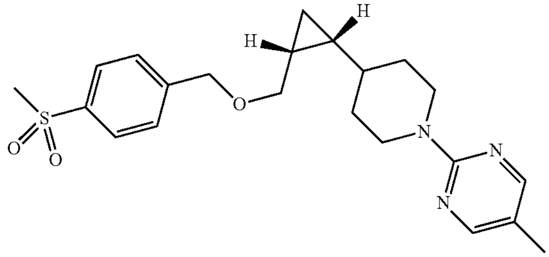 | 416 [M + H]$^+$ | 1.6 nM |
| 22 | 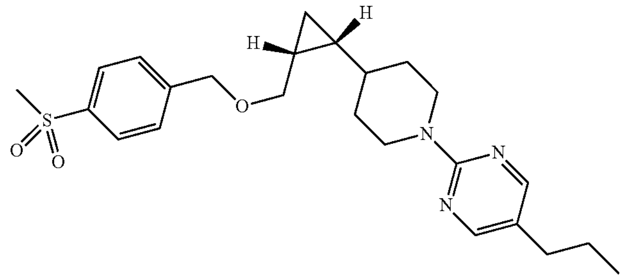 [SMILES: CCCc1cnc(N2CCC([C@H]3C[C@H]3COCc3ccc(S(C)(=O)=O)cc3)CC2)nc1] | 444 [M + H]$^+$ | 0.3 nM |

Example 23

Preparation of 5-isopropyl-2-{4-[(1R,2R)-2-({[4-(methylsulfonyl)benzyl]oxy}methyl)cyclopropyl]piperidin-1-yl}pyrimidine

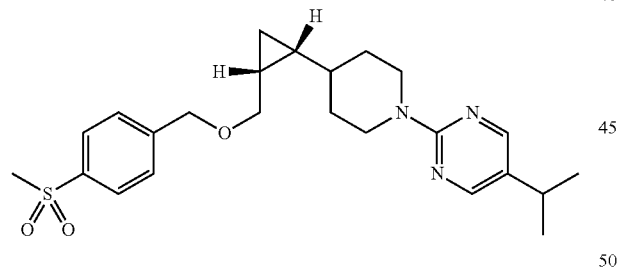

Step A: {(1R,2R)-2-[1-(5-isopropenylpyrimidin-2-yl)piperidin-4-yl]cyclopropyl}methanol

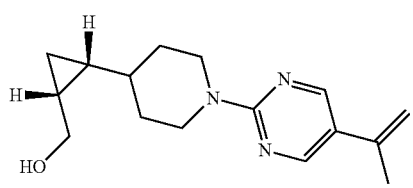 [SMILES: C=C(C)c1cnc(N2CCC([C@H]3C[C@H]3CO)CC2)nc1]

The product of Intermediate 7, step B (300 mg, 0.96 mmol), Pd(dppf)Cl2 (78 mg, 0.096 mmol), K$_3$PO$_4$ (612 mg, 2.9 mmol), and the 2-isoprenyl-4,4,5,5-tetramethyl-1,3,2-dioxaborolane (296 mg, 1.8 mmol) were dissolved in DME/H$_2$O (17 mL/1.7 mL), and the resulting solution was stirred at 100° C. for 15 hours. The solution was concentrated in vacuo, and the residue was diluted with brine and extracted with DCM. The organic layer was dried over Na$_2$SO$_4$, filtered, and concentrated in vacuo. The residue was purified via silica gel column chromatography (20/1 DCM/MeOH), yielding the title compound.

Step B: {(1R,2R)-2-[1-(5-isopropylpyrimidin-2-yl)piperidin-4-yl]cyclopropyl}methanol

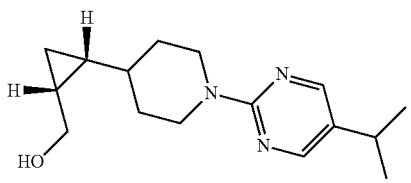 [SMILES: CC(C)c1cnc(N2CCC([C@H]3C[C@H]3CO)CC2)nc1]

The product of step A (170 mg, 0.62 mmol) and 5% Pd/C (20 mg) were dissolved in EtOH (5 mL). The mixture was stirred under 1 atm of H$_2$ for 1 hour. The mixture was filtered and the filtrate concentrated in vacuo, yielding the title compound.

Step C: 2-{4-[(1R,2R)-2-(iodomethyl)cyclopropyl]piperidin-1-yl}-5-isopropylpyrimidine

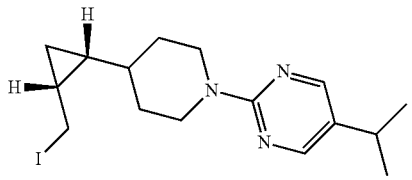 [SMILES: CC(C)c1cnc(N2CCC([C@H]3C[C@H]3CI)CC2)nc1]

The product of step B was converted to the iodide using the conditions outlined for intermediate 8, step A.

Step D: 5-isopropyl-2-{4-[(1R,2R)-2-({[4-(methylsulfonyl)benzyl]oxy}methyl)cyclopropyl]piperidin-1-yl}pyrimidine

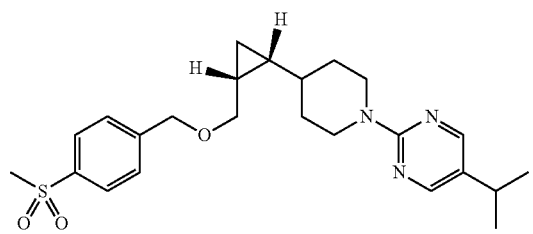 [SMILES: CC(C)c1cnc(N2CCC([C@H]3C[C@H]3COCc3ccc(S(C)(=O)=O)cc3)CC2)nc1]

Using the procedure outlined in intermediate 8 (step B) the product from step C was reacted with 4-(methylsulfonyl)benzyl alcohol to yield the title compound. MS (ESI) m/z 444 [M+H]$^+$. GPR119 Human EC50: 0.26 nM Examples 24-32

Preparation of 1-(3-isopropyl-1,2,4-oxadiazol-5-yl)-4-[(1R,2R)-2-({[4-(methylsulfonyl)benzyl]oxy}methyl)cyclopropyl]piperidine

24

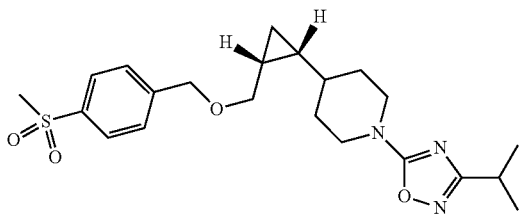

Intermediate 9 (79 mg, 0.23 mmol) and N'-hydroxy-2-methylpropanimidamide (46.3 mg, 0.453 mmol) were dissolved in tetrahydrofuran (2 mL). Zinc dichloride (1M in diethyl ether, 0.462 mL) was added dropwise at room temperature. The reaction was stirred for 3 hours at room temperature. 1,4-Dioxane (4 mL) was added and 4 M HCl in 1,4-dioxane (0.5 mL, 2 mmol) was added. The reaction was heated at 90° C. for 1 hour. The reaction was cooled to room temperature, CH$_2$Cl$_2$ was added, and the reaction was concentrated in vacuo. Methanol was added to the residue and the solution was concentrated. The reaction was partitioned between EtOAc and saturated aqueous NaHCO$_3$. The aqueous layer was discarded and the organic layer was washed with brine, dried over anhydrous sodium sulfate, filtered and evaporated. The residue was purified by preparative HPLC (C18 reversed phase, gradient elution 10% to 100% MeCN in water with 0.1% formic acid) to yield title compound as a colorless, viscous oil. MS (ESI) m/z 434 [M+H]$^+$. GPR119 Human EC50: 0.92 nM The Examples in Table 8 were synthesized according to the method described in the prior example 24 employing intermediates 9, 10, and 11 and the appropriate N-hydroxyalkylimidamide reagents.

TABLE 8

| Example # | Chemical Structure | Observed Mass | GPR119 Human EC$_{50}$ |
|---|---|---|---|
| 25 | 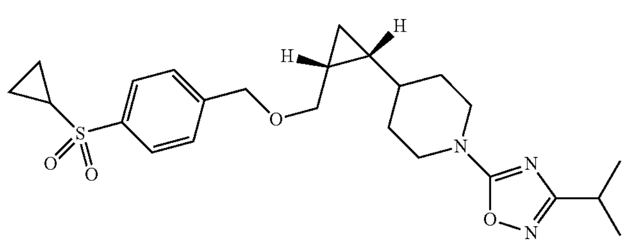 [SMILES: CC(C)c1noc(N2CCC([C@H]3C[C@H]3COCc3ccc(S(=O)(=O)C4CC4)cc3)CC2)n1] | 460 [M + H]$^+$ | 18 nM |
| 26 | 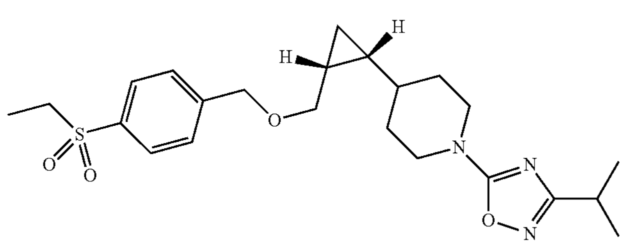 [SMILES: CCS(=O)(=O)c1ccc(COC[C@@H]2C[C@@H]2C2CCN(c3nc(C(C)C)no3)CC2)cc1] | 448 [M + H]$^+$ | 3.1 nM |

TABLE 8-continued

| Example # | Chemical Structure | Observed Mass | GPR119 Human EC$_{50}$ |
|---|---|---|---|
| 27 | 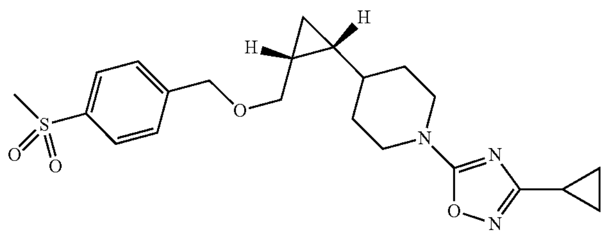 [SMILES: CS(=O)(=O)c1ccc(COC[C@@H]2C[C@@H]2C2CCN(c3nc(C4CC4)no3)CC2)cc1] | 432 [M + H]$^+$ | 3.2 nM |
| 28 | 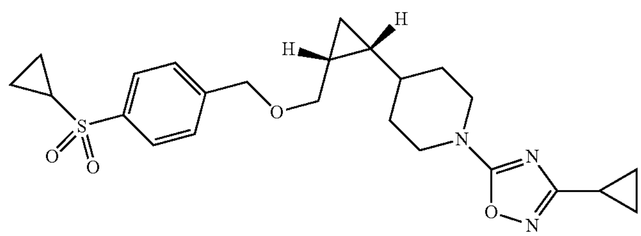 [SMILES: O=S(=O)(c1ccc(COC[C@@H]2C[C@@H]2C2CCN(c3nc(C4CC4)no3)CC2)cc1)C1CC1] | 458 [M + H]$^+$ | 12 nM |
| 29 | 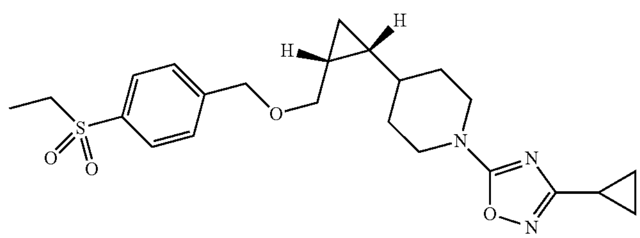 [SMILES: CCS(=O)(=O)c1ccc(COC[C@@H]2C[C@@H]2C2CCN(c3nc(C4CC4)no3)CC2)cc1] | 446 [M + H]$^+$ | 2.3 nM |
| 30 | 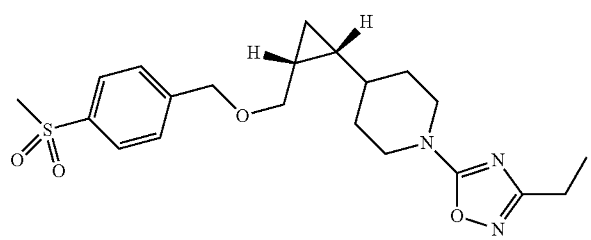 [SMILES: CCc1noc(N2CCC([C@H]3C[C@H]3COCc3ccc(S(C)(=O)=O)cc3)CC2)n1] | 420 [M + H]$^+$ | 2.8 nM |
| 31 | 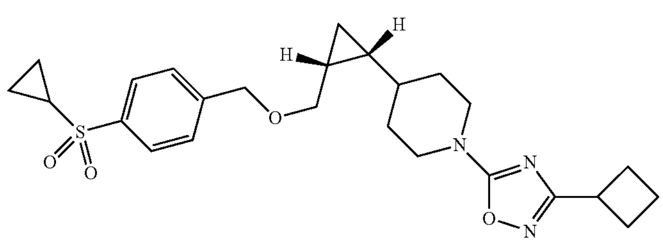 [SMILES: O=S(=O)(c1ccc(COC[C@@H]2C[C@@H]2C2CCN(c3nc(C4CCC4)no3)CC2)cc1)C1CC1] | 472 [M + H]$^+$ | 7 nM |
| 32 | 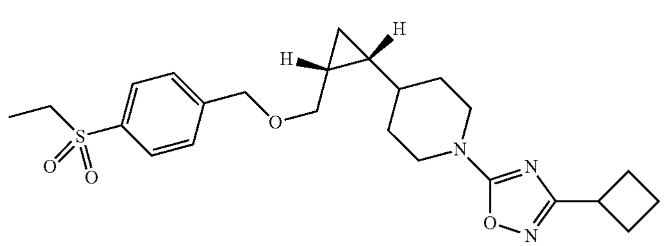 | 472 [M + H]$^+$ | 0.8 nM |

Example 33

Preparation of tert-butyl 4-[(1R,2R)-2-({[3-fluoro-4-(methylsulfonyl)benzyl]oxy}methyl)cyclopropyl]piperidine-1-carboxylate

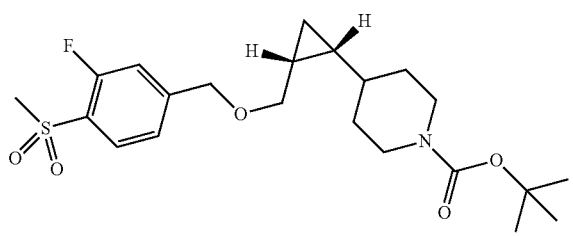

Step A: tert-butyl 4-[(1R,2R)-2-({[3-fluoro-4-(methylthio)benzyl]oxy}methyl)cyclopropyl]piperidine-1-carboxylate

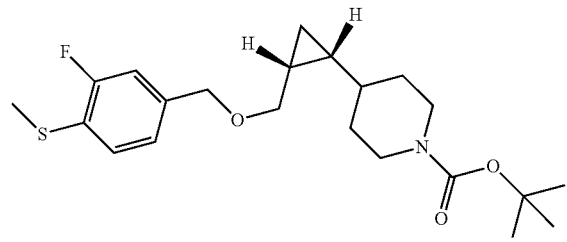 [SMILES: CSc1ccc(COC[C@@H]2C[C@@H]2C2CCN(C(=O)OC(C)(C)C)CC2)cc1F]

Intermediate 13 (1.00 g, 2.26 mmol) was dissolved in diethyl ether (10 mL) and was cooled to −78° C. A solution of n-butyllithium in hexanes (2.5 M, 0.998 mL, 2.5 mmol) was added at −78° C. The reaction was stirred for 60 minutes at −78° C. Dimethyl disulfide (0.209 mL, 2.36 mmol) was added. The reaction was stirred for 60 minutes at −78° C. and then for 45 minutes at 0° C. Water was added to the reaction, followed by Et$_2$O. The aqueous layer was discarded and the organic layer was washed twice with brine, dried over anhydrous magnesium sulfate, filtered, and evaporated to yield a crude material, which was purified by silica gel chromatography (gradient elution 0% to 100% EtOAc in hexanes) to yield the title compound. NMR (500 MHz, CDCl$_3$) δ 7.26 (m, 1H), 7.09 (d, J 8.0 Hz, 1H), 7.05 (d, J 10.5 Hz, 1H), 4.54 (d, J 12.5 Hz, 1H), 4.45 (d, J 12.5 Hz, 1H), 4.28-4.00 (br m, 2H), 3.59-3.53 (m 1H), 3.43-3.38 (m, 1H), 2.75-2.60 (m, 2H), 2.48 (s, 3H), 1.89-1.83 (m, 1H), 1.76-1.69 (m, 1H), 1.49 (s, 9H), 1.38-1.25 (m, 2H), 1.25-1.18 (m, 1H), 0.96-0.88 (m, 1H), 0.78-0.66 (m, 2H), 0.04-0.00 (m, 1H).

Step B: tert-butyl 4-[(1R,2R)-2-({[3-fluoro-4-(methylsulfonyl)benzyl]oxy}methyl)cyclopropyl]piperidine-1-carboxylate

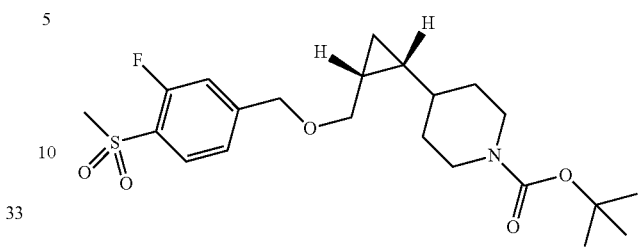

The product of step A was oxidized according to the procedure described in intermediate 5 (step D). $^1$H NMR (500 MHz, CDCl$_3$) δ 7.92 (m, 1H), 7.26 (m, 2H), 4.61 (d, J 13.5 Hz, 1H), 4.55 (d, J 13.5 Hz, 1H), 4.15-3.97 (br m, 2H), 3.58-3.47 (m 2H), 3.21 (s, 3H), 2.71-2.58 (m, 2H), 1.89-1.77 (m, 1H), 1.73-1.67 (m, 1H), 1.45 (s, 9H), 1.36-1.17 (m, 3H), 0.95-0.85 (m, 1H), 0.79-0.68 (m, 2H), 0.05-0.01 (m, 1H). MS (ESI) m/z 444 [M+H]$^+$. GPR119 Human EC50: 1.1 nM

Example 34

Preparation of tert-butyl 4-[(1R,2R)-2-({[4-(ethylsulfonyl)-3-fluorobenzyl]oxy}methyl)cyclopropyl]piperidine-1-carboxylate

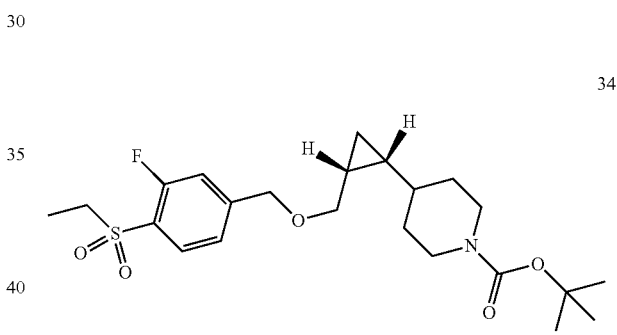

This compound was prepared according to the procedures outlined in example 33, using intermediate 13 and replacing dimethyl disulfide with diethyl disulfide in step A. MS (ESI) m/z 456 [M+H]$^+$. GPR119 Human EC50: 0.1 nM

Examples 35-43

Preparation of 4-[(1R,2R)-2-({[3-fluoro-4-(methylsulfonyl)benzyl]oxy}methyl)cyclopropyl]-1-(3-isopropyl-1,2,4-oxadiazol-5-yl)piperidine

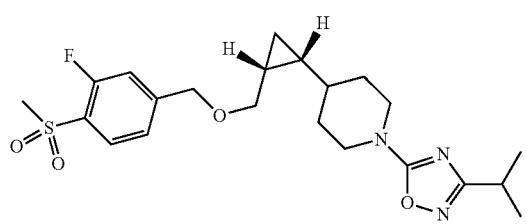

Step A: 4-[(1R,2R)-2-({[3-fluoro-4-(methylsulfonyl)benzyl]oxy}methyl)cyclopropyl]piperidine trifluoroacetate

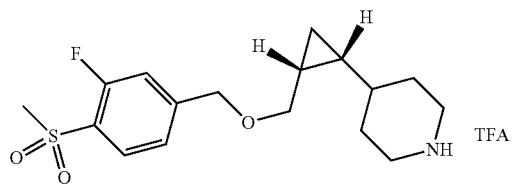 [SMILES: CS(=O)(=O)c1ccc(COC[C@@H]2C[C@@H]2C2CCNCC2)cc1F]

This compound was prepared from example 33 using the procedure outlined for intermediate 7 (step A).

Step B: 4-[(1R,2R)-2-({[3-fluoro-4-(methylsulfonyl)benzyl]oxy}methyl)cyclopropyl]piperidine-1-carbonitrile

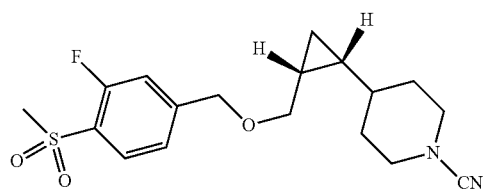 [SMILES: CS(=O)(=O)c1ccc(COC[C@@H]2C[C@@H]2C2CCN(C#N)CC2)cc1F]

This compound was prepared from the product of step A using the procedure outlined for intermediate 9 (step C).

Step C: 4-[(1R,2R)-2-({[3-fluoro-4-(methylsulfonyl)benzyl]oxy}methyl)cyclopropyl]-1-(3-isopropyl-1,2,4-oxadiazol-5-yl)piperidine

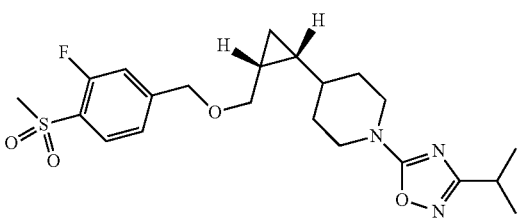 [SMILES: CC(C)c1noc(N2CCC([C@H]3C[C@H]3COCc3ccc(S(C)(=O)=O)c(F)c3)CC2)n1]

This compound was prepared from the product of step B and N'-hydroxy-2-methylpropanimidamide according to the procedure for example 24. MS (ESI) m/z 452 [M+H]$^+$.

GPR119 Human EC50: 0.2 nM

The Examples in Table 9 were synthesized from examples 33 and 34 according to the procedure of example 35 and using the appropriate N-hydroxyalkylimidamide reagents.

TABLE 9

| Example # | Chemical Structure | Observed Mass | GPR119 Human EC$_{50}$ |
|---|---|---|---|
| 36 | 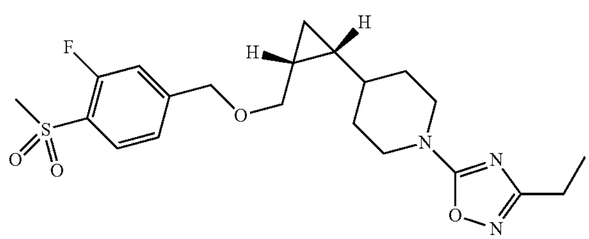 [SMILES: CCc1noc(N2CCC([C@H]3C[C@H]3COCc3ccc(S(C)(=O)=O)c(F)c3)CC2)n1] | 438 [M + H]$^+$ | 1.9 nM |
| 37 | 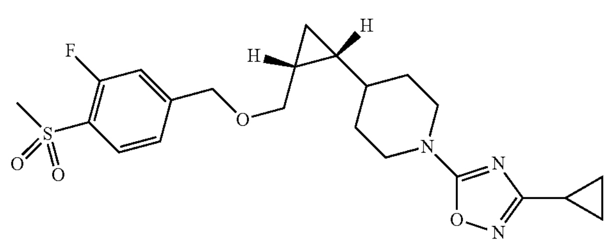 [SMILES: CS(=O)(=O)c1ccc(COC[C@@H]2C[C@@H]2C2CCN(c3nc(C4CC4)no3)CC2)cc1F] | 450 [M + H]$^+$ | 0.6 nM |
| 38 | 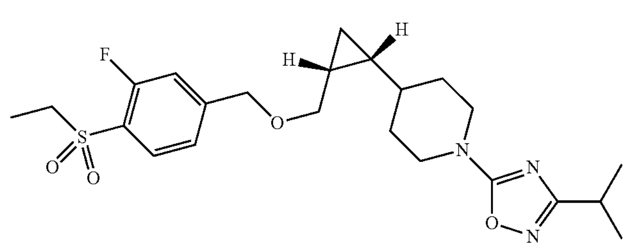 [SMILES: CCS(=O)(=O)c1ccc(COC[C@@H]2C[C@@H]2C2CCN(c3nc(C(C)C)no3)CC2)cc1F] | 466 [M + H]$^+$ | 0.4 nM |

TABLE 9-continued

| Example # | Chemical Structure | Observed Mass | GPR119 Human EC$_{50}$ |
|---|---|---|---|
| 39 | 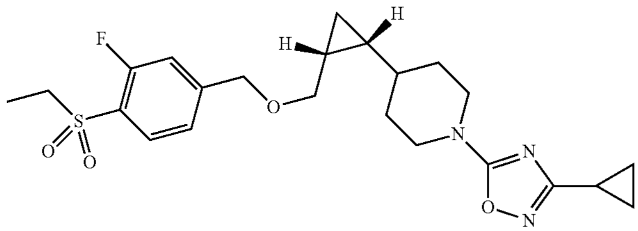 [SMILES: CCS(=O)(=O)c1ccc(COC[C@@H]2C[C@@H]2C2CCN(c3nc(C4CC4)no3)CC2)cc1F] | 464 [M + H]$^+$ | 0.6 nM |

The Examples in Table 10 were synthesized employing the intermediate from example 35, step A and the appropriate 2-chloropyrimidine, chloroformate or hydroxysuccinimide reagent according to the procedures from examples 1 and 8.

TABLE 10

| Example # | Chemical Structure | Observed Mass | GPR119 Human EC$_{50}$ |
|---|---|---|---|
| 40 | 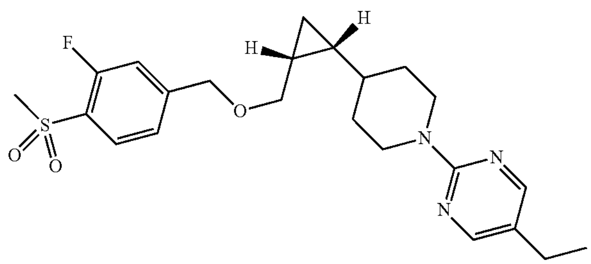 [SMILES: CCc1cnc(N2CCC([C@H]3C[C@H]3COCc3ccc(S(C)(=O)=O)c(F)c3)CC2)nc1] | 448 [M + H]$^+$ | 0.2 nM |
| 41 | 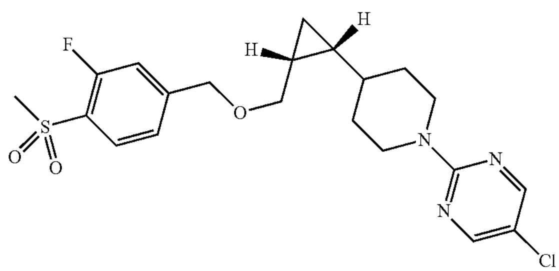 [SMILES: CS(=O)(=O)c1ccc(COC[C@@H]2C[C@@H]2C2CCN(c3ncc(Cl)cn3)CC2)cc1F] | 454 [M + H]$^+$ | 0.4 nM |
| 42 | 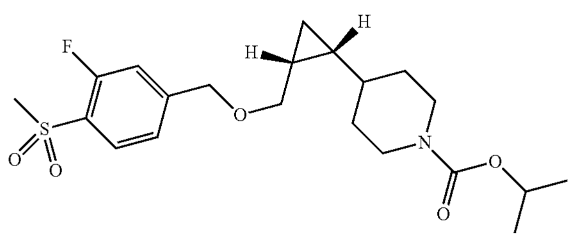 [SMILES: CC(C)OC(=O)N1CCC([C@H]2C[C@H]2COCc2ccc(S(C)(=O)=O)c(F)c2)CC1] | 428 [M + H]$^+$ | 8.5 nM |
| 43 | 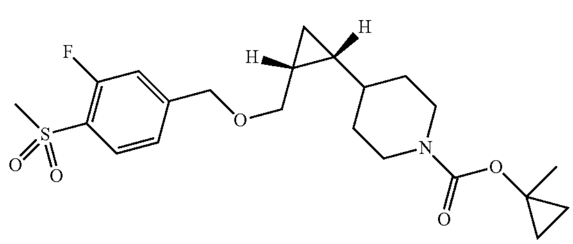 [SMILES: CC1(OC(=O)N2CCC([C@H]3C[C@H]3COCc3ccc(S(C)(=O)=O)c(F)c3)CC2)CC1] | 440 [M + H]$^+$ | 4.7 nM |

Example 44

Preparation of tert-butyl 4-[(1R,2R)-2-({[3,5-difluoro-4-(methylsulfonyl)benzyl]oxy}methyl)cyclopropyl]piperidine-1-carboxylate

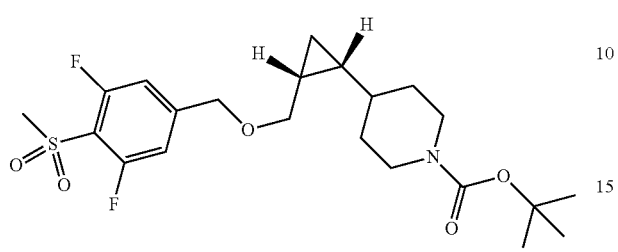

Step A: tert-butyl 4-[(1R,2R)-2-({[3,5-difluoro-4-(methylthio)benzyl]oxy}methyl)cyclopropyl]piperidine-1-carboxylate

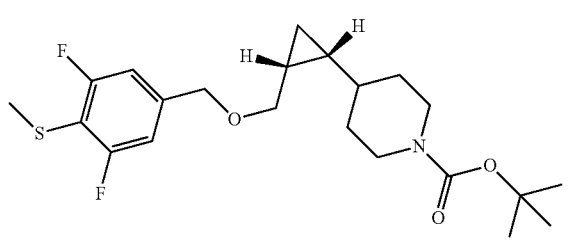 [SMILES: CSc1c(F)cc(COC[C@@H]2C[C@@H]2C2CCN(C(=O)OC(C)(C)C)CC2)cc1F]

This compound was prepared from tert-butyl 4-[(1R,2R)-2-(hydroxymethyl)cyclopropyl]piperidine-1-carboxylate (intermediate 4) and intermediate 15 according to the conditions outlined in intermediate 5 (step B). $^1$H NMR (500 MHz, CDCl$_3$) δ 6.87 (d, J 7.5 Hz, 2H), 4.49 (d, J 13.0 Hz, 1H), 4.41 (d, J 13.0 Hz, 1H), 4.15-3.95 (br m, 2H), 3.57-3.47 (m, 1H), 3.47-3.38 (m, 1H), 2.70-2.57 (m, 2H), 2.41 (s, 3H), 1.85-1.77 (m, 1H), 1.72-1.63 (m, 1H), 1.43 (s, 9H), 1.35-1.13 (m, 3H), 0.92-0.83 (m, 1H), 0.76-0.63 (m, 2H), 0.03-0.03 (m, 1H).

Step B: tert-butyl 4-[(1R,2R)-2-({[3,5-difluoro-4-(methylsulfonyl)benzyl]oxy}methyl)cyclopropyl]piperidine-1-carboxylate

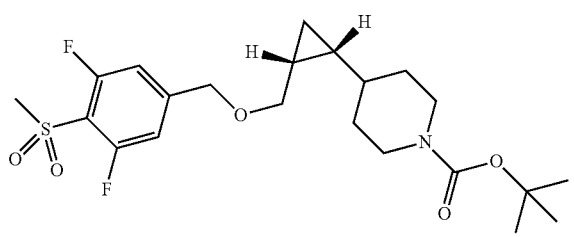 [SMILES: CC(C)(C)OC(=O)N1CCC([C@H]2C[C@H]2COCc2cc(F)c(S(C)(=O)=O)c(F)c2)CC1]

The product of step A was oxidized according to the procedure outlined in intermediate 5 (step D) to yield the title compound. $^1$H NMR (500 MHz, CDCl$_3$) δ 7.05 (d, J 9.7 Hz, 2H), 4.58 (d, J 13.9 Hz, 1H), 4.52 (d, J 13.9 Hz, 1H), 4.15-4.00 (br m, 2H), 3.56-3.49 (m, 2H), 3.29 (s, 3H) 2.72-2.59 (m, 2H), 1.81-1.75 (m, 1H), 1.75-1.68 (m, 1H), 1.46 (s, 9H), 1.37-1.18 (m, 3H), 0.95-0.88 (m, 1H), 0.80-0.69 (m, 2H), 0.07-0.02 (m, 1H). MS (ESI) m/z 460 [M+H]$^+$.

GPR119 Human EC50: 14.8 nM

Examples 45-50

Preparation of 5-chloro-2-{4-[(1R,2R)-2-({[3,5-difluoro-4-(methylsulfonyl)benzyl]oxy}methyl)cyclopropyl]piperidin-1-yl}pyrimidine

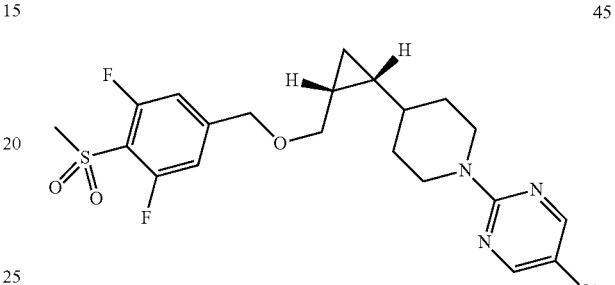

Step A: 4-[(1R,2R)-2-({[3,5-difluoro-4-(methylsulfonyl)benzyl]oxy}methyl)cyclopropyl]piperidine trifluoroacetate

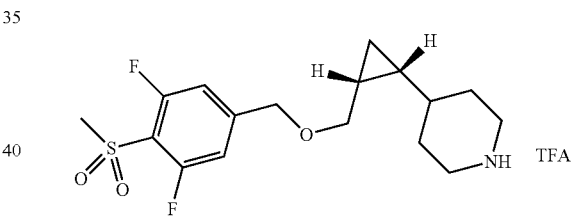

This compound was prepared from example 44 using the procedure outlined in intermediate 7 (step A). MS (ESI) m/z 360 [M+H]$^+$.

Step B: 5-chloro-2-{4-[(1R,2R)-2-({[3,5-difluoro-4-(methylsulfonyl)benzyl]oxy}methyl)cyclopropyl]piperidin-1-yl}pyrimidine

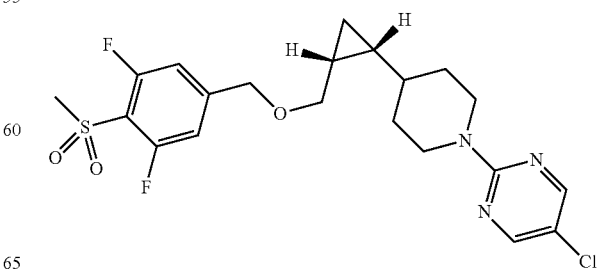

This compound prepared from the product of step A and 2,5-dichloropyrimidine according to the procedure from example 1. ¹H NMR (500 MHz, CDCl₃) δ 8.19 (s, 2H), 7.05 (d, J 9.5 Hz, 2H), 4.68-4.51 (m, 4H), 3.60-3.52 (m, 2H), 3.29 (s, 3H) 2.88-2.79 (m, 2H), 1.89 (d, J 13.5 Hz, 1H), 1.82 (d, J 13.0 Hz, 1H), 1.42-1.31 (m, 2H), 1.27-1.18 (m, 1H), 1.11-1.01 (m, 1H), 0.82-0.68 (m, 2H), 0.09-0.06 (m, 1H). MS (ESI) m/z 472 [M+H]⁺.

GPR119 Human EC50: 0.6 nM

The Examples in Table 11 were synthesized employing intermediate from example 45, step A and the appropriate 2-chloropyrimidine, chloroformate or hydroxysuccinimide reagent according to the procedures from examples 1 and 8.

TABLE 11

| Example # | Chemical Structure | Observed Mass | GPR119 Human EC₅₀ |
|---|---|---|---|
| 46 | 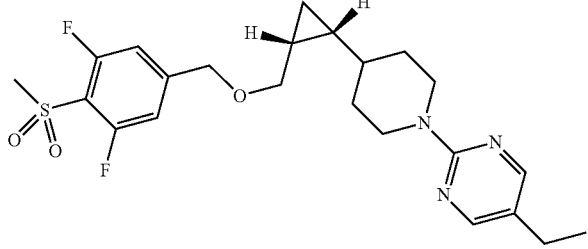 | 466 [M + H]⁺ | 0.4 nM |
| 47 | 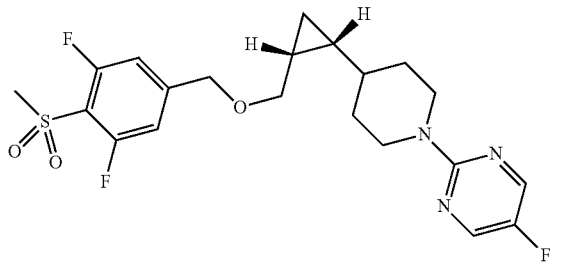 [SMILES: CS(=O)(=O)c1c(F)cc(COC[C@@H]2C[C@@H]2C2CCN(c3ncc(F)cn3)CC2)cc1F] | 456 [M + H]⁺ | 3.2 nM |
| 48 | 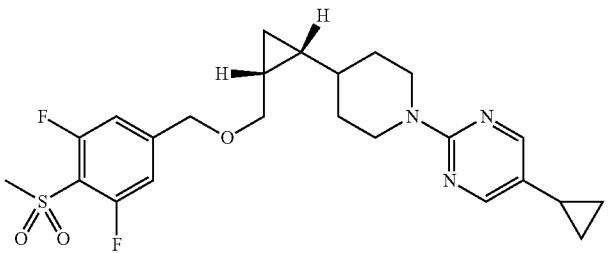 [SMILES: CS(=O)(=O)c1c(F)cc(COC[C@@H]2C[C@@H]2C2CCN(c3ncc(C4CC4)cn3)CC2)cc1F] | 478 [M + H]⁺ | 0.6 nM |
| 49 | 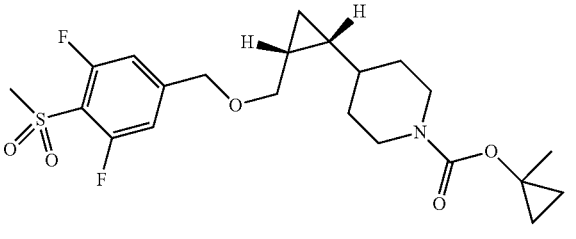 [SMILES: CC1(OC(=O)N2CCC([C@H]3C[C@H]3COCc3cc(F)c(S(C)(=O)=O)c(F)c3)CC2)CC1] | 458 [M + H]⁺ | 11.7 nM |
| 50 | 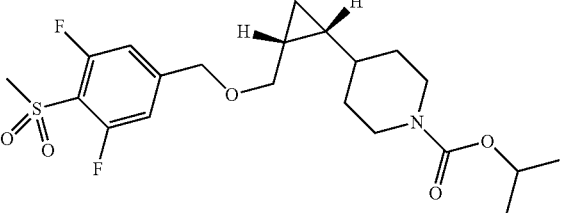 | 446 [M + H]⁺ | 20.5 nM |

Example 51

Preparation of 4-[((1R,2R)-2-[1-(5-chloropyrimidin-2-yl)piperidin-4-yl]cyclopropyl}methoxy)methyl]-2-fluorophenyl}(cyclopropyl)methanone

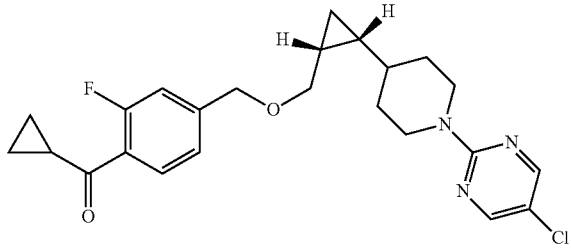

Step A: 4-[({(1R,2R))-2-[1-(tert-butoxycarbonyl)piperidin-4-yl]cyclopropyl}methoxy)methyl]-2-fluorobenzoic acid

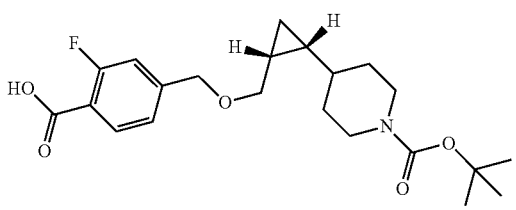 [SMILES: CC(C)(C)OC(=O)N1CCC([C@H]2C[C@H]2COCc2ccc(C(=O)O)c(F)c2)CC1]

Intermediate 13 (100 mg, 0.23 mmol) was dissolved in THF (3 mL) and was cooled to −78° C. A solution of n-BuLi in hexanes (1.6M, 0.30 mL, 0.475 mmol) was added and the reaction was stirred for 30 min. Carbon dioxide (generated from dry ice) was bubbled through the reaction for 5 minutes. The reaction was warmed to RT and stirred for 10 minutes. Water was added to quench the reaction and the resulting mixture was extracted with EtOAc. The combined organic extracts were concentrated to yield the desired carboxylic acid. $^1$H NMR (500 MHz, CDCl$_3$) δ 8.01 (m, 1H), 7.21-7.16 (m, 2H), 4.63 (d, 1H), 4.56 (d, 1H), 4.11-4.03 (br m, 2H), 3.58-3.52 (m, 1H), 3.52-3.47 (m, 1H), 2.72-2.62 (m, 2H), 1.96-1.91 (d, 1H), 1.86-1.79 (d, 1H), 1.47 (s, 9H), 1.38-1.21 (m, 3H), 0.96-0.87 (m, 1H), 0.80-0.65 (m, 2H), 0.06-0.02 (m, 1H). MS (ESI) m/z 352 [M+H−56]$^+$.

Step B: tert-butyl 4-((1R,2R)-2-{[(3-fluoro-4-{[methoxy(methyl)amino]carbonyl}benzyl)oxy]methyl}cyclopropyl)piperidine-1-carboxylate

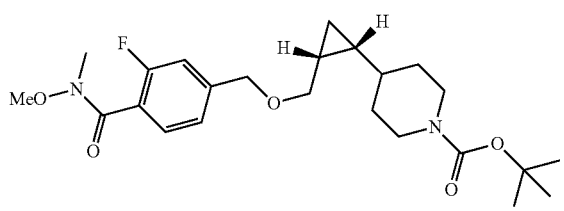 [SMILES: CON(C)C(=O)c1ccc(COC[C@@H]2C[C@@H]2C2CCN(C(=O)OC(C)(C)C)CC2)cc1F]

A solution of the product from the previous step (80 mg, 0.20 mmol) in CH$_2$Cl$_2$ was treated with EDCI (75 mg, 0.39 mmol), HOBt.H$_2$O (60 mg, 0.39 mmol) and iPr$_2$NEt (0.17 mL, 0.98 mmol). After 15 minutes, N, O-dimethylhydroxylamine hydrochloride (96 mg, 0.98 mmol) was added and the resulting reaction mixture was stirred overnight at room temperature. The reaction was then concentrated and subjected to silica gel chromatography (gradient elution, 0-80% EtOAc in hexanes) to yield the title compound. MS (ESI) m/z 451 [M+H]$^+$.

Step C: 4-[({(1R,2R)-2-[1-(5-chloropyrimidin-2-yl)piperidin-4-yl]cyclopropyl}methoxy)methyl]-2-fluoro-N-methoxy-N-methylbenzamide

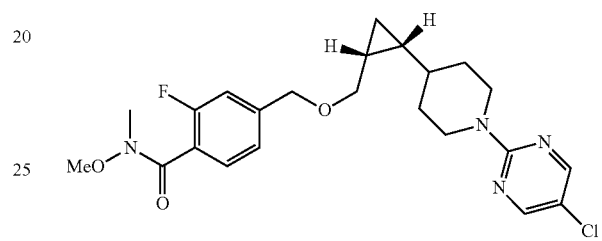

TFA (1 mL) was added to a solution of product from step B (35 mg, 0.078 mmol) in DCM (1 mL) and the resulting mixture stirred at RT for 15 min. The mixture was evaporated and the residue dissolved in DMF (1 mL) and Cs$_2$CO$_3$ (76 mg, 0.233 mmol) and 2,5-dichloropyrimidine (13.89 mg, 0.093 mmol) added. The resultant mixture was stirred at RT overnight, diluted with water and extracted with EtOAc. The organic layer was dried over MgSO$_4$, filtered and concentrated in vacuo. The residue was purified by silica gel chromatography (eluent EtOAc/hexanes 0-100%) to yield the title compound. $^1$H NMR (500 MHz, CDCl$_3$) δ 8.02 (s, 1H), 7.44 (m, 1H), 7.17 (d, 1H), 7.13 (d, 1H), 4.72-4.62 (m, 2H), 4.61 (d, 1H), 4.55 (d, 1H), 3.66-3.53 (m, 4H), 3.53-3.47 (m, 1H), 3.38 (br s, 3H), 2.89-2.81 (m, 2H), 1.97 (d, 1H), 1.93 (d, 1H), 1.43-1.31 (m, 2H), 1.29-1.20 (m, 1H), 1.11-1.02 (m, 1H), 0.81-0.69 (m, 2H), 0.09-0.04 (m, 1H). MS (ESI) m/z 463 [M+H]$^+$.

Step D: 4-[(1R,2R)-2-[1-(5-chloropyrimidin-2-yl)piperidin-4-yl]cyclopropyl}methoxy)methyl]-2-fluorophenyl}(cyclopropyl)methanone

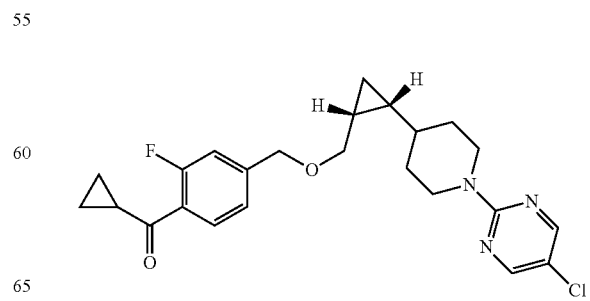

The product from step C (35 mg, 0.08 mmol) was dissolved in THF (2 mL) and cyclopropylmagnesium bromide (0.45 mL of a 0.5 M solution, 0.23 mmol) was added. After stirring at RT for 30 minutes, the solution was quenched with 2 N HCl$_{(aq.)}$ and extracted with EtOAc. The combined organic layers were dried (Na$_2$SO$_4$), filtered, and concentrated in vacuo. The residue was purified via silica gel column chromatography (0-40% EtOAc in hexanes) which provided the title compound. $^1$H NMR (500 MHz, CDCl$_3$) δ 8.00 (s, 1H), 7.77 (m, 1H), 7.20-7.16 (m, 2H), 4.71-4.61 (m, 3H), 4.55 (d, 1H), 3.63-3.58 (m, 1H), 3.51-3.47 (m, 1H), 2.90-2.80 (m, 2H), 2.71-2.64 (m, 1H), 1.96 (d, 1H), 1.83 (d, 1H), 1.43-1.31 (m, 2H), 1.31-1.20 (m, 3H), 1.11-1.01 (m, 3H), 0.81-0.69 (m, 2H), 0.07-0.03 (m, 1H). MS (ESI) m/z 444 [M+H]$^+$. GPR119 Human EC50: 3.7 nM Example 52

Preparation of tert-butyl 4-[(1R,2R)-2-({[4-(cyclopropylcarbonyl)-3,5-difluorobenzyl]oxy}methyl)cyclopropyl]piperidine-1-carboxylate

52

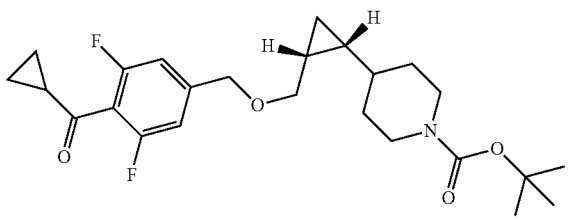

Step A: tert-butyl 4-[(1R,2R)-2-[({4-[cyclopropyl(hydroxy)methyl]-3,5-difluorobenzyl}oxy)methyl]cyclopropyl}piperidine-1-carboxylate

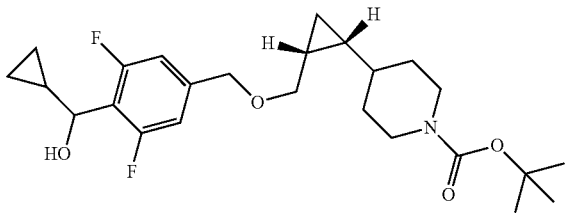 [SMILES: CC(C)(C)OC(=O)N1CCC([C@H]2C[C@H]2COCc2cc(F)c(C(O)C3CC3)c(F)c2)CC1]

Intermediate 14 (78 mg, 0.204 mmol) was dissolved in THF (3 mL) and cooled to −78° C. whereupon a solution of n-BuLi in hexanes (1.6M, 0.139 mL, 0.223 mmol) was added and the reaction was stirred for 1 hour at −78° C. Cyclopropanecarbaldehyde (0.014 mL, 0.185 mmol) was added to the reaction and the resulting mixture was stirred at −78° C. for 1 hour and RT for 2 hours. The reaction was quenched with sat. NaHCO$_3$ and was extracted with EtOAc. The combined organic extracts were concentrated to yield the desired product. $^1$H NMR (500 MHz, CDCl$_3$) δ 6.89 (m, 2H), 4.57 (d, 1H), 4.46 (d, 1H), 4.29 m (d, 1H), 4.20-4.00 (br m, 2H), 3.60-3.50 (m, 1H), 3.50-3.42 (m, 1H), 2.76-2.59 (m, 2H), 1.84 (m, 1H), 1.72 (d, 1H), 1.57-1.44 (m, 10H), 1.40-1.18 (m, 3H), 0.97-0.87 (m, 1H), 0.82-0.67 (m, 2H), 0.58-0.47 (m, 2H), 0.38-0.30 (m, 1H), 0.09-0.01 (m, 1H).

Step B: tert-butyl 4-[(1R,2R)-2-({[4-(cyclopropylcarbonyl)-3,5-difluorobenzyl]oxy}methyl)cyclopropyl]piperidine-1-carboxylate

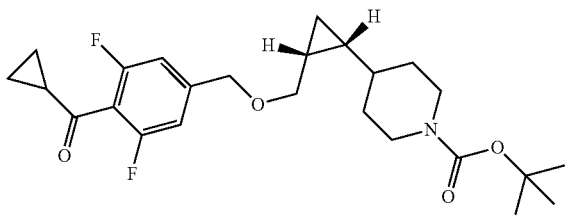 [SMILES: CC(C)(C)OC(=O)N1CCC([C@H]2C[C@H]2COCc2cc(F)c(C(=O)C3CC3)c(F)c2)CC1]

Oxalyl chloride (0.09 mL of a 2M soln in DCM, 0.177 mmol) was dissolved in DCM (0.8 mL) at −78° C. DMSO (35 mg, 0.44 mmol) was added, and the resulting solution was stirred at −78° C. for 5 minutes. A solution of the product from step A (40 mg, 0.09 mmol) in DCM (1 mL) was added followed by Et$_3$N (90 mg, 0.89 mmol). The reaction was warmed to room temperature, and stirred at that temperature for 15 minutes. The reaction was quenched with sat. NH$_4$Cl$_{(aq.)}$, and extracted with DCM. The combined organic layers were dried (Na$_2$SO$_4$), filtered, and concentrated in vacuo. The residue was purified via silica gel column chromatography (0-15% EtOAc in hexanes) which provided title compound. $^1$H NMR (500 MHz, CDCl$_3$) δ 6.94 (dd, 2H), 4.58 (d, 1H), 4.49 (d, 1H), 4.18-4.00 (br m, 2H), 3.58-3.46 (m, 2H), 2.74-2.61 (m, 2H), 1.83 (d, 1H), 1.73 (d, 1H), 1.47 (s, 9H), 1.38-1.19 (m, 5H), 1.13-1.09 (m, 2H), 0.97-0.88 (m, 1H), 0.80-0.68 (m, 2H), 0.06-0.00 (m, 1H). MS (ESI) m/z 450 [M+H]$^+$.

GPR119 Human EC50: 2.4 nM

Example 53

Preparation of 4-[(1R,2R)-2-[1-(5-chloropyrimidin-2-yl)piperidin-4-yl]cyclopropyl}methoxy)methyl]-2,6-difluorophenyl}(cyclopropyl)methanone

53

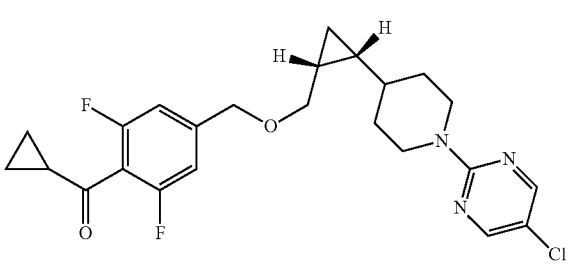

Example 53 was prepared from example 52 using the method outlined in example 51 (step C). $^1$H NMR (500 MHz, CDCl$_3$) δ 8.22 (s, 2H), 6.96 (dd, 2H), 4.72-4.64 (m, 2H), 4.59 (d, 1H), 4.51 (d, 1H), 3.61-3.56 (m, 1H), 3.53-3.49 (m 1H), 2.91-2.82 (m, 2H), 2.41-2.36 (m, 1H), 1.95 (d, 1H), 1.84 (d, 1H), 1.45-1.22 (m, 5H), 1.13-1.03 (m, 3H), 0.91-0.84 (m, 2H), 0.81-0.70 (m, 2H), 0.10-0.06 (m, 1H). MS (ESI) m/z 462 [M+H]+. GPR119 Human EC50: 1.0 nM

Example 54

Preparation of 5-ethyl-2-{4-[(1R,2R)-2-({[4-(1,3-oxazol-2-yl)benzyl]oxy}methyl)cyclopropyl]piperidin-1-yl}pyrimidine

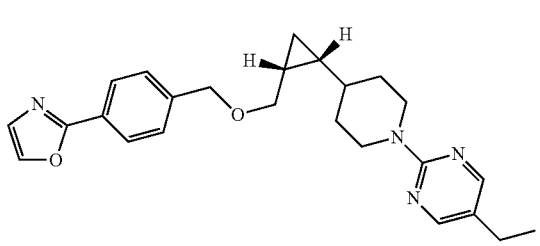

Step A: 2-[4-((1R,2R)-2-{[(4-bromobenzyl)oxy]methyl}cyclopropyl)piperidin-1-yl]-5-ethyl pyrimidine

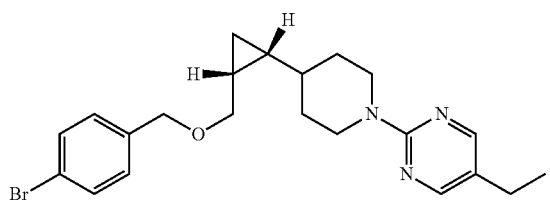 [SMILES: CCc1cnc(N2CCC([C@H]3C[C@H]3COCc3ccc(Br)cc3)CC2)nc1]

This compound was prepared from the product of intermediate 9 (step B) and 2-chloro-5-ethylpyrimidine according to the procedure outlined in intermediate 7 (step B). 1H NMR (500 MHz, CDCl3) δ 8.19 (s, 2H), 7.50 (d, J 8.2 Hz, 2H), 7.24 (d, J 8.2 Hz, 2H), 4.73-4.65 (m, 2H), 4.55 (d, J 12.2 Hz, 1H), 4.45 (d, J 12.2 Hz, 1H), 3.59 (dd, J 10.0 &6.5 Hz, 1H), 3.47-3.43 (m 1H), 2.87-2.77 (m, 2H), 2.47 (q, J 7.6 Hz, 2H), 1.96 (d, J 13.0 Hz, 1H), 1.82 (d, J 13.0 Hz, 1H), 1.43-1.34 (m, 2H), 1.26-1.18 (m, 4H), 1.08-0.98 (m, 1H), 0.79-0.68 (m, 2H), 0.07-0.03 (m, 1H).

Step B: 5-ethyl-2-{4-[(1R,2R)-2-({[4-(1,3-oxazol-2-yl)benzyl]oxy}methyl)cyclopropyl]piperidin-1-yl}pyrimidine

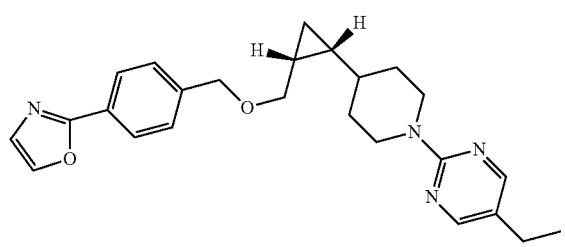 [SMILES: CCc1cnc(N2CCC([C@H]3C[C@H]3COCc3ccc(-c4ncco4)cc3)CC2)nc1]

The product of step A (100 mg, 0.2 mmol), Pd(PPh3)2Cl2 (16 mg, 0.02 mmol), and 2-(tributylstannyl)oxazole (125 mg, 0.35 mmol) were dissolved in toluene (2.5 mL), and the solution was heated at 90° C. for 18 h. Silica gel was added, and the slurry was subjected to silica gel column chromatography (2/1 EtOAc/hexanes) to provide the title compound. MS (ESI) m/z 419 [M+H]+. GPR119 Human EC50: 12 nM

Example 55

Preparation of 5-ethyl-2-{4-[(1R,2R)-2-({[4-(1,3-thiazol-5-yl)benzyl]oxy}methyl)cyclopropyl]piperidin-1-yl}pyrimidine

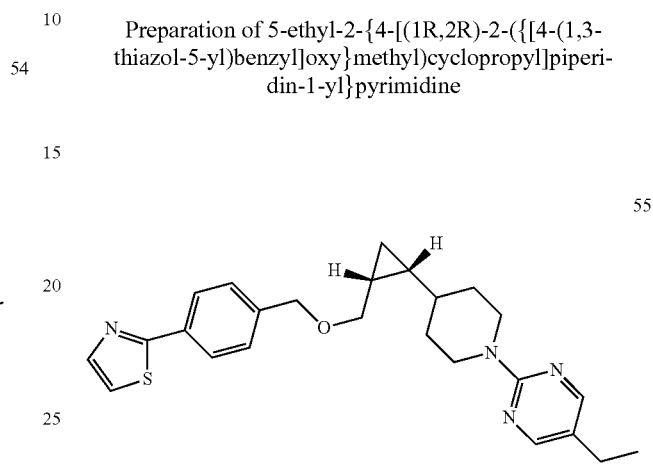

This compound was prepared according to the procedure for example 54, replacing 2-(tributylstannyl)oxazole with 5-(tributylstannyl)thiazole. MS (ESI) m/z 435 [M+H]+. GPR119 Human EC50: 2.2 nM

Example 56

Preparation of 2-{4-[(1R,2R)-2-({[4-(cyclopropylsulfonyl)benzyl]oxy}methyl)cyclopropyl]piperidin-1-yl}-5-ethylpyrimidine

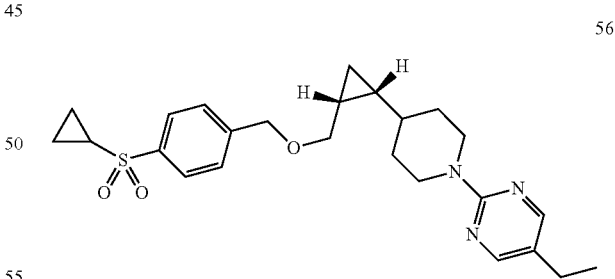

The product of example 54 (step A) (100 mg, 0.2 mmol), sodium cyclopropanesulfinate (36 mg, 0.28 mmol), copper (I) trifluoromethanesulfonate benzene complex (6 mg, 0.012 mmol), and N,N'-dimethylethylenediamine (2 mg, 0.02 mmol) were dissolved in DMSO (1 mL), and the solution was heated at 120° C. The solution was partitioned between water and Et2O. The aqueous layer was extracted with Et2O. The combined organic layers were washed with brine, dried (Na2SO4), filtered, and concentrated in vacuo. The residue was purified via silica gel column chromatography (2/1

EtOAc/hexanes) to provide the title compound. MS (ESI) m/z 456 [M+H]+. GPR119 Human EC50: 1.2 nM

Example 57

Preparation of. 5-ethyl-2-{4-[(1R,2R)-2-({[4-(ethylsulfonyl)benzyl]oxy}methyl)cyclopropyl]piperidin-1-yl}pyrimidine

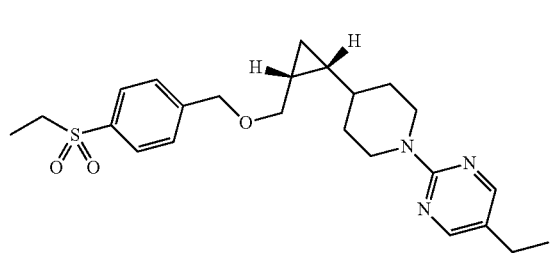

This compound was prepared from the product of example 54 (step A), and sodium ethanesulfinate according to the procedure from example 56. MS (ESI) m/z 444 [M+H]+.
GPR119 Human EC50: 0.3 nM

Example 58

Preparation of (2R)-1-{4-[({(1R,2R)-2-[1-(5-ethylpyrimidin-2-yl)piperidin-4-yl]cyclopropyl}methoxy)methyl]phenyl}propan-2-ol

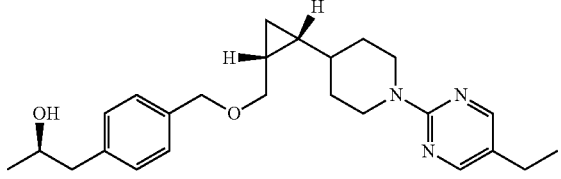

The product of example 54 (step A) (100 mg, 0.2 mmol), was dissolved in THF (2.3 mL), and the solution was cooled to −78° C. under N$_2$. n-Butyl lithium (0.1 mL of a 2.5 M solution in hexane, 0.25 mmol) was added dropwise at 78° C. The solution was stirred at −78° C. for 20 minutes. (R)-propylene oxide (16 mg, 0.028 mmol) and BF$_3$.Et$_2$O (33 mg, 0.23 mmol) were then added. The solution was stirred at −78° C. for 30 minutes, and then at RT for 1 h. The solution was partitioned between water and DCM. The aqueous layer was extracted with DCM. The combined organic layers were dried (Na$_2$SO$_4$), filtered, and concentrated in vacuo. The residue was purified via silica gel column chromatography (2/1 hexanes/EtOAc) to provide the title compound. MS (ESI) m/z 410 [M+H]+. GPR119 Human EC50: 11 nM

Example 59

Preparation of (2S)-1-{4-[({(1R,2R)-2-[1-(5-ethylpyrimidin-2-yl)piperidin-4-yl]cyclopropyl}methoxy)methyl]phenyl}propan-2-ol

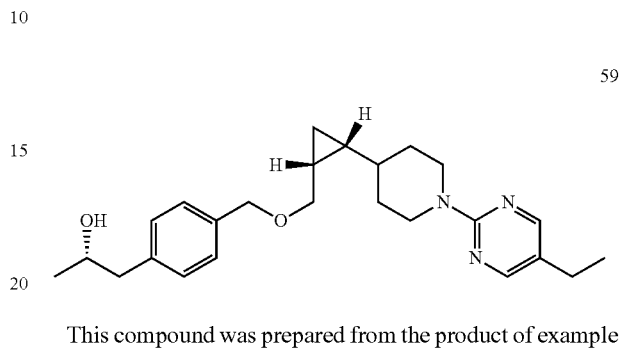

This compound was prepared from the product of example 54 (step A), and (S)-propylene oxide according to the procedure from example 58. MS (ESI) m/z 410 [M+H]+. GPR119 Human EC50: 1.6 nM

Example 60

Preparation of 2-{4-[({(1R,2R)-2-[1-(5-ethylpyrimidin-2-yl)piperidin-4-yl]cyclopropyl}methoxy)methyl]phenyl}ethanol

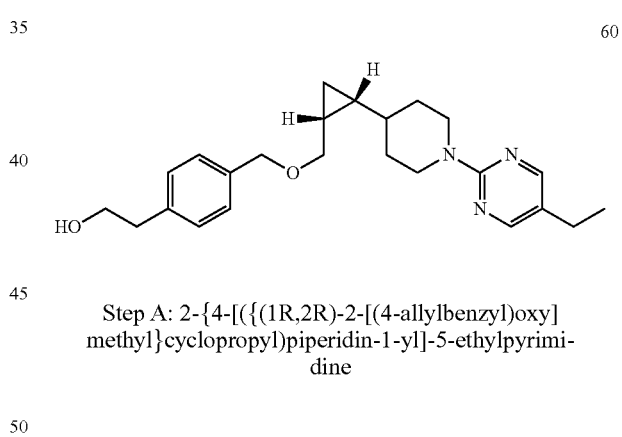

Step A: 2-{4-[({(1R,2R)-2-[(4-allylbenzyl)oxy]methyl}cyclopropyl)piperidin-1-yl]-5-ethylpyrimidine

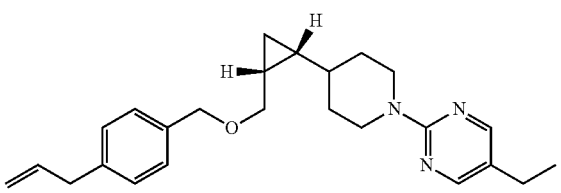 [SMILES: C=CCc1ccc(COC[C@@H]2C[C@@H]2C2CCN(c3ncc(CC)cn3)CC2)cc1]

The product of example 54 (step A) (500 mg, 1.17 mmol), Pd$_2$(dba)$_3$ (53 mg, 0.06 mmol), tri(2-furyl)phosphine (91 mg, 0.4 mmol), and allyltributylstannane (423 mg, 1.28 mmol) were dissolved in toluene (12 mL), and the solution was heated at 100° C. for 15 h. The solution was cooled to RT and diluted with Et$_2$O. A saturated solution of KF$_{(aq.)}$ was added. After stirring at RT for 1 h, the mixture was filtered. The filtrate was diluted with water and extracted with DCM. The organic layers were dried (Na₂SO₄), filtered, and concentrated in vacuo. The residue was purified via silica gel column chromatography (10/1 hexanes/EtOAc) yielding the title compound.

Step B: {4-[({(1R,2R)-2-[1-(5-ethylpyrimidin-2-yl)piperidin-4-yl]cyclopropyl}methoxy)methyl]phenyl}acetaldehyde

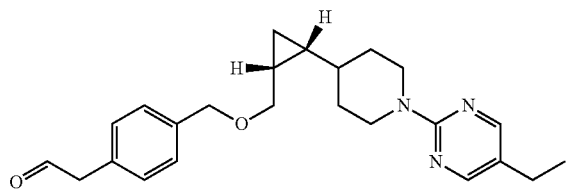 [SMILES: CCc1cnc(N2CCC([C@H]3C[C@H]3COCc3ccc(CC=O)cc3)CC2)nc1]

The product of step A (210 mg, 0.54 mmol), OsO₄ (3 drops of a 4% solution in water), and 4-methylmorpholine N-oxide (188 mg, 1.6 mmol) were dissolved in acetone/water (4/1, 5 mL), and stirred at RT for 15 h. The solution was quenched with a 10% Na₂S₂O₃ (aq.) solution. After stirring at RT for 1 h, the solution was extracted with EtOAc. The combined organic layers were dried (Na₂SO₄), filtered, and concentrated in vacuo. The residue was dissolved in acetone/water (4/1, 10 mL), and sodium periodate (229 mg, 1.07 mmol) was added. The solution was stirred at RT for 1 h. The solid was filtered and washed with EtOAc. The organic layers were dried (Na₂SO₄), filtered, and concentrated. The residue was purified via silica gel column chromatography (2/1 hexanes/EtOAc) yielding the title compound.

Step C: 2-{4-[({(1R,2R)-2-[1-(5-ethylpyrimidin-2-yl)piperidin-4-yl]cyclopropyl}methoxy)methyl]phenyl}ethanol

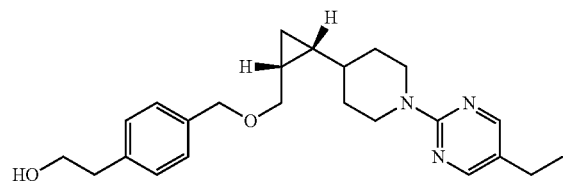 [SMILES: CCc1cnc(N2CCC([C@H]3C[C@H]3COCc3ccc(CCO)cc3)CC2)nc1]

The product of step B (70 mg, 0.18 mmol) was dissolved in DCM/MeOH (1/1, 4 mL) at 0° C., and sodium borohydride (30 mg, 0.8 mmol) added. The solution was stirred at 0° C. for 1 h. The solution was partitioned between water and DCM. The aqueous layer was extracted with DCM. The combined organic layers were dried (Na₂SO₄), filtered, and concentrated. The residue was purified via silica gel column chromatography (2/1 hexanes/EtOAc) followed by reverse phase HPLC (C18, 10-100% water/acetonitrile with 0.1% formic acid gradient) which yielded the title compound. MS (ESI) m/z 396 [M+H]⁺. GPR119 Human EC50: 2.5 nM Example 61

Preparation of 5-ethyl-2-{4-[(1R,2R)-2-({[4-(1H-tetrazol-1-yl)benzyl]oxy}methyl)cyclopropyl]piperidin-1-yl}pyrimidine

61

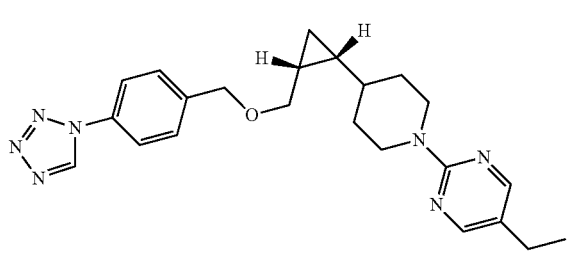 [SMILES: CCc1cnc(N2CCC([C@H]3C[C@H]3COCc3ccc(-n4cnnn4)cc3)CC2)nc1]

Step A: 4-[({(1R,2R)-2-[1-(5-ethylpyrimidin-2-yl)piperidin-4-yl]cyclopropyl}methoxy)methyl]aniline

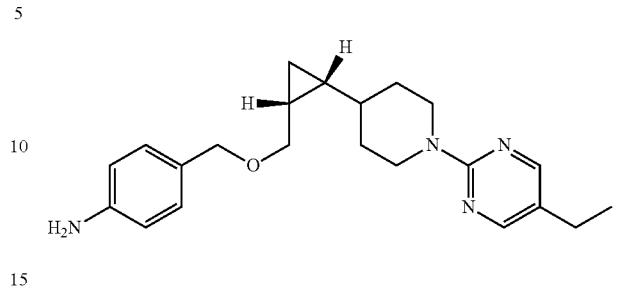

The product of example 54 (step A) (100 mg, 0.2 mmol), Pd₂(dba)₃ (21 mg, 0.023 mmol), (2-biphenyl)di-tert-butylphosphine (14 mg, 0.046 mmol), NaOtBu (48 mg, 0.5 mmol), and benzophenone imine (50 mg, 0.28 mmol) were dissolved in toluene (1.5 mL), and the solution was heated under N₂ at 60° C. for 6 hours. The mixture was filtered and the filtrate concentrated in vacuo. The residue was dissolved in MeOH (3 mL), and sodium acetate (38 mg, 0.46 mmol) and hydroxylamine hydrochloride (32 mg, 0.46 mmol) were added. The solution was stirred at RT for 1 h. The solution was partitioned between sat. NaHCO₃ (aq.) and EtOAc. The aqueous layer was extracted with EtOAc. The combined organic layers were dried (Na₂SO₄), filtered, and concentrated. The residue was purified via silica gel column chromatography (2/1 hexanes/EtOAc) which provided the title compound.

Step B: 5-ethyl-2-{4-[(1R,2R)-2-({[4-(1H-tetrazol-1-yl)benzyl]oxy}methyl)cyclopropyl]piperidin-1-yl}pyrimidine

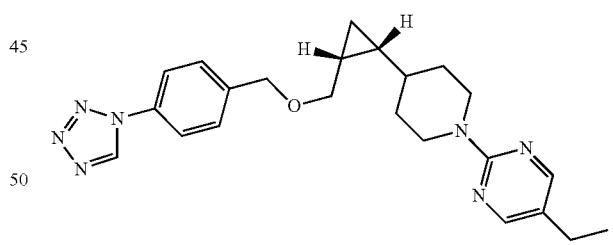

The product of step A (60 mg, 0.16 mmol), sodium azide (13 mg, 0.2 mmol), trimethyl orthoformate (0.3 mL, 2.7 mmol), and acetic acid (0.15 mL, 2.6 mmol) were heated at 80° C. for 6 hours. The solution was cooled and diluted with water. The solution was neutralized with NaHCO₃ and extracted with DCM. The organic layers were dried (Na₂SO₄), filtered, and concentrated. The residue was purified via reverse-phase HPLC (C18: gradient 10-100 water/acetonitrile 0.1% formic acid) which yielded the title compound. MS (ESI) m/z 420 [M+H]⁺. GPR119 Human EC50: 0.07 nM

Example 62

Preparation of 5-ethyl-2-{4-[(1R,2R)-2-({[4-(1H-1,2,3-triazol-1-yl)benzyl]oxy}methyl)cyclopropyl]piperidin-1-yl}pyrimidine

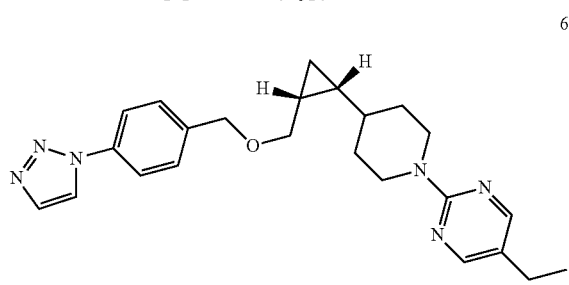

The product of example 54 (step A) (100 mg, 0.232 mmol), CuI (44 mg, 0.232 mmol), triazole (48 mg, 0.697 mmol), NaOtBu (67 mg, 0.697 mmol) and N,N'-dimethylethylene diamine (61 mg, 0.697 mmol) in NMP (1 mL) was heated at 130° C. for 15 h. The reaction was cooled to room temperature, diluted with EtOAc and washed with H$_2$O (×3). The organic layer was dried over anhydrous MgSO$_4$, filtered, and concentrated under vacuum to leave a residue which was purified by silica gel column chromatography (elution with 2:1 hexane:ethyl acetate) to yield the title compound. MS (ESI) m/z 419 [M+H]$^+$. GPR119 Human EC50: 0.3 nM

Example 63

Preparation of 5-ethyl-2-{4-[(1R,2R)-2-({[4-(1,2,4-oxadiazol-5-yl)benzyl]oxy}methyl)cyclopropyl]piperidin-1-yl}pyrimidine

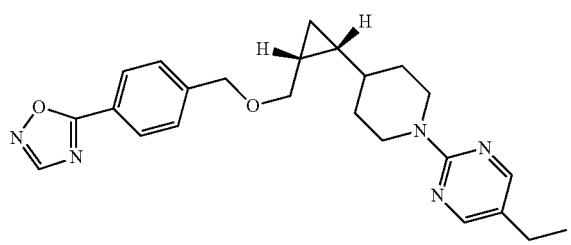

Step A: 4-[({(1R,2R)-2-[1-(5-ethylpyrimidin-2-yl)piperidin-4-yl]cyclopropyl}methoxy)methyl]benzonitrile

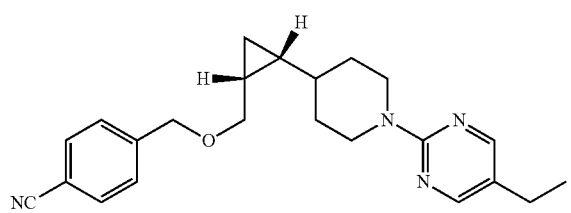 [SMILES: CCc1cnc(N2CCC([C@H]3C[C@H]3COCc3ccc(C#N)cc3)CC2)nc1]

The product of example 54 (step A) (500 mg, 1.17 mmol), Pd$_2$(dba)$_3$ (43 mg, 0.046 mmol), dppf (51.5 mg, 0.093 mmol), Zn(CN)$_2$ (89 mg, 0.755 mmol) and zinc dust (18 mg, 0.278 mmol) in DMA (1 mL) was evacuated and back-filled with argon (×3). The mixture was stirred at 100° C. for 4 h. The reaction was cooled to room temperature, diluted with Et$_2$O and filtered through a pad of silica. The filtrate was concentrated under vacuum to leave a residue which was purified by silica gel column chromatography (elution with 5:1 hexane:ethyl acetate) to yield the title compound as a colorless gum. MS (ESI) m/z 377 [M+H]$^+$.

Step B: 4-[({(1R,2R)-2-[1-(5-ethylpyrimidin-2-yl)piperidin-4-yl]cyclopropyl}methoxy)methyl]benzamide

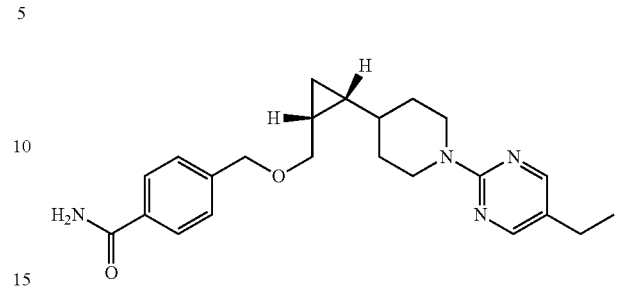

The product of step A (150 mg, 0.398 mmol), acetamide (101 mg, 1.71 mmol) and Pd(OAc)$_2$ (13.4 mg, 0.02 mmol) in THF (4.5 mL) and H$_2$O (1.5 mL) was heated at 65° C. for 24 h. The mixture was cooled to RT and diluted with H$_2$O. The solution was extracted with EtOAc (×3). The combined organic layers were washed with brine (1×), dried over anhydrous MgSO$_4$, filtered, and concentrated under vacuum to leave a residue which was purified by silica gel column chromatography (elution with 20:1 DCM:MeOH) to yield the desired compound. MS (ESI) m/z 395 [M+H]$^+$.

Step C: 5-ethyl-2-{4-[(1R,2R)-2-({[4-(1,2,4-oxadiazol-5-yl)benzyl]oxy}methyl)cyclopropyl]piperidin-1-yl}pyrimidine

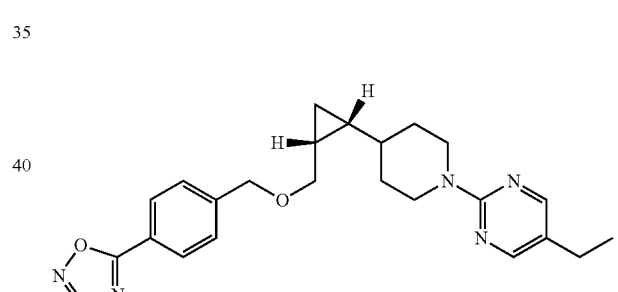

A solution of the product of step B (80 mg, 0.203 mmol) in N,N-dimethylformamide dimethyl acetal (2 mL) was stirred at 120° C. for 4 h. Upon cooling to RT, the solvent was removed under vacuum to leave a residue. The resulting residue was dissolved in 1,4-dioxane (1 mL) followed by the addition of NH$_2$OH (0.016 mL of 50% solution in H$_2$O, 0.243 mmol) and HOAc (0.5 mL). The reaction was stirred at 90° C. for 4 h before being cooled to RT. The reaction was quenched with a saturated aqueous solution of NaHCO$_3$ and the layer was extracted with EtOAc (×3). The combined organic layers were washed with brine (1×), dried over MgSO$_4$, filtered, and concentrated under vacuum to leave a residue which was purified by silica gel column chromatography (elution with 5:1 hexane:ethyl acetate) to give the title compound. MS (ESI) m/z 420 [M+H]$^+$. GPR119 Human EC50: 5.5 nM

Example 64

Preparation of (2S)-)-4-({4-[({(1R,2R)-2-[1-(5-ethylpyrimidin-2-yl)piperidin-4-yl]cyclopropyl}methoxy)methyl]phenyl}sulfonyl)butan-2-ol

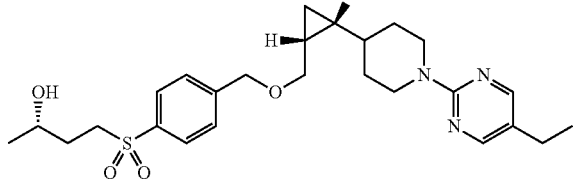

To a cold (−78° C.), stirred solution of example 21 (0.1 g, 0.23 mmol) in THF (2.5 mL) was added n-BuLi (0.1 mL of 2.5M solution in hexane, 0.26 mmol) dropwise. After being stirred at −78° C. for 20 min, (S)-propylene oxide (20 mg, 0.35 mmol) was added neat. The cold bath was removed and the mixture was stirred at RT for 2 h before being quenched with a saturated aqueous solution of NH$_4$Cl. The layer was extracted with EtOAc (×3). The combined organic layers were washed with brine (1×), dried over anhydrous MgSO$_4$, filtered, and concentrated under vacuum to leave a residue which was purified by column chromatography on silica (elution with 3:2 hexanes:ethyl acetate) to yield the title compound as a colorless gum. MS (ESI) m/z 488 [M+H]$^+$. GPR119 Human EC50: 0.6 nM

Example 65

Preparation of 5-ethyl-2-{4-[(1R,2R)-2-((1R)-2-methoxy-1-{[4-(methylsulfonyl)benzyl]oxyethyl)cyclopropyl]piperidin-1-yl}pyrimidine

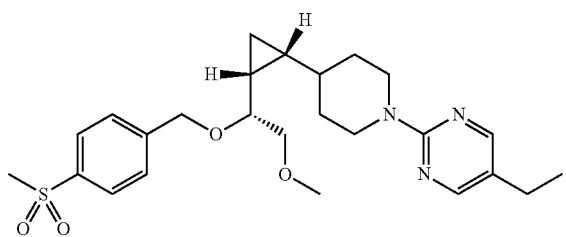

Step A: {(1R,2R)-2-[1-(5-ethylpyrimidin-2-yl)piperidin-4-yl]cyclopropyl}methanol

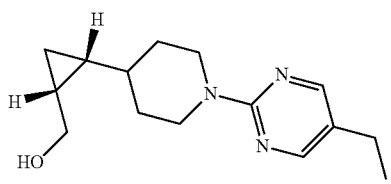 [SMILES: CCc1cnc(N2CCC([C@H]3C[C@H]3CO)CC2)nc1]

To a cold (0° C.), stirred solution tert-butyl 4-[(1R,2R)-2-(hydroxymethyl)cyclopropyl]piperidine-1-carboxylate (intermediate 4, 5.0 g, 19.58 mmol) in dichloromethane (100 mL) was added trifluoroacetic acid (100 mL) slowly over 10 minutes. After being stirred at 0° C. for 1 h, the mixture was concentrated under vacuum. Residual TFA was further removed by stripping twice from dichloromethane followed by drying in vacuum. The resulting residue was dissolved in DMF (40 ml) followed by the addition of cesium carbonate (35.09 g, 107.69 mmol) and 2-chloro-5-ethylpyrimidine (5.6 g, 39.15 mmol). The mixture was stirred at RT for 15 h before being quenched with H$_2$O. The aqueous layer was extracted with EtOAc (2×). The combined organic layers were washed with H$_2$O (2×), brine (1×), dried over anhydrous MgSO$_4$, filtered, and concentrated under vacuum to leave a residue which was purified by column chromatography on silica (elution with 2:1→1:1 hexane:ethyl acetate) to yield the title compound. H NMR (500 MHz, CDCl$_3$) δ 8.18 (s, 2H), 4.74-4.65 (m, 2H), 3.74-3.67 (m, 2H), 2.89-2.81 (m, 2H), 2.47 (q, J 7.6 Hz, 2H), 1.91-1.82 (m, 2H), 1.46-1.34 (m, 2H), 1.23-1.16 (M, 4H), 1.16-1.07 (m 1H), 0.77-0.70 (m, 2H), 0.09-0.04 (m, 1H). MS (ESI) m/z 262 [M+H]$^+$.

Step B: (1R,2R)-2-[1-(5-ethylpyrimidin-2-yl)piperidin-4-yl]cyclopropanecarbaldehyde

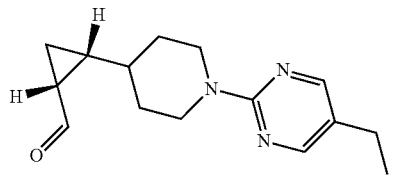 [SMILES: CCc1cnc(N2CCC([C@H]3C[C@H]3C=O)CC2)nc1]

A mixture of the product of step A (5 g, 19.6 mmol), powdered 4 Å activated molecular sieves (10 g) and N-methylmorpholine oxide (3.5 g, 29.4 mmol) was stirred in DCM (100 mL) for 15 min at RT. Then the mixture was cooled to 0° C. and tetrapropylammonium perruthenate (0.69 g, 0.196 mmol) was added in one portion. The cold bath was removed and the mixture was stirred at RT for 1 h. The reaction was diluted with Et$_2$O and stirred for 15 min at RT. The mixture was filtered through a plug of silica gel which was washed thoroughly with 2:1 hexane: ethyl acetate. The filtrate was concentrated to get a residue which was purified by column chromatography on silica (elution with 2:1 hexane:ethyl acetate) to yield the desired aldehyde. MS (ESI) m/z 260 [M+H]$^+$.

Step C: 5-ethyl-2-{4-[(1R,2S)-2-vinylcyclopropyl]piperidin-1-yl}pyrimidine

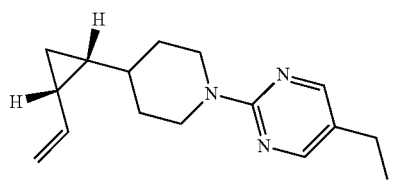 [SMILES: C=C[C@@H]1C[C@@H]1C1CCN(c2ncc(CC)cn2)CC1]

To a cold (−78° C.), stirred suspension of triphenylmethyl phosphonium bromide (10.5 g, 29.4 mmol) in THF (80 mL) was added n-BuLi (11.4 mL of a 2.5M solution in hexanes, 28.4 mmol) dropwise. Upon stirring the resulting orange suspension for 45 min at −78° C., a solution of the product of step B (3.8 g, 14.7 mmol) in THF (25 mL) was added dropwise. The cold bath was removed and the mixture was stirred at RT for 2 h before being quenched with a saturated aqueous solution of NH₄Cl. The organic layer was separated and the aqueous layer was extracted with Et₂O (3×). The combined organic layers were washed with brine (1×), dried over anhydrous MgSO₄, filtered, and concentrated under vacuum to leave a residue which was purified by column chromatography on silica (elution with 5:1 hexane:ethyl acetate) to yield the desired alkene. MS (ESI) m/z 258 [M+H]⁺.

Step D: (1R)-2-{[tert-butyl(dimethyl)silyl]oxy}-1-{(1R,2R)-2-[1-(5-ethylpyrimidin-2-yl)piperidin-4-yl]cyclopropyl}ethanol and (1S)-2-{[tert-butyl(dimethyl)silyl]oxy}-1-{(1R,2R)-2-[1-(5-ethylpyrimidin-2-yl)piperidin-4-yl]cyclopropyl}ethanol

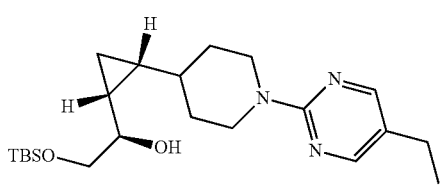

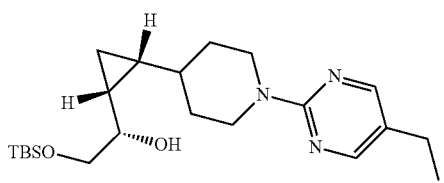

To a cold (0° C.) solution of the product of step C (1.80 g, 7.03 mmol) in t-BuOH (35 mL) and H₂O (35 mL) was added ADmix-β. The mixture was stirred for 20 h, allowing the mixture to warm to RT. The reaction was cooled to 0° C. and Na₂SO₃ (10 g) was added. The mixture was then stirred at RT for 1 h before being diluted with H₂O. The mixture was extracted with EtOAc (×5). The combined organic layers were dried over anhydrous MgSO₄, filtered, and concentrated under vacuum to leave a residue which was purified by column chromatography on silica (elution with 20:1 DCM:MeOH) to yield the diol as a mixture of diastereomers (LCMS calc: 291.2; obs: 292.2 (M+1)). To a cold (0° C.), stirred solution of diols (1.95 g, 6.69 mmol), imidazole (0.68 g, 10.04 mmol) and DMAP (100 mg, 0.8 mmol) in methylene chloride (20 mL) was added tert-butyldimethylsilyl chloride (1.10 g, 7.36 mmol) in one portion. The resulting cloudy solution was stirred at 0° C. for 2 h before being quenched with H₂O. The organic layer was separated and the aqueous layer was extracted with DCM (×3). The combined organic layers were dried over anhydrous MgSO₄, filtered, and concentrated under vacuum to leave a residue which was purified by column chromatography on silica (elution with 5:1 hexane:ethyl acetate) to yield two separate diastereomers (1R)-2-{[tert-butyl(dimethyl)silyl]oxy}-1-{(1R,2R)-2-[1-(5-ethylpyrimidin-2-yl) piperidin-4-yl]cyclopropyl}ethanol (major) and (1S)-2-{[tert-butyl(dimethyl)silyl]oxy}-1-{(1R,2R)-2-[1-(5-ethylpyrimidin-2-yl)piperidin-4-yl]cyclopropyl}ethanol (minor MS (ESI) m/z 406 [M+H]⁺.

Step E: 2-{4-[(1R,2R)-2-((1R)-1-[(4-bromobenzyl)oxy]-2-{[tert-butyl(dimethyl)silyl]oxy}ethyl)cyclopropyl]piperidin-1-yl}-5-ethylpyrimidine

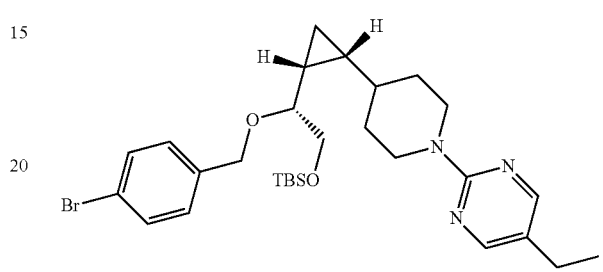

To a cold (−78° C.), stirred solution of the major diastereoisomer prepared in step D (0.95 g, 2.35 mmol) in THF (9 mL) was added NaHMDS (2.6 mL of 1.0 M solution in THF, 2.58 mmol) dropwise via syringe. Upon stirring at −78° C. for 0.5 h, 1-bromo-4-(bromomethyl)benzene (0.88 g, 3.51 mmol) added followed by tetra-n-butylammonium iodide (100 mg, 0.27 mmol). The cold bath was removed and the mixture was stirred at RT for 4 h before being quenched with a saturated aqueous solution of NH₄Cl. The layer was extracted with EtOAc (×3). The combined organic layers were dried over anhydrous MgSO₄, filtered, and concentrated under vacuum to leave a residue which was purified by column chromatography on silica (elution with 10:1 hexane:ethyl acetate) to yield the title compound. LCMS calc: MS (ESI) m/z 574/576 [M+H]⁺.

Step F: (2R)-2-[(4-bromobenzyl)oxy]-2-{(1R,2R)-2-[1-(5-ethylpyrimidin-2-yl)piperidin-4-yl]cyclopropyl}ethanol

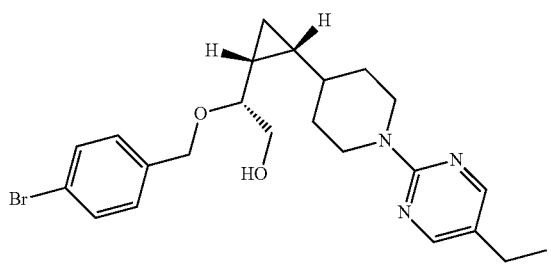 [SMILES: CCc1cnc(N2CCC([C@H]3C[C@H]3[C@H](CO)OCc3ccc(Br)cc3)CC2)nc1]

To a stirred solution of the compound prepared in step E (0.37 g, 0.64 mmol) in THF (3 mL) was added TBAF (0.96 mL of 1.0 M solution in THF, 0.96 mmol). Upon stirring at RT for 1 h, silica gel was added to the reaction mixture and a slurry was prepared, which was purified by column chromatography on silica (elution with 2:1 hexane:ethyl acetate) to yield the desired compound. MS (ESI) m/z 460/462 [M+H]+.

Step G: 2-[4-((1R,2R)-2-{(1R)-1-[(4-bromobenzyl)oxy]-2-methoxyethyl}cyclopropyl)piperidin-1-yl]-5-ethylpyrimidine

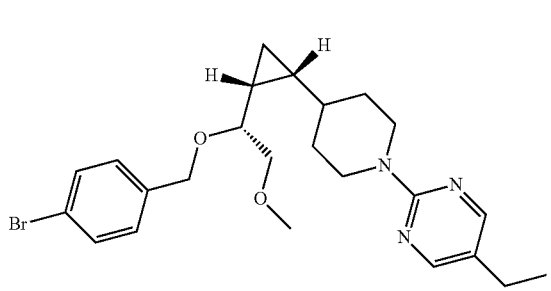 [SMILES: CCc1cnc(N2CCC([C@H]3C[C@H]3[C@H](COC)OCc3ccc(Br)cc3)CC2)nc1]

To a cold (−78° C.), stirred solution of the product of step F (0.70 g, 1.52 mmol) in THF (6 mL) was added NaHMDS (1.6 mL of 1.0 M solution in THF, 1.60 mmol) dropwise. Upon stirring at −78° C. for 15 min the mixture was warmed to 0° C. when MeI (0.43 g, 3.04 mmol) was added. The cold bath was removed and the mixture was stirred at RT for 3 h before being quenched with a saturated aqueous solution of NH₄Cl. The solution was extracted with Et₂O (×3). The combined organic layers were dried over anhydrous MgSO₄, filtered, and concentrated under vacuum to leave a residue which was purified by column chromatography on silica (elution with 5:1 hexane:ethyl acetate) to yield the title compound. MS (ESI) m/z 474/476 [M+H]+.

Step H: 5-ethyl-2-{4-[(1R,2R)-2-((1R)-2-methoxy-1-{[4-(methylthio)benzyl]oxy}ethyl)cyclopropyl]piperidin-1-yl}pyrimidine

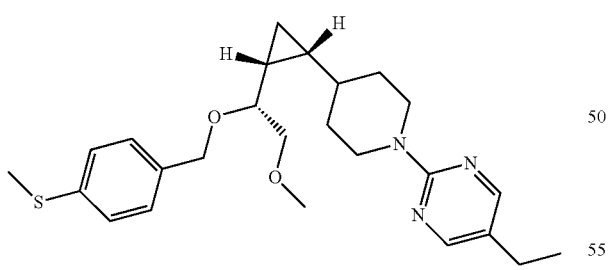

To a cold (−78° C.), stirred solution of the product of step G (90 mg, 0.190 mmol) in THF (1.9 mL) was added n-BuLi (0.9 mL of 2.5 M solution in hexane, 0.228 mmol). After 10 min, dimethyldisulfide (23.2 mg, 0.247 mmol) was added and the mixture stirred for 45 min at −78° C. The reaction was quenched with a saturated aqueous solution of NH₄Cl, and the aqueous layer was extracted with EtOAc (×3). The combined organic layers were dried over anhydrous MgSO₄, filtered, and concentrated under vacuum to leave a residue which was purified by column chromatography on silica (elution with 5:1 hexane:ethyl acetate) to yield the title compound. MS (ESI) m/z 442 [M+H]+.

Step I: 5-ethyl-2-{4-[(1R,2R)-2-((1R)-2-methoxy-1-{[4-(methylsulfonyl)benzyl]oxyethyl)cyclopropyl]piperidin-1-yl}pyrimidine

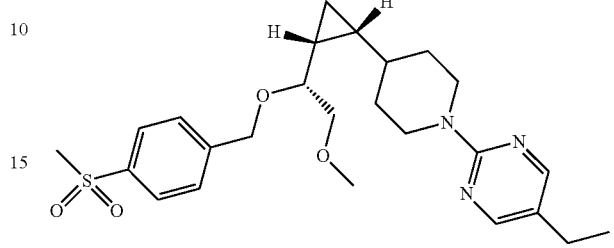

The product of step H was oxidized according to the procedure described in intermediate 5 (step D). MS (ESI) m/z 474 [M+H]+. GPR119 Human EC50: 850 nM Example 66

Preparation of 5-ethyl-2-{4-[(1R,2R)-2-((1S)-2-methoxy-1-{[4-(methylsulfonyl)benzyl]oxyethyl)cyclopropyl]piperidin-1-yl}pyrimidine

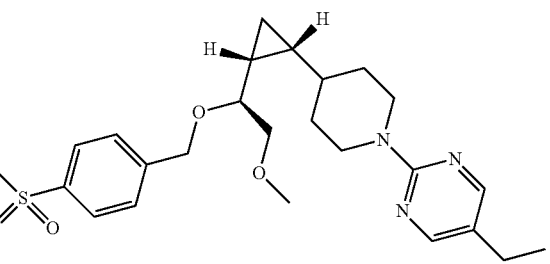

66

This compound was prepared from the minor diastereoisomer prepared in example 65, step D using the procedures described in example 65, steps E, F, G, H, and I to give the title compound. MS (ESI) m/z 474 [M+H]+. GPR119 Human EC50: 0.19 nM Example 67

Preparation of 5-ethyl-2-{4-[(1R,2R)-2-((1S)-2-methoxy-1-{[4-(ethylsulfonyl)benzyl]oxyethyl)cyclopropyl]piperidin-1-yl}pyrimidine

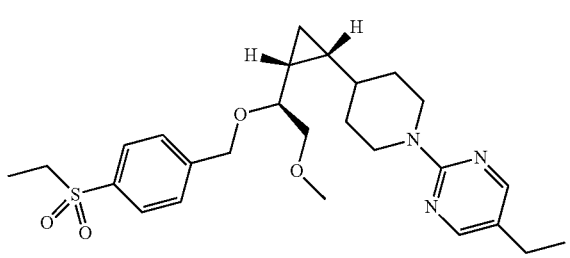

67

To a solution of the product of example 66, step G (66 mg, 0.139 mmol) in DMSO (1.4 mL) were added ethanesulfinic acid, sodium salt (24 mg, 0.209 mmol), copper trifluoromethanesulfonate benzene complex (14 mg, 0.029 mmol) and N,N'-dimethylethylene diamine (4.9 mg, 0.056 mmol), and the solution was stirred at 120° C. for 15 h. The mixture was cooled to RT and diluted with EtOAc. The layer was washed with $H_2O$ (×3), brine, dried over anhydrous $MgSO_4$, filtered, and concentrated under vacuum to leave a residue which was purified by column chromatography on silica (elution with 1:1 hexane:ethyl acetate) to yield the title compound. MS (ESI) m/z 488 [M+H]$^+$. GPR119 Human EC50: 0.16 nM Examples 68-76

Preparation of 5-chloro-2-{4-[(1R,2R)-2-({[3,5-difluoro-4-(methylsulfonyl)benzyl]oxy}methyl)cyclopropyl]piperidin-1-yl}pyrimidine

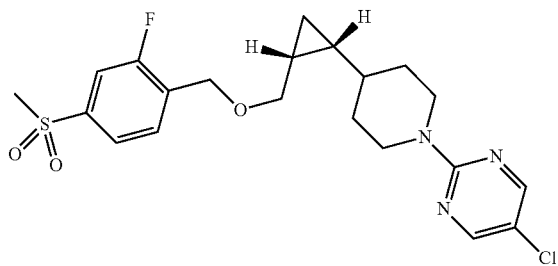

68

Step A: tert-butyl 4-[(1R,2R)-2-({[2-fluoro-4-(methylthio)benzyl]oxy}methyl)cyclopropyl]piperidine-1-carboxylate

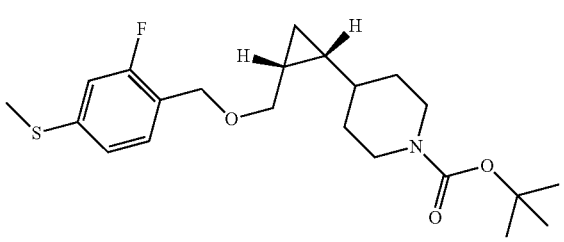 [SMILES: CSc1ccc(COC[C@@H]2C[C@@H]2C2CCN(C(=O)OC(C)(C)C)CC2)c(F)c1]

This compound was prepared from intermediate 13, according to the procedures described in example 33 (step A). $^1$H NMR (500 MHz, CDCl$_3$) δ 7.31 (m, 1H), 7.03 (dd, 1H), 6.95 (dd, 1H), 4.58 (d, 1H), 4.49 (d, 1H), 4.19-3.96 (br m, 2H), 3.62 (dd, 1H), 3.42-3.37 (m, 1H), 2.71-2.57 (m, 2H), 2.50 (s, 3H), 1.84 (d, 1H), 1.71 (d, 1H), 1.48 (s, 9H), 1.36-1.18 (m, 3H), 0.94-0.84 (m, 1H), 0.76-0.64 (m, 2H), 0.03-0.00 (m, 1H).

Step B: tert-butyl 4-[(1R,2R)-2-({[2-fluoro-4-(methylsulfonyl)benzyl]oxy}methyl)cyclopropyl]piperidine-1-carboxylate

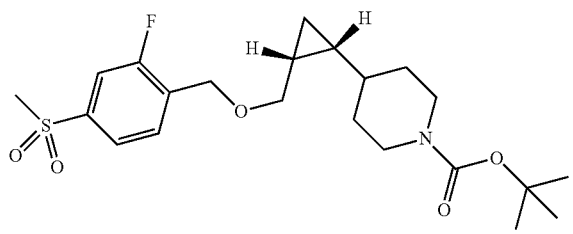 [SMILES: CC(C)(C)OC(=O)N1CCC([C@H]2C[C@H]2COCc2ccc(S(C)(=O)=O)cc2F)CC1]

This compound was prepared from the product of step A, according to the procedures described in intermediate 5 (step D). $^1$H NMR (500 MHz, CDCl$_3$) δ 7.78 (dd, 1H), 7.71 (m, 1H), 7.66 (dd, 1H), 4.71 (d, 1H), 4.64 (d, 1H), 4.18-4.00 (br m, 2H), 3.67-3.63 (m, 1H), 3.57-3.52 (m, 1H), 3.09 (s, 3H), 2.75-2.60 (m, 2H), 1.83 (d, 1H), 1.75 (d, 1H), 1.49 (s, 9H), 1.31-1.22 (m, 3H), 0.99-0.90 (m, 1H), 0.82-0.70 (m, 2H), 0.10-0.05 (m, 1H).

Step C: 4-[(1R,2R)-2-({[2-fluoro-4-(methylsulfonyl)benzyl]oxy}methyl)cyclopropyl]piperidine trifluoroacetate

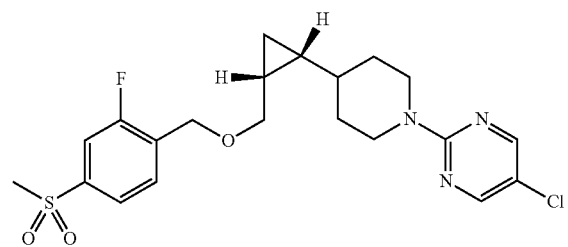 [SMILES: CS(=O)(=O)c1ccc(COC[C@@H]2C[C@@H]2C2CCN(c3ncc(Cl)cn3)CC2)c(F)c1]

This compound was prepared from the product of step B, according to the procedure described in intermediate 7 (step A). $^1$H NMR (500 MHz, CDCl$_3$) δ 7.78 (dd, 1H), 7.70-7.65 (m, 2H), 4.64 (q, 2H), 4.64 (d, 1H), 3.79-3.73 (m, 1H), 3.46-3.33 (m, 3H), 3.10 (s, 3H), 2.92-2.78 (m, 2H), 2.15 (d, 1H), 1.97 (d, 1H), 1.79-1.69 (m, 2H), 1.36-1.27 (m 2H), 1.14-1.05 (m, 1H), 0.85-0.00 (m, 2H), 0.10-0.06 (m, 1H).

Step D: 5-chloro-2-{4-[(1R,2R)-2-({[3,5-difluoro-4-(methylsulfonyl)benzyl]oxy}methyl)cyclopropyl]piperidin-1-yl}pyrimidine This compound was prepared from the product of step D, and 2,5-dichloropyrimidine according to the procedure described in example 1. $^1$H NMR (500 MHz, CDCl$_3$) δ 8.23 (s, 2H), 7.78 (dd, 1H), 7.72 (m, 1H), 7.67 (dd, 1H), 4.75-4.61 (m, 4H), 3.72-3.68 (m, 1H), 3.58-3.53 (m, 1H), 3.09 (s, 3H), 2.91-2.79 (m, 2H), 1.95 (d, 1H), 1.80 (d, 1H), 1.43-1.33 (m, 2H), 1.31-1.23 (m 1H), 1.13-1.03 (m, 1H), 0.83-0.72 (m, 2H), 0.13-0.08 (m, 1H). MS (ESI) m/z 454 [M+H]$^+$.

GPR119 Human EC50: 0.18 nM

The Examples in Table 12 were synthesized according to the method described in the prior example 82 employing the appropriate 2-chloropyrimidine, or chloropyrazine reagent.

TABLE 12

| Example # | Chemical Structure | Observed Mass | GPR119 Human EC$_{50}$ |
|---|---|---|---|
| 69 | 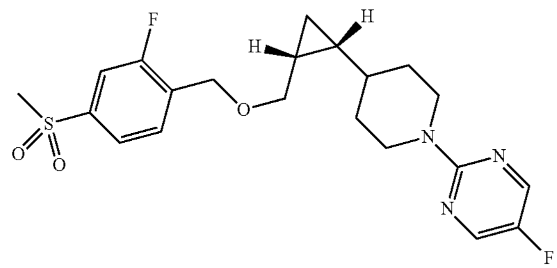 [SMILES: CS(=O)(=O)c1ccc(COC[C@@H]2C[C@@H]2C2CCN(c3ncc(F)cn3)CC2)c(F)c1] | 438 [M + H]$^+$ | 2.4 nM |
| 70 | 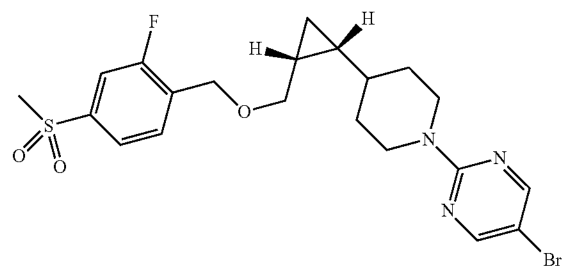 [SMILES: CS(=O)(=O)c1ccc(COC[C@@H]2C[C@@H]2C2CCN(c3ncc(Br)cn3)CC2)c(F)c1] | 498/500 [M + H]$^+$ | 0.19 nM |
| 71 | 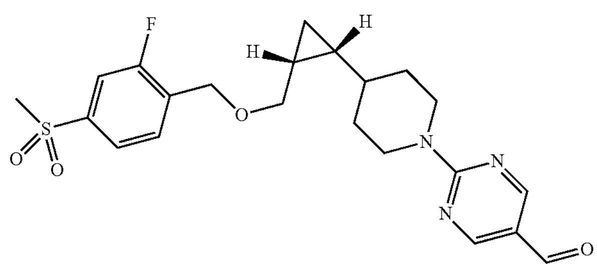 [SMILES: CS(=O)(=O)c1ccc(COC[C@@H]2C[C@@H]2C2CCN(c3ncc(C=O)cn3)CC2)c(F)c1] | 448 [M + H]$^+$ | 13.6 nM |
| 72 | 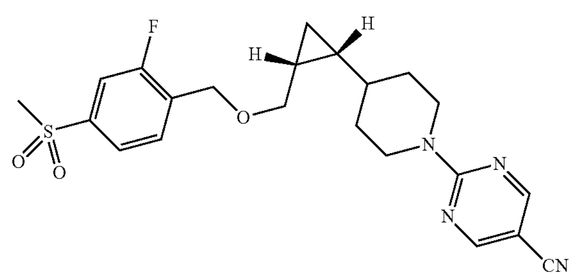 [SMILES: CS(=O)(=O)c1ccc(COC[C@@H]2C[C@@H]2C2CCN(c3ncc(C#N)cn3)CC2)c(F)c1] | 445 [M + H]$^+$ | 9.3 nM |
| 73 | 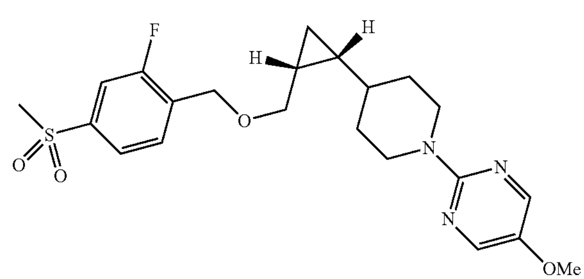 [SMILES: COc1cnc(N2CCC([C@H]3C[C@H]3COCc3ccc(S(C)(=O)=O)cc3F)CC2)nc1] | 450 [M + H]$^+$ | 4.5 nM |

TABLE 12-continued

| Example # | Chemical Structure | Observed Mass | GPR119 Human EC$_{50}$ |
|---|---|---|---|
| 74 | 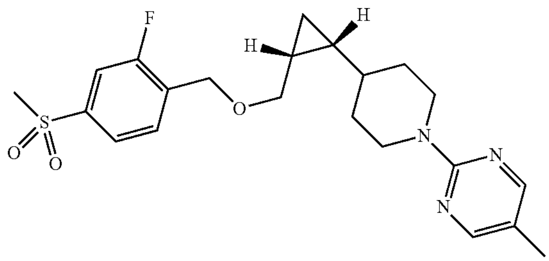 | 434 [M + H]$^+$ | 4.3 nM |
| 75 | 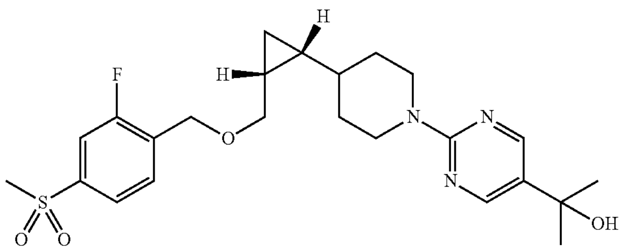 [SMILES: CC(C)(O)c1cnc(N2CCC([C@H]3C[C@H]3COCc3ccc(S(C)(=O)=O)cc3F)CC2)nc1] | 478 [M + H]$^+$ | 25 nM |
| 76 | 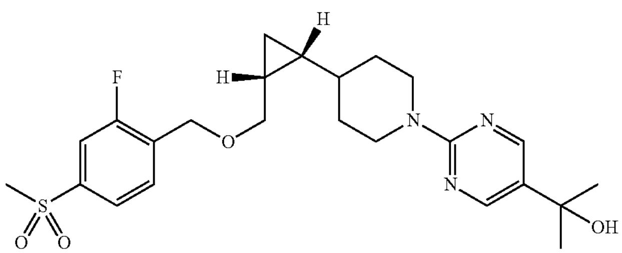 [SMILES: CC(C)(O)c1cnc(N2CCC([C@H]3C[C@H]3COCc3ccc(S(C)(=O)=O)cc3F)CC2)nc1] | 478 [M + H]$^+$ | 15 nM |

Example 77

Preparation of 2-{4-[(1R,2R)-2-({[2-fluoro-4-(methylsulfonyl)benzyl]oxy}methyl)cyclopropyl]piperidin-1-yl}-5-(methoxymethyl)pyrimidine

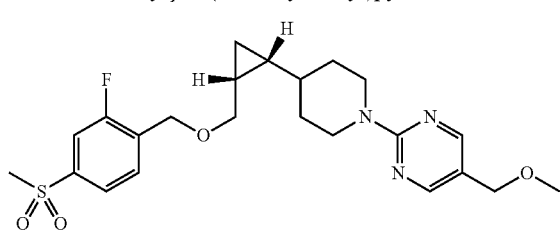

77

Step A: (2-{4-[(1R,2R)-2-({[2-fluoro-4-(methylsulfonyl)benzyl]oxy}methyl)cyclopropyl]piperidin-1-yl}pyrimidin-5-yl)methanol

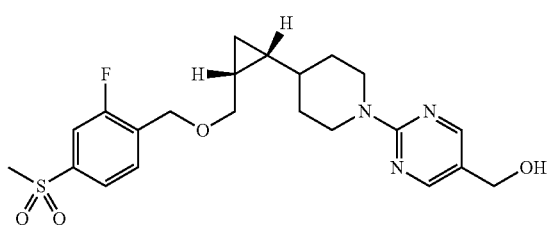 [SMILES: CS(=O)(=O)c1ccc(COC[C@@H]2C[C@@H]2C2CCN(c3ncc(CO)cn3)CC2)c(F)c1]

Example 85 (26 mg, 0.058 mmol) was dissolved in MeOH (4 mL) at RT under N$_2$ and NaBH$_4$ (8.61 mg, 0.23 mmol) was added. The mixture was stirred at RT for 10 mins then the mixture was diluted with EtOAc, washed with water, dried over MgSO$_4$, filtered and evaporated in vacuo to yield the title compound. MS (ESI) m/z 450 [M+H]$^+$.

Step B: 2-{4-[(1R,2R)-2-({[2-fluoro-4-(methylsulfonyl)benzyl]oxy}methyl)cyclopropyl]piperidin-1-yl}-5-(methoxymethyl)pyrimidine

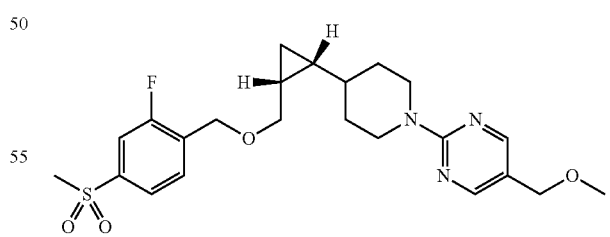

The product of step A (20 mg, 0.044 mmol) was dissolved in acetonitrile (4 mL) at RT under N$_2$ and sodium hydride (10 mg of a 60% dispersion in oil, 0.25 mmol) was added followed by CH$_3$I (31.6 mg, 0.222 mmol). The mixture was stirred at RT overnight. The mixture was diluted with EtOAc, washed with sat. NH$_4$Cl, dried over MgSO$_4$, filtered and evaporated in vacuo. The crude material was purified by preparative thin-layer chromatography (70% EtOAc in hexane) to yield the title compound. ¹H NMR (500 MHz, CDCl₃) δ 8.30 (s, 2H), 7.78 (dd, 1H), 7.73 (m, 1H), 7.67 (dd, 1H), 4.80-4.64 (m, 4H), 4.28 (s, 2H), 3.71 (dd, 1H), 3.61-3.54 (m, 1H), 3.37 (s, 3H), 3.08 (s, 3H), 2.93-2.80 (m, 2H), 1.96 (d, 1H), 1.85 (d, 1H), 1.43-1.22 (m, 3H), 1.15-1.04 (m, 1H), 0.94-0.71 (m, 2H), 0.12-0.08 (m, 1H). MS (ESI) m/z 464 [M+H]⁺. GPR119 Human EC50: 1.6 nM

Example 78

Preparation of 4-[(1R,2R)-2-({[2-fluoro-4-(methylsulfonyl)benzyl]oxy}methyl)cyclopropyl]-1-(3-isopropyl-1,2,4-oxadiazol-5-yl)piperidine

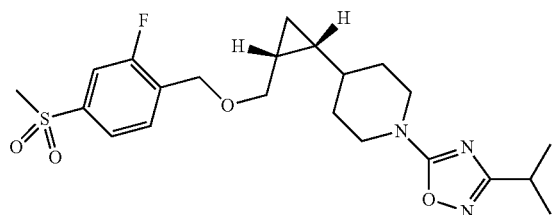

78

Step A: 4-[(1R,2R)-2-({[2-fluoro-4-(methylsulfonyl)benzyl]oxy}methyl)cyclopropyl]piperidine trifluoroacetate

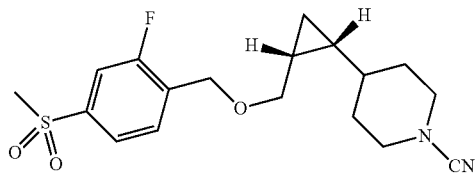 [SMILES: CS(=O)(=O)c1ccc(COC[C@@H]2C[C@@H]2C2CCN(C#N)CC2)c(F)c1]

This compound was prepared from the product of example 68 (step A) using the procedure outlined for intermediate 9 (step C). ¹H NMR (500 MHz, CDCl₃) δ 7.78 (dd, 1H), 7.71-7.64 (m, 2H), 4.66 (q, 2H), 3.68 (dd, 1H), 3.49-3.39 (m, 3H), 3.09 (s, 3H), 3.03-2.91 (m, 2H), 1.94 (d, 1H), 1.81 (d, 1H), 1.59-1.49 (m, 2H), 1.32-1.24 (m, 1H), 0.97-0.88 (m, 1H), 0.83-0.74 (m, 2H), 0.07-0.04 (m, 1H).

Step B: 4-[(1R,2R)-2-({[2-fluoro-4-(methylsulfonyl)benzyl]oxy}methyl)cyclopropyl]-1-(3-isopropyl-1,2,4-oxadiazol-5-yl)piperidine

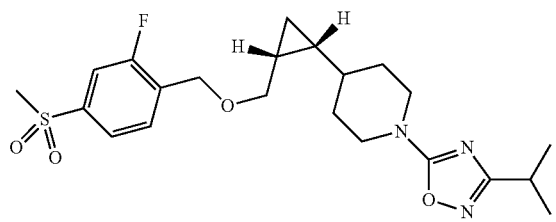 [SMILES: CC(C)c1noc(N2CCC([C@H]3C[C@H]3COCc3ccc(S(C)(=O)=O)cc3F)CC2)n1]

This compound was prepared from the product of step A and N'-hydroxy-2-methylpropanimidamide according to the procedure for example 24. ¹H NMR (500 MHz, CDCl₃) δ 7.78 (dd, 1H), 7.71 (m, 1H), 7.61 (dd, 1H), 4.67 (q, 2H), 4.18-4.09 (m, 2H), 3.71 (dd, 1H), 3.51 (dd, 1H), 3.09 (s, 3H), 3.07-2.95 (m, 2H), 2.90 (sept, 1H), 1.99 (d, 1H), 1.86 (d, 1H), 1.53-1.43 (m, 2H), 1.31 (d, 6H), 1.32-1.24 (m, 1H), 1.09-1.00 (m, 1H), 0.83-0.74 (m, 2H), 0.07-0.04 (m, 1H). MS (ESI) m/z 452 [M+H]⁺. GPR119 Human EC50: 4.9 nM

Example 79

Preparation of tert-butyl 4-{(1R,2R)-2-[({2-fluoro-4-[(2-hydroxyethyl)sulfonyl]benzyl}oxy)methyl]cyclopropyl}piperidine-1-carboxylate

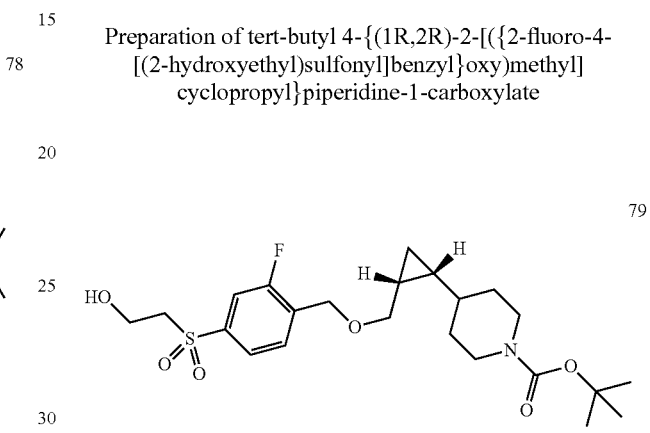

79

Step A: tert-butyl 4-{(1R,2R)-2-[({2-fluoro-4-[(2-hydroxyethyl)thio]benzyl}oxy)methyl]cyclopropyl}piperidine-1-carboxylate

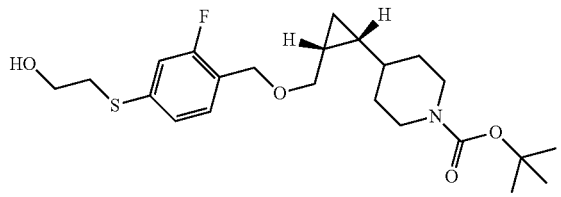 [SMILES: CC(C)(C)OC(=O)N1CCC([C@H]2C[C@H]2COCc2ccc(SCCO)cc2F)CC1]

To a solution of intermediate 12 (415 mg, 0.938 mmol) in 1,4-dioxane (10 mL) was added Hunig's base (0.328 mL, 1.876 mmol). The mixture was evacuated and backfilled with N₂ (3×). Pd₂dba₃ (25.8 mg, 0.028 mmol), 4,5-bis(diphenylphosphino)-9,9-dimethylxanthene (54.3 mg, 0.094 mmol) and 2-mercaptoethanol (73.3 mg, 0.94 mmol) were added sequentially and the mixture was degassed (2×). The mixture was heated to reflux for 2 h, the mixture cooled and evaporated. The residue was purified by silica gel column chromatography (gradient 15~40% EtOAC in hexane) to yield the title compound. ¹H NMR (500 MHz, CDCl₃) δ 7.33 (m, 1H), 7.15 (dd, 1H), 7.08 (dd, 1H), 4.59 (d, 1H), 4.48 (d, 1H), 4.18-3.96 (m, 2H), 3.82-3.77 (m, 2H), 3.41-3.36 (m, 1H), 3.15 (t, 2H), 2.70-2.63 (m, 1H), 1.82 (d, 1H), 1.79 (d, 1H), 1.48 (s, 9H), 1.36-1.17 (m, 3H), 0.92-0.83 (m, 1H), 0.77-0.64 (m, 2H), 0.04-0.00 (m, 1H).

Step B: tert-butyl 4-{(1R,2R)-2-[({2-fluoro-4-[(2-hydroxyethyl)sulfonyl]benzyl}oxy)methyl]cyclopropyl}piperidine-1-carboxylate

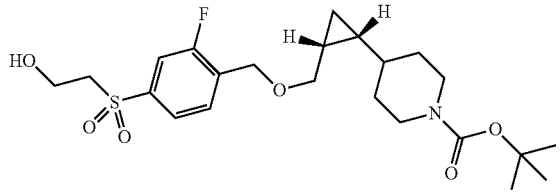 [SMILES: CC(C)(C)OC(=O)N1CCC([C@H]2C[C@H]2COCc2ccc(S(=O)(=O)CCO)cc2F)CC1]

This compound was prepared from the product of step A, according to the procedure described in intermediate 5 (step D). ¹H NMR (500 MHz, CDCl₃) δ 7.78-7.70 (m, 2H), 7.66 (dd, 1H), 4.71 (d, 1H), 4.63 (d, 1H), 4.17-3.98 (m, 4H), 3.68 (dd, 1H), 3.56-3.51 (m, 1H), 3.40 (t, 2H), 2.73-2.65 (m, 2H), 1.82 (d, 1H), 1.73 (d, 1H), 1.48 (s, 9H), 1.36-1.22 (m, 3H), 0.98-0.89 (m, 1H), 0.82-0.71 (m, 2H), 0.09-0.06 (m, 1H). MS (ESI) m/z 494 [M+Na]⁺. GPR119 Human EC50: 7.1 nM Examples 80-84

Preparation of 2-({4-[({(1R,2R))-2-[1-(5-chloropyrimidin-2-yl)piperidin-4-yl]cyclopropyl}methoxy)methyl]-3-fluorophenyl}sulfonyl)ethanol

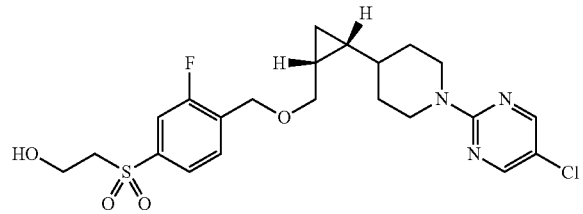 [SMILES: O=S(=O)(CCO)c1ccc(COC[C@@H]2C[C@@H]2C2CCN(c3ncc(Cl)cn3)CC2)c(F)c1]

Step A: 2-{[3-fluoro-4-({[(1R,2R)-2-piperidin-4-ylcyclopropyl]methoxy}methyl)phenyl]sulfonyl}ethanol

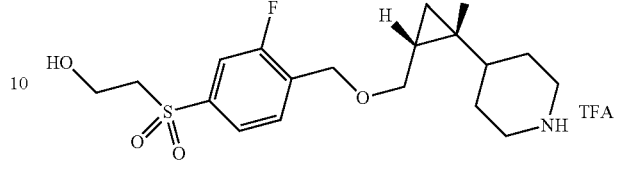

This compound was prepared from example 79 according to the procedure described in intermediate 7 (step A). ¹H NMR (500 MHz, CDCl₃) δ 9.25 (br s, 1H), 8.78 (br s, 1H), 7.77 (dd, 1H), 7.68-7.63 (m, 2H), 4.72 (d, 1H), 4.57 (d, 1H), 4.08-3.99 (m, 2H), 3.81 (dd, 1H), 3.43-3.37 (m, 2H), 3.37-3.27 (m, 2H), 2.90-2.79 (m, 1H), 2.79-2.69 (m, 1H), 2.15 (d, 1H), 1.94 (d, 1H), 1.75-1.60 (m, 2H), 1.37-1.27 (m 1H), 1.06-0.95 (m, 1H), 0.84-0.77 (m, 2H), 0.07-0.03 (m, 1H). MS (ESI) m/z 372 [M+H]⁺.

Step B: 2-({4-[({(1R,2R))-2-[1-(5-chloropyrimidin-2-yl)piperidin-4-yl]cyclopropyl}methoxy)methyl]-3-fluorophenyl}sulfonyl)ethanol

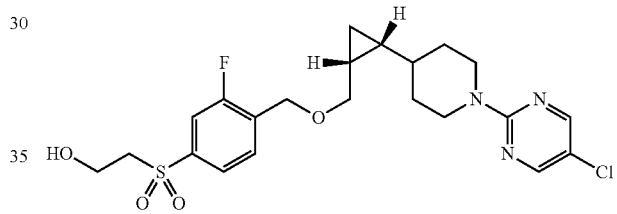

This compound was prepared from the product of step A, and 2,5-dichloropyrimidine according to the procedure described in example 1. ¹H NMR (500 MHz, CDCl₃) δ 8.23 (s, 2H), 7.79-7.72 (m, 2H), 7.66 (dd, 1H), 4.75-4.58 (m, 4H), 4.08-4.03 (m, 2H), 3.73 (dd, 1H), 3.57 (t, 1H), 3.40 (t, 2H), 2.92-2.84 (m, 1H), 2.84-2.71 (m 1H), 1.95 (d, 1H), 1.85 (d, 1H), 1.43-1.23 (m, 3H), 1.14-1.04 (m, 1H), 0.84-0.72 (m, 2H), 0.13-0.09 (m, 1H). MS (ESI) m/z 484 [M+H]⁺.
GPR119 Human EC50: 2.3 nM
The Examples in Table 13 were synthesized from example 79 according to the method described for example 80 employing the appropriate 2-chloropyrimidine reagent.

TABLE 13

| Example # | Chemical Structure | Observed Mass | GPR119 Human EC₅₀ |
|---|---|---|---|
| 81 | ![structure] | 528/530 [M + H]⁺ | 1.7 nM |

TABLE 13-continued

| Example # | Chemical Structure | Observed Mass | GPR119 Human EC$_{50}$ |
|---|---|---|---|
| 82 | 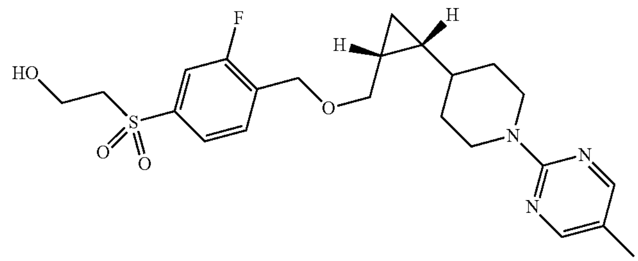 [SMILES: Cc1cnc(N2CCC([C@H]3C[C@H]3COCc3ccc(S(=O)(=O)CCO)cc3F)CC2)nc1] | 464 [M + H]$^+$ | 11.7 nM |
| 83 | 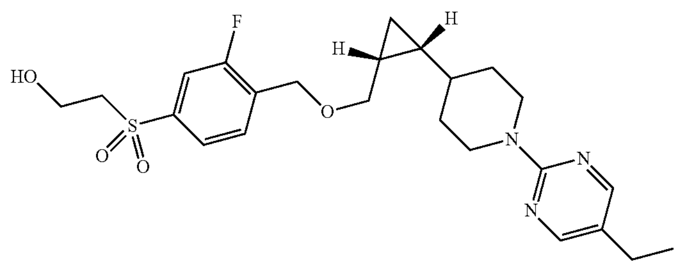 [SMILES: CCc1cnc(N2CCC([C@H]3C[C@H]3COCc3ccc(S(=O)(=O)CCO)cc3F)CC2)nc1] | 478 [M + H]$^+$ | 21 nM |
| 84 | 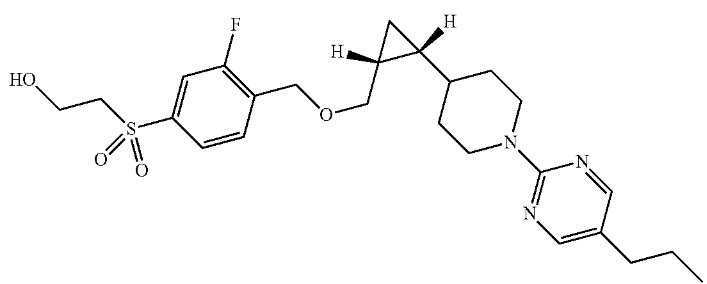 [SMILES: CCCc1cnc(N2CCC([C@H]3C[C@H]3COCc3ccc(S(=O)(=O)CCO)cc3F)CC2)nc1] | 492 [M + H]$^+$ | 1.3 nM |

Examples 85-90

Preparation of 2-[(3-fluoro-4-{[(((1R,2R)-2-{1-[5-(3-furyl)pyrimidin-2-yl]piperidin-4-yl}cyclopropyl)methoxy]methyl}phenyl)sulfonyl]ethanol

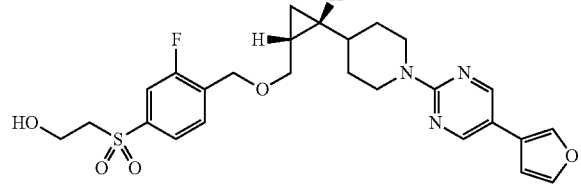

Example 81 (32 mg, 0.06 mmol), 3-furanboronic acid (10.16 mg, 0.09 mmol), Pd(dppf)Cl$_2$ (4 mg, 0.006 mmol) and 50% K$_3$PO$_4$ (0.2 mL) were dissolved in DMF (1.5 mL) and the mixture was microwaved at 90° C. for 1 h. The mixture was diluted with EtOAc, washed with sat. NH$_4$Cl, evaporated and purified by preparative thin layer chromatography (60% EtOAc in hexane) to yield the title compound. $^1$H NMR (500 MHz, CDCl$_3$) δ 8.44 (s, 2H), 7.79-7.72 (m, 2H), 7.68-7.64 (m, 2H), 7.50 (d, 1H), 6.62 (d, 1H), 4.81-4.71 (m, 2H), 4.68-4.62 (m, 2H), 4.07-4.03 (m, 2H), 3.78-3.72 (m, 1H), 3.58-3.53 (m, 1H), 3.43-3.38 (m, 2H), 2.92-2.86 (m, 1H), 2.83-2.77 (m, 1H), 1.96 (d, 1H), 1.86 (d, 1H), 1.46-1.22 (m, 3H), 1.14-1.04 (m, 1H), 0.83-0.72 (m, 2H), 0.14-0.08 (m, 1H). MS (ESI) m/z 516 [M+H]$^+$. GPR119 Human EC50: 3.8 nM The Examples in Table 14 were synthesized from intermediate 6, according to the method described for example 1 employing the appropriate 2-chloropyrimidine reagent.

TABLE 14
| Example # | Chemical Structure | Observed Mass | GPR119 Human EC$_{50}$ |
|---|---|---|---|
| 86 | 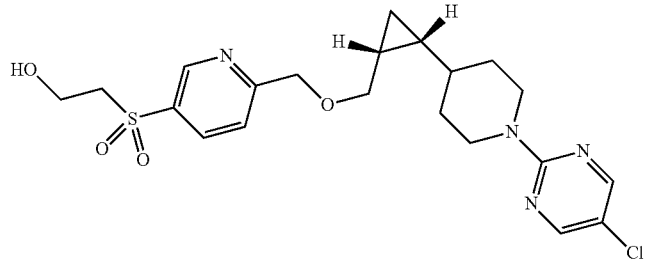 [SMILES: O=S(=O)(CCO)c1ccc(COC[C@@H]2C[C@@H]2C2CCN(c3ncc(Cl)cn3)CC2)nc1] | 467 [M + H]$^+$ | 22 nM |
| 87 | 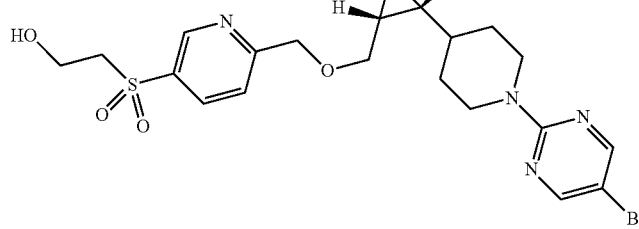 | 511/513 [M + H]$^+$ | 10.7 nM |
| 88 | 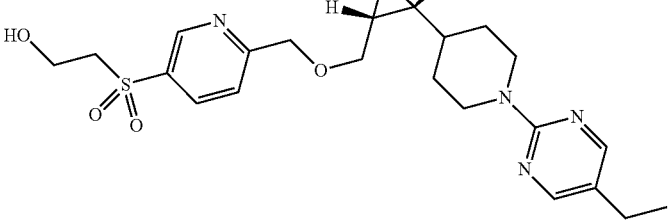 | 461 [M + H] | 17 nM |
| 89 | 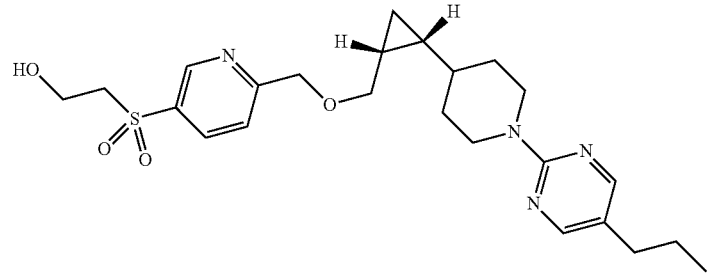 [SMILES: CCCc1cnc(N2CCC([C@H]3C[C@H]3COCc3ccc(S(=O)(=O)CCO)cn3)CC2)nc1] | 475 [M + H]$^+$ | 10 nM |
| 90 | 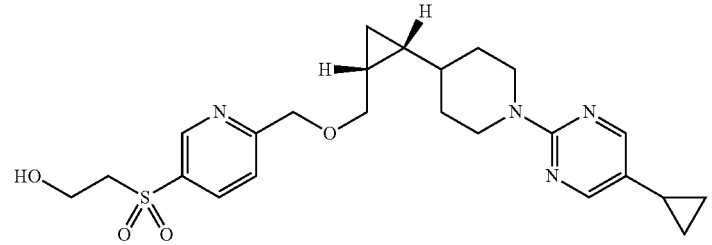 [SMILES: O=S(=O)(CCO)c1ccc(COC[C@@H]2C[C@@H]2C2CCN(c3ncc(C4CC4)cn3)CC2)nc1] | 473 [M + H]$^+$ | 23 nM |

Examples 91 and 92

Preparation of tert-butyl 4-(1R,2R)-2-[({4-[(2-oxo-propyl)thio]benzyl}oxy)methyl]cyclopropyl}piperidine-1-carboxylate and tert-butyl 4-(1R,2R)-2-[({4-[(2-hydroxy-2-methylpropyl)thio]benzyl}oxy)methyl]cyclopropyl}piperidine-1-carboxylate

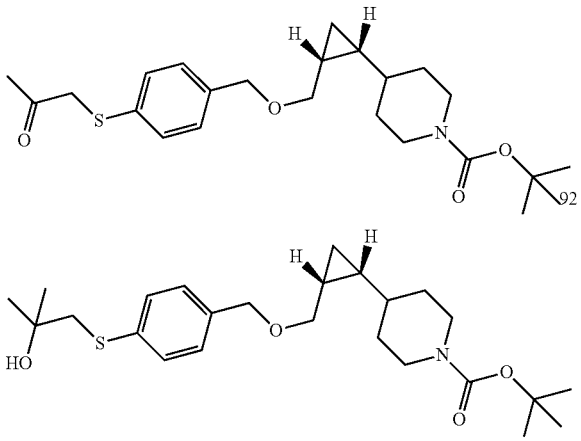

91

92

Step A: 4-(1R,2R)-2-[[[4-[(2-methoxy-2-oxoethyl)thio]phenyl]methoxy]methyl]cyclopropyl]-1-piperidinecarboxylic acid-1,1-dimethylethyl ester

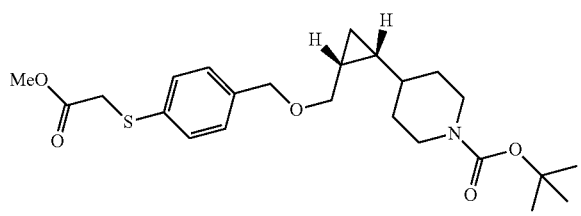 [SMILES: COC(=O)CSc1ccc(COC[C@@H]2C[C@@H]2C2CCN(C(=O)OC(C)(C)C)CC2)cc1]

This compound was prepared from intermediate 12 and methyl mercaptoacetate according to the procedure described in intermediate 6 (step A). $^1$H NMR (500 MHz, CDCl$_3$) δ 7.38 (m, 1H), 7.17 (dd, 1H), 7.12 (dd, 1H), 4.69 (d, 1H), 4.52 (d, 1H), 4.18-4.00 (br m, 2H), 3.77 (s, 3H), 3.69 (s, 2H), 3.61 (dd, 1H), 3.42 (t, 2H), 2.72-2.68 (m, 2H), 1.84 (d, 1H), 1.71 (d, 1H), 1.48 (s, 9H), 1.36-1.17 (m, 3H), 0.94-0.86 (m, 1H), 0.77-0.67 (m, 2H), 0.04-0.00 (m, 1H).

Step B: tert-butyl 4-(1R,2R)-2-[({4-[(2-oxopropyl)thio]benzyl}oxy)methyl]cyclopropyl}piperidine-1-carboxylate and tert-butyl 4-(1R,2R)-2-[({4-[(2-hydroxy-2-methylpropyl)thio]benzyl}oxy)methyl]cyclopropyl}piperidine-1-carboxylate

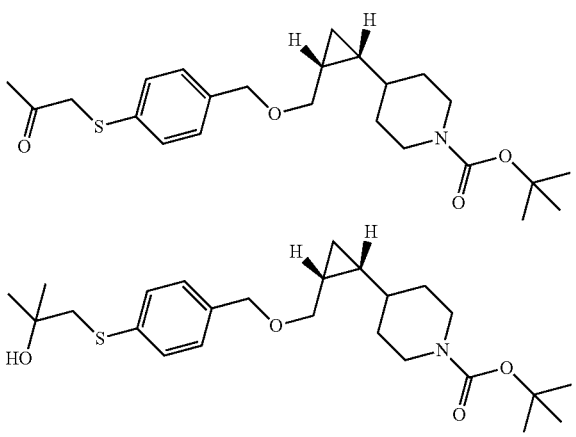

The product of step A (580 mg, 1.240 mmol) was dissolved in THF (10 mL) and the mixture was cooled to 0° C. Methylmagnesium chloride (2.067 mL of a 3.0M solution in THF, 6.20 mmol) was added dropwise. The mixture was warmed up to RT and quenched by the addition of MeOH and water. The mixture was extracted with EtOAc, and the organic phase was washed with water and brine, dried over MgSO$_4$, filtered and evaporated. The residue was purified by silica gel column chromatography (eluent: gradient 10~30% EtOAc in hexane) to yield the title compounds.

The less polar compound is tert-butyl 4-(1R,2R)-2-[({4-[(2-oxopropyl)thio]benzyl}oxy)methyl]cyclopropyl}piperidine-1-carboxylate $^1$H NMR (500 MHz, CDCl$_3$) δ 7.37-7.33 (m, 1H), 7.11 (dd, 1H), 7.04 (dd, 1H), 4.58 (d, 1H), 4.50 (d, 1H), 4.17-3.98 (br m, 2H), 3.72 (s, 2H), 3.61 (dd, 1H), 3.41 (t, 2H), 2.73-2.56 (br m, 2H), 2.31 (s, 3H), 1.84 (d, 1H), 1.71 (d, 1H), 1.48 (s, 9H), 1.38-1.18 (m, 3H), 0.95-0.86 (m, 1H), 0.77-0.65 (m, 2H), 0.04-0.00 (m, 1H). MS (ESI) m/z 474 [M+Na]$^+$. GPR119 Human EC50: 14.9 nM The more polar compound is tert-butyl 4-(1R,2R)-2-[({4-[(2-hydroxy-2-methylpropyl)thio]benzyl}oxy)methyl]cyclopropyl}piperidine-1-carboxylate $^1$H NMR (500 MHz, CDCl$_3$) δ 7.34-7.29 (m, 1H), 7.18 (dd, 1H), 7.11 (dd, 1H), 4.59 (d, 1H), 4.49 (d, 1H), 4.18-3.98 (br m, 2H), 3.63 (dd, 1H), 3.39 (t, 2H), 3.14 (s, 2H), 2.70-2.63 (m, 2H), 1.84 (d, 1H), 1.70 (d, 1H), 1.48 (s, 9H), 1.15 (s, 6H), 1.30-1.17 (m, 3H), 0.93-0.84 (m, 1H), 0.76-0.66 (m, 2H), 0.04-0.00 (m, 1H). MS (ESI) m/z 468 [M+H]$^+$. GPR119 Human EC50: 20.3 nM

Example 93

Preparation of tert-butyl 4-(1R,2R)-2-[({4-[(2R/S-hydroxypropyl)thio]benzyl}oxy)methyl]cyclopropyl}piperidine-1-carboxylate

93

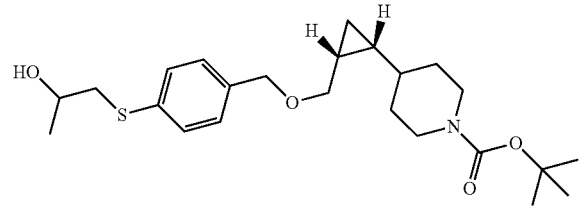

This compound was prepared from intermediate 12 and 1-mercapto-2-propanol according to the procedure described in intermediate 6 (step A). $^1$H NMR (500 MHz, CDCl$_3$) δ 7.36-7.31 (m, 1H), 7.16 (dd, 1H), 7.09 (dd, 1H), 4.59 (d, 1H), 4.49 (d, 1H), 4.16-3.98 (br m, 2H), 3.96-3.89 (m, 1H), 3.67-3.61 (m, 1H), 3.39 (t, 1H), 3.16-3.10 (m, 1H), 2.96-2.88 (m, 1H), 2.71-2.63 (m, 1H), 1.83 (d, 1H), 1.70 (d, 1H), 1.49 (s, 9H), 1.32 (d, 3H), 1.32-1.18 (m, 3H), 0.94-0.84 (m, 1H), 0.77-0.66 (m, 2H), 0.04-0.00 (m, 1H). MS (ESI) m/z 454 [M+H]$^+$. GPR119 Human EC50: 22 nM

Examples 94-98

Preparation of tert-butyl 4-(1R,2R)-2-[({4-[(2R/S-hydroxypropyl)sulfonyl]benzyl}oxy)methyl]cyclopropyl}piperidine-1-carboxylate

94

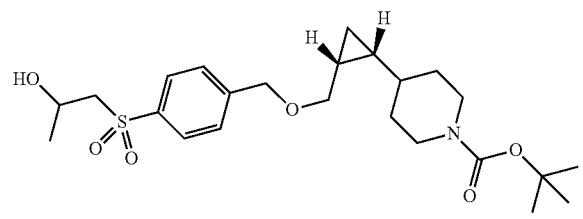

This compound was prepared from example 93, according to the procedure described in intermediate 5 (step D). ¹H NMR (500 MHz, CDCl₃) δ 7.78-7.71 (m, 2H), 7.64 (dd, 1H), 4.71 (d, 1H), 4.64 (d, 1H), 4.41-4.33 (m, 1H), 4.18-4.00 (m, 2H), 3.66 (dd, 1H), 3.53 (t, 1H), 3.37-3.26 (m, 2H), 3.20 (dd, 2H), 2.74-2.65 (m, 1H), 1.83 (d, 1H), 1.74 (d, 1H), 1.48 (s, 9H), 1.38-1.22 (m, 6H), 0.99-0.90 (m, 1H), 0.82-0.70 (m, 2H), 0.09-0.05 (m, 1H). MS (ESI) m/z 486 [M+H]⁺.

GPR119 Human EC50: 9.5 nM

The Examples in Table 15 were synthesized from example 94 according to the method described for example 80 employing the appropriate 2-chloropyrimidine or 2-chloropyrazine reagent.

TABLE 15

| Example # | Chemical Structure | Observed Mass | GPR119 Human EC$_{50}$ |
|---|---|---|---|
| 95 | 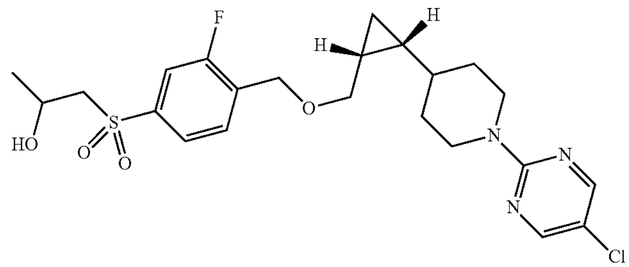 [SMILES: CC(O)CS(=O)(=O)c1ccc(COC[C@@H]2C[C@@H]2C2CCN(c3ncc(Cl)cn3)CC2)c(F)c1] | 498 [M + H]⁺ | 2.4 nM |
| 96 | 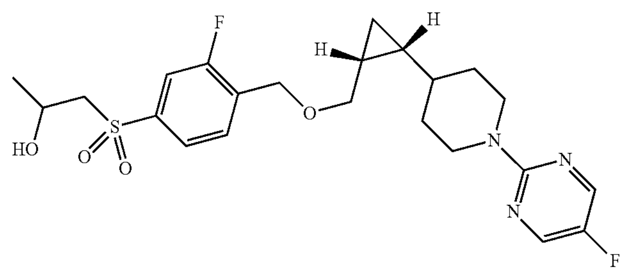 [SMILES: CC(O)CS(=O)(=O)c1ccc(COC[C@@H]2C[C@@H]2C2CCN(c3ncc(F)cn3)CC2)c(F)c1] | 482 [M + H]⁺ | 21.9 nM |
| 97 | 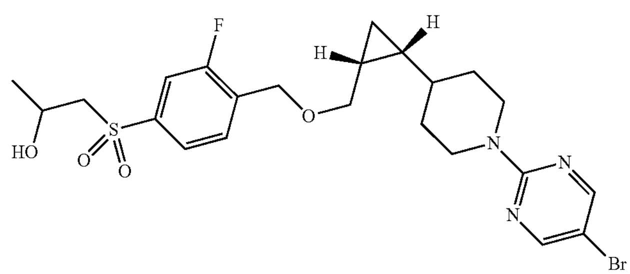 [SMILES: CC(O)CS(=O)(=O)c1ccc(COC[C@@H]2C[C@@H]2C2CCN(c3ncc(Br)cn3)CC2)c(F)c1] | 542/544 [M + H]⁺ | 1.6 nM |
| 98 | 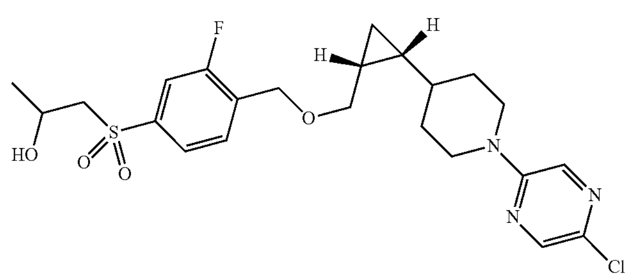 [SMILES: CC(O)CS(=O)(=O)c1ccc(COC[C@@H]2C[C@@H]2C2CCN(c3cnc(Cl)cn3)CC2)c(F)c1] | 498 [M + H]⁺ | 7.3 nM |

Examples 99-123

Preparation of 3-{4-[({(1R,2R)-2-[1-(5-ethylpyrimidin-2-yl)piperidin-4-yl]cyclopropyl}methoxy)methyl]-3-fluorophenyl}pyridazine

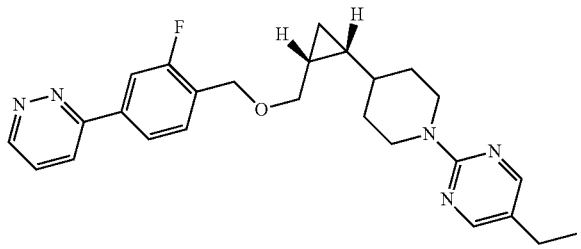

A mixture of intermediate 16 (100 mg, 0.2 mmol), 3-chloropyridazine hydrochloride (46.2 mg, 0.4 mmol), and 2M $Na_2CO_3$ (0.22 mL, 0.44 mmol) in 1,4-dioxane (3 mL) was degassed by passing nitrogen through for 10 mins. $Pd(PPh_3)_4$ (12 mg, 0.01 mmol) added and nitrogen bubbled through for a further 5 mins. Mixture heated in a microwave reactor at 140° C. for 1 hour. Mixture filtered and filtrate purified by mass-directed reverse phase preparative HPLC (C18: gradient 10-100% $CH_3CN$ in water+0.05% TFA), to yield the title compound 27 mg (Yield 30%). $^1$H NMR (500 MHz, $CDCl_3$) δ 9.21 (d, J 4.4 Hz, 1H), 7.91-7.86 (m, 3H), 7.64-7.59 (m, 4H), 4.75-4.65 (m, 4H), 3.71 (dd, J 10.0 & 6.4 Hz, 1H), 3.53 (t, J 9.6 Hz, 1H), 2.89-2.79 (m, 2H), 2.01 (d, J 13.2 Hz, 1H), 1.84 (d, J 12.9 Hz, 1H), 1.44-1.35 (m, 2H), 1.30-1.24 (m, 1H), 1.21 (t, J 7.5 Hz, 3H), 1.12-1.03 (m, 1H), 0.81-0.71 (m, 2H), 0.12-0.07 (m, 1H). MS (ESI) m/z 448 [M+H]$^+$. GPR119 Human EC50: 0.1 nM The Examples in Table 16 were synthesized from intermediates, 16, 17, and 18 according to the method described for example 99 employing the appropriate heteroaryl halide reagent.

TABLE 16

| Example # | Chemical Structure | Observed Mass | GPR119 Human EC$_{50}$ |
|---|---|---|---|
| 100 | 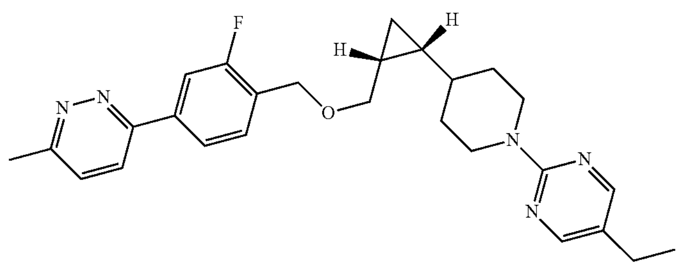 [SMILES: CCc1cnc(N2CCC([C@H]3C[C@H]3COCc3ccc(-c4ccc(C)nn4)cc3F)CC2)nc1] | 462 [M + H]$^+$ | 1.0 nM |
| 101 | 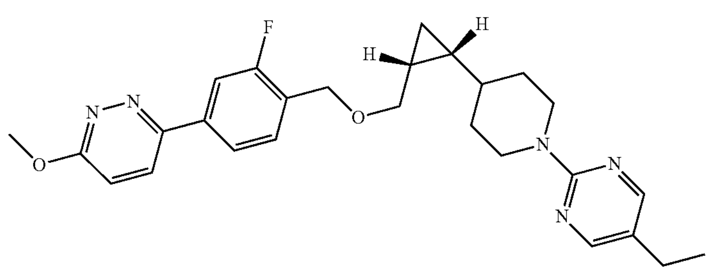 [SMILES: CCc1cnc(N2CCC([C@H]3C[C@H]3COCc3ccc(-c4ccc(OC)nn4)cc3F)CC2)nc1] | 478 [M + H]$^+$ | 0.8 nM |
| 102 | 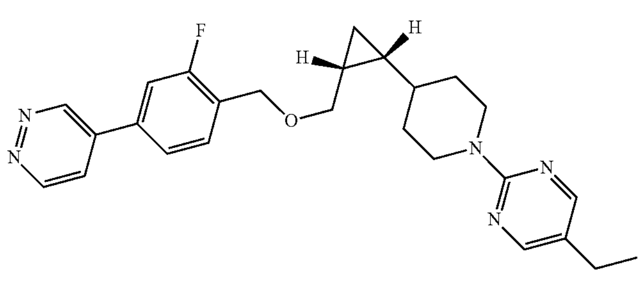 [SMILES: CCc1cnc(N2CCC([C@H]3C[C@H]3COCc3ccc(-c4ccnnc4)cc3F)CC2)nc1] | 448 [M + H]$^+$ | 0.6 nM |

TABLE 16-continued

| Example # | Chemical Structure | Observed Mass | GPR119 Human EC$_{50}$ |
|---|---|---|---|
| 103 | 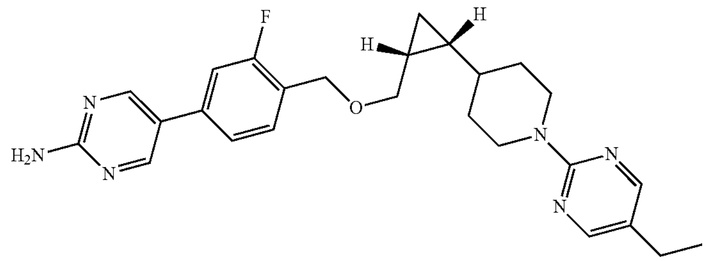 [SMILES: CCc1cnc(N2CCC([C@H]3C[C@H]3COCc3ccc(-c4cnc(N)nc4)cc3F)CC2)nc1] | 463 [M + H]$^+$ | 2.5 nM |
| 104 | 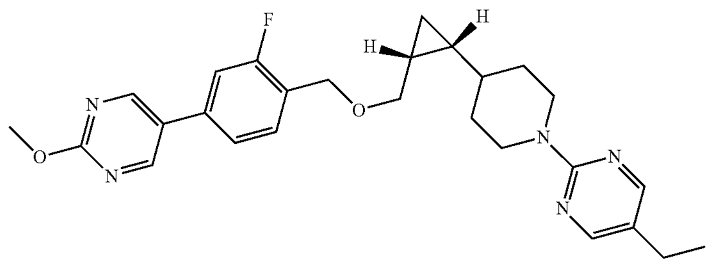 | 478 [M + H]$^+$ | 8.8 nM |
| 105 | 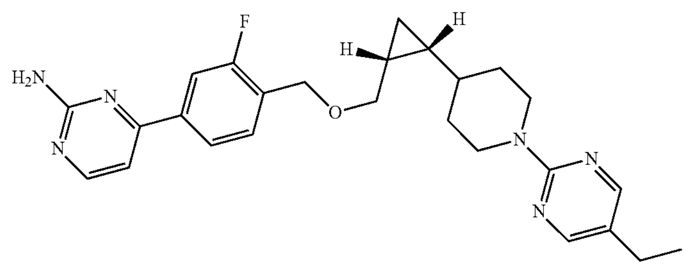 [SMILES: CCc1cnc(N2CCC([C@H]3C[C@H]3COCc3ccc(-c4ccnc(N)n4)cc3F)CC2)nc1] | 463 [M + H]$^+$ | 10.8 nM |
| 106 | 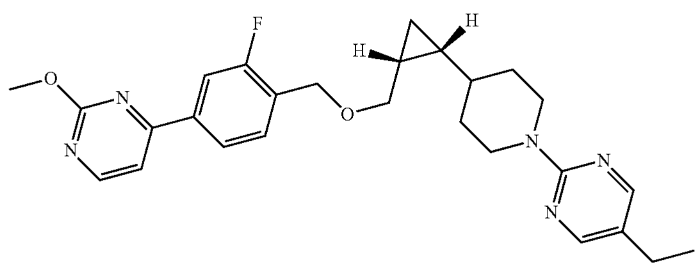 [SMILES: CCc1cnc(N2CCC([C@H]3C[C@H]3COCc3ccc(-c4ccnc(OC)n4)cc3F)CC2)nc1] | 478 [M + H]$^+$ | 2.9 nM |
| 107 | 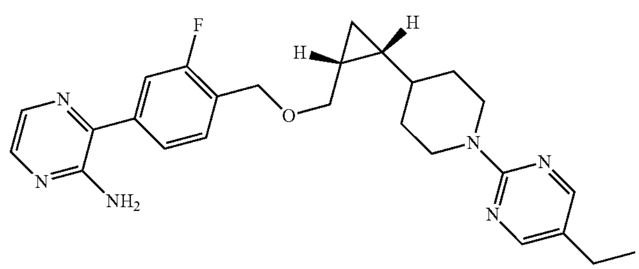 [SMILES: CCc1cnc(N2CCC([C@H]3C[C@H]3COCc3ccc(-c4nccnc4N)cc3F)CC2)nc1] | 463 [M + H]$^+$ | 2.0 nM |
| 108 | 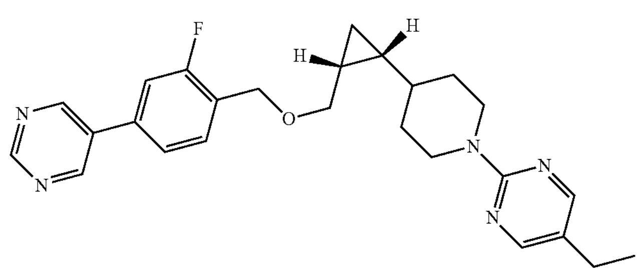 | 448 [M + H]$^+$ | 1.1 nM |

TABLE 16-continued

| Example # | Chemical Structure | Observed Mass | GPR119 Human EC$_{50}$ |
|---|---|---|---|
| 109 | 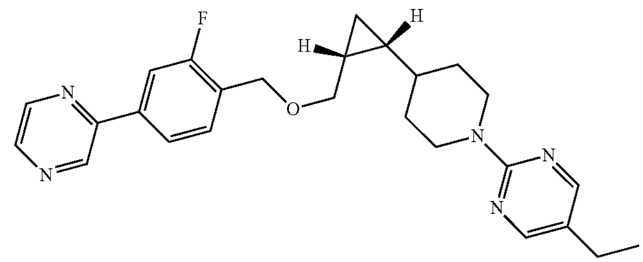 [SMILES: CCc1cnc(N2CCC([C@H]3C[C@H]3COCc3ccc(-c4cnccn4)cc3F)CC2)nc1] | 448 [M + H]$^+$ | 2.3 nM |
| 110 | 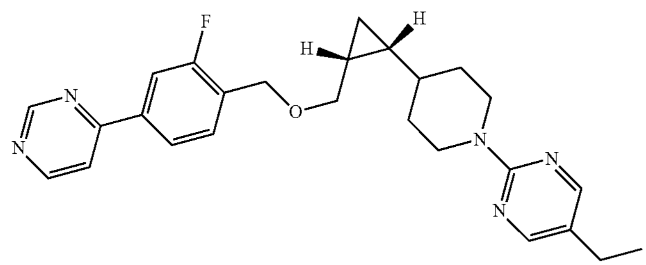 [SMILES: CCc1cnc(N2CCC([C@H]3C[C@H]3COCc3ccc(-c4ccncn4)cc3F)CC2)nc1] | 448 [M + H]$^+$ | 1.5 nM |
| 111 | 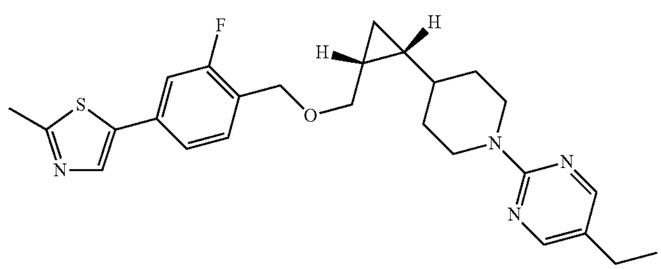 [SMILES: CCc1cnc(N2CCC([C@H]3C[C@H]3COCc3ccc(-c4cnc(C)s4)cc3F)CC2)nc1] | 467 [M + H]$^+$ | 4.0 nM |
| 112 | 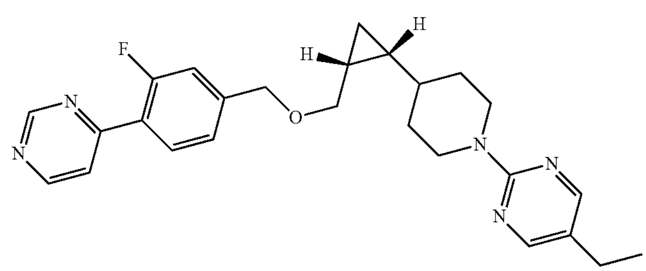 [SMILES: CCc1cnc(N2CCC([C@H]3C[C@H]3COCc3ccc(-c4ccncn4)c(F)c3)CC2)nc1] | 448 [M + H]$^+$ | 3.0 nM |
| 113 | 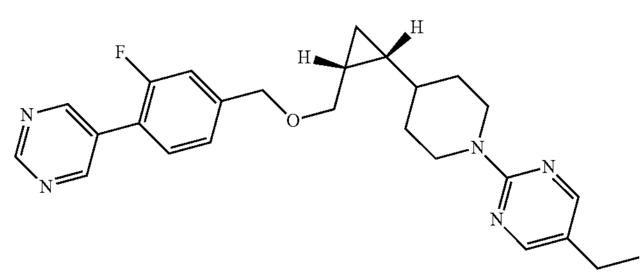 [SMILES: CCc1cnc(N2CCC([C@H]3C[C@H]3COCc3ccc(-c4cncnc4)c(F)c3)CC2)nc1] | 448 [M + H]$^+$ | 2.0 nM |

TABLE 16-continued

| Example # | Chemical Structure | Observed Mass | GPR119 Human EC$_{50}$ |
|---|---|---|---|
| 114 | 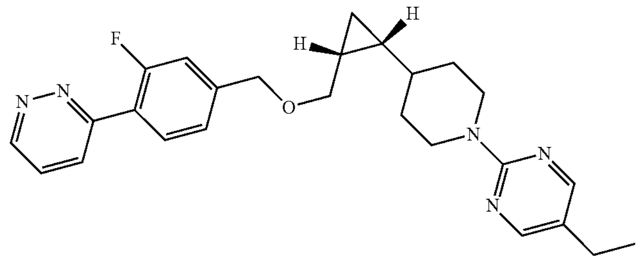 [SMILES: CCc1cnc(N2CCC([C@H]3C[C@H]3COCc3ccc(-c4cccnn4)c(F)c3)CC2)nc1] | 448 [M + H]$^+$ | 3.0 nM |
| 115 | 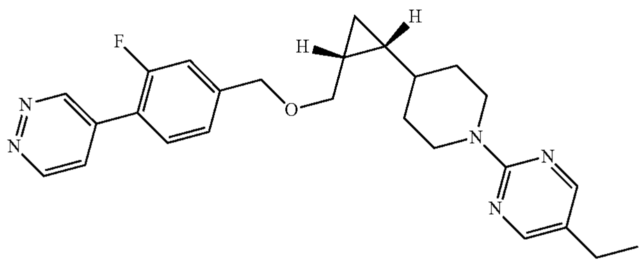 [SMILES: CCc1cnc(N2CCC([C@H]3C[C@H]3COCc3ccc(-c4ccnnc4)c(F)c3)CC2)nc1] | 448 [M + H]$^+$ | 1.0 nM |
| 116 | 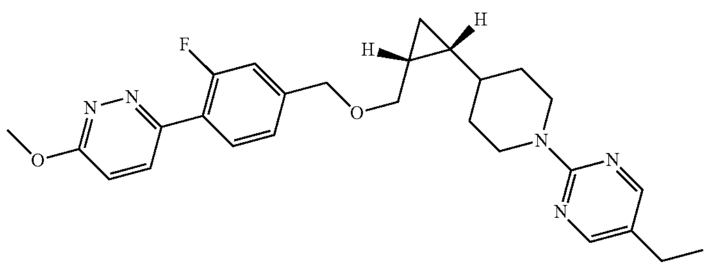 [SMILES: CCc1cnc(N2CCC([C@H]3C[C@H]3COCc3ccc(-c4ccc(OC)nn4)c(F)c3)CC2)nc1] | 478 [M + H]$^+$ | 0.9 nM |
| 117 | 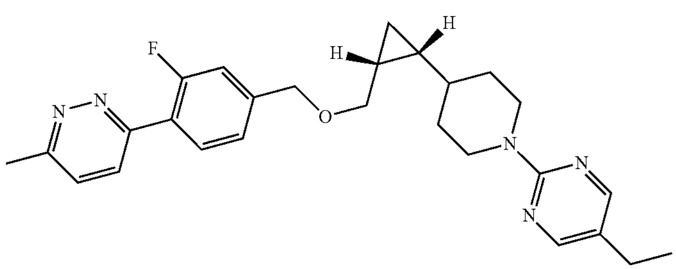 [SMILES: CCc1cnc(N2CCC([C@H]3C[C@H]3COCc3ccc(-c4ccc(C)nn4)c(F)c3)CC2)nc1] | 462 [M + H]$^+$ | 0.2 nM |
| 118 | 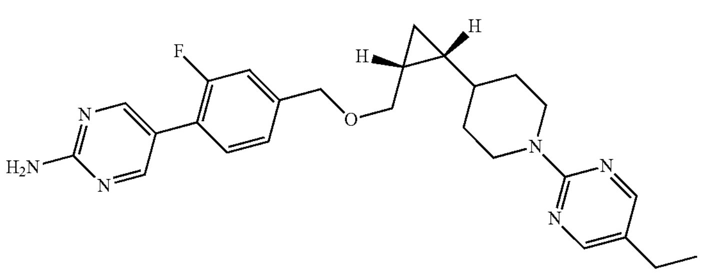 [SMILES: CCc1cnc(N2CCC([C@H]3C[C@H]3COCc3ccc(-c4cnc(N)nc4)c(F)c3)CC2)nc1] | 463 [M + H]$^+$ | 5.9 nM |
| 119 | 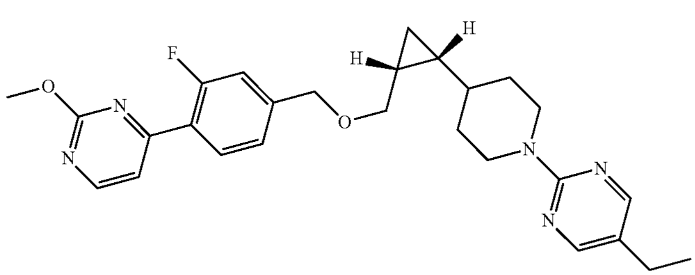 [SMILES: CCc1cnc(N2CCC([C@H]3C[C@H]3COCc3ccc(-c4ccnc(OC)n4)c(F)c3)CC2)nc1] | 478 [M + H]$^+$ | 4.8 nM |

TABLE 16-continued

| Example # | Chemical Structure | Observed Mass | GPR119 Human EC$_{50}$ |
|---|---|---|---|
| 120 | 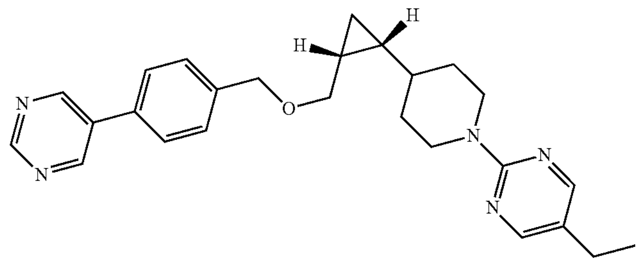 [SMILES: CCc1cnc(N2CCC([C@H]3C[C@H]3COCc3ccc(-c4cncnc4)cc3)CC2)nc1] | 430 [M + H]$^+$ | 1.9 nM |
| 121 | 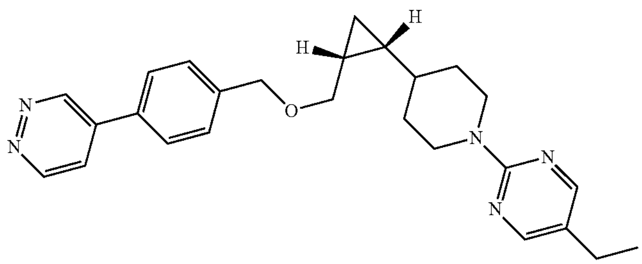 [SMILES: CCc1cnc(N2CCC([C@H]3C[C@H]3COCc3ccc(-c4ccnnc4)cc3)CC2)nc1] | 430 [M + H]$^+$ | 1.9 nM |
| 122 | 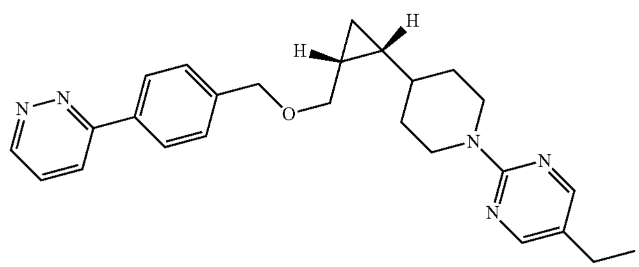 [SMILES: CCc1cnc(N2CCC([C@H]3C[C@H]3COCc3ccc(-c4cccnn4)cc3)CC2)nc1] | 430 [M + H]$^+$ | 1.1 nM |
| 123 | 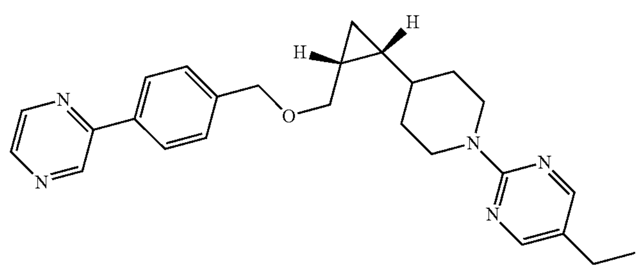 [SMILES: CCc1cnc(N2CCC([C@H]3C[C@H]3COCc3ccc(-c4cnccn4)cc3)CC2)nc1] | 430 [M + H]$^+$ | 9.8 nM |

Example 124

Preparation of 2-(4-((1R,2R)-2-(((2-fluoro-4-(methylsulfonyl)benzyl)oxy)methyl)cyclopropyl)piperidin-1-yl)-5-(methoxymethyl)pyrimidine

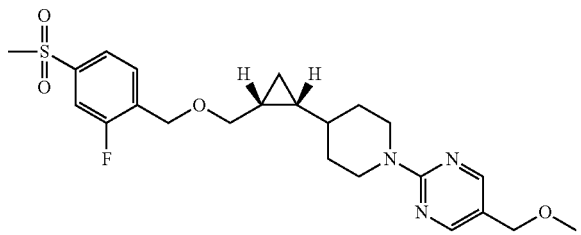

Step A: tert-Butyl 4-((1R,2R)-2-(((4-bromo-2-fluorobenzyl)oxy)methyl)cyclopropyl)piperidine-1-carboxylate

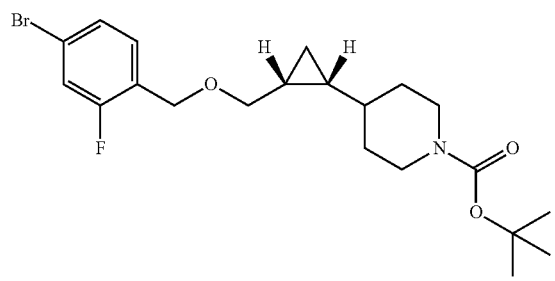 [SMILES: CC(C)(C)OC(=O)N1CCC([C@H]2C[C@H]2COCc2ccc(Br)cc2F)CC1]

tert-butyl 4-((1R,2R)-2-(hydroxymethyl)cyclopropyl)piperidine-1-carboxylate (Intermediate 4, 4 g, 15.7 mmol) was dissolved in 45 mL of DMF. The mixture was cooled to 0° C. and NaH (60% dispersion, 0.94 g, 23.5 mmol) was added portionwise. The mixture was stirred for 5 min and 4-bromo-1-(bromomethyl)-2-fluorobenzene in DMF (15 mL) was added dropwise. The mixture was stirred at 0° C. for 30 min and at RT overnight. The mixture was quenched with sat. NaHCO₃ and extracted with EtOAc. The EtOAc phase was washed with water and brine, dried over MgSO₄, and concentrated. The crude material was purified by flash column (100 g SNAP, 0~30% EtOAc in hexane) to afford 6.88 g (99%) of the product. Rf was 0.5 @ 20% EtOAc in hexanes (blue spot on CAM stain).

Step B: tert-Butyl 4-((1R,2R)-2-(((2-fluoro-4-(methylthio)benzyl)oxy)methyl)cyclopropyl)piperidine-1-carboxylate

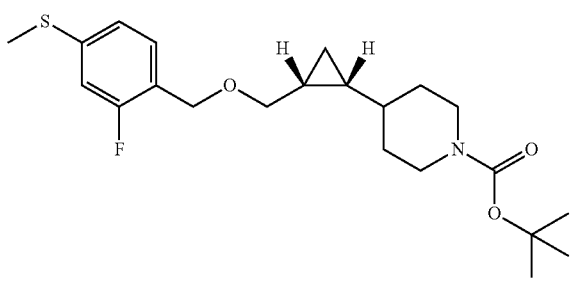 [SMILES: CSc1ccc(COC[C@@H]2C[C@@H]2C2CCN(C(=O)OC(C)(C)C)CC2)c(F)c1]

tert-Butyl 4-((1R,2R)-2-(((4-bromo-2-fluorobenzyl)oxy)methyl)cyclopropyl)piperidine-1-carboxylate (Step A product, 1.3 g, 2.94 mmol) was dissolved in diethyl ether (13 ml) and cooled to −78° C. The mixture was stirred for 5 min, then n-butyllithium in hexane (2.5 M, 1.293 ml, 3.23 mmol) was added dropwise. The mixture was stirred at −78° C. for 10 min and dimethyl disulfide (0.313 ml, 3.53 mmol) was added dropwise. The mixture was stirred at −78° C. for 30 min. before it was quenched with sat. NH₄Cl at −78° C. The reaction mixture was warmed up to rt and extracted with EtOAc (2×). The EtOAc phase was washed with brine, dried over MgSO₄, and concentrated. The crude material was purified by flash column (25 g, SNAP, 0~20% EtOAc in hexane) to afford 1.2 g (100%) of the product. Rf was 0.4 @ 20% EtOAc in hexanes (blue spot on CAM stain).

Step C: tert-Butyl 4-((1R,2R)-2-(((2-fluoro-4-(methylsulfonyl)benzyl)oxy)methyl)cyclopropyl)piperidine-1-carboxylate

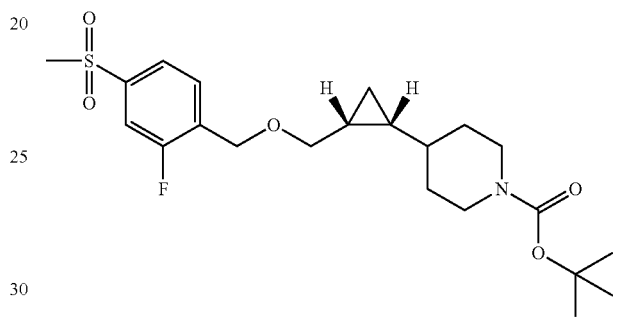

tert-Butyl 4-((1R,2R)-2-(((2-fluoro-4-(methylthio)benzyl)oxy)methyl)cyclopropyl)piperidine-1-carboxylate (Step B product, 1.2 g, 2.93 mmol) was dissolved in MeOH (15 ml) at RT. To this mixture was added a solution of oxone potassium peroxymonosulfate (5.40 g, 8.79 mmol) in water (30 ml). The mixture was stirred at RT for 1 h. TLC showed no starting material left. The mixture was diluted with DCM, washed with brine, dried over MgSO₄, and concentrated. The crude material was purified by flash column (25 g, SNAP, 20~60% EtOAc in hexane) to afford 1.13 g (87%) of the product. LC/MS (m/z): 442 (M+H)⁺. Rf was 0.4 @ 50% EtOAc in hexanes (blue spot on CAM stain).

Step D: 4-((1R,2R)-2-(((2-fluoro-4-(methylsulfonyl)benzyl)oxy)methyl)cyclopropyl)piperidine hydrochloride

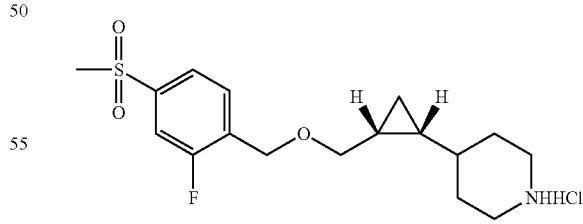

tert-Butyl 4-((1R,2R)-2-(((2-fluoro-4-(methylsulfonyl)benzyl)oxy)methyl)cyclopropyl)piperidine-1-carboxylate (Step C product, 1.13 g, 2.56 mmol) was dissolved in DCM (20 ml) and HCl in dioxane (4 M solution, 9.60 ml, 38.4 mmol) was added. The mixture was stirred at RT for 1 h. The solvents were evaporated to afford 0.97 g of the desired product (100%) which will be used without further purification. LC/MS (m/z): 378 (M+H)⁺.

Step E: 2-(4-((1R,2R)-2-(((2-fluoro-4-(methylsulfonyl)benzyl)oxy)methyl)cyclopropyl)piperidin-1-yl)pyrimidine-5-carbaldehyde

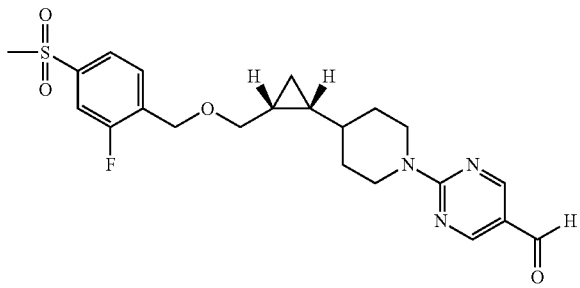 [SMILES: CS(=O)(=O)c1ccc(COC[C@@H]2C[C@@H]2C2CCN(c3ncc(C=O)cn3)CC2)c(F)c1]

4-((1R,2R)-2-(((2-fluoro-4-(methylsulfonyl)benzyl)oxy)methyl)cyclopropyl)piperidine hydrochloride (Step D product) was dissolved in DMSO (7 ml) at RT under N2 and Cs$_2$CO$_3$ (539 mg, 1.654 mmol) was added. The mixture was stirred at RT for 5 min and chloropyrimidine aldehyde (113 mg, 0.794 mmol) in DMSO (1 mL) was added. The mixture was stirred at RT overnight. The mixture was diluted with EtOAc, washed with sat. NH4Cl, dried over MgSO4, evaporated to dryness. The crude material was purified by flash column (25 g SNAP, 25~60% EtOAc in hexane) to afford 200 mg of the desired product (67.6%) as a white solid. LC/MS (m/z): 448 (M+H)$^+$.

Step F: (2-(4-((1R,2R)-2-(((2-fluoro-4-(methylsulfonyl)benzyl)oxy)methyl)cyclopropyl)piperidin-1-yl)pyrimidin-5-yl)methanol

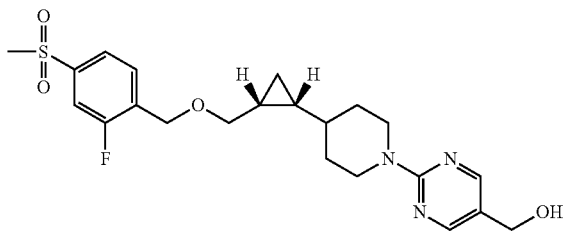 [SMILES: CS(=O)(=O)c1ccc(COC[C@@H]2C[C@@H]2C2CCN(c3ncc(CO)cn3)CC2)c(F)c1]

2-(4-((1R,2R)-2-(((2-fluoro-4-(methylsulfonyl)benzyl)oxy)methyl)cyclopropyl) piperidin-1-yl)pyrimidine-5-carbaldehyde (Step E product, 200 mg, 0.447 mmol) was dissolved in MeOH (20 ml) at RT and NaBH$_4$ (66.2 mg, 0.670 mmol) was added. The mixture was stirred at RT for 30 min and TLC showed the SM was completely consumed. The mixture was diluted with EtOAc, washed with water, dried over MgSO$_4$, evaporated to afford 198 mg of the product (99%) which was used for the next step. LC/MS (m/z): 450 (M+H)$^+$.

Step G: 2-(4-((1R,2R)-2-(((2-fluoro-4-(methylsulfonyl)benzyl)oxy)methyl)cyclopropyl)piperidin-1-yl)-5-(methoxymethyl)pyrimidine

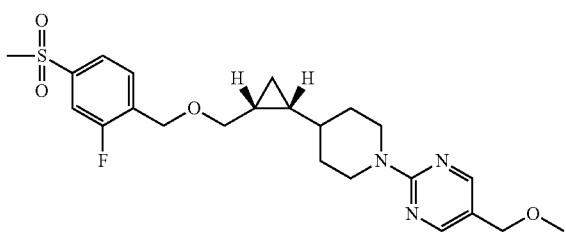

(2-(4-((1R,2R)-2-(((2-fluoro-4-(methylsulfonyl)benzyl)oxy)methyl)cyclopropyl)piperidin-1-yl)pyrimidin-5-yl)methanol (Step F product, 198 mg, 0.44 mmol) was dissolved in Acetonitrile (6 mL) at room temperature under N$_2$ and sodium hydride (26 mg of a 60% dispersion in oil, 0.66 mmol) was added followed by CH$_3$I (313 mg, 2.2 mmol). The mixture was stirred at RT overnight. The mixture was diluted with EtOAc, washed with sat. NH$_4$Cl, dried over MgSO$_4$, filtered and evaporated in vacuo. The crude material was purified by column chromatography (SNAP, 10 g, 70% EtOAc in hexane) to afford the title compound. $^1$H NMR (500 MHz, CDCl$_3$) δ 8.30 (s, 2H), 7.78 (dd, 1H), 7.73 (m, 1H), 7.67 (dd, 1H), 4.80-4.64 (m, 4H), 4.28 (s, 2H), 3.71 (dd, 1H), 3.61-3.54 (m, 1H), 3.37 (s, 3H), 3.08 (s, 3H), 2.93-2.80 (m, 2H), 1.96 (d, 1H), 1.85 (d, 1H), 1.43-1.22 (m, 3H), 1.15-1.04 (m, 1H), 0.94-0.71 (m, 2H), 0.12-0.08 (m, 1H). MS (ESI) m/z 464 [M+H]$^+$. GPR119 Human EC$_{50}$: 1.6 nM.

Example 125

Preparation of 2-(4-((1R,2R)-2-(((2-fluoro-4-(methylsulfonyl)benzyl)oxy)methyl)cyclopropyl)piperidin-1-yl)-5-(1-methoxyethyl)pyrimidine

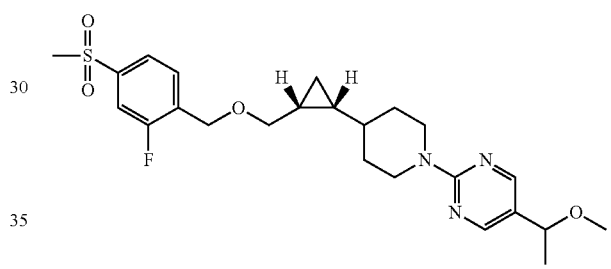

Step A: 1-(2-(4-((1R,2R)-2-(((2-fluoro-4-(methylsulfonyl)benzyl)oxy)methyl)cyclopropyl)piperidin-1-yl)pyrimidin-5-yl)ethanol

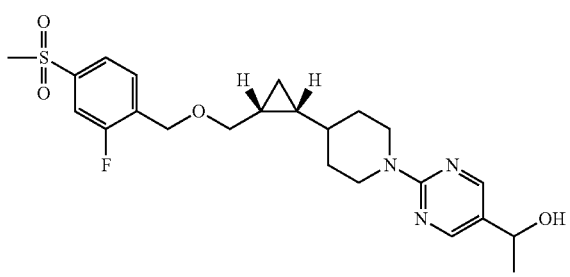 [SMILES: CC(O)c1cnc(N2CCC([C@H]3C[C@H]3COCc3ccc(S(C)(=O)=O)cc3F)CC2)nc1]

2-(4-((1R,2R)-2-(((2-fluoro-4-(methylsulfonyl)benzyl)oxy)methyl)cyclopropyl) piperidin-1-yl)pyrimidine-5-carbaldehyde (Step E product of Example 124, 130 mg, 0.29 mmol) was dissolved in THF (5 ml) at 0° C. under N$_2$ and CH$_3$MgCl (3 M solution, 0.145 ml, 0.436 mmol) was added. The mixture was stirred at RT for 30 min and TLC showed the SM was completely consumed. The mixture was diluted with EtOAc, washed with water, dried over MgSO4, and concentrated to afford 134 mg (100%) of the product. Rf was 0.4 @ 50% EtOAc in hexanes (blue spot on CAM stain). LC/MS (m/z): 464 (M+H)$^+$.

Step B: 2-(4-((1R,2R)-2-(((2-fluoro-4-(methylsulfonyl)benzyl)oxy)methyl)cyclopropyl)piperidin-1-yl)-5-(1-methoxyethyl)pyrimidine

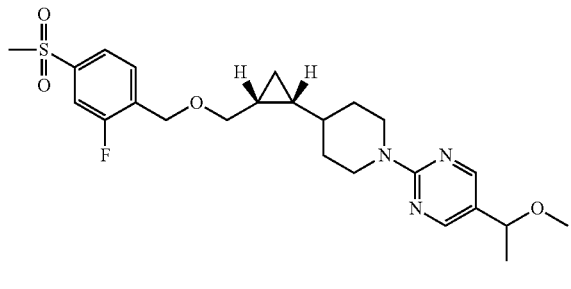

1-(2-(4-((1R,2R)-2-(((2-fluoro-4-(methylsulfonyl)benzyl)oxy)methyl)cyclopropyl)piperidin-1-yl)pyrimidin-5-yl)ethanol (Step A product, 110 mg, 0.24 mmol) was dissolved in CH$_3$CN (5 mL) at RT and NaH (60% dispersion, 28.5 mg, 0.712 mmol) was added followed by IODOMETHANE (0.148 ml, 2.373 mmol). The mixture was stirred at RT for 2 h. TLC showed SM was almost consumed. The mixture was diluted with EtOAc, washed with sat. NH$_4$Cl, dried over MgSO4, and evaporated. The crude material was purified by prep TLC (50% EtOAc in hexane) to afford 92 mg (81%) of the product. Rf was 0.5 @ 50% EtOAc in hexanes (blue spot on CAM stain). The diastereoisomer mixture was resolved by chiral HPLC to obtain two pure diastereomers. The faster diastereomer was the title compound. $^1$H NMR (500 MHz, CDCl$_3$) δ 8.25 (s, 2H), 7.78 (m, 2H), 7.70 (d, 1H), 4.80-4.64 (m, 4H), 4.18 (m, 1H), 3.71 (dd, 1H), 3.61 (m, 2H), 3.25 (s, 3H), 3.08 (s, 3H), 2.93-2.80 (m, 2H), 1.96-1.80 (m, 2H), 1.43 (d, 3H), 1.4-1.0 (m, 5H), 0.8 (m, 2H), 0.12-0.08 (m, 1H). MS (ESI) m/z 478 [M+H]$^+$. GPR119 Human EC$_{50}$: 0.36 nM.

Example 126

Preparation of 2-(4-((1R,2R)-2-(((2-fluoro-4-(methylsulfonyl)benzyl)oxy)methyl)cyclopropyl)piperidin-1-yl)-5-(1-methoxyethyl)pyrimidine

126

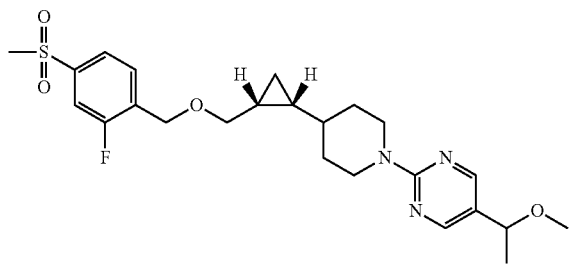

The slower diastereomer from Step B of Example 125 was the title compound. $^1$H NMR (500 MHz, CDCl$_3$) δ 8.25 (s, 2H), 7.78 (m, 2H), 7.70 (d, 1H), 4.80-4.64 (m, 4H), 4.18 (m, 1H), 3.71 (dd, 1H), 3.61 (m, 2H), 3.25 (s, 3H), 3.08 (s, 3H), 2.93-2.80 (m, 2H), 1.96-1.80 (m, 2H), 1.43 (d, 3H), 1.4-1.0 (m, 5H), 0.8 (m, 2H), 0.12-0.08 (m, 1H). MS (ESI) m/z 478 [M+H]$^+$.
GPR119 Human EC$_{50}$: 1.5 nM.

Example 127

Preparation of 2-(4-((1R,2R)-2-(((4-(ethylsulfonyl)-2-fluorobenzyl)oxy)methyl)cyclopropyl)piperidin-1-yl)-5-(methoxymethyl)pyrimidine

127

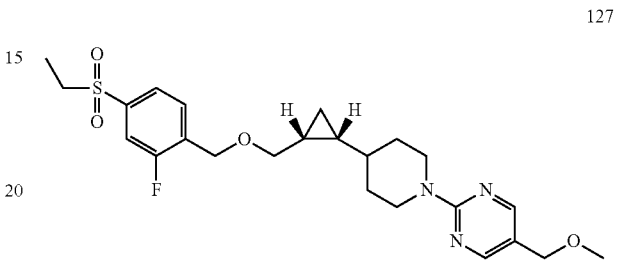

The title compound was prepared following the procedure described for Example 124 with the minor modification of Step B, where dimethyl disulfide was replaced by diethyl disulfide. $^1$H NMR (500 MHz, CDCl$_3$) δ 8.30 (s, 2H), 7.78 (m, 2H), 7.73 (d, 1H), 4.70-4.60 (m, 4H), 4.28 (s, 2H), 3.71-3.60 (m, 2H), 3.37 (s, 3H), 3.08 (m, 2H), 2.93-2.80 (m, 2H), 1.96 (d, 1H), 1.85 (d, 1H), 1.40-1.22 (m, 6H), 1.15-1.04 (m, 1H), 0.94-0.71 (m, 2H), 0.12-0.08 (m, 1H). MS (ESI) m/z 478 [M+H]$^+$. GPR119 Human EC$_{50}$: 2.8 nM.

Example 128

Preparation of 2-(4-((1R,2R)-2-(((3,5-difluoro-4-(methylsulfonyl)benzyl)oxy)methyl)cyclopropyl)piperidin-1-yl)-5-(methoxymethyl)pyrimidine

128

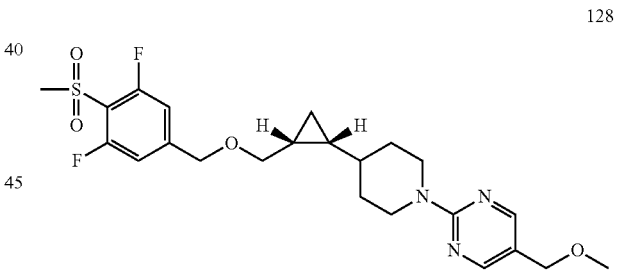

Step A: tert-butyl 4-((1R,2R)-2-(((3,5-difluoro-4-(methylthio)benzyl)oxy)methyl)cyclopropyl)piperidine-1-carboxylate

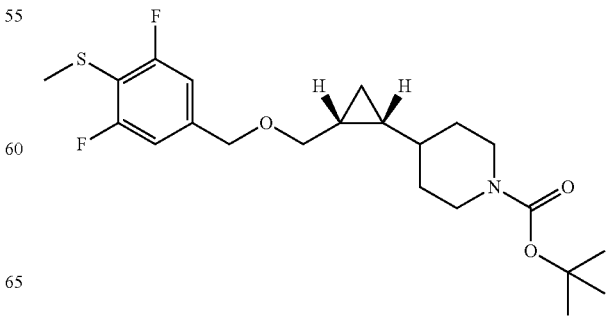

tert-butyl 4-((1R,2R)-2-(hydroxymethyl)cyclopropyl)piperidine-1-carboxylate (Intermediate 4, 1.7 g, 6.66 mmol) was dissolved in 20 mL of DMF. The mixture was cooled to 0° C. and NaH (60% dispersion, 0.4 g, 10 mmol) was added portionwise. The mixture was stirred for 5 min and (4-(bromomethyl)-2,6-difluorophenyl)(methyl)sulfane (Intermediate 15A, 1.05 equiv) in DMF (3 mL) was added dropwise. The mixture was stirred at 0° C. for 30 min and at RT overnight. The mixture was quenched with sat. NaHCO$_3$, extracted with EtOAc. The EtOAc phase was washed with water and brine, dried over MgSO4, and concentrated. The crude material was purified by flash column (50 g SNAP, 10~50% EtOAc in hexane) to afford 2.77 g (97%) of the designed product. Rf was 0.3 @ 20% EtOAc in hexanes (blue spot on CAM stain).

Step B: tert-butyl 4-((1R,2R)-2-(((3,5-difluoro-4-(methylsulfonyl)benzyl)oxy)methyl)cyclopropyl)piperidine-1-carboxylate

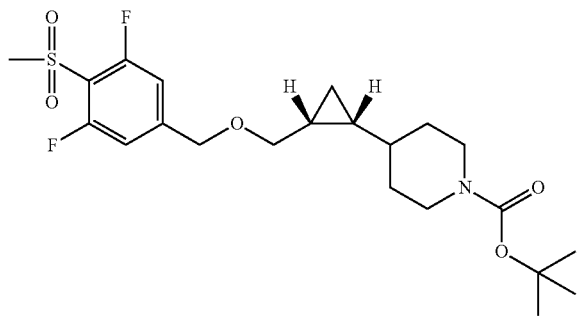 [SMILES: CC(C)(C)OC(=O)N1CCC([C@H]2C[C@H]2COCc2cc(F)c(S(C)(=O)=O)c(F)c2)CC1]

tert-butyl 4-((1R,2R)-2-(((3,5-difluoro-4-(methylthio)benzyl)oxy)methyl)cyclopropyl)piperidine-1-carboxylate (Step A product, 2.77 g, 6.48 mmol) was dissolved in CH$_2$Cl$_2$ (40 ml) at RT. To this mixture was added 3-CHLOROPEROXYBENZOIC ACID (3.91 g, 22.68 mmol). The mixture was stirred at RT overnight. LC-MS showed no SM left. The mixture was diluted with EtOAc, washed with sat. Na$_2$S$_2$O$_3$ (2×), sat. NaHCO$_3$ (2×), brine, dried over MgSO4, and evaporated to dryness. The crude material was purified by flash column (50 g, SNAP, 20~50% EtOAc in hexane) to afford 1.85 g (62%) of the desired product. Rf was 0.4 @ 50% EtOAc in hexanes (blue spot on CAM stain).

Step C: 4-((1R,2R)-2-(((3,5-difluoro-4-(methylsulfonyl)benzyl)oxy)methyl)cyclopropyl)piperidine hydrochloride

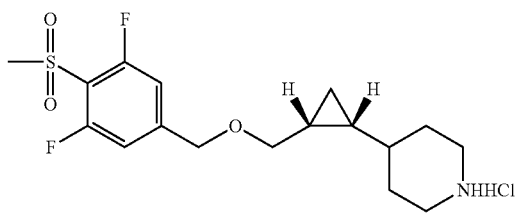

tert-butyl 4-((1R,2R)-2-(((3,5-difluoro-4-(methylsulfonyl)benzyl)oxy)methyl)cyclopropyl)piperidine-1-carboxylate (Step B product, 1.85 g, 4.03 mmol) was dissolved in DCM (20 ml) and HCl in dioxane (4 M solution, 10.60 ml, 40 mmol) was added. The mixture was stirred at RT for 1 h. The solvents were evaporated to afford 1.6 g (100%) of the desired product which was used without further purification. LC/MS (m/z): 360 (M+H)$^+$.

Step D: 2-(4-((1R,2R)-2-(((3,5-difluoro-4-(methylsulfonyl)benzyl)oxy)methyl)cyclopropyl)piperidin-1-yl)-5-(methoxymethyl)pyrimidine

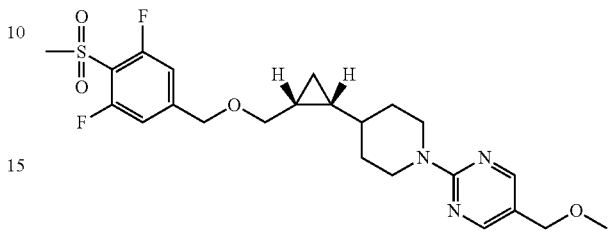

4-((1R,2R)-2-(((3,5-difluoro-4-(methylsulfonyl)benzyl)oxy)methyl)cyclopropyl)piperidine hydrochloride (Step C product, 100 mg, 0.25 mmol) was dissolved in DMSO (3 ml) at RT under N$_2$ and Cs$_2$CO$_3$ (288 mg, 0.884 mmol) was added. The mixture was stirred at RT for 5 min and 2-chloro-5-methoxymethylpyrimidine (Intermediate 18, 48 mg, 0.3 mmol) in DMSO (0.5 mL) was added. The mixture was stirred at 60° C. overnight. The mixture was diluted with EtOAc, washed with sat. NH$_4$Cl, dried over MgSO$_4$, and evaporated to dryness. The crude material was purified by preparative TLC (60% EtOAc in hexane) to afford 50.5 mg (41.5%) of the desired product. LC/MS (m/z): 482 (M+H) ±$^1$H NMR (500 MHz, CDCl$_3$) δ 8.30 (s, 2H), 7.15 (dd, 2H), 4.80-4.64 (m, 4H), 4.25 (s, 2H), 3.60 (m, 2H), 3.37 (s, 3H), 3.35 (s, 3H), 2.93-2.80 (m, 2H), 1.96-1.80 (m, 2H), 1.40-1.10 (m, 4H), 0.94-0.71 (m, 2H), 0.12-0.08 (m, 1H).

GPR119 Human EC$_{50}$: 4.5 nM.

Example 129

Preparation of 5-ethoxy-2-(4-((1R,2R)-2-(((3-fluoro-4-(methylsulfonyl)benzyl)oxy)methyl)cyclopropyl)piperidin-1-yl)pyrimidine

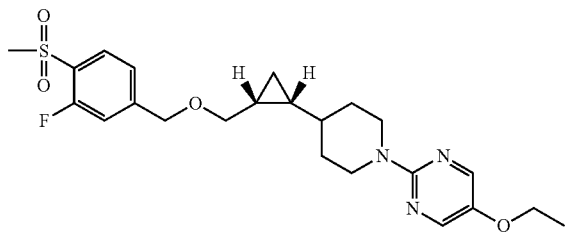 [SMILES: CCOc1cnc(N2CCC([C@H]3C[C@H]3COCc3ccc(S(C)(=O)=O)c(F)c3)CC2)nc1]

Step A: tert-butyl 4-((1R,2R)-2-(((4-bromo-3-fluorobenzyl)oxy)methyl)cyclopropyl)piperidine-1-carboxylate

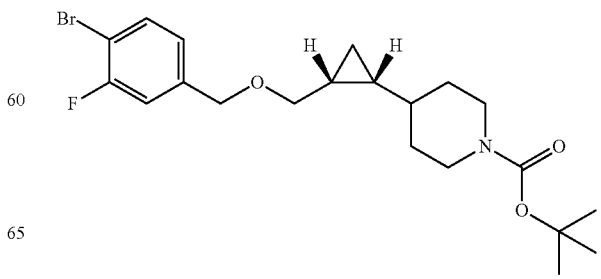

tert-butyl 4-((1R,2R)-2-(hydroxymethyl)cyclopropyl)piperidine-1-carboxylate (Intermediate 4, 4.5 g, 17.6 mmol) was dissolved in 50 mL of DMF. The mixture was cooled to 0° C. and NaH (60% dispersion, 1 g, 26.4 mmol) was added portionwise. The mixture was stirred for 5 min and 1-bromo-4-(bromomethyl)-2-fluorobenzene (Step B of Intermediate 13, 5.67 g, 21.1 mmol) in DMF (15 mL) was added dropwise. The mixture was stirred at 0° C. for 30 min and at RT overnight. The mixture was quenched with sat. NaHCO₃, extracted with EtOAc. The EtOAc phase was washed with water and brine, dried over MgSO₄, and evaporated to dryness. The crude material was purified by flash column (100 g SNAP, 10~50% EtOAc in hexane) to afford 7.7 g (99%) of the designed product. Rf was 0.5 @ 20% EtOAc in hexanes (blue spot on CAM stain).

Step B: tert-butyl 4-((1R,2R)-2-(((3-fluoro-4-(methylthio)benzyl)oxy)methyl)cyclopropyl)piperidine-1-carboxylate

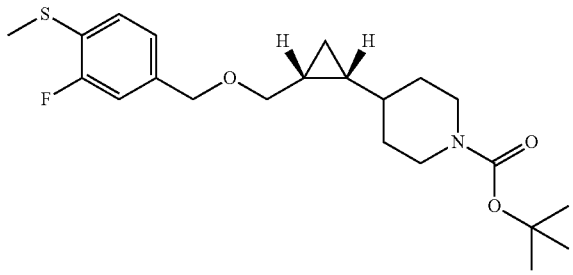 [SMILES: CSc1ccc(COC[C@@H]2C[C@@H]2C2CCN(C(=O)OC(C)(C)C)CC2)cc1F]

tert-butyl 4-((1R,2R)-2-(((4-bromo-3-fluorobenzyl)oxy)methyl)cyclopropyl)piperidine-1-carboxylate (Step A product, 7.7 g, 17.4 mmol) was dissolved in Diethyl ether (70 ml) and cooled to −78° C. The mixture was stirred for 5 min, then n-Butyllithium in hexane (2.5 M, 7.66 ml, 19.15 mmol) was added dropwise. The mixture was stirred at −78° C. for 10 min and dimethyl disulfide (1.85 ml, 20.9 mmol) was added dropwise. The mixture was stirred at −78° C. for 30 min and TLC showed the SM was almost consumed. The mixture was quenched with sat. NH₄Cl at −78° C., extracted with EtOAc (2×). The EtOAc phase was washed with brine, dried over MgSO4, and concentrated to afford 7.13 g (100%) of the designed product. This crude product was used for the next step without further purification.

Step C: tert-butyl 4-((1R,2R)-2-(((3-fluoro-4-(methylsulfonyl)benzyl)oxy)methyl)cyclopropyl)piperidine-1-carboxylate

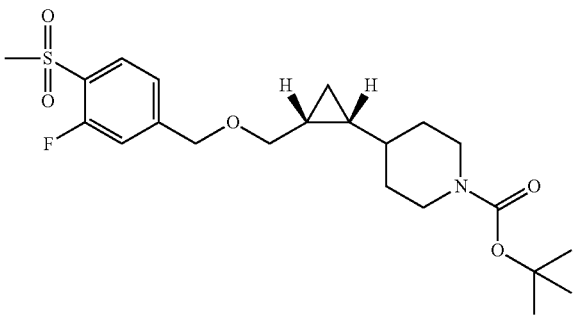 [SMILES: CC(C)(C)OC(=O)N1CCC([C@H]2C[C@H]2COCc2ccc(S(C)(=O)=O)c(F)c2)CC1]

tert-butyl 4-((1R,2R)-2-(((3-fluoro-4-(methylthio)benzyl)oxy)methyl)cyclopropyl) piperidine-1-carboxylate (Step B product, 7.2 g, 17.58 mmol) was dissolved in CH₂Cl₂ (100 ml) at RT. To this mixture was added 3-CHLOROPEROXY-BENZOIC ACID (10.62 g, 61.5 mmol). The mixture was stirred at RT for 2 h. LC-MS showed no SM left. The mixture was diluted with DCM, washed with sat. Na₂S₂O₃ (2×), sat. NaHCO₃ (2×), brine, dried over MgSO₄, and evaporated to dryness. The crude material was purified by flash column (100 g, SNAP, 20~50% EtOAc in hexane) to afford 2.7 g (34.8%) of the desired product. LC/MS (m/z): 442 (M+H)⁺. Rf was 0.3 @ 50% EtOAc in hexanes (blue spot on CAM stain)

Step D: 4-((1R,2R)-2-(((3-fluoro-4-(methylsulfonyl)benzyl)oxy)methyl)cyclopropyl)piperidine hydrochloride

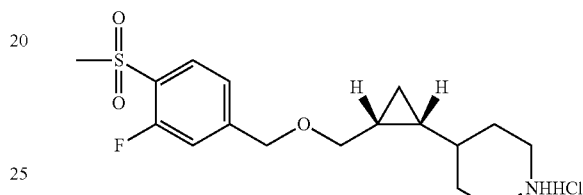

tert-butyl 4-((1R,2R)-2-(((3-fluoro-4-(methylsulfonyl)benzyl)oxy)methyl)cyclopropyl) piperidine-1-carboxylate (Step C product, 2.7 g, 6.11 mmol) was dissolved in DCM (45 ml) and HCl in dioxane (4 M solution, 15.3 ml, 61.1 mmol) was added. The mixture was stirred at RT for 1 h. The solvents were evaporated to afford 2.3 g (100%) of the desired product which was used without further purification. LC/MS (m/z): 342 (M+H)⁺.

Step E: 5-ethoxy-2-(4-((1R,2R)-2-(((3-fluoro-4-(methylsulfonyl)benzyl)oxy)methyl)cyclopropyl)piperidin-1-yl)pyrimidine

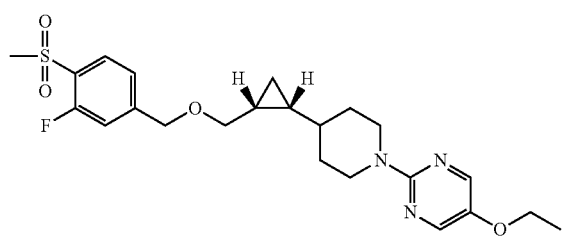 [SMILES: CCOc1cnc(N2CCC([C@H]3C[C@H]3COCc3ccc(S(C)(=O)=O)c(F)c3)CC2)nc1]

4-((1R,2R)-2-(((3-fluoro-4-(methylsulfonyl)benzyl)oxy)methyl)cyclopropyl)piperidine hydrochloride (Step D product, 200 mg, 0.53 mmol) was dissolved in DMSO (5 ml) at RT under N₂ and Cs₂CO₃ (517 mg, 1.588 mmol) was added. The mixture was stirred at RT for 5 min and 2-chloro-5-ethoxy-pyrimidine (101 mg, 0.635 mmol) in DMSO (0.5 mL) was added. The mixture was stirred at 100° C. overnight. The mixture was diluted with EtOAc, washed with sat. NH₄Cl, dried over MgSO₄, evaporated. The crude material was purified by flash column (25 g SNAP, 15~50% EtOAc in hexane) to afford 56 mg (23%) of the title compound. ¹H NMR (500 MHz, CDCl₃) δ 8.10 (s, 2H), 7.90 (m, 1H), 7.30 (m, 2H), 4.60 (m, 4H), 4.00 (t, 2H), 3.60 (m, 2H), 3.20 (s, 3H), 2.93-2.80 (m, 2H), 1.96 (d, 1H), 1.85 (d, 1H), 1.43 (m, 5H), 1.25 (m, 1H), 1.15 (m, 1H), 0.80-0.71 (m, 2H), 0.12-0.08 (m, 1H). MS (ESI) m/z 464 [M+H]⁺. GPR119 Human EC₅₀: 1.65 nM.

Examples 130 and 131 were prepared similarly using the procedure described for Examples 125 and 126.

Example 130

Preparation of 2-(4-((1R,2R)-2-(((3-fluoro-4-(methylsulfonyl)benzyl)oxy)methyl)cyclopropyl)piperidin-1-yl)-5-(-methoxyethyl)pyrimidine

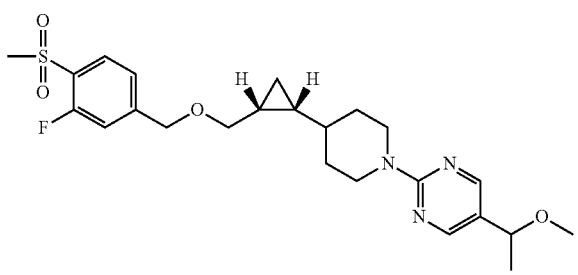

Slower diastereomer. $^1$H NMR (500 MHz, CDCl$_3$) δ 8.15 (s, 2H), 7.90 (m, 1H), 7.30 (m, 2H), 4.80-4.60 (m, 4H), 4.20 (m, 1H), 3.60 (m, 2H), 3.22 (s, 3H), 3.20 (s, 3H), 2.93-2.80 (m, 2H), 1.96 (d, 1H), 1.85 (d, 1H), 1.43 (m, 5H), 1.25 (m, 1H), 1.15 (m, 1H), 0.80-0.71 (m, 2H), 0.12-0.08 (m, 1H). MS (ESI) m/z 478 [M+H]$^+$. GPR119 Human EC$_{50}$: 0.72 nM.

Example 131

Preparation of 2-(4-((1R,2R)-2-(((3-fluoro-4-(methylsulfonyl)benzyl)oxy)methyl)cyclopropyl)piperidin-1-yl)-5-(methoxyethyl)pyrimidine

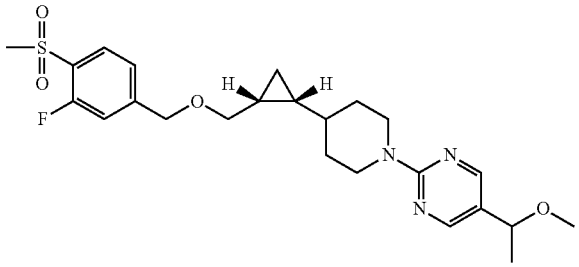

Faster diastereomer. $^1$H NMR (500 MHz, CDCl$_3$) δ 8.15 (s, 2H), 7.90 (m, 1H), 7.30 (m, 2H), 4.80-4.60 (m, 4H), 4.20 (m, 1H), 3.60 (m, 2H), 3.22 (s, 3H), 3.20 (s, 3H), 2.93-2.80 (m, 2H), 1.96 (d, 1H), 1.85 (d, 1H), 1.43 (m, 5H), 1.25 (m, 1H), 1.15 (m, 1H), 0.80-0.71 (m, 2H), 0.12-0.08 (m, 1H). MS (ESI) m/z 478 [M+H]$^+$. GPR119 Human EC$_{50}$: 1.03 nM.

Examples 132-133

Preparation of 2-(4-((1R,2R)-2-(((3-fluoro-4-(1H-tetrazol-1-yl)benzyloxy)methyl)cyclopropyl)piperidin-1-yl)-5-(methoxymethyl)pyrimidine

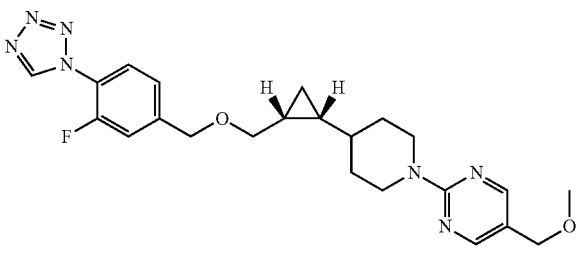

Step A: tert-butyl 4-((1R,2R)-2-((4-bromo-3-fluorobenzyloxy)methyl)cyclopropyl)piperidine-1-carboxylate

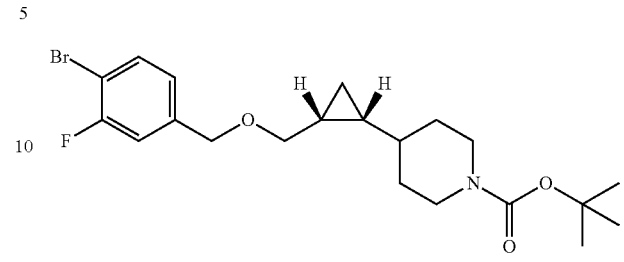

Sodium hydride (235 mg, 5.87 mmol) was added to a stirring solution of tert-butyl 4-((1R,2R)-2-(hydroxymethyl)cyclopropyl)piperidine-1-carboxylate (Intermediate 4, 1 g, 3.92 mmol) in DMF (10 mL) that had been cooled to 0° C. in an ice bath and placed under an inert atmosphere. 10 min later 1-bromo-4-(bromomethyl)-2-fluorobenzene (Step B product of Intermediate 13, 1.1 g, 4.11 mmol) was introduced to the mixture. The ice bath was removed and the reaction warmed to rt. The reaction was aged for 1 hr then diluted with EtOAc (20 mL) and neutralized by the slow addition of saturated aqueous ammonium chloride solution (20 mL). The layers were cut and the aqueous phase extracted with EtOAc (20 mL×2). The combined organic layers were dried over MgSO$_4$, filtered, and concentrated under reduced pressure. The residue was loaded onto a silica column (KP-Sil 50 g SNAP column, Biotage system) eluting with a range of 0-20% EtOAc/Hex over 12 CV to give the desired compound (1.73 g, 91%). LC/MS (m/z): 442 (M+H)$^+$.

Step B: tert-butyl 4-((1R,2R)-2-((4-amino-3-fluorobenzyloxy)methyl)cyclopropyl)piperidine-1-carboxylate

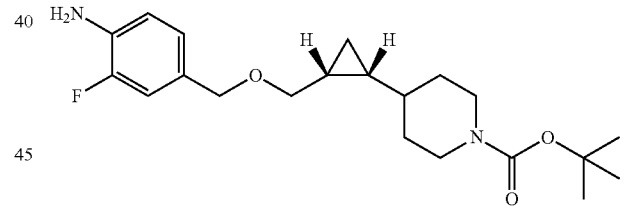

Ammonium hydroxide (14.9 mL, 107 mmol) was quickly added to a solution of tert-butyl 4-((1R,2R)-2-((4-bromo-3-fluorobenzyloxy)methyl)cyclopropyl)piperidine-1-carboxylate (Step A product, 1.58 g, 3.57 mmol), (2S,4R)-4-hydroxypyrrolidine-2-carboxylic acid (1.3 g, 7.86 mmol), Copper(I) iodide (1.36 g, 7.14 mmol), and potassium carbonate (1.53 g, 11.1 mmol) in DMSO (12 mL) that had been placed under an inert atmosphere in a sealed tube. The reaction mixture was subsequently heated at 85° C. for 48 hrs in the sealed tube. The solution was cooled to rt and diluted with EtOAc (25 mL) and water (25 mL). The layers were cut and the aqueous phase extracted with EtOAc (25 mL×2). The combined organic layers were dried over MgSO$_4$, filtered, and concentrated under reduced pressure. The residue was loaded onto a silica column (KP-Sil 50 g SNAP column, Biotage system) initially eluting with a range of 10-20% EtOAc/Hex over 6 CV, followed by a range of 25-60% EtOAc/Hex over 7 CV to give the desired compound (802 mg, 59%). LC/MS (m/z): 379 (M+H)$^+$.

Step C: tert-butyl 4-((1R,2R)-2-((3-fluoro-4-(1H-tetrazol-1-yl)benzyloxy)methyl)cyclopropyl)piperidine-1-carboxylate

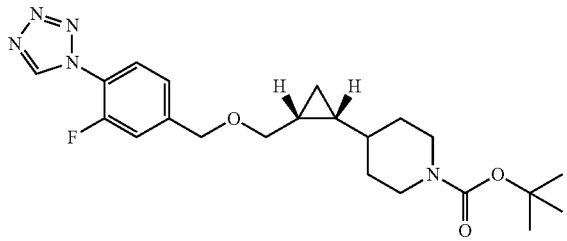 [SMILES: CC(C)(C)OC(=O)N1CCC([C@H]2C[C@H]2COCc2ccc(-n3cnnn3)c(F)c2)CC1]

A solution of tert-butyl 4-((1R,2R)-2-((4-amino-3-fluorobenzyloxy)methyl)cyclopropyl)piperidine-1-carboxylate (Step B product, 400 mg, 1.06 mmol), triethyl orthoformate (880 uL, 5.28 mmol), and sodium azide (344 mg, 5.28 mmol) in acetic acid (4.3 mL) that had been placed under an inert atmosphere was heat in a sealed vial at 100° C. for 3 hrs. The reaction mixture was cooled to rt and concentrated under reduced pressure. The resulting crude was partitioned between EtOAc (20 mL) and water (20 mL) and the layers were cut. The aqueous phase was extracted with EtOAc (20 mL×2) and the combined organic layers were dried over MgSO$_4$, filtered, and concentrated under reduced pressure. The residue was loaded onto a silica column (KP-Sil 25 g SNAP column, Biotage system) eluting with a range of 20-60% EtOAc/Hex over 12 CV to give the desired compound (415 mg, 91%). LC/MS (m/z): 432 (M+H)$^+$.

Step D: 4-((1R,2R)-2-((3-fluoro-4-(1H-tetrazol-1-yl)benzyloxy)methyl)cyclopropyl)piperidinium chloride

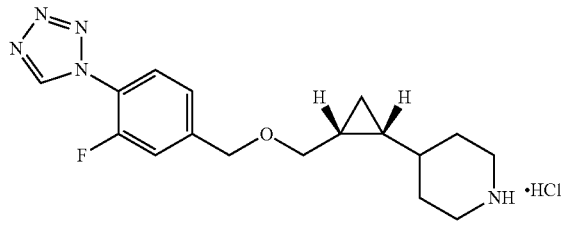 [SMILES: Fc1cc(COC[C@@H]2C[C@@H]2C2CCNCC2)ccc1-n1cnnn1 ; Cl]

A solution of 4 M HCl in dioxane (2.4 mL, 9.62 mmol) was added to a solution of tert-butyl 4-((1R,2R)-2-((3-fluoro-4-(1H-tetrazol-1-yl)benzyloxy)methyl)cyclopropyl)piperidine-1-carboxylate (Step C product, 415 mg, 0.962 mmol) in DCM (3 mL). This mixture was stirred at rt for 1 hr. The reaction mixture was subsequently concentrated under reduced pressure to afford the title compound (351 mg, 99%) as a crude product to be used for the next step. LC/MS (m/z): 332 (M+H)$^+$.

Step E: 2-(4-((1R,2R)-2-((3-fluoro-4-(1H-tetrazol-1-yl)benzyloxy)methyl)cyclopropyl)piperidin-1-yl)-5-(methoxymethyl)pyrimidine

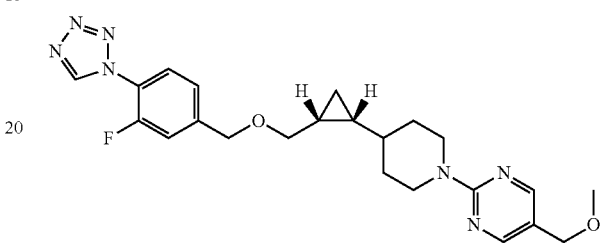

4-((1R,2R)-2-((3-fluoro-4-(1H-tetrazol-1-yl)benzyloxy)methyl)cyclopropyl)piperidinium chloride (Step D product, 45 mg, 0.122 mmol) and 2-chloro-5-(methoxymethyl)pyrimidine (Intermediate 18, 22 mg, 0.136 mmol) were dissolved in DMF (600 uL), to which was added cesium carbonate (100 mg, 0.306 mmol). The reaction was heated at 55° C. overnight. The reaction mixture was cooled to rt and diluted with EtOAc (5 mL) and water (5 mL). The layers were cut and the aqueous phase extracted with EtOAc (5 mL×2). The combined organic layers were dried over MgSO$_4$, filtered, and concentrated under reduced pressure. The residue was loaded onto 2×2000 micron silica preparative TLC plates (uv 254 active) which were developed using 50% EtOAc/Hex as the solvent system. The desired silica (Rf=0.4 @ 50% EtOAc/Hex) was collected and extracted to give the title compound (32 mg, 57%). $^1$H NMR (500 MHz, CDCl$_3$) δ 9.14 (s, 1H), 8.39 (s, 2H), 7.94 (t, 1H), 7.40 (dd, 2H), 4.73 (t, 2H), 4.65 (q, 2H), 4.29 (s, 2H), 3.61 (td, 2H), 3.38 (s, 3H), 2.95 (m, 2H), 1.95 (dd, 2H), 1.43 (m, 2H), 1.28 (m, 1H), 1.22 (m, 1H), 0.85-0.73 (m, 2H), 0.11 (q, 1H). LC/MS (m/z): 454 (M+H)+, GPR119 Human EC$_{50}$: 1.1 nM.

The example in Table 17 was synthesized according to the methods described in Example 132 employing the appropriate reagents and solvents.

TABLE 17

| Example # | Chemical Structure | Observed Mass | GPR119 Human EC$_{50}$ |
|---|---|---|---|
| 133 | 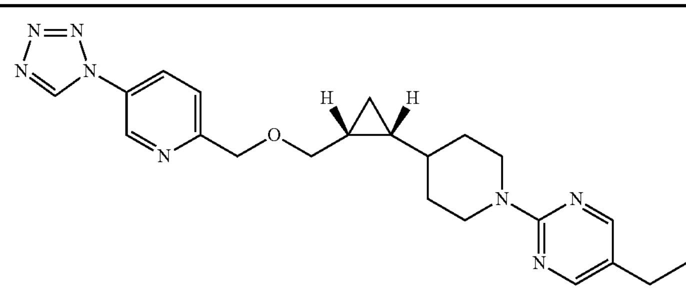 | 421 [M + H]$^+$ | 5.6 nM |

Examples 134-135

Preparation of 5-(4-(((1R,2R)-2-((2-fluoro-4-(1H-tetrazol-1-yl)benzyloxy)methyl)cyclopropyl)piperidin-1-yl)-3-isopropyl-1,2,4-oxadiazole

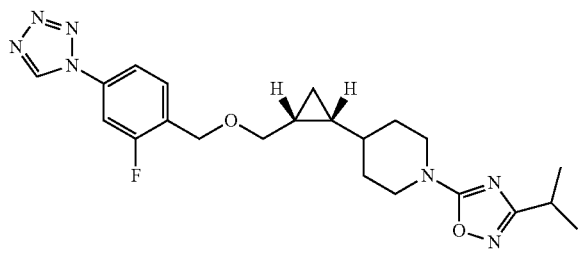

134

Step A: 4-(((1R,2R)-2-((2-fluoro-4-(1H-tetrazol-1-yl)benzyloxy)methyl)cyclopropyl)piperidinium chloride

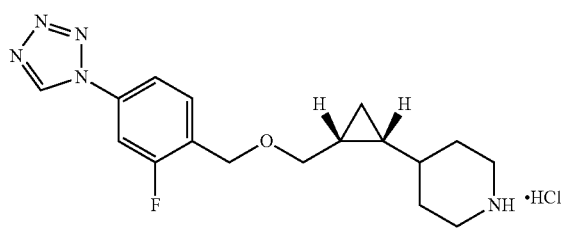 [SMILES: Fc1cc(-n2cnnn2)ccc1COC[C@@H]1C[C@@H]1C1CCNCC1 ; Cl]

The product in this step was synthesized according to the methods described in Step D of Example 132 employing the appropriate reagents and solvents. LC/MS (m/z): 332 (M+H)+.

Step B: 4-(((1R,2R)-2-((3-fluoro-4-(1H-tetrazol-1-yl)benzyloxy)methyl)cyclopropyl)piperidine-1-carbonitrile

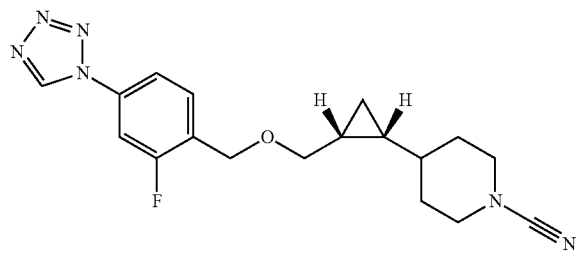 [SMILES: N#CN1CCC([C@H]2C[C@H]2COCc2ccc(-n3cnnn3)cc2F)CC1]

A solution of 3 M cyanogen bromide in DCM (120 uL, 0.359 mmol) was added to a preformed mixture of 4-(((1R,2R)-2-(((3-fluoro-4-(1H-tetrazol-1-yl)benzyloxy)methyl)cyclopropyl)piperidinium chloride (Step A product, 120 mg, 0.326 mmol) and sodium bicarbonate (69 mg, 0.816 mmol) in DCM (1.5 mL) and water (1.5 mL) that had been cooled to 0° C. in an ice bath. The reaction was stirred at 0° C. for 30 min then warmed to rt and stirred for 1 hr. The layers were cut and the aqueous phase extracted with DCM (2 mL×2). The combined organic layers were dried over MgSO$_4$, filtered, and concentrated under reduced pressure to afford the title compound (105 mg, 90%) as a crude product to be used for the next step. LC/MS (m/z): 357 (M+H)+.

Step C: 5-(4-(((1R,2R)-2-((2-fluoro-4-(1H-tetrazol-1-yl)benzyloxy)methyl)cyclopropyl)piperidin-1-yl)-3-isopropyl-1,2,4-oxadiazole

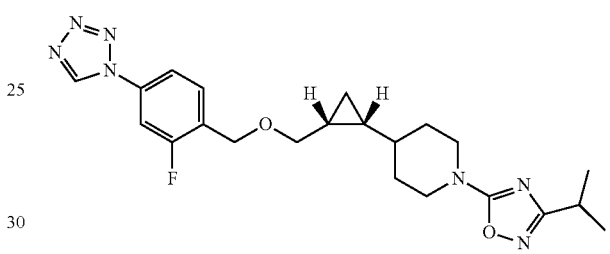

A solution of 0.5 M zinc chloride in THF (505 uL, 0.253 mmol) was introduced to a mixture of 4-(((1R,2R)-2-((3-fluoro-4-(1H-tetrazol-1-yl)benzyloxy)methyl)cyclopropyl)piperidine-1-carbonitrile (Step B product, 60 mg, 0.168 mmol), N-hydroxyisobutyrimidamide (26 mg, 0.253 mmol) and p-toluenesulfonic acid monohydrate (96 mg, 0.505 mmol) in THF (1 mL). The reaction vessel was fitted with a reflux condenser and refluxed for 3 hrs. The reaction mixture was cooled to rt, diluted with EtOAc (5 mL) and neutralized by the addition of saturated aqueous sodium bicarbonate solution (5 mL). The layers were cut and the aqueous phase extracted with EtOAc (5 mL×2). The combined organic layers were dried over MgSO$_4$, filtered, and concentrated under reduced pressure. The residue was loaded onto 2×2000 micron silica preparative TLC plates (uv 254 active) which were developed using 50% EtOAc/Hex as the solvent system. The desired silica (Rf=0.4 @ 50% EtOAc/Hex) was collected and extracted to give the title compound (12 mg, 16%). $^1$H NMR (500 MHz, CDCl$_3$) 9.04 (s, 1H), 7.72 (t, 1H), 7.55 (d, 2H), 4.66 (q, 2H), 4.14 (q, 2H), 3.72 (t, 1H), 3.49 (t, 1H), 2.99 (p, 2H), 2.91 (p, 1H), 2.01 (d, 1H), 1.85 (d, 1H), 1.47 (m, 2H), 1.29 (m, 7H), 1.04 (m, 1H), 0.84-0.73 (m, 2H), 0.09 (q, 1H). LC/MS (m/z): 442 (M+H)+, GPR119 Human EC$_{50}$: 1.7 nM.

The example in Table 18 was synthesized according to the methods described Example 134 employing the appropriate reagents and solvents.

TABLE 18

| Example # | Chemical Structure | Observed Mass | GPR119 Human EC$_{50}$ |
|---|---|---|---|
| 135 | 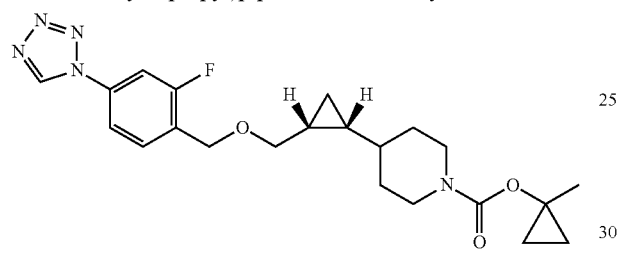 | 444 [M + H]$^+$ | 9.8 nM |

Example 136

Preparation of 1-methylcyclopropyl 4-((1R,2R)-2-((2-fluoro-4-(1H-tetrazol-1-yl)benzyloxy)methyl)cyclopropyl)piperidine-1-carboxylate

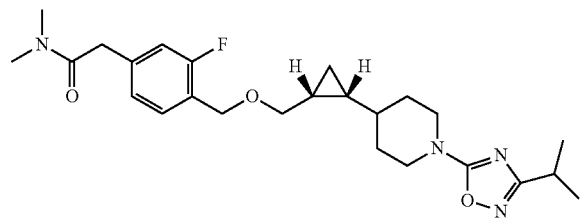 [SMILES: CC(C)c1noc(N2CCC([C@H]3C[C@H]3COCc3ccc(CC(=O)N(C)C)cc3F)CC2)n1]

A solution of 4-((1R,2R)-2-((3-fluoro-4-(1H-tetrazol-1-yl)benzyloxy)methyl)cyclopropyl)piperidinium chloride (Step A product of Example 134, 50 mg, 0.136 mmol), 2,5-dioxopyrrolidin-1-yl 1-methylcyclopropyl carbonate (Intermediate 2, 48 mg, 0.177 mmol), and triethylamine (48 uL, 0.34 mmol) in anhydrous ACN (1.4 mL) was stirred for 1 hr at rt. The reaction mixture was concentrated under reduced pressure then diluted with EtOAc (5 mL) and water (5 mL). The layers were cut and the aqueous phase extracted with EtOAc (5 mL×2). The combined organic layers were dried over MgSO$_4$, filtered, and concentrated under reduced pressure. The residue was loaded onto 2×2000 micron silica preparative TLC plates (uv 254 active) which were developed using 50% EtOAc/Hex as the solvent system. The desired silica (Rf=0.5 @ 50% EtOAc/Hex) was collected and extracted to give the title compound (35 mg, 59%). $^1$H NMR (500 MHz, CD$_3$CN) δ 9.38 (s, 1H), 7.64 (m, 3H), 4.61 (q, 2H), 4.08-3.80 (m, 2H), 3.66 (dd, 1H), 3.42 (dd, 1H), 2.63 (m, 2H), 1.83 (d, 1H), 1.67 (d, 1H), 1.49 (s, 3H), 1.23-1.11 (m, 3H), 0.97 (m, 1H), 0.79 (t, 2H), 0.69-0.63 (m, 2H), 0.58 (t, 2H), 0.01 (d, 1H). LC/MS (m/z): 430 (M+H)+, GPR119 Human EC$_{50}$: 4.8 nM.

Example 137

Preparation of 2-(3-fluoro-4-((((1R,2R)-2-(1-(3-isopropyl-1,2,4-oxadiazol-5-yl)piperidin-4-yl)cyclopropyl)methoxy)methyl)phenyl)-N,N-dimethylacetamide

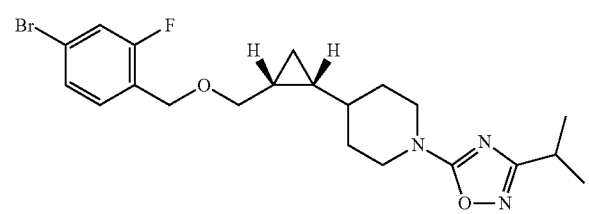

Step A: ((1R,2R)-2-(1-(3-isopropyl-1,2,4-oxadiazol-5-yl)piperidin-4-yl)cyclopropyl)methanol

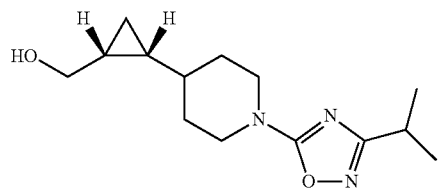 [SMILES: CC(C)c1noc(N2CCC([C@H]3C[C@H]3CO)CC2)n1]

The compound in this step was prepared from Intermediate 4 following the procedures described in Steps A-C of Example 134. LC/MS (m/z): 266 (M+H)$^+$.

Step B: 5-(4-((1R,2R)-2-((4-bromo-2-fluorobenzyloxy)methyl)cyclopropyl)piperidin-1-yl)-3-isopropyl-1,2,4-oxadiazole Sodium hydride (203 mg, 5.09 mmol) was added to a stirring solution of ((1R,2R)-2-(1-(3-isopropyl-1,2,4-oxadiazol-5-yl)piperidin-4-yl)cyclopropyl)methanol (Step A product, 900 mg, 3.39 mmol) in DMF (9 mL) that had been cooled to 0° C. in an ice bath and placed under an inert atmosphere. 10 min later 4-bromo-1-(bromomethyl)-2-fluorobenzene (1 g, 3.73 mmol) was introduced to the mixture. The ice bath was removed and the reaction warmed to rt. The reaction was aged for 1 hr then diluted with EtOAc (20 mL) and neutralized by the slow addition of saturated aqueous ammonium chloride solution (20 mL). The layers were cut and the aqueous phase extracted with EtOAc (20 mL×2). The combined organic layers were dried over MgSO$_4$, filtered, and concentrated under reduced pressure. The residue was loaded onto a silica column (KP-Sil 50 g SNAP column, Biotage system) eluting with a range of 0-45% EtOAc/Hex over 12 CV to give the desired compound (1.36 g, 89%). LC/MS (m/z): 452 (M+H)$^+$.

Step C: tert-butyl 2-(3-fluoro-4-((((1R,2R)-2-(1-(3-isopropyl-1,2,4-oxadiazol-5-yl)piperidin-4-yl)cyclopropyl)methoxy)methyl)phenyl)acetate

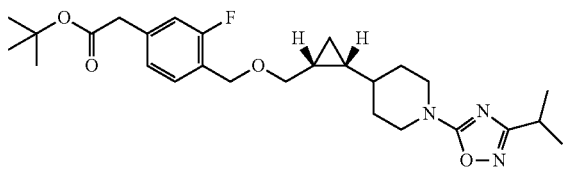 [SMILES: CC(C)c1noc(N2CCC([C@H]3C[C@H]3COCc3ccc(CC(=O)OC(C)(C)C)cc3F)CC2)n1]

A 0.5 M solution of 2-(tert-butyloxy)-2-oxoethylzinc chloride in Et₂O (14.6 mL, 7.3 mmol) was added to a mixture of 5-(4-((1R,2R)-2-((4-bromo-2-fluorobenzyloxy)methyl)cyclopropyl)piperidin-1-yl)-3-isopropyl-1,2,4-oxadiazole (Step B product, 1.1 g, 2.43 mmol), Pd₂(dba)₃ (110 mg, 0.122 mmol), and X-PHOS (116 mg, 0.243 mmol) in anhydrous THF (3 mL). The reaction mixture was stirred and heated at 65° C. overnight. The following morning the mixture was cooled to rt and filtered through a plug of celite, washing with EtOAc. The volatiles were removed under reduced pressure and the residue was loaded onto a silica column (KP-Sil 50 g SNAP column, Biotage system) eluting with a range of 5-45% EtOAc/Hex over 13 CV to give the desired compound (910 mg, 78%). LC/MS (m/z): 488 (M+H)⁺.

Step D: 2-(3-fluoro-4-((((1R,2R)-2-(1-(3-isopropyl-1,2,4-oxadiazol-5-yl)piperidin-4-yl)cyclopropyl)methoxy)methyl)phenyl)acetic acid

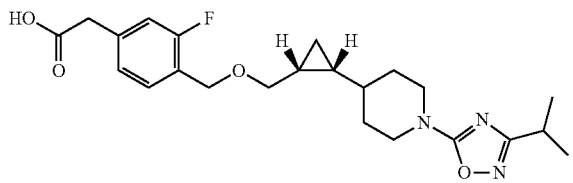 [SMILES: CC(C)c1noc(N2CCC([C@H]3C[C@H]3COCc3ccc(CC(=O)O)cc3F)CC2)n1]

A solution of 4 M HCl in dioxane (3.85 mL, 15.4 mmol) was added to a solution of tert-butyl 2-(3-fluoro-4-((((1R,2R)-2-(1-(3-isopropyl-1,2,4-oxadiazol-5-yl)piperidin-4-yl)cyclopropyl)methoxy)methyl)phenyl)acetate (Step C product, 750 mg, 1.54 mmol) in DCM (4 mL). This mixture was stirred at 35° C. for 4 hrs. The reaction mixture was subsequently concentrated under reduced pressure to afford the title compound (1.05 g, 97%) as a crude product to be used for the next step. LC/MS (m/z): 432 (M+H)⁺.

Step E: 2-(3-fluoro-4-((((1R,2R)-2-(1-(3-isopropyl-1,2,4-oxadiazol-5-yl)piperidin-4-yl)cyclopropyl)methoxy)methyl)phenyl)-N,N-dimethylacetamide

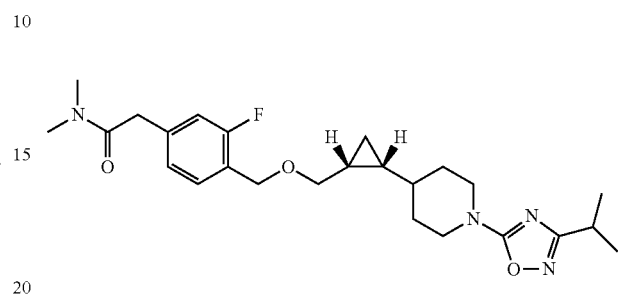

A solution of 2-(3-fluoro-4-((((1R,2R)-2-(1-(3-isopropyl-1,2,4-oxadiazol-5-yl)piperidin-4-yl)cyclopropyl)methoxy)methyl)phenyl)acetic acid (Step D product, 60 mg, 0.139 mmol), HOBT.H₂O (32 mg, 0.209 mmol), and EDC.HCl (40 mg, 0.209 mmol) dissolved in DCM (1 mL) was stirred at rt for 30 min. Dimethylamine hydrochloride (35 mg, 0.431 mmol) was added to this solution and the reaction aged at rt for 3 hrs. The reaction mixture was then diluted with DCM (1 mL) and the residue loaded directly onto 2×2000 micron silica preparative TLC plates (uv 254 active) which were developed using 100% EtOAc as the solvent system. The desired silica (Rf=0.4 @ 100% EtOAc) was collected and extracted to give the title compound (37 mg, 58%). ¹H NMR (500 MHz, CD₃CN) δ 7.37 (t, 1H), 7.06 (d, 1H), 6.99 (d, 1H), 4.52 (q, 2H), 3.99 (dd, 2H), 3.69 (s, 2H), 3.64 (q, 1H), 3.27 (t, 1H), 3.02 (s, 3H), 3.01-2.90 (m, 2H), 2.88 (s, 3H), 2.84 (t, 1H), 1.94 (d, 1H), 1.78 (d, 1H), 1.41-1.26 (m, 2H), 1.23 (s, 6H), 1.20-1.14 (m, 1H), 1.06-0.96 (m, 1H), 0.77 (p, 2H), 0.02 (q, 1H). LC/MS (m/z): 459 (M+H)+, GPR119 Human EC₅₀: 1.6 nM.

Examples 138-144

The examples in Table 19 were synthesized according to the methods described in Example 137 employing the appropriate reagents and solvents.

TABLE 19

| Example # | Chemical Structure | Observed Mass | GPR119 Human EC₅₀ |
|---|---|---|---|
| 138 | 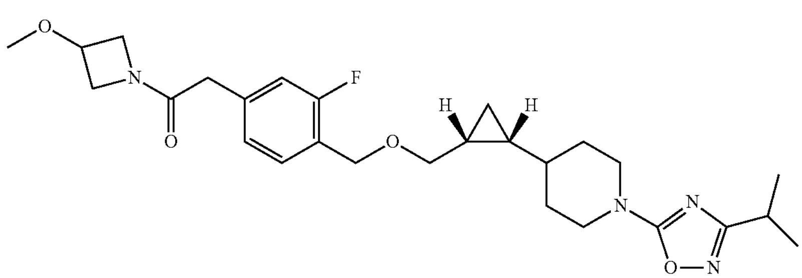 [SMILES: COC1CN(C(=O)Cc2ccc(COC[C@@H]3C[C@@H]3C3CCN(c4nc(C(C)C)no4)CC3)c(F)c2)C1] | 501 [M + H]⁺ | 2.2 nM |

TABLE 19-continued
| Example # | Chemical Structure | Observed Mass | GPR119 Human EC$_{50}$ |
|---|---|---|---|
| 139 | 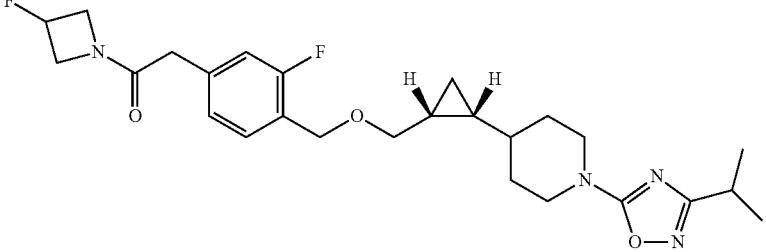 | 489 [M + H]$^+$ | 0.89 nM |
| 140 | 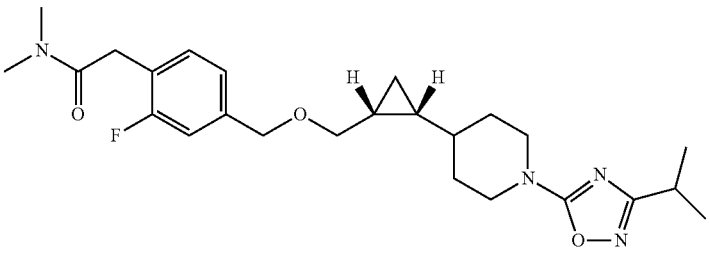 [SMILES: CC(C)c1noc(N2CCC([C@H]3C[C@H]3COCc3ccc(CC(=O)N(C)C)c(F)c3)CC2)n1] | 459 [M + H]$^+$ | 0.66 nM |
| 141 | 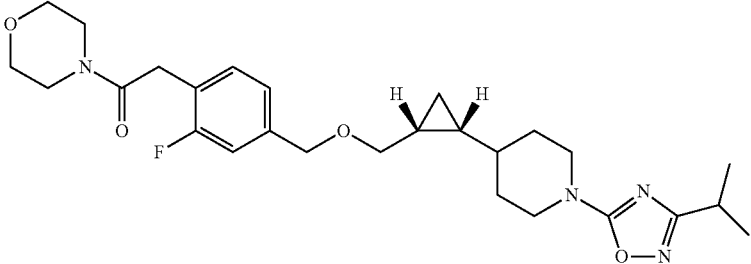 [SMILES: CC(C)c1noc(N2CCC([C@H]3C[C@H]3COCc3ccc(CC(=O)N4CCOCC4)c(F)c3)CC2)n1] | 501 [M + H]$^+$ | 1.2 nM |
| 142 | 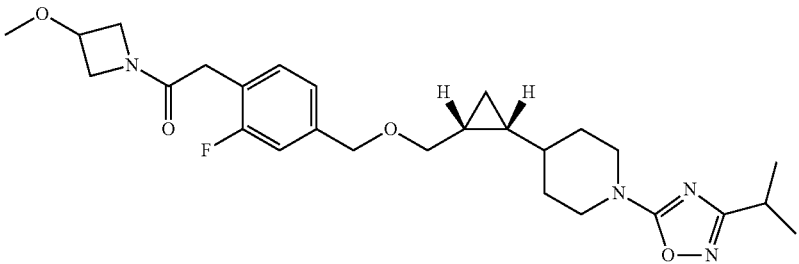 [SMILES: COC1CN(C(=O)Cc2ccc(COC[C@@H]3C[C@@H]3C3CCN(c4nc(C(C)C)no4)CC3)cc2F)C1] | 501 [M + H]$^+$ | 0.95 nM |
| 143 | 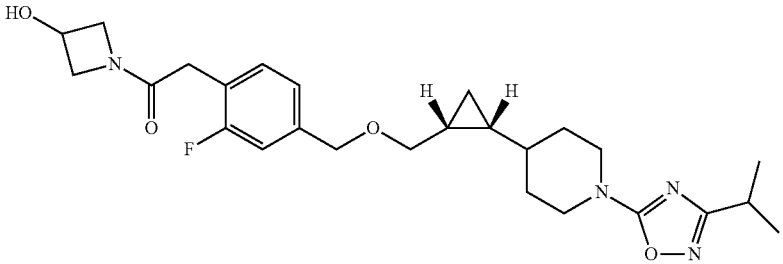 [SMILES: CC(C)c1noc(N2CCC([C@H]3C[C@H]3COCc3ccc(CC(=O)N4CC(O)C4)c(F)c3)CC2)n1] | 487 [M + H]$^+$ | 6.3 nM |

TABLE 19-continued

| Example # | Chemical Structure | Observed Mass | GPR119 Human EC$_{50}$ |
|---|---|---|---|
| 144 | 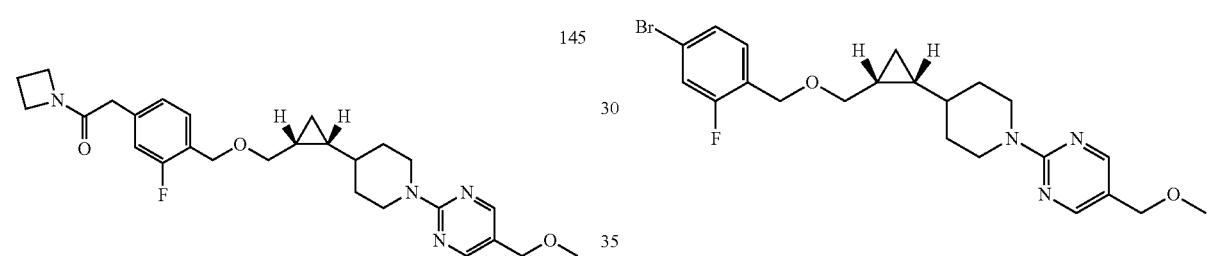 | 473 [M + H]$^+$ | 11.4 nM |

Examples 145-148

Preparation of 1-(azetidin-1-yl)-2-(3-fluoro-4-(((((1R,2R)-2-(1-(5-(methoxymethyl)pyrimidin-2-yl)piperidin-4-yl)cyclopropyl)methoxy)methyl)phenyl)ethanone

145

Step A: ((1R,2R)-2-(1-(5-(methoxymethyl)pyrimidin-2-yl)piperidin-4-yl)cyclopropyl)methanol

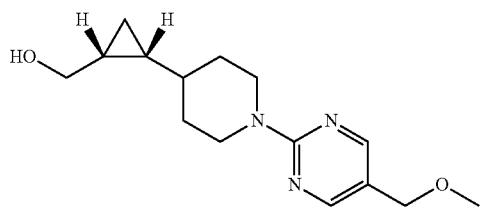 [SMILES: COCc1cnc(N2CCC([C@H]3C[C@H]3CO)CC2)nc1]

The product in this step was prepared from Intermediate 4 following the procedures described in Steps C and D of Example 128. LC/MS (m/z): 278 (M+H)$^+$.

Step B: 2-(4-(((1R,2R)-2-(((4-bromo-2-fluorobenzyl)oxy)methyl)cyclopropyl)piperidin-1-yl)-5-(methoxymethyl)pyrimidine ((1R,2R)-2-(1-(5-(methoxymethyl)pyrimidin-2-yl)piperidin-4-yl)cyclopropyl)methanol (Step A product, 1 g, 3.61 mmol) was dissolved in 10 mL of DMF. The mixture was cooled to 0° C. and NaH (60% dispersion, 0.22 g, 5.41 mmol) was added portionwise. The mixture was stirred for 5 min and 4-bromo-1-(bromomethyl)-2-fluorobenzene in DMF (2 mL) was added dropwise. The mixture was stirred at 0° C. for 30 min and at RT overnight. The mixture was quenched with sat. NaHCO$_3$ and extracted with EtOAc. The EtOAc phase was washed with water and brine, dried over MgSO4, and evaporated. The crude material was purified by flash column (25 g SNAP, 10~50% EtOAc in hexane) to afford 1.6 g (96%) of the product. Rf was 0.5 @ 50% EtOAc in hexanes (blue spot on CAM stain).

Step C: tert-butyl 2-(3-fluoro-4-(((((1R,2R)-2-(1-(5-(methoxymethyl)pyrimidin-2-yl) piperidin-4-yl)cyclopropyl)methoxy)methyl)phenyl)acetate

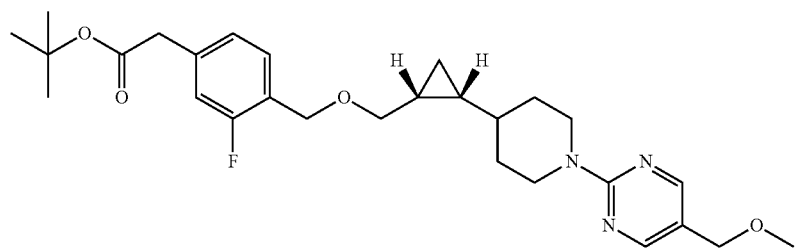 [SMILES: COCc1cnc(N2CCC([C@H]3C[C@H]3COCc3ccc(CC(=O)OC(C)(C)C)cc3F)CC2)nc1]

2-(4-(((1R,2R)-2-(((4-bromo-2-fluorobenzyl)oxy)methyl)cyclopropyl)piperidin-1-yl)-5-(methoxymethyl)pyrimidine (Step B product, 1.0 g, 2.15 mmol) was dissolved in anhydrous THF (3 ml). The mixture was stirred for 5 min and TRIS(DIBENZYLIDENEACETONE)DIPALLADIUM(0) (0.099 g, 0.108 mmol) and X-PHOS (0.103 g, 0.215 mmol) were added, followed by (2-(tert-butoxy)-2-oxoethyl)zinc(II) bromide (0.5 M solution in ether, 12.92 ml, 6.46 mmol). The mixture was heated at 60° C. overnight. The reaction mixture was quenched with aqueous NH₄Cl, and the aqueous layer was extracted with EtOAc. The organic extracts were washed with brine, dried, and evaporated to give the crude product, which was purified by flash column (25 g SNAP, 5~30% EtOAc in hexane) to afford 1.05 g (98%) of the desired product. Rf was 0.3 @ 20% EtOAc in hexanes (blue spot on CAM stain).

Step D: 2-(3-fluoro-4-((((1R,2R)-2-(1-(5-(methoxymethyl)pyrimidin-2-yl)piperidin-4-yl)cyclopropyl)methoxy)methyl)phenyl)acetic acid

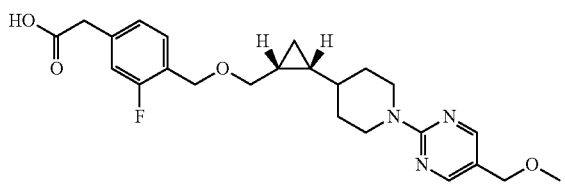 [SMILES: COCc1cnc(N2CCC([C@H]3C[C@H]3COCc3ccc(CC(=O)O)cc3F)CC2)nc1]

tert-butyl 2-(3-fluoro-4-((((1R,2R)-2-(1-(5-(methoxymethyl)pyrimidin-2-yl) piperidin-4-yl)cyclopropyl)methoxy)methyl)phenyl)acetate (Step C product, 1 g, 2.0 mmol) was dissolved in DCM (10 ml) and TFA (5.80 ml, 78 mmol) was added. The mixture was stirred at RT for 2 h. The solvents were evaporated to afford 1.5 g of the crude material. This crude material was dissolved in EtOAc (50 mL), washed with 20 mL of sat. NaHCO₃ and sat. NH₄Cl. The combined water phase was extracted with EtOAc (30 mL). The combined EtOAc phases were dried over MgSO4, evaporated to afford 0.9 g (100%) of the desired acid. LC/MS (m/z): 444 (M+H)⁺. Rf was 0 @ 50% EtOAc in hexanes (blue spot on CAM stain)

Step E: 1-(azetidin-1-yl)-2-(3-fluoro-4-((((1R,2R)-2-(1-(5-(methoxymethyl) pyrimidin-2-yl)piperidin-4-yl)cyclopropyl)methoxy)methyl)phenyl)ethanone

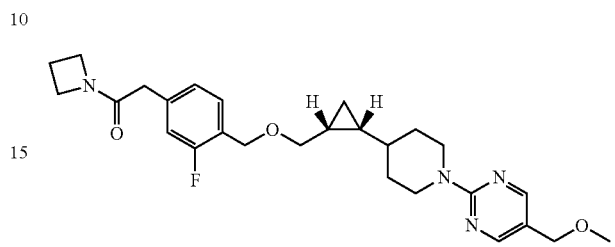

2-(3-Fluoro-4-((((1R,2R)-2-(1-(5-(methoxymethyl)pyrimidin-2-yl)piperidin-4-yl)cyclopropyl)methoxy)methyl)phenyl)acetic acid (Step D product, 70 mg, 0.158 mmol), 1-HYDROXYBENZOTRIAZOLE HYDRATE (36.3 mg, 0.237 mmol) and (E)-3-(ETHYLDIAZENYL)-N,N-DIMETHYLPROPAN-1-AMINE HYDROCHLORIDE (42.5 mg, 0.237 mmol) were dissolved in CH₂Cl₂ (3 ml). The mixture was stirred at RT for 10 min., to which was added AZETIDINE (0.016 ml, 0.237 mmol). The reaction mixture was stirred at RT overnight. TLC and LC-MS showed the SM was completely consumed. The mixture was diluted with DCM, washed with water, dried over MgSO₄, and evaporated to dryness. The crude product was purified by prep TLC (pure EtOAc) to afford 58.2 mg (76%) of the title compound. ¹H NMR (500 MHz, CDCl₃) δ 8.30 (S, 2H), 7.38 (m, 1H), 7.05 (m, 2H), 4.70 (m, 2H), 4.60-4.50 (m, 2H), 4.25 (s, 2H), 4.10~4.00 (m, 4H), 3.70 (m, 1H), 3.40 (m, 3H), 3.32 (s, 3H), 2.83 (m, 2H), 2.25 (m, 2H), 2.05 (m, 2H), 1.82 (m, 1H), 1.40-1.20 (m, 3H), 1.05 (m, 1H), 0.70 (m, 2H), 0.40 (m, 1H). LC/MS (m/z): 483 (M+H)⁺, GPR119 Human EC₅₀: 5.16 nM.

The Examples in Table 20 were synthesized according to the methods described Example 145 employing the appropriate reagents and solvents.

TABLE 20

| Example # | Chemical Structure | Observed Mass | GPR119 Human EC$_{50}$ |
|---|---|---|---|
| 146 | 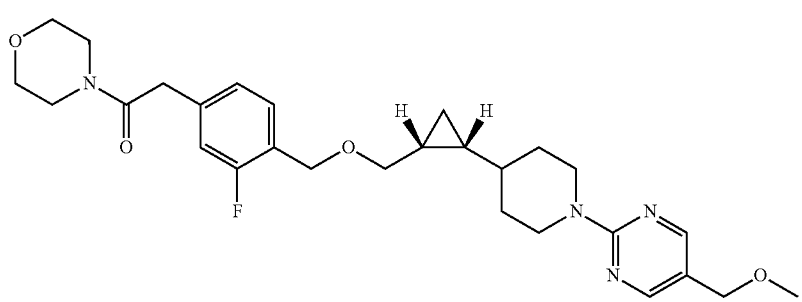 [SMILES: COCc1cnc(N2CCC([C@H]3C[C@H]3COCc3ccc(CC(=O)N4CCOCC4)cc3F)CC2)nc1] | 513 [M + H]⁺ | 3.23 nM |

TABLE 20-continued

| Example # | Chemical Structure | Observed Mass | GPR119 Human EC$_{50}$ |
|---|---|---|---|
| 147 | 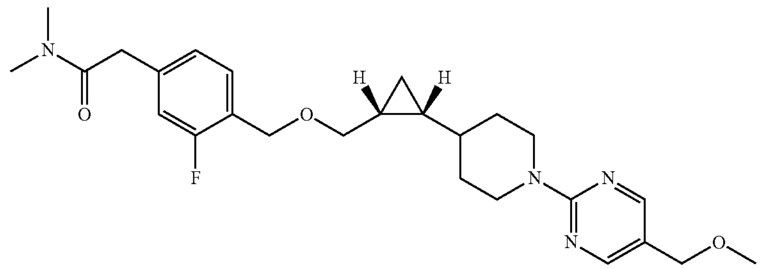 | 471 [M + H]$^+$ | 2.52 nM |
| 148 | 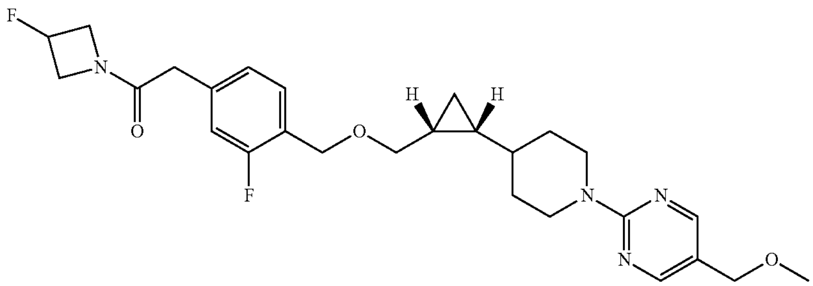 [SMILES: COCc1cnc(N2CCC([C@H]3C[C@H]3COCc3ccc(CC(=O)N4CC(F)C4)cc3F)CC2)nc1] | 501 [M + H]$^+$ | 3.56 nM |

Compounds of the present invention were shown to be biologically active in one or more of the following assays:

Measurement of GPR119 Signaling Using LANCE 384-Well cAMP Kit

Human embryonic kidney (HEK) 293 cell lines stably transfected with human GPR119 were maintained in DMEM media containing FBS, penicillin-streptomycin, HEPES, and hygromycin. For the cAMP assay, the transfected cells were harvested using a non-enzymatic cell dissociation solution (GIBCO 2672), pelleted and resuspended in stimulation buffer (DMEM, 25 mM Hepes, 0.1% BSA, pH 7.4 in the presence of 100 μM phosphodiesterase inhibitors). The adenylate cyclase assay was constructed following the LANCE™ cAMP Kit (Perkin Elmer, AD0264) instructions. Briefly, cells with Alexa Fluor® 647-anti cAMP antibody were incubated with 10 point series diluted test article in stimulation buffer with a final concentration of 2.5% DMSO for 45 minutes. The reaction was stopped by incubating with the supplied detection buffer containing the europium chelate of the Eu-SA/Biotin-cAMP tracer for 3 hours. The assay was performed in duplicate in a 384 well plate for duplicate plates. Fluorescence at 665 nm was measured using a PHERAstar instrument. Basal activity was determined using a DMSO control and maximum response was defined as cAMP stimulation produced by an internal agonist control. Standard cAMP concentrations were assayed concurrently for conversion of fluorescence signal to cAMP level. The data was analyzed using 4-parameter curve fit in Microsoft Excel.

Measurement of GPR119 Signaling Using a Cyclic AMP (cAMP) Homogenous Time Resolved Fluorescence (HTRF) Assay Chinese hamster ovary (CHO) cell lines stably transfected with the permissive guanine nucleotide binding protein alpha 15 (Gα15) and murine GPR119 were maintained in DMEM media containing FBS, penicillin-streptomycin, puromycin, and G418 (geneticin). Alternatively, human embryonic kidney (HEK)293 Flp-In cells (Invitrogen, Carlsbad, Calif.) were stably transfected with a human SNP variant (S309L) of GPR119 and maintained in DMEM media containing FBS, penicillin-streptomycin, and hygromycin. Agonist activation of the GPR119 receptor was measured in receptor transfected cells described above, treated with compounds of this invention, using a commercial homogenous time resolved fluorescence (HTRF) kit for measurement of cAMP (CisBio, Bedford, Mass.). The assay was performed in 96-well half-volume plates (murine) or 384-well plates (human) following the manufacturers instructions. Briefly, suspended cells were incubated with a dose titration of test compound at RT for 60 min, lysed, and incubated with HTRF reagents for an additional 60 min. The plate was read using an Envision multilabel reader (Perkin Elmer) adjusted to read time resolved fluorescence and the cAMP concentrations were extrapolated from a cAMP calibration curve. GPR119 agonists will exhibit a concentration-dependent increase in intracellular cAMP. The concentration of test compound required to stimulate a half-maximal response (EC50), and efficacy as compared to an internal agonist control, was determined from a sigmoidal 4-parameter curve fit of the resulting plot of normalized activity versus compound concentration.

Evaluation of Glucose Dependent Insulin Secretion (GDIS) in Static Isolated Mouse Islets.

Pancreatic islets of Langerhans were isolated from the pancreata of 10-12 wk-old C57BL/6 mice by collagenase digestion and discontinuous Ficoll gradient separation, a modification of the original method of Lacy and Kostianovsky (Lacy & Kostianovsky, 1967 Diabetes 16-35-39). The islets were cultured overnight in RPMI 1640 medium (11 mM glucose, 10% FCS) before experimental treatment. The acute effects of compounds of this invention on GDIS were determined by 60-min static incubation with islets in Krebs-Ringers' bicarbonate (KRB) medium. The KRB medium contained, in mM, 143.5 Na$^+$, 5.8 K$^+$, 2.5 Ca$^{2+}$, 1.2 Mg$^{2+}$, 124.1 Cl$^-$, 1.2 PO$_4^{3-}$, 1.2 SO$_4^{2+}$, 25 CO$_3^{2-}$, and 10 HEPES, pH 7.4, in addition to 2 mg/ml bovine serum albumin, and either 2 (G2) or 16 (G16) mM glucose (pH 7.4). The static incubation was performed with round-bottomed 96-well plates (one islet/well with 200 μl KRB medium). The compounds were added to KRB medium just before the initiation of the 60-min incubation. Insulin concentration in aliquots of the incubation buffer was measured by the ultra-sensitive rat insulin EIA kit from ALPCO Diagnostics (Windham, N.H.).

Example of a Pharmaceutical Formulation

As a specific embodiment of an oral composition of a compound of the present invention, 50 mg of any of the examples is formulated with sufficient finely divided lactose to provide a total amount of 580 to 590 mg to fill a size O hard gelatin capsule.

While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:
1. A compound represented by the formula:

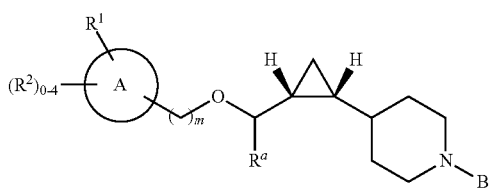

I or a pharmaceutically acceptable salt thereof, wherein:
ring A represents a 5- or 6-membered aryl or heteroaryl ring, the heteroaryl ring containing 1-4 heteroatoms, 1-4 of which are nitrogen atoms, and 0-1 of which are oxygen or sulfur atoms;
m is an integer selected from 1-3;
$R^a$ is selected from: H; $C_{1-4}$alkyl; hydroxy$C_{1-4}$alkyl; or $C_{1-4}$alkoxy$C_{1-4}$alkyl;
$R^1$ is selected from:
  $C_{1-6}$alkyl;
  $OC_{1-6}$alkyl;
  $C(O)C_{1-6}$alkyl;
  $C(O)C_{3-6}$cycloalkyl;
  $C(O)NHC_{1-6}$alkyl;
  $S(O)_{0-2}C_{1-6}$alkyl;
  $SO_2C_{3-6}$cycloalkyl;
  $SO_2NR^bR^c$, wherein $R^b$ and $R^c$ are independently selected from H or $C_{1-6}$alkyl; —$CH_2CONR^dR^e$ wherein $R^d$ and $R^e$ are independently selected from the group consisting of H, $C_{1-6}$alkyl, $C_{3-6}$cycloalkyl, halo$C_{1-6}$alkyl, halo$C_{3-6}$cycloalkyl, $C_{1-6}$alkoxy, and $C_{3-6}$cycloalkyl$C_{1-6}$alkoxy; wherein $R^d$ and $R^e$, if individually alkyl or alkoxy, can together form a 4-6-membered saturated heterocyclic ring having 1 nitrogen atom which 4-6-membered ring may be optionally substituted with 1-3 substituents independently selected from halogen, hydroxy, oxo, $C_{1-6}$alkoxy; or $CO_2C_{1-6}$alkyl;
  —$CH_2$-heteroaryl, wherein the heteroaryl is a 5-6 membered heteroaryl ring containing 1-4 heteroatoms independently selected from nitrogen or oxygen;
  —$CH_2CH_3CONR^dR^e$, with $R^d$ and $R^e$ defined above;
  or a 5-6 membered heteroaryl ring containing 1-4 heteroatoms, 1-4 of which are nitrogen atoms, and 0-1 of which are oxygen or sulfur atoms, wherein the $R^1$ alkyl, cycloalkyl and heteroaryl moiety is optionally substituted with 1-3 of halogen; hydroxy; $C_{1-6}$alkyl; $NH^2$; and $O$—$C_{1-6}$alkyl;
each $R^2$ is independently selected from halogen, CN, $C_{1-6}$alkyl or halo$C_{1-6}$alkyl;
B represents (a) a 6 membered aryl ring or a 5-6 membered heteroaryl ring containing 1-4 heteroatoms, 1-4 of which are nitrogen atoms, and 0-1 of which are oxygen or sulfur atoms, said ring being optionally substituted with 1-3 groups selected from $R^3$, wherein each $R^3$ is independently selected from
  halogen;
  hydroxyl;
  $C_{1-6}$alkyl;
  $C(O)OC_{1-6}$alkyl;
  C=O;
  CN;
  $C_{1-6}$alkoxy;
  $C_{3-6}$cycloalkyl;
  $C(=O)$—$(O)_n$—$R'$, wherein n is an integer from 0-3 and $R'$ is $C_{1-6}$alkyl or H;
  5-6 membered heteroaryl ring containing 1-4 heteroatoms independently selected from nitrogen or oxygen;
  $C(=O)$—$R^f$, wherein $R^f$ is 5-6 membered heteroaryl ring containing 1-4 heteroatoms independently selected from nitrogen or oxygen;
  or halo$C_{1-6}$alkoxy;
wherein the $R^3$ alkyl moiety is optionally substituted with 1-3 substituents independently selected from:
  halogen,
  hydroxy,
  $C_{1-6}$alkyl, or
  $C_{1-6}$alkoxy;
  or b) $CO_2R^4$, wherein
  $R^4$ is selected from:
    $C_{1-6}$alkyl; or
    $C_{3-6}$cycloalkyl,
  wherein the alkyl and cycloalkyl are optionally substituted with 1-3 substituents independently selected from:
    halogen,
    $C_{1-6}$alkyl, or
    $C_{3-6}$ cycloalkyl.

2. The compound of claim 1 in accordance with formula I-a:

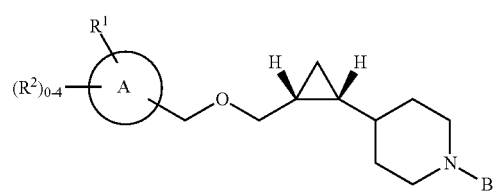

I-a or a pharmaceutically acceptable salt thereof, wherein:
ring A is substituted phenyl or pyridyl;
B represents a) a pyrimidine ring optionally substituted with 1-2 groups selected from $R^3$, wherein each $R^3$ is independently selected from:
  halogen;
  hydroxyl;
  $C_{1-6}$alkyl;
  $C(O)OC_{1-6}$alkyl;
  C=O;
  CN;

$C_{1-6}$alkoxy;
$C_{3-6}$cycloalkyl;
C(=O)—(O)$_n$—R', wherein n is an integer from 0-3 and R' is $C_{1-6}$alkyl or H;
5-6 membered heteroaryl ring containing 1-4 heteroatoms independently selected from nitrogen or oxygen;
C(=O)—R$^f$, wherein R$^f$ is a 5-6 membered heteroaryl ring containing 1-4 heteroatoms independently selected from nitrogen or oxygen;
or halo$C_{1-6}$alkoxy;
wherein the R$^3$ alkyl moiety is optionally substituted with 1-3 substituents independently selected from:
halogen,
hydroxy,
$C_{1-6}$alkyl, or
$C_{1-6}$alkoxy;
b) 1,2,4-oxadiazol optionally substituted with 1-3 substituents independently selected from:
$C_{1-6}$alkyl;
$C_{1-6}$alkoxy; or
$C_{3-6}$cycloalkyl,
wherein the alkyl, alkoxy and cycloalkyl are optionally substituted with 1-3 substituents independently selected from:
halogen,
$C_{1-6}$alkyl, or
$C_{3-6}$cycloalkyl;
or c) $CO_2R^4$, wherein
R$^4$ is selected from:
$C_{1-6}$alkyl; or
$C_{3-6}$cycloalkyl,
wherein the alkyl and cycloalkyl are optionally substituted with 1-3 substituents independently selected from:
halogen,
$C_{1-6}$alkyl, or
$C_{3-6}$cycloalkyl;
R$^1$ is selected from the group consisting of
$C_{1-6}$alkyl;
$OC_{1-6}$alkyl;
$C(O)C_{1-6}$alkyl;
$C(O)C_{3-6}$cycloalkyl;
$C(O)NHC_{1-6}$alkyl;
$S(O)_{0-2}C_{1-6}$alkyl;
$SO_2C_{3-6}$cycloalkyl;
—CH$_2$CONR$^d$R$^e$ wherein R$^d$ and R$^e$ are independently selected from H, $C_{1-6}$alkyl, $C_{3-6}$cycloalkyl, halo$C_{1-6}$alkyl, halo$C_{3-6}$cycloalkyl, $C_{1-6}$alkoxy, or $C_{3-6}$cycloalkyl$C_{1-6}$alkoxy; wherein R$^d$ and R$^e$, if individually alkyl or alkoxy, can together form a 4-6-membered saturated heterocyclic ring having 1 nitrogen atom which 4-6-membered ring may be optionally substituted with 1-3 substituents independently selected from halogen, hydroxy, oxo, $C_{1-6}$alkyl, $C_{1-6}$alkoxy; or $CO_2C_{1-6}$alkyl;
—CH$_2$-heteroaryl, wherein the heteroaryl is a 5-6 membered heteroaryl ring containing 1-4 heteroatoms independently selected from nitrogen or oxygen
—CH$_2$CH$_3$CONR$^d$R$^e$, with R$^d$ and R$^e$ defined above;
or a 5-6 membered heteroaryl ring containing 1-4 heteroatoms, 1-4 of which are nitrogen atoms, and 0-1 of which are oxygen or sulfur atoms,
wherein the R$^1$ alkyl and cycloalkyl moiety is optionally substituted with 1-3 substituents selected from: halogen; hydroxy; $C_{1-6}$alkyl; NH$^2$; or O—$C_{1-6}$alkyl;
and R$^2$ is halogen which is further selected from fluoro or chloro.

3. The compound of claim 1 or a pharmaceutically acceptable salt thereof, wherein ring A is pyridyl.

4. The compound of claim 1 or a pharmaceutically acceptable salt thereof, wherein ring A is phenyl.

5. The compound of claim 1 or a pharmaceutically acceptable salt thereof, wherein B represents (b) $CO_2R^4$, wherein R$^4$ is
$C_{1-6}$alkyl, or
$C_{3-6}$cycloalkyl,
wherein the alkyl and cycloalkyl are optionally substituted with 1-3 substituents independently selected from:
halogen,
$C_{1-6}$alkyl,
or $C_{3-6}$ cycloalkyl.

6. The compound of claim 1 or a pharmaceutically acceptable salt thereof, wherein B is pyrimidine, optionally substituted with 1-3 substituents independently selected from:
halogen;
hydroxyl;
$C_{1-6}$alkyl;
$C(O)OC_{1-6}$alkyl;
C=O;
CN;
$C_{1-6}$alkoxy;
$C_{3-6}$cycloalkyl;
C(=O)—(O)$_n$—R', wherein n is an integer from 0-3 and R' is $C_{1-6}$alkyl or H;
5-6 membered heteroaryl ring containing 1-4 heteroatoms independently selected from nitrogen or oxygen;
C(=O)—R$^f$, wherein R$^f$ is a 5-6 membered heteroaryl ring containing 1-4 heteroatoms independently selected from nitrogen or oxygen;
or halo$C_{1-6}$alkoxy;
wherein the alkyl moiety is optionally substituted with 1-3 substituents independently selected from:
halogen,
hydroxy,
$C_{1-6}$alkyl, or
$C_{1-6}$alkoxy.

7. The compound of claim 1 or a pharmaceutically acceptable salt thereof, wherein B is 1,2,4-oxadiazol optionally substituted with 1-3 substituents independently selected from
$C_{1-6}$alkyl;
$C_{1-6}$alkoxy; or
$C_{3-6}$cycloalkyl,
wherein the alkyl, alkoxy and cycloalkyl are optionally substituted with 1-3 substituents independently selected from:
halogen,
$C_{1-6}$alkyl, or
$C_{3-6}$cycloalkyl.

8. The compound of claim 1 or a pharmaceutically acceptable salt thereof, wherein each R$^3$ is independently selected from halogen which is further selected from F, Cl, or Br, $C_{1-4}$alkyl, $C_{1-3}$ alkoxy or $C_{3-6}$ cycloalkyl.

9. The compound of claim 1 or a pharmaceutically acceptable salt thereof, wherein B is methoxymethylpyrimidine.

10. The compound of claim 1 or a pharmaceutically acceptable salt thereof, wherein R$^2$ is halogen which is further selected from fluoro or chloro.

11. The compound of claim 1 or a pharmaceutically acceptable salt thereof, wherein R$^1$ is at the 4 position and is selected from $C_{1-6}$alkyl; $OC_{1-6}$alkyl; $C(O)C_{1-6}$alkyl; $C(O)C_{3-6}$cycloalkyl; $C(O)NHC_{1-6}$alkyl; $S(O)_{0-2}C_{1-6}$alkyl; $SO_2C_{3-6}$cycloalkyl; $SO_2NR^bR^c$, wherein R$^b$ and R$^c$ are selected from H or $C_{1-6}$alkyl; or a 5-6 membered heteroaryl ring containing 1-4 heteroatoms, 1-4 of which are nitrogen atoms, and 0-1 of which are oxygen or sulfur atoms, wherein the R¹ alkyl, cycloalkyl and heteroaryl moiety is optionally substituted with 1-3 substituents independently selected from: halogen; hydroxy; $C_{1-6}$alkyl or O—$C_{1-6}$alkyl.

12. The compound of claim 1 or a pharmaceutically acceptable salt thereof, wherein R¹ is methylsulfonyl.

13. A compound which is:

5-chloro-2-{4-[(1R,2R)-2-({[5-(methylsulfonyl)pyridin-2-yl]methoxy}methyl)cyclopropyl]piperidin-1-yl}pyrimidine;

5-methyl-2-{4-[(1R,2R)-2-({[5-(methylsulfonyl)pyridin-2-yl]methoxy}methyl)cyclopropyl]piperidin-1-yl}pyrimidine;

5-ethyl-2-{4-[(1R,2R)-2-({[5-(methylsulfonyl)pyridin-2-yl]methoxy}methyl)cyclopropyl]piperidin-1-yl}pyrimidine;

5-bromo-2-{4-[(1R,2R)-2-({[5-(methylsulfonyl)pyridin-2-yl]methoxy}methyl)cyclopropyl]piperidin-1-yl}pyrimidine;

5-fluoro-2-{4-[(1R,2R)-2-({[5-(methylsulfonyl)pyridin-2-yl]methoxy}methyl)cyclopropyl]piperidin-1-yl}pyrimidine;

5-methoxy-2-{4-[(1R,2R)-2-({[5-(methylsulfonyl)pyridin-2-yl]methoxy}methyl)cyclopropyl]piperidin-1-yl}pyrimidine;

2-{4-[(1R,2S)-24 {5-(methylsulfonyl)pyridin-2-yl]methoxy}methyl)cyclopropyl]piperidin-1-yl}-5-(1H)-pyrazol-4-yl)pyrimidine;

propyl 4-[(1R,2R)-2-({[4(methylsulfonyl)benzyl]oxy}methyl)cyclopropyl]piperidine-1-carboxylate;

isopropyl 4-[(1R,2R)-2-({[4(methylsulfonyl)benzyl]oxy}methyl)cyclopropyl]piperidine-1-carboxylate;

isobutyl 4-[(1R,2R)-2-({[4(methylsulfonyl)benzyl]oxy}methyl)cyclopropyl]piperidine-1-carboxylate;

1-methylcyclopropyl 4-[(1R,2R)-2-({[4-(methylsulfonyl)benzyl]oxy}methyl)cyclopropyl]piperidine-1-carboxylate;

cyclobutyl 4-[(1R,2R)-2-({[4-(methylsulfonyl)benzyl]oxy}methyl)cyclopropyl]piperidine-1-carboxylate;

cyclopropylmethyl 4-[(1R,2R)-2-({[4-(methylsulfonyl)benzyl]oxy}methyl)cyclopropyl]piperidine-1-carboxylate;

5-chloro-2-{4-[(1R,2R)-2-({[4-(methylsulfonyl)benzyl]oxy}methyl)cyclopropyl]piperidin-1-yl}pyrimidine;

5-methoxy-2-{4-[(1R,2R)-2-({[4-(methylsulfonyl)benzyl]oxy}methyl)cyclopropyl]piperidin-1-yl}pyrimidine;

5-fluoro-2-{4-[(1R,2R)-2-({[4-(methylsulfonyl)benzyl]oxy}methyl)cyclopropyl]piperidin-1-yl}pyrimidine;

methyl 2-{4-[(1R,2R)-2-({[4-(methylsulfonyl)benzyl]oxy}methyl)cyclopropyl]piperidine-1-yl}pyrimidine-5-carboxylate;

5-cyclopropyl-2-{4-[(1R,2R)-2-({[4-(methylsulfonyl)benzyl]oxy}methyl)cyclopropyl]piperidin-1-yl}pyrimidine;

5-isobutyl-2-{4-[(1R,2R)-2-({[4-(methylsulfonyl)benzyl]oxy}methyl)cyclo-propyl]piperidin-1-yl}pyrimidine;

5-ethyl-2-{4-[(1R,2R)-2-({[4-(methylsulfonyl)benzyl]oxy}methyl)cyclopropyl]piperidin-1-yl}pyrimidine;

5-methyl-2-{4-[(1R,2R)-2-({[4-(methylsulfonyl)benzyl]oxy}methyl)cyclopropyl]piperidin-1-yl}pyrimidine;

2-{4-[(1R,2R)-2-({[4-(methylsulfonyl)benzyl]oxy}methyl)cyclopropyl]piperidin-1-yl}-5-propylpyrimidine;

5-isopropyl-2-{4-[(1R,2R)-2-({[4-(methylsulfonyl)benzyl]oxy}methyl)cyclo propyl]piperidin-1-yl}pyrimidine;

1-(3-isopropyl-1,2,4-oxadiazol-5-yl)-4-[(1R,2R)-2-({[4-(methylsulfonyl)benzyl]oxy}methyl)cyclo propyl]piperidine;

4-[(1R,2R))-2-({[4-(cyclopropylsulfonyl)benzyl]oxy}methyl)cyclopropyl]-1-(3-isopropyl-1,2,4-oxadiazol-5-yl)piperidine;

4-[(1R,2R)-2-({[4-(ethylsulfonyl)benzyl]oxy}methyl)cyclopropyl]-1-(3-isopropyl-1,2,4-oxadiazol-5-yl)piperidine;

1-(3-cyclopropyl-1,2,4-oxadiazol-5-yl)-4-[(1R,2R)-2-({[4-(methylsulfonyl)benzyl]oxy}methyl)cyclopropyl]piperidine;

1-(3-cyclopropyl-1,2,4-oxadiazol-5-yl)-4-[(1R,2R)-2-({[4-(cyclopropylsulfonyl)benzyl]oxy}methyl)cyclopropyl]piperidine;

1-(3-cyclopropyl-1,2,4-oxadiazol-5-yl)-4-[(1R,2R)-2-({[4-(ethylsulfonyl)benzyl]oxy}methyl)cyclopropyl]piperidine;

1-(3-ethyl-1,2,4-oxadiazol-5-yl)-4-[(1R,2R)-2-({[4-(methylsulfonyl)benzyl]oxy}methyl)cyclopropyl]piperidine;

1-(3-cyclobutyl-1,2,4-oxadiazol-5-yl)-4-[(1R,2R)-2-({[4-(cyclopropylsulfonyl)benzyl]oxy}methyl)cyclopropyl]piperidine;

1-(3-cyclobutyl-1,2,4-oxadiazol-5-yl)-4-[(1R,2R)-2-({[4-(ethylsulfonyl)benzyl]oxy}methyl)cyclopropyl]piperidine;

tert-butyl 4-[(1R,2R)-2-({[3-fluoro-4-(methylsulfonyl)benzyl]oxy}methyl)cyclopropyl]piperidine-1-carboxylate;

tert-butyl 4-[(1R,2R)-2-({[4-(ethylsulfonyl)-3-fluorobenzyl]oxy}methyl)cyclopropyl]piperidine-1-carboxylate;

4-[(1R,2R)-2-({[3-fluoro-4-(methylsulfonyl)benzyl]oxy}methyl)cyclopropyl]-1-(3-isopropyl-1,2,4-oxadiazol-5-yl)piperidine;

1-(3-ethyl-1,2,4-oxadiazol-5-yl)-4-[(1R,2R)-2-({[3-fluoro-4-(methylsulfonyl)benzyl]oxy}methyl)cyclopropyl]piperidine;

1-(3-cyclopropyl-1,2,4-oxadiazol-5-yl)-4-[(1R,2R)-2-({[3-fluoro-4-(methylsulfonyl)benzyl]oxy}methyl)cyclopropyl]piperidine;

4-[(1R,2R)-2-({[3-fluoro-4-(ethylsulfonyl)benzyl]oxy}methyl)cyclopropyl]-1-(3-isopropyl-1,2,4-oxadiazol-5-yl)piperidine;

1-(3-cyclopropyl-1,2,4-oxadiazol-5-yl)-4-[(1R,2R)-2-({[3-fluoro-4-(ethylsulfonyl)benzyl]oxy}methyl)cyclopropyl]piperidine;

5-ethyl-2-{4-[(1R,2R)-2-({[3-fluoro-4-(methylsulfonyl)benzyl]oxy}methyl)cyclopropyl]piperidin-1-yl}pyrimidine;

5-chloro-2-{4-[(1R,2R)-2-({[3-fluoro-4-(methylsulfonyl)benzyl]oxy}methyl)cyclopropyl]piperidin-1-yl}pyrimidine;

isopropyl 4-[(1R,2R)-2-({[3-fluoro-4-(methylsulfonyl)benzyl]oxy}methyl)cyclopropyl]piperidine-1-carboxylate;

1-methylcyclopropyl 4-[(1R,2R)-2-({[3-fluoro-4-(methylsulfonyl)benzyl]oxy}methyl)cyclopropyl]piperidine-1-carboxylate;

tert-butyl 4-[(1R,2R)-2-({[3,5-difluoro-4-(methylsulfonyl)benzyl]oxy}methyl)cyclopropyl]piperidine-1-carboxylate;

5-chloro-2-{4-[(1R,2R)-2-({[3,5-difluoro-4-(methylsulfonyl)benzyl]oxy}methyl)cyclopropyl]piperidin-1-yl}pyrimidine;

5-chloro-2-{4-[(1R,2R)-2-({[3,5-difluoro-4-(methylsulfonyl)benzyl]oxy}methyl)cyclopropyl]piperidin-1-yl}pyrimidine;

2-{4-[(1R,2R)-2-({[3,5-difluoro-4-(methylsulfonyl)benzyl]oxy}methyl)cyclopropyl]piperidin-1-yl}-5-fluoropyrimidine;

5-cyclopropyl-2-{4-[(1R,2R)-2-({[3,5-difluoro-4-(methylsulfonyl)benzyl]oxy}methyl)cyclopropyl]piperidin-1-yl}pyrimidine;

1-methylcyclopropyl 4-[(1R,2R)-2-({[3,5-difluoro-4-(methylsulfonyl)benzyl]oxy}methyl)cyclopropyl]piperidine-1-carboxylate;

isopropyl 4-[(1R,2R)-2-({[3,5-difluoro-4-(methylsulfonyl)benzyl]oxy}methyl)cyclopropyl]piperidine-1-carboxylate;

4-[(1R,2R)-2-[1-(5-chloropyrimidin-2-yl)piperidin-4-yl]cyclopropyl}methoxy)methyl]-2-fluoro phenyl}(cyclopropyl)methanone;

tert-butyl 4-[(1R,2R)-2-({[4-(cyclopropylcarbonyl)-3,5-difluorobenzyl]oxy}methyl)cyclopropyl]piperidine-1-carboxylate;

4-[(1R,2R)-2-[1-(5-chloropyrimidin-2-yl)piperidin-4-yl]cyclopropyl}methoxy)methyl]-2,6-difluoro phenyl}(cyclopropyl)methanone;

5-ethyl-2-{4-[(1R,2R)-2-({[4-(1,3-oxazol-2-yl)benzyl]oxy}methyl)cyclopropyl]piperidin-1-yl}pyrimidine;

5-ethyl-2-{4-[(1R,2R)-2-({[4-(1,3-thiazol-5-yl)benzyl]oxy}methyl)cyclopropyl]piperidin-1-yl}pyrimidine;

2-{4-[(1R,2R)-2-({[4-(cyclopropylsulfonyl)benzyl]oxy}methyl)cyclopropyl]piperidin-1-yl}-5-ethyl pyrimidine;

5-ethyl-2-{4-[(1R,2R)-2-({[4-(ethylsulfonyl)benzyl]oxy}methyl)cyclopropyl]piperidin-1-yl}pyrimidine;

(2R)-1-{4-[({(1R,2R)-2-[1-(5-ethylpyrimidin-2-yl)piperidin-4-yl]cyclopropyl}methoxy)methyl]phenyl}propan-2-ol;

(2S)-1-{4-[({(1R,2R)-2-[1-(5-ethylpyrimidin-2-yl)piperidin-4-yl]cyclopropyl}methoxy)methyl]phenyl}propan-2-ol;

2-{4-[({(1R,2R)-2-[1-(5-ethylpyrimidin-2-yl)piperidin-4-yl]cyclopropyl}methoxy)methyl]phenyl}ethanol;

5-ethyl-2-{4-[(1R,2R)-2-({[4-(1H-tetrazol-1-yl)benzyl]oxy}methyl)cyclopropyl]piperidin-1-yl}pyrimidine;

5-ethyl-2-{4-[(1R,2R)-2-({[4-(1H-1,2,3-triazol-1-yl)benzyl]oxy}methyl)cyclopropyl]piperidin-1-yl}pyrimidine;

5-ethyl-2-{4-[(1R,2R)-2-({[4-(1,2,4-oxadiazol-5-yl)benzyl]oxy}methyl)cyclopropyl]piperidin-1-yl}pyrimidine;

(2S)-)-4-({4-[({(1R,2R)-2-[1-(5-ethylpyrimidin-2-yl)piperidin-4-yl]cyclopropyl}methoxy)methyl]phenyl}sulfonyl)butan-2-ol;

5-ethyl-2-{4-[(1R,2R)-2-((1R)-2-methoxy-1-{[4-(methylsulfonyl)benzyl]oxy ethyl)cyclopropyl]piperidin-1-yl}pyrimidine;

5-ethyl-2-{4-[(1R,2R)-2-((1S)-2-methoxy-1-{[4-(methylsulfonyl)benzyl]oxy ethyl)cyclopropyl]piperidin-1-yl}pyrimidine;

5-ethyl-2-{4-[(1R,2R)-2-((1S)-2-methoxy-1-{[4-(ethylsulfonyl)benzyl]oxy ethyl)cyclopropyl]piperidin-1-yl}pyrimidine;

5-chloro-2-{4-[(1R,2R)-2-({[3,5-difluoro-4-(methylsulfonyl)benzyl]oxy}methyl)cyclopropyl]piperidin-1-yl}pyrimidine;

5-fluoro-2-{4-[(1R,2R)-2-({[3,5-difluoro-4-(methylsulfonyl)benzyl]oxy}methyl)cyclopropyl]piperidin-1-yl}pyrimidine;

5-bromo-2-{4-[(1R,2R)-2-({[3,5-difluoro-4-(methylsulfonyl)benzyl]oxy}methyl)cyclopropyl]piperidin-1-yl}pyrimidine;

2-{4-[(1R,2R)-2-({[2-fluoro-4-(methylsulfonyl)benzyl]oxy}methyl)cyclopropyl]piperidin-1-yl}pyrimidine-5-carbaldehyde;

5-cyano-2-{4-[(1R,2R)-2-({[3,5-difluoro-4-(methylsulfonyl)benzyl]oxy}methyl)cyclopropyl]piperidin-1-yl}pyrimidine;

5-methoxy-2-{4-[(1R,2R)-2-({[3,5-difluoro-4-(methylsulfonyl)benzyl]oxy}methyl)cyclopropyl]piperidin-1-yl}pyrimidine;

5-methyl-2-{4-[(1R,2R)-2-({[3,5-difluoro-4-(methylsulfonyl)benzyl]oxy}methyl)cyclopropyl]piperidin-1-yl}pyrimidine;

2-(2-{4-[(1R,2R)-2-({[2-fluoro-4-(methylsulfonyl)benzyl]oxy}methyl)cyclopropyl]piperidin-1-yl}pyrimidin-5-yl)propan-2-ol;

2-(5-{4-[(1R,2R))-2-({[2-fluoro(methylsulfonyl)benzyl]oxy}methyl)cyclopropyl]piperidin-1-yl}pyrazin-2-yl)propan-2-ol;

2-{4-[(1R,2R)-2-({[2-fluoro-4-(methylsulfonyl)benzyl]oxy}methyl)cyclopropyl]piperidin-1-yl}-5-(methoxymethyl)pyrimidine;

4-[(1R,2R)-2-({[2-fluoro-4-(methylsulfonyl)benzyl]oxy}methyl)cyclopropyl]-1-(3-isopropyl-1,2,4-oxadiazol-5-yl)piperidine;

tert-butyl 4-{(1R,2R)-2-[({2-fluoro-4-[(2-hydroxyethyl)sulfonyl]benzyl}oxy)methyl]cyclopropyl}piperidine-1-carboxylate;

2-({4-[({(1R,2R))-2-[1-(5-chloropyrimidin-2-yl)piperidin-4-yl]cyclopropyl-1}methoxy)methyl]-3-fluorophenyl}sulfonyl)ethanol;

2-({4-[({(1R,2R))-2-[1-(5-bromopyrimidin-2-yl)piperidin-4-yl]cyclopropyl}methoxy)methyl]-3-fluorophenyl}sulfonyl)ethanol;

2-({4-[({(1R,2R))-2-[1-(5-methylpyrimidin-2-yl)piperidin-4-yl]cyclopropyl}methoxy)methyl]-3-fluorophenyl}sulfonyl)ethanol;

2-({4-[({(1R,2R))-2-[1-(5-ethylpyrimidin-2-yl)piperidin-4-yl]cyclopropyl}methoxy)methyl]-3-fluorophenyl}sulfonyl)ethanol;

2-({4-[({(1R,2R))-2-[1-(5-propylpyrimidin-2-yl)piperidin-4-yl]cyclopropyl}methoxy)methyl]-3-fluorophenyl}sulfonyl)ethanol;

2-[(3-fluoro-4-{[((1R,2R)-2-{1-[5-(3-furyl)pyrimidin-2-yl]piperidin-4-yl}cyclopropyl)methoxy]methyl}phenyl)sulfonyl]ethanol;

2-({6-[({(1R,2R)-2-[1-(5-chloropyrimidin-2-yl)piperidin-4-yl]cyclopropyl}methoxy)methyl]pyridin-3-yl}sulfonyl)ethanol;

2-({6-[({(1R,2R)-2-[1-(5-bromopyrimidin-2-yl)piperidin-4-yl]cyclopropyl}methoxy)methyl]pyridin-3-yl}sulfonyl)ethanol;

2-({6-[({(1R,2R)-2-[1-(5-ethylpyrimidin-2-yl)piperidin-4-yl]cyclopropyl}methoxy)methyl]pyridin-3-yl}sulfonyl)ethanol;

2-({6-[({(1R,2R)-2-[1-(5-propylpyrimidin-2-yl)piperidin-4-yl]cyclopropyl}methoxy)methyl]pyridin-3-yl}sulfonyl)ethanol;

2-({6-[({(1R,2R)-2-[1-(5-cyclopropylpyrimidin-2-yl)piperidin-4-yl]cyclopropyl}methoxy)methyl]pyridin-3-yl}sulfonyl)ethanol;

tert-butyl 4-(1R,2R)-2-[({4-[(2-oxopropyl)thio]benzyl}oxy)methyl]cyclopropyl}piperidine-1-carboxylate;

tert-butyl 4-(1R,2R)-2-[({4-[(2-hydroxy-2-methylpropyl) thio]benzyl}oxy)methyl]cyclopropyl}piperidine-1-carboxylate;

tert-butyl 4-(1R,2R)-2-[({4-[(2R/S-hydroxypropyl)thio] benzyl}oxy)methyl]cyclo propyl}piperidine-1-carboxylate;

tert-butyl 4-(1R,2R)-2-[({4-[(2R/S-hydroxypropyl)sulfonyl]benzyl}oxy)methyl]cyclopropyl}piperidine-1-carboxylate;

1-({4-[({(1R,2R)-2-[1-(5-chloropyrimidin-2-yl)piperidin-4-yl]cyclopropyl}methoxy)methyl]-3-fluoro phenyl}sulfonyl)propan-2-ol;

1-({4-[({(1R,2R)-2-[1-(5-fluoropyrimidin-2-yl)piperidin-4-yl]cyclopropyl}methoxy)methyl]-3-fluoro phenyl}sulfonyl)propan-2-ol;

1-({4-[({(1R,2R)-2-[1-(5-bromopyrimidin-2-yl)piperidin-4-yl]cyclopropyl}methoxy)methyl]-3-fluoro phenyl}sulfonyl)propan-2-ol;

1-({4-[({(1R,2R)-2-[1-(5-chloropyrazin-2-yl)piperidin-4-yl]cyclopropyl}methoxy)methyl]-3-fluoro phenyl}sulfonyl)propan-2-ol;

3-{4-[({(1R,2R)-2-[1-(5-ethylpyrimidin-2-yl)piperidin-4-yl]cyclopropyl}methoxy)methyl]-3-fluorophenyl}pyridazine;

3-{4-[({(1R,2R)-2-[1-(5-ethylpyrimidin-2-yl)piperidin-4-yl]cyclopropyl}methoxy)methyl]-3-fluorophenyl}-6-methylpyridazine;

3-{4-[({(1R,2R)-2-[1-(5-ethylpyrimidin-2-yl)piperidin-4-yl]cyclopropyl}methoxy)methyl]-3-fluorophenyl}-6-methoxypyridazine;

4-{4-[({(1R,2R)-2-[1-(5-ethylpyrimidin-2-yl)piperidin-4-yl]cyclopropyl}methoxy)methyl]-3-fluorophenyl}pyridazine;

5-{4-[({(1R,2R)-2-[1-(5-ethylpyrimidin-2-yl)piperidin-4-yl]cyclopropyl}methoxy)methyl]-3-fluorophenyl}pyrimidin-2-amine;

5-{4-[({(1R,2R)-2-[1-(5-ethylpyrimidin-2-yl)piperidin-4-yl]cyclopropyl}methoxy)methyl]-3-fluorophenyl}-2-methoxypyrimidine;

4-{4-[({(1R,2R)-2-[1-(5-ethylpyrimidin-2-yl)piperidin-4-yl]cyclopropyl}methoxy)methyl]-3-fluorophenyl}pyrimidin-2-amine;

4-{4-[({(1R,2R)-2-[1-(5-ethylpyrimidin-2-yl)piperidin-4-yl]cyclopropyl}methoxy)methyl]-3-fluorophenyl}-2-methoxypyrimidine;

2-{4-[({(1R,2R)-2-[1-(5-ethylpyrimidin-2-yl)piperidin-4-yl]cyclopropyl}methoxy)methyl]-3-fluorophenyl}pyrazin-2-amine;

5-{4-[({(1R,2R)-2-[1-(5-ethylpyrimidin-2-yl)piperidin-4-yl]cyclopropyl}methoxy)methyl]-3-fluorophenyl}pyrimidine;

2-{4-[({(1R,2R)-2-[1-(5-ethylpyrimidin-2-yl)piperidin-4-yl]cyclopropyl}methoxy)methyl]-3-fluorophenyl}pyrazine;

4-{4-[({(1R,2R)-2-[1-(5-ethylpyrimidin-2-yl)piperidin-4-yl]cyclopropyl}methoxy)methyl]-3-fluorophenyl}pyrimidine;

5-ethyl-2-{4-[(1R,2R)-2-({[2-fluoro-4-(2-methyl-1,3-thiazol-5-yl)benzyl]oxy}methyl)cyclopropyl]piperidin-1-yl}pyrimidine;

4-{4-[({(1R,2R)-2-[1-(5-ethylpyrimidin-2-yl)piperidin-4-yl]cyclopropyl}methoxy)methyl]-2-fluorophenyl}pyrimidine;

5-{4-[({(1R,2R)-2-[1-(5-ethylpyrimidin-2-yl)piperidin-4-yl]cyclopropyl}methoxy)methyl]-2-fluorophenyl}pyrimidine;

3-{4-[({(1R,2R)-2-[1-(5-ethylpyrimidin-2-yl)piperidin-4-yl]cyclopropyl}methoxy)methyl]-2-fluorophenyl}pyridazine;

4-{4-[({(1R,2R)-2-[1-(5-ethylpyrimidin-2-yl)piperidin-4-yl]cyclopropyl}methoxy)methyl]-2-fluorophenyl}pyridazine;

4-{4-[({(1R,2R)-2-[1-(5-ethylpyrimidin-2-yl)piperidin-4-yl]cyclopropyl}methoxy)methyl]-2-fluorophenyl}-6-methoxypyridazine;

4-{4-[({(1R,2R)-2-[1-(5-ethylpyrimidin-2-yl)piperidin-4-yl]cyclopropyl}methoxy)methyl]-2-fluorophenyl}-6-methylpyridazine;

5-{4-[({(1R,2R)-2-[1-(5-ethylpyrimidin-2-yl)piperidin-4-yl]cyclopropyl}methoxy)methyl]-2-fluorophenyl}pyrimidin-2-amine;

4-{4-[({(1R,2R)-2-[1-(5-ethylpyrimidin-2-yl)piperidin-4-yl]cyclopropyl}methoxy)methyl]-3-fluorophenyl}-2-methoxypyrimidine;

5-ethyl-2-[4-((1R,2R))-2-{[(4-pyrimidin-5-ylbenzyl)oxy] methyl}cyclopropyl)piperidin-1-yl]pyrimidine;

5-ethyl-2-[4-((1R,2R))-2-{[(4-pyridazin-4-ylbenzyl)oxy] methyl}cyclopropyl)piperidin-1-yl]pyrimidine;

5-ethyl-2-[4-((1R,2R))-2-{[(4-pyridazin-4-ylbenzyl)oxy] methyl}cyclopropyl)piperidin-1-yl]pyrimidine; and 5-ethyl-2-[4-((1R,2R))-2-{[(4-pyrazin-2-ylbenzyl)oxy] methyl}cyclopropyl)piperidin-1-yl]pyrimidine;

2-(4-((1R,2R)-2-(((2-fluoro-4-(methylsulfonyl)benzyl) oxy)methyl)cyclopropyl)piperidin-1-yl)-5-(methoxymethyl)pyrimidine;

2-(4-((1R,2R)-2-(((2-fluoro-4-(methylsulfonyl)benzyl) oxy)methyl)cyclopropyl)piperidin-1-yl)-5-(1-methoxyethyl)pyrimidine;

2-(4-((1R,2R)-2-(((4-(ethylsulfonyl)-2-fluorobenzyl)oxy) methyl)cyclopropyl)piperidin-1-yl)-5-(methoxymethyl)pyrimidine;

2-(4-((1R,2R)-2-(((3,5-difluoro-4-(methylsulfonyl)benzyl)oxy)methyl)cyclopropyl)piperidin-1-yl)-5-(methoxymethyl)pyrimidine;

5-ethoxy-2-(4-((1R,2R)-2-(((3-fluoro-4-(methylsulfonyl) benzyl)oxy)methyl)cyclopropyl)piperidin-1-yl)pyrimidine;

2-(4-((1R,2R)-2-(((3-fluoro-4-(methylsulfonyl)benzyl) oxy)methyl)cyclopropyl)piperidin-1-yl)-5-(-methoxyethyl)pyrimidine;

2-(4-((1R,2R)-2-(((3-fluoro-4-(1H-tetrazol-1-yl)benzyloxy)methyl)cyclopropyl)piperidin-1-yl)-5-(methoxymethyl)pyrimidine;

2-(4-((1R,2R)-2-(((5-(1H-tetrazol-1-yl)pyridin-2-yl) methoxy)methyl)cyclopropyl)piperidin-1-yl)-5-ethylpyrimidine;

5-(4-((1R,2R)-2-(((2-fluoro-4-(1H-tetrazol-1-yl)benzyloxy)methyl)cyclopropyl)piperidin-1-yl)-3-isopropyl-1,2,4-oxadiazole;

5-(4-((1R,2R)-2-(((2-fluoro-4-(1H-tetrazol-1-yl)benzyl) oxy)methyl)cyclopropyl)piperidin-1-yl)-3-(methoxymethyl)-1,2,4-oxadiazole;

1-methylcyclopropyl 4-((1R,2R)-2-((2-fluoro-4-(1H-tetrazol-1-yl)benzyloxy)methyl)cyclopropyl)piperidine-1-carboxylate;

2-(3-fluoro-4-((((1R,2R)-2-(1-(3-isopropyl-1,2,4-oxadiazol-5-yl)piperidin-4-yl)cyclopropyl)methoxy)methyl) phenyl)-N,N-dimethylacetamide;

2-(3-fluoro-4-((((1R,2R)-2-(1-(3-isopropyl-1,2,4-oxadiazol-5-yl)piperidin-4-yl)cyclopropyl)methoxy)methyl) phenyl)-1-(3-methoxyazetidin-1-yl)ethanone;

2-(3-fluoro-4-((((1R,2R)-2-(1-(3-isopropyl-1,2,4-oxadiazol-5-yl)piperidin-4-yl)cyclopropyl)methoxy)methyl)phenyl)-1-(3-fluoroazetidin-1-yl) ethanone;

2-(2-fluoro-4-((((1R,2R)-2-(1-(3-isopropyl-1,2,4-oxadiazol-5-yl)piperidin-4-yl)cyclopropyl)methoxy)methyl)phenyl)-N—N-dimethylacetamide;

2-(2-fluoro-4-((((1R,2R)-2-(1-(3-isopropyl-1,2,4-oxadiazol-5-yl)piperidin-4-yl)cyclopropyl)methoxy)methyl)phenyl)-1-morpholinoethanone;

2-(2-fluoro-4-((((1R,2R)-2-(1-(3-isopropyl-1,2,4-oxadiazol-5-yl)piperidin-4-yl)cyclopropyl)methoxy)methyl)phenyl)-1-(3-methoxyazetidin-1-yl)ethanone;

2-(2-fluoro-4-((((1R,2R)-2-(1-(3-isopropyl-1,2,4-oxadiazol-5-yl)piperidin-4-yl)cyclopropyl)methoxy)methyl)phenyl)-1-(3-hydroxyazetidin-1-yl)ethanone;

2-(2-fluoro-4-((((1R,2R)-2-(1-(3-(methoxymethyl)-1,2,4-oxadiazol-5-yl)piperidin-4-yl)cyclopropyl)methoxy)methyl)phenyl)-1-(3-hydroxyazetidin-1-yl)ethanone;

1-(azetidin-1-yl)-2-(3-fluoro-4-((((1R,2R)-2-(1-(5-(methoxymethyl) pyrimidin-2-yl)piperidin-4-yl)cyclopropyl)methoxy)methyl)phenyl)ethanone;

2-(3-fluoro-4-((((1R,2R)-2-(1-(5-(methoxymethyl)pyrimidin-2-yl)piperidin-4-yl)cyclopropyl)methoxy)methyl)phenyl)-1-morpholinoethanone;

2-(3-fluoro-4-((((1R,2R)-2-(1-(5-(methoxymethyl)pyrimidin-2-yl)piperidin-4-yl)cyclopropyl)methoxy)methyl)phenyl)-N,N-dimethylacetamide;

2-(3-fluoro-4-((((1R,2R)-2-(1-(5-(methoxymethyl)pyrimidin-2-yl)piperidin-4-yl)cyclopropyl)methoxy)methyl)phenyl)-1-(3-fluoroazetidin-1-yl)ethanone;

or a pharmaceutically acceptable salt thereof.

14. The compound of claim 1, which is

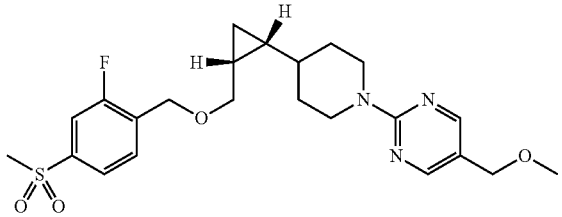

or a pharmaceutically acceptable salt thereof.

15. The compound of claim 1, which is

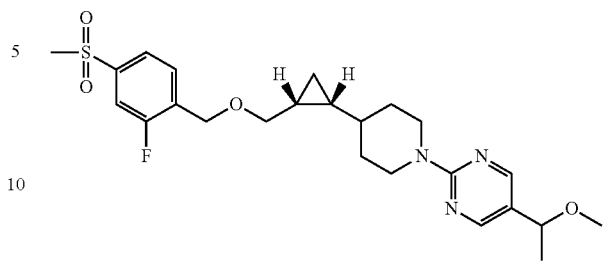

or a pharmaceutically acceptable salt thereof.

16. A pharmaceutical composition comprising a compound of claim 1 or a pharmaceutically acceptable salt thereof, and a pharmaceutically acceptable carrier.

17. A method for the treatment of a condition selected from obesity or diabetes comprising administering to an individual a pharmaceutical composition comprising the compound of claim 1 or a pharmaceutically acceptable salt thereof.

18. The compound of claim 1, which is

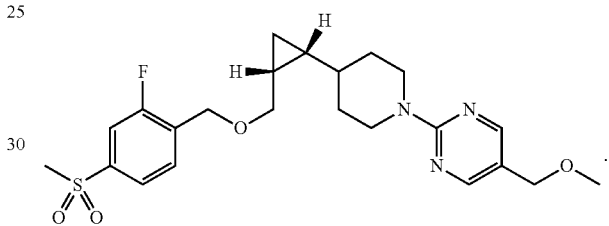

19. The compound of claim 1, which is

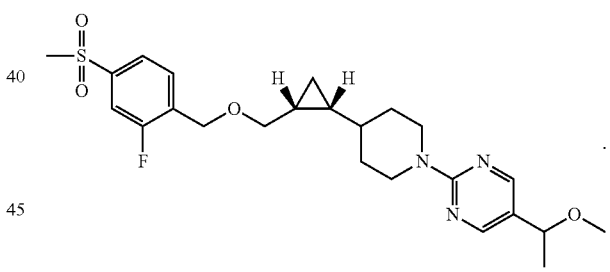

* * * * *